US009096909B2

(12) United States Patent
Preuss et al.

(10) Patent No.: US 9,096,909 B2

(45) Date of Patent: Aug. 4, 2015

(54) ***SORGHUM* CENTROMERE SEQUENCES AND MINICHROMOSOMES**

(75) Inventors: Daphne Preuss, Chicago, IL (US); Pierluigi Barone, Charleston, IL (US); Shawn R. Carlson, Bondville, IL (US); Gregory P. Copenhaver, Chapel Hill, NC (US); Song Luo, Chicago, IL (US); Jennifer M. Mach, Chicago, IL (US)

(73) Assignee: CHROMATIN, INC., Chicago, IL (US)

( * ) Notice: Subject to any disclaimer, the term of this patent is extended or adjusted under 35 U.S.C. 154(b) by 525 days.

(21) Appl. No.: 13/383,699

(22) PCT Filed: Jul. 23, 2010

(86) PCT No.: PCT/US2010/043065

§ 371 (c)(1), (2), (4) Date: May 7, 2012

(87) PCT Pub. No.: WO2011/011693

PCT Pub. Date: Jan. 27, 2011

(65) Prior Publication Data

US 2012/0255072 A1 Oct. 4, 2012

Related U.S. Application Data

(60) Provisional application No. 61/228,015, filed on Jul. 23, 2009.

(51) Int. Cl.

| | |
|---|---|
| ***C12N 15/82*** | (2006.01) |
| ***C12N 15/63*** | (2006.01) |
| ***C12N 15/09*** | (2006.01) |
| ***A01H 5/00*** | (2006.01) |
| ***C12Q 1/68*** | (2006.01) |

(52) U.S. Cl.

CPC .......... *C12Q 1/6895* (2013.01); *C12N 15/8245* (2013.01)

(58) Field of Classification Search

CPC .... C12N 15/09; C12N 15/82; C12N 15/8245; C12Q 1/6895

See application file for complete search history.

(56) References Cited

U.S. PATENT DOCUMENTS

| | | | |
|---|---|---|---|
| 4,889,806 | A | 12/1989 | Olson et al. |
| 5,270,201 | A | 12/1993 | Richards et al. |
| 5,288,625 | A | 2/1994 | Hadlaczky |
| 5,316,931 | A | 5/1994 | Donson et al. |
| 5,491,076 | A | 2/1996 | Carrington et al. |
| 5,530,187 | A | 6/1996 | Lamb et al. |
| 5,589,379 | A | 12/1996 | Kridl et al. |
| 5,608,149 | A | 3/1997 | Barry et al. |
| 5,650,303 | A | 7/1997 | Kridl et al. |
| 5,695,967 | A | 12/1997 | Van Bokkelen et al. |
| 5,712,134 | A | 1/1998 | Hadlaczky et al. |
| 5,721,118 | A | 2/1998 | Scheffler |
| 5,733,744 | A | 3/1998 | Hamilton |
| 5,766,885 | A | 6/1998 | Carrington et al. |
| 5,773,705 | A | 6/1998 | Vierstra et al. |
| 5,866,793 | A | 2/1999 | Baga et al. |
| 5,869,294 | A | 2/1999 | Harrington et al. |
| 5,877,402 | A | 3/1999 | Maliga et al. |
| 5,891,625 | A | 4/1999 | Buchardt et al. |
| 5,891,691 | A | 4/1999 | Hadlaczky et al. |
| 5,925,808 | A | 7/1999 | Oliver et al. |
| 5,977,439 | A | 11/1999 | Hamilton |
| 5,977,441 | A | 11/1999 | Oliver et al. |
| 6,025,155 | A | 2/2000 | Hadlaczky et al. |
| 6,048,692 | A | 4/2000 | Maracas et al. |
| 6,077,697 | A | 6/2000 | Hadlaczky et al. |
| 6,127,171 | A | 10/2000 | Slilaty et al. |
| 6,156,953 | A | 12/2000 | Preuss et al. |
| 6,162,963 | A | 12/2000 | Kucherlapati et al. |
| 6,265,211 | B1 | 7/2001 | Choo et al. |
| 6,277,608 | B1 | 8/2001 | Hartley et al. |
| 6,277,632 | B1 | 8/2001 | Harney |
| 6,291,243 | B1 | 9/2001 | Fogarty et al. |
| 6,337,431 | B1 | 1/2002 | Tricoli et al. |
| 6,348,353 | B1 | 2/2002 | Harrington et al. |
| 6,365,377 | B1 | 4/2002 | Patten et al. |
| 6,369,296 | B1 | 4/2002 | Ratcliff et al. |
| 6,376,234 | B1 | 4/2002 | Grimsley et al. |
| 6,376,745 | B1 | 4/2002 | Atabekov et al. |
| 6,388,168 | B1 | 5/2002 | Maliga et al. |

(Continued)

FOREIGN PATENT DOCUMENTS

| | | |
|---|---|---|
| EP | 0 320 500 A2 | 6/1989 |
| EP | 0 338 266 A2 | 10/1989 |

(Continued)

OTHER PUBLICATIONS

Bedell et al., *Sorghum* genome sequencing by methylation filtration, *PLOS Biol.*, 3:104-15 (2005).
Carlson et al., Meiotic transmission of an in vitro-assembled autonomous maise minichromosome, *PLOS Gen.*, 3:1965-74 (2007).
Miller et al., Retrotransposon-related DNA sequences in the centromeres of grass chromosomes, *Genetics*, 150:1615-23 (1998).
Zwick et al., Distribution and sequence analysis of the centromere-associated repetitive element CEN38 of *Sorghum bicolor* (Poaceae), *Am. J. Botany*, 87:1757-64 (2000).
Extended European Search Report, European Patent Office, EP10802957, dated Aug. 21, 2013.
Abdullah et al., Efficient plant regeneration from rice protoplasts through somatic embryogenesis, *BioTechnology*, 4: 1087-90 (1986).
Abel et al., Delay of disease development in transgenic plants that express the tobacco mosaic virus coat protein Gene, *Science*, 232: 738-43 (1986).

(Continued)

*Primary Examiner* — Brent T Page

(74) *Attorney, Agent, or Firm* — Marshall, Gerstein & Borun LLP

(57) ABSTRACT

The invention is generally related to MCs containing sorghum centromere sequences. In addition, the invention provides for methods of generating plants transformed with these MCs. MCs with novel compositions and structures are used to transform plants cells which are in turn used to generate the plant. Methods for generating the plant include methods for delivering the MC into plant cell to transform the cell, methods for selecting the transformed cell, and methods for isolating plants transformed with the MC.

19 Claims, No Drawings

(56) References Cited

U.S. PATENT DOCUMENTS

| | | | |
|---|---|---|---|
| 6,391,639 | B1 | 5/2002 | Schenk et al. |
| 6,455,315 | B1 | 9/2002 | Baszczynski et al. |
| 6,472,586 | B1 | 10/2002 | Maliga et al. |
| 6,475,798 | B2 | 11/2002 | Fogarty et al. |
| 6,495,318 | B2 | 12/2002 | Harney |
| 6,514,693 | B1 | 2/2003 | Lansdorp |
| 6,573,427 | B1 | 6/2003 | Atabekov et al. |
| 6,900,012 | B1 | 5/2005 | Preuss et al. |
| 6,942,771 | B1 | 9/2005 | Kayyem |
| 6,972,197 | B1 | 12/2005 | Preuss et al. |
| 7,119,250 | B2 | 10/2006 | Keith et al. |
| 7,226,782 | B2 | 6/2007 | Mach et al. |
| 7,227,057 | B2 | 6/2007 | Mach et al. |
| 7,235,716 | B2 | 6/2007 | Mach et al. |
| 7,456,013 | B2 | 11/2008 | Mach et al. |
| 7,534,331 | B2 | 5/2009 | Kayyem |
| 2001/0008025 | A1 | 7/2001 | Hadlaczky et al. |
| 2002/0028513 | A1 | 3/2002 | Fogarty et al. |
| 2002/0034814 | A1 | 3/2002 | Atabekov et al. |
| 2002/0059660 | A1 | 5/2002 | Tricoli et al. |
| 2002/0072097 | A1 | 6/2002 | Delcardayre et al. |
| 2002/0076811 | A1 | 6/2002 | Okazaki et al. |
| 2002/0094574 | A1 | 7/2002 | Hartley et al. |
| 2002/0108146 | A1 | 8/2002 | Pang et al. |
| 2002/0111930 | A1 | 8/2002 | Battles |
| 2002/0123053 | A1 | 9/2002 | Luo et al. |
| 2002/0123145 | A1 | 9/2002 | Ow |
| 2002/0128457 | A1 | 9/2002 | Anderson et al. |
| 2002/0132348 | A1 | 9/2002 | Bradshaw et al. |
| 2002/0151058 | A1 | 10/2002 | Perkins et al. |
| 2002/0155530 | A1 | 10/2002 | Szybalski et al. |
| 2002/0160410 | A1 | 10/2002 | Hadlaczky et al. |
| 2002/0160970 | A1 | 10/2002 | Hadlaczky et al. |
| 2002/0172997 | A1 | 11/2002 | Hartley et al. |
| 2002/0174453 | A1 | 11/2002 | Daniell et al. |
| 2002/0192819 | A1 | 12/2002 | Hartley et al. |
| 2003/0003435 | A1 | 1/2003 | DeJong et al. |
| 2003/0003466 | A1 | 1/2003 | Harrington et al. |
| 2003/0022204 | A1 | 1/2003 | Lansdorp |
| 2003/0032186 | A1 | 2/2003 | Jorgensen et al. |
| 2003/0033617 | A1 | 2/2003 | Hadlaczky et al. |
| 2003/0041353 | A1 | 2/2003 | Daniell et al. |
| 2003/0049665 | A1 | 3/2003 | Szybalski et al. |
| 2003/0064509 | A1 | 4/2003 | Marynen et al. |
| 2003/0077804 | A1 | 4/2003 | Byrd et al. |
| 2003/0083293 | A1 | 5/2003 | Hadlaczky et al. |
| 2003/0084482 | A1 | 5/2003 | Hall et al. |
| 2003/0088081 | A1 | 5/2003 | Maliga et al. |
| 2003/0097678 | A1 | 5/2003 | Kushinov et al. |
| 2003/0101480 | A1 | 5/2003 | Hadlaczky et al. |
| 2003/0108914 | A1 | 6/2003 | Hadlaczky |
| 2003/0124561 | A1 | 7/2003 | Mach et al. |
| 2005/0268359 | A1 | 12/2005 | Mach et al. |
| 2007/0271629 | A1 | 11/2007 | Ananiev et al. |

FOREIGN PATENT DOCUMENTS

| | | | |
|---|---|---|---|
| EP | 0 442 174 | A1 | 8/1991 |
| EP | 0 552 829 | A1 | 7/1993 |
| EP | 0 712 272 | A1 | 5/1996 |
| EP | 0 959 134 | A1 | 11/1999 |
| EP | 1 033 405 | A2 | 9/2000 |
| WO | WO-89/09219 | A1 | 10/1989 |
| WO | WO-91/02066 | A1 | 2/1991 |
| WO | WO-91/13994 | A1 | 9/1991 |
| WO | WO-92/07080 | A1 | 4/1992 |
| WO | WO-93/05165 | A1 | 3/1993 |
| WO | WO-95/02319 | A1 | 1/1995 |
| WO | WO-95/12669 | A1 | 5/1995 |
| WO | WO-96/40965 | A1 | 12/1996 |
| WO | WO-97/06250 | A1 | 2/1997 |
| WO | WO-97/14026 | A2 | 4/1997 |
| WO | WO-97/40183 | A2 | 10/1997 |
| WO | WO-98/02562 | A2 | 1/1998 |
| WO | WO-98/08964 | A1 | 3/1998 |
| WO | WO-98/37223 | A1 | 8/1998 |
| WO | WO-98/51790 | A1 | 11/1998 |
| WO | WO-98/54342 | A1 | 12/1998 |
| WO | WO-98/55637 | A1 | 12/1998 |
| WO | WO-99/06581 | A1 | 2/1999 |
| WO | WO-99/21977 | A1 | 5/1999 |
| WO | WO-99/67374 | A1 | 12/1999 |
| WO | WO-00/06715 | A1 | 2/2000 |
| WO | WO-00/07431 | A1 | 2/2000 |
| WO | WO-00/18941 | A1 | 4/2000 |
| WO | WO-00/40723 | A2 | 7/2000 |
| WO | WO-00/46350 | A1 | 8/2000 |
| WO | WO-00/52155 | A2 | 9/2000 |
| WO | WO-00/52183 | A1 | 9/2000 |
| WO | WO-00/55325 | A2 | 9/2000 |
| WO | WO-00/75289 | A1 | 12/2000 |
| WO | WO-00/75299 | A1 | 12/2000 |
| WO | WO-00/78985 | A1 | 12/2000 |
| WO | WO-01/00858 | A1 | 1/2001 |
| WO | WO-01/05962 | A1 | 1/2001 |
| WO | WO-01/11020 | A1 | 2/2001 |
| WO | WO-01/20011 | A1 | 3/2001 |
| WO | WO-01/27241 | A2 | 4/2001 |
| WO | WO-01/29241 | A2 | 4/2001 |
| WO | WO-01/59091 | A2 | 8/2001 |
| WO | WO-01/64024 | A1 | 9/2001 |
| WO | WO-01/77357 | A2 | 10/2001 |
| WO | WO-01/78976 | A1 | 10/2001 |
| WO | WO-02/00842 | A2 | 1/2002 |
| WO | WO-02/04629 | A2 | 1/2002 |
| WO | WO-02/08409 | A2 | 1/2002 |
| WO | WO-02/12555 | | 2/2002 |
| WO | WO-02/29068 | A2 | 4/2002 |
| WO | WO-02/50288 | A1 | 6/2002 |
| WO | WO-02/057464 | A2 | 7/2002 |
| WO | WO-02/059296 | A2 | 8/2002 |
| WO | WO-02/059330 | A2 | 8/2002 |
| WO | WO-02/067655 | A1 | 9/2002 |
| WO | WO-02/072849 | A2 | 9/2002 |
| WO | WO-02/081710 | A1 | 10/2002 |
| WO | WO-02/086144 | A2 | 10/2002 |
| WO | WO-02/086146 | A2 | 10/2002 |
| WO | WO-02/096923 | A1 | 12/2002 |
| WO | WO-03/028014 | A1 | 4/2003 |
| WO | WO-2005/010142 | A2 | 2/2005 |
| WO | WO-2005/010187 | A1 | 2/2005 |
| WO | WO-2005/083096 | A1 | 9/2005 |
| WO | WO-2007/030510 | A2 | 3/2007 |
| WO | WO-2007/137114 | A2 | 11/2007 |

OTHER PUBLICATIONS

Adam et al., Retrofitting YACs for direct DNA transfer into plant cells, *Plant J.*, 11: 1349-58 (1997).

Alfenito et al., Molecular characterization of a maize B chromosome centric sequence, *Genetics*, 135: 589-97 (1993).

Alonso-Blanco et al., Development of AFLP based linkage map of L*er*, Col and Cvi *Arabidopsis thaliana* ecotypes and construction of a L*er*/Cvi recombinant inbred line population, *Plant J.*, 14: 259-71 (1998).

Ananiev et al., A knob-associated tandem repeat in maize capable of forming fold-back DNA segments:Are chromosome knobs megatransposons? *Proc. Natl. Acad. Sci. USA*, 95: 10785-90 (1998).

Ananiev et al., Chromosome-specific molecular organization of maize (*Zea mays* L.) centromeric regions, *Proc. Natl. Acad. Sci. USA*, 95: 13073-8 (1998).

Ananiev et al., Complex structure of knob DNA on maize chromosome 9: Retrotransposon invasion into heterochromatin, *Genetics*, 149: 2025-37 (1998).

Ananiev et al., Complex structure of knobs and centromeric regions in maize chromosomes, *Tsitol Genet.*, 34: 11-5 (2000).

Aragon-Alcaide et al., A cereal centromeric sequence, *Chromosoma*, 105: 261-8 (1996).

Araki et al., Site-specific recominanse, R, encoded by yeast plasmid pSR1, *J. Mol. Biol.*, 225: 25-37 (1992).

Areshchenkova et al., Long tomato microsatellites are predominantly associated with centromeric regions, *Genome*, 42: 536-44 (1999).

(56) References Cited

OTHER PUBLICATIONS

Armstrong et al., Physical mapping of DNA repetitive sequences to mitotic and meiotic chromosomes of *Brassica oleracea* var. alboglabra by fluorescence in situ hybridization, *Heredity*, 81: 666-73 (1998).
Avramova et al., Heterochromatin in animals and plants. Similarities and differences. *Plant Physiol.*, 129: 40-9 (2002).
Barki-Golan et al., Studies on growth inhibition by lectins of penicillia and aspergilli, *Arch. Microbiol.*, 116: 119-24 (1978).
Baum et al., The centromeric K-type repeat and the central core are together sufficient to establish a functional *Schizosaccharomyces pombe* centromere, *Molec. Biol. Cell*, 5: 747-61 (1994).
Bell et al., Assignment of 30 microsatellite loci to the linkage map of *Arabidopsis, Genomics*, 19: 137-44 (1994).
Bernal-Lugo et al., Changes in soluble carbohydrates during seed storage, *Plant Physiol.*, 98: 1207-10 (1992).
Berzal-Herranz et al., In vitro selection of active hairpin ribozymes by sequential RNA-catalyzed cleavage and ligation reactions, *Genes Dev.*, 6: 129-34 (1992).
Bevan et al., Clearing a path through the jungle: Progress in *Arabidopsis* genomics, *BioEssays*, 21: 110-20 (1999).
Bevan et al., Structure and transcription of the nopaline synthase gene region of T-DNA, *Nucl. Acids Res.*, 11: 369-85 (1983).
Birchler, Do these sequences make CENs yet? *Genome Res.*, 7: 1035-7 (1997).
Blackman et al., Maturation proteins and sugars in dessiccation tolerance of developing soybean seeds, *Plant Physiol.*, 100: 225-30 (1992).
Bloom, The Centromere frontier: Kinetochore components, microtubule-based motility, and the CEN-value paradox, *Cell*, 73: 621-4 (1993).
Bol et al., Plant pathogenesis-related proteins induced by virus infection, *Annu. Rev. Phytopath.*, 28: 113-38 (1990).
Bowler et al., Superoxide dismutase and stress tolerance, *Annu. Rev. Plant Physiol. Plant Mol. Biol.*, 43: 83-116 (1992).
Brandes et al., Multiple repetitive DNA sequences in the paracentromeric regions of *Arabidopsis thaliana* L., *Chromosome Res.*, 5: 238-46 (1997).
Branson et al., Potential for utilizing resistance from relatives of cultivated crops, *Proc. N. Cent. Branch Entomol. Soc. Am.*, 27: 91-5 (1972).
Brisson et al., Expression of a bacterial gene in plants by using a viral vector, *Nature*, 310: 511-6 (1984).
Broach et al., Transformation in yeast: Development of a hybrid cloning vector and isolation of the CAN1 gene, *Gene*, 8: 121-33 (1979).
Broekaert et al., A chitin-binding lectin from stinging nettle rhizomes with antifungal properties, *Science*, 245: 1100-2 (1989).
Broun et al., Characterization and genetic mapping of simple repeat sequences in the tomato genome, *Mol. Gen. Genet.*, 250: 39-49 (1996).
Bryant et al., Origins and complexes: The initiation of DNA replication. *J. Exp. Biol.*, 52: 193-202 (2001).
Buchowicz, Nuclear extrachromosomal DNA of higher plants, *Acta Biochim Pol.*, 44: 13-9 (1977).
Burke et al., Cloning of large segments of exogenous DNA into yeast by means of artificial chromosome vectors, *Science*, 236: 806-12 (1987).
Bytebier et al., T-DNA organization in tumor cultures and transgenic plants of the monocotyledon *Asparagus officinalis, Proc. Natl. Acad. Sci. USA*, 84: 5345-9 (1987).
Callis et al., Introns increase gene expression in cultured maize cells, *Genes Dev.*, 1: 1183-200 (1987).
Cambareri et al., Structure of the chromosome VII centromere region in *Neurospora crassa*: Degenerate transposons and simple repeats, *Molec. Cell. Biol.*, 18: 5465-77 (1998).
Campbell, The production and characterization of rodent and human hybridomas, *Lab. Tech. Biochem. Molec. Biol.*, 13: 75-83 (1984).
Capecchi, High efficiency transformation by direct microinjection of DNA into cultured mammalian cells, *Cell*, 22: 479-88 (1980).
Carbon et al., Centromere structure and function in budding and fission yeasts, *New Biologist*, 2: 10-9 (1990).
Carbon et al., Recombinant molecules: Impact on science and society, Raven Press: 335-78 (1977).
Carbon et al., Structural and functional analysis of a yeast centromere (CEN3), *J. Cell Sci.*, Suppl. 1, 43-58 (1984).
Carlson et al., Meiotic transmission of an in vitro-assembled autonomous maize minichromosome. *PLoS Genet.*, 3(10): 1965-74 (2007).
Carpenter et al., On the control of the distribution of meiotic exchange in *Drosophila melanogaster, Genetics*, 101: 81-9 (1982).
Cech et al., In vitro splicing of the ribosomal RNA precursor of tetrahymena: Involvement of a guanosine nucleotide in the excision of the intervening sequence, *Cell*, 27: 487-96 (1981).
Cepko et al., Construction and applications of a highly transmissible murine retrovirus shuttle vector, *Cell*, 37: 1053-62 (1984).
Chandler et al., Two regulatory genes of the maize anthocyanin pathway are homologous: Isolation of *B* utilizing *R* genomic sequences, *Plant Cell*, 1: 1175-83 (1989).
Chang et al., Restriction fragment length polymorphism linkage map for *Arabidopsis thaliana, Proc. Natl. Acad. Sci USA*, 85: 6856-60 (1988).
Charlesworth et al., The evolution of restricted recombination and the accumulation of repeated DNA sequences, *Genetics*, 112: 947-62 (1986).
Charlesworth et al., The evolutionary dynamics of repetitive DNA in eukaryotes, *Nature*, 371: 215-20 (1994).
Cheng et al., Functional rice centromeres are marked by a satellite repeat and a centromere-specific retrotransposon, *Plant Cell.*, 14: 1691-704 (2002).
Choi et al., Construction and characterization of a bacterial artificial chromosome library of *Arabidopsis thaliana, Plant Molec., Biol. Reporter*, 13: 124-9 (1995).
Choo, Turning on the centromere, *Nat. Genet.*, 18: 3-4 (1998).
Choo, Why is the centromere so cold? *Genome Res.*, 8: 81-2 (1998).
Chowrira et al., In vitro and in vivo comparison of hammerhead, hairpin, and hepatitis delta virus self-processing ribozyme cassettes, *J. Biol. Chem.*, 269: 25856-64 (1994).
Christou et al., Stable transformation of soybean callus by DNA-coated gold particles, *Plant Physiol.*, 87: 671-4 (1988).
Chu et al., Separation of large DNA molecules by contour-clamped homogenous electric fields, *Science*, 234: 1582-5 (1986).
Chye et al., Characterization of *TSCL*, a nonviral retroposon from *Arabidopsis thaliana, Plant Molec. Biol.*, 35: 893-904 (1997).
Clapp, Somatic gene therapy into hemotopoietic cells, *Clinics Perinatol.*, 20: 155-68 (1993).
Clarke et al., Analysis of centromeric DNA in the fission yeast *Schizosaccharomyces pombe, Proc. Natl. Acad. Sci. USA.*, 83: 8253-7 (1986).
Clarke et al., Centromeres: Proteins, protein complexes, and repeated domains at centromeres of simple eukaryotes, *Genet. Dev.*, 8:212-8 (1998).
Clarke et al., Isolation of a yeast centromere and construction of functional small circular chromosomes, *Nature*, 287: 504-9 (1980).
Co et al., Generation of transgenic mice and germline transmission of a mammalian artificial chromosome introduced into embryos by pronuclear microinjection. *Chrom. Res.*, 8: 183-91 (2000).
Cohen et al., Construction of biologically functional bacterial plasmids in vitro, *Proc. Nat. Acad. Sci. USA*, 70: 3240-4 (1973).
Conkling et al., Isolation of transcriptionally regulated root-specific genes from tobacco, *Curr. Opin. Plant Physiol.*, 93: 1203-11 (1990).
Copenhaver et al., Assaying genome-wide recombination and centromere functions with *Arabidopsis* tetrads,*Proc. Natl. Acad. Sci. USA*, 95: 247-52 (1998).
Copenhaver et al., Centromeres in the genomic era: Unraveling paradoxes, *Plant Biol.*, 2: 104-8 (1999).
Copenhaver et al., Genetic definition and sequence analysis of *Arabidopsis* Centromeres, *Science*, 286: 2468-74 (1999).
Copenhaver et al., RFLP and physical mapping with an rDNA-specific endonuclease reveals that nucleolus organizer regions of *Arabidopsis thaliana* adjoin the telemores on chromosomes 2 and 4, *Plant J.*, 9: 259-76 (1996).
Copenhaver et al., Tetrad analysis in higher plants: A budding technology, *Plant Physiol.*, 124: 7-16 (2000).

(56) References Cited

OTHER PUBLICATIONS

Copenhaver et al., Two-dimensional RFLP analyses reveal megabase-sized clusters of rRNA gene variants in *Arabidopsis thaliana*, suggesting local spreading of variants as the mode for gene homogenization during concerted evolution, *Plant J.*, 9: 273-82 (1996).
Copenhaver et al., Use of RFLPs larger than 100 kbp to map position and internal organization of the nucleolus organizer region on chromosome 2 in *Arabidopsis thaliana, Plant J.*, 7: 273-86 (1995).
Copenhaver, Using *Arabidopsis* to understand centromere function: Progress and prospects, *Chromosome Res.* 2993(11): 255-62 (2003).
Coxson et al., Pulse release of sugars and polyols from canopy bryophytes in tropical montane rain forest (Guadeloupe, French West Indies), *Biotropica*, 24: 121-33 (1992).
Cramer et al., Restriction endonuclease analysis of ribosomal DNA from *Saccharomyces cerevisae. Molec. Genet.* 148: 233-41 (1976).
Creusot et al., The CIC Library: A large insert YAC library for genome mapping in *Arabidopsis thaliana, Plant J.*, 8: 763-70 (1995).
Cristou et al., Stable transformation of soybean callus by DNA-coated gold particles, *Plant Physiol.*, 87: 671-4 (1988).
Cuozzo et al., Viral protection in transgenic tobacco plants expressing the cucumber mosaic virus coat protein or its antisense RNA, *BioTechnology*, 6: 549-57 (1988).
Curiel et al., Adenovirus enhancement of transferrin-polylysine-mediated gene delivery, *Proc. Natl. Acad. Sci. USA*, 88: 8850-4 (1991).
Curiel et al., High-efficiency gene transfer mediated by adenovirus coupled to DNA-polylysine complexes, *Hum. Gen. Ther.*, 3: 147-54 (1992).
Cutler et al. , Winter flounder antifreeze protein improves the cold hardiness of plant tissues, *J. Plant Physiol.*, 135: 351-4 (1989).
Czapla et al., Effect of plant lectins on the larval development of European corn borer (Lepidoptera: Pyralidae) and southern corn rootworm (Coleoptera: Chrysomelidae), *J. Econ Entomol.*, 83: 2480-5 (1990).
Davies et al., Leaf senescence in a nonyellowing mutant of *Festuca pratensis, Plant Physiol.*, 93: 588-95 (1990).
Dawe et al., Centromeres put epigenetics in the driver's seat. *Trend Biochem. Sci.*, 31: 662-9 (2006).
Dellaporta et al., Molecular cloning of the maize R-nj allele by transposon tagging with Ac: Chromosome structure and function: impact of new concepts, 18th Stadler Genetics Symposium 11: 263-82 (1988).
Dennis et al., Knob heterochromatin homology in maize and its relatives, *J. Mol. Evol.*, 20: 341-50 (1984).
Depicker et al., A negative selection scheme for tobacco protoplast-derived cells expressing the T-DNA gene 2, *Plant Cell Reports*, 7: 63-6 (1988).
Di Laurenzio et al., The Scarecrow gene regulates an asymmetric cell division that is essential for generating the radial organization of the *Arabidopsis* Root, *Cell*, 86: 423-33 (1996).
Discussion with David Baltimore as Moderator, Recombinant Molecules: Impact on Science and Society: 337-352, New York (1977).
Donahue et al., The nucleotide sequence of the *HIS4* region of yeast, *Gene*, 18: 47-59 (1982).
Dong et al., Rice (*Oryza sativa*) centromeric regions consist of complex DNA, *Proc. Natl. Acad. Sci. USA*, 95: 8135-40 (1998).
Dure III et al., Common amino acid sequence domains among the LEA proteins of higher plants, *Plant Molec. Biol.*, 12: 475-86 (1989).
Dusart et al., A functional neo-centromere formed through activation of a latent human centromere and consisting of non-alpha satellite DNA, *Nat. Genet.*, 16: 144-53 (1997).
Earnshaw et al, Proteins of the inner and outer centromere of mitotic chromosomes, *Genome*, 31: 541-52 (1989).
Earnshaw et al., When is a centromere not a kinetochore? *J. Cell Sci.*, 99: 1-4 (1991).
Ebert et al., Identification of an essential upstream element in the nopaline synthase promoter by stable and transient assays, *Proc. Natl. Acad. Sci. USA*, 84: 5745-9 (1987).
Ecker, PFGE and YAC analysis of the *Arabidopsis* genome, *Methods* I: 186-94 (1990).
Eglitis et al., Retroviral vectors for introduction of genes into mammalian cells, *BioTechniques*, 6: 608-14 (1988).
Eglitis et al., Retroviral-mediated gene transfer into hemapoietic cells, *Avd. Exp. Med. Biol.*, 241: 19-27 (1988).
EMBI Accession No. AC183942, *Zea mays* chromosome unknown clone CH201-2403; ZMMBBc0024003, *Sequencing in Progress*, 19 unordered pieces, dated Mar. 26, 2006.
EMBL Accession No. AC006161, *Arabidopsis thaliana* chromosome II section 37 of 255 of the complete sequence. Sequences from clones T12H3, T14A4, HTG, dated Dec. 11, 1998.
EMBL Accession No. AC006217, *Arabidopsis thaliana* chromosome II section 41 of 255 of the complete sequence. Sequence from clones T25N22, T13E11, dated Dec. 14, 1998.
EMBL Accession No. AC006586, *Arabidopsis thaliana* chromosome II section 50 of 255 of the complete sequence. Sequence from clones F7B19, T15D9, HTG, dated Mar. 11, 1999.
EMBL Accession No. AC012392, Genomic Sequence for *Arabidopsis thaliana* clone C17L7, Chromosome IV, complete sequence, dated Oct. 28, 1999.
EMBL Accession No. AC138570, *Zea mays* genetic clone ZM16H10, finished contig 37375, complete sequence, Jan. 11, 2003.
EMBL Accession No. AC185251, *Zea mays* chromosome 4 clone CH201-478E6; ZMMBBc0478E06, Apr. 15, 2006.
EMBL Accession No. AF072897, *Arabidopsis thaliana* BAC T8A17 chromosome IV, complete sequence, dated Jun. 29, 1998.
EMBL Accession No. AF074021, *Arabidopsis thaliana* BAC F4H6, chromosome IV, complete sequence, dated Jul. 13, 1998.
EMBL Accession No. AF076274, *Arabidopsis thaliana* BAC T27D20, dated Jul. 8, 1998.
EMBL Accession No. AF162444, *Arabidopsis thaliana* BAC T32N4, dated Jun. 30, 1999.
EMBL Accession No. AF297984, *Glycine max* clone TRS2 tandem representative repeat region, Dec. 2, 2000.
EMBL Accession No. AF297985, *Glycine max* clone TRS3 tandem representative repeat region, Dec. 2, 2000.
EMBL Accession No. AY321491, *Zea mays* centromeric repeat CentC27, complete sequence, Jul. 21, 2003.
EMBL Accession No. AY530242, *Zea mays* clone CentC27 centromeric repeat sequence, Feb. 28, 2004.
EMBL Accession No. AY530257, *Zea mays* clone CentC42 centromeric repeat sequence, Feb. 28, 2004.
EMBL Accession No. B97084, T31F11TR TAMU *Arabidopsis thaliana* genomic clone T31F11, genomic survey sequence, dated Apr. 3, 1998.
EMBL Accession No. CC062798, *Glycine max* genomic clone ugma002f001g10, DNA sequence, Apr. 16, 2003.
EMBL Accession No. U11026, *Glycine max* BSR-101 satellite SB92 genomic sequence, Jul. 14, 1994.
EMBL Accession No. Z26334, *G. max* satellite DNA, dated Sep. 21, 1993.
Enomoto et al., Mapping of the *pin* locus coding for a site-specific recombinase that causes flagellar-phase variation in *Escherichia coli* K-12, *J. Bacteriol.*, 156: 663-8 (1983).
Erdmann et al., Glycosylglycerol accumulation during salt acclimination of two unicellular cyanobacteria, *J. Gen. Microbiol.*, 138: 363-8 (1992).
Ferrin et al., Selective cleavage of human DNA: RecA-assisted restriction endonuclease (RARE) cleavage, *Science*, 254: 1494-7 (1991).
Fitzpatrick, Pleiotropic gene found in barley plant gene. *Engin. News*, 13(5): 1-22 (1993).
Flavell, Repeated sequences and genome architecture. Structure and Function of Plant Genomes, Ciferri & Dure III (Eds.) pp. 1-14 (1983).
Fleig. et al., Functional selection for the centromere DNA from yeast chromosome VIII, *Nucl. Acids. Res.*, 23: 922-4 (1995).
Forster et al., Self-cleavage of plus and minus RNAs of a virusoid and a structural model for the active sites, *Cell*, 49: 211-20 (1987).
Fraley et al., The SEV system: A new disarmed TI plasmid vector system for plant transformation, *BioTechnology*, 3: 629-35 (1985).
Fransz et al., Cytogenetics for the model system *Arabidopsis thaliana, Plant J.*, 13: 867-76 (1998).

(56) References Cited

OTHER PUBLICATIONS

Fransz et al., Integrated cytogenetic map of chromosome arm 4S of *A. thaliana*:Structural organization of heterochromatic knob and centromere region, *Cell*, 100: 367-76 (2000).
Frary et al., Molecular mapping of the centromeres of tomato chromosomes 7 and 9, *Mol. Gen. Genet.*, 250: 295-304 (1996).
Fromm et al., Expression of genes transferred into monocot and dicot plant cells by electroporation, *Proc. Nat. Acad. Sci. USA*, 82: 5824-8 (1985).
Fromm et al., Stable transformation of maize after gene transfer by electroporation, *Nature*, 319: 791-3 (1986).
Fujimara et al, Regeneration of rice plants from protoplasts, *Plant Tissue Culture Letters*, 2: 74 (1985).
Fukui et al., Physical arrangement of retrotransposon-related repeats in centromeric regions of wheat, *Plant Cell Physiol.*, 42: 189-96 (2004).
Fynan et al., DNA vaccines: Protective immunizations by parenteral, mucosal, and gene-gun inoculations, *Proc. Natl. Acad. Sci. USA*, 90:11478-82 (1993).
Ganal et al., A molecular and cytogenetic survey of major repeated DNA sequences in tomato (*Lycopersicon esculentum*), *Mol. Gen. Genet.*, 213: 262-8 (1988).
Gatehouse et al., Effect of seed lectins from *Phaseolus vulgaris* on the development of larvae of *Callosobruchus maculatus*; Mechanism of Toxicity, *J. Sci. Food. Agric.*, 35: 373-80 (1984).
Gefter et al., A simple method for polyethylene glycol-promoted hybridization of mouse myeloma cells, *Somatic Cell Genet.*, 3: 231-6 (1977).
Genbank Accession No. AC169373.2, *Sorghum bicolor* clone SB_BBc0188M08, complete sequence, nucleotides 126110-132443, dated Mar. 1, 2006.
GenBank Accession No. AC196831.1, *Sorghum bicolor* clone SB_BBc0060K10, Working Draft Sequence, 6 unordered pieces, nucleotides 9604-9473, dated Jan. 17, 2007.
GenBank Accession No. AF139910, dated Jun. 1, 1999.
GenBank Accession No. AF013103, dated Nov. 3, 1997.
GenBank Accession No. AF049110, dated Feb. 2, 1999.
GenBank Accession No. AF050437, dated Aug. 26, 1998.
GenBank Accession No. AF050438, dated Aug. 26, 1998.
GenBank Accession No. AF050452, dated Aug. 26, 1998.
GenBank Accession No. AF050453, dated Aug. 26, 1998.
GenBank Accession No. AF071126, dated Oct. 8, 1998.
GenBank Accession No. AF078917, dated Oct. 4, 1998.
GenBank Accession No. AF078922, dated Oct. 4, 1998.
GenBank Accession No. AF078923, dated Oct. 4, 1998.
GenBank Accession No. AF090447, dated Jan. 12, 1999.
GenBank Accession No. AF123535, dated Mar. 19, 2000.
GenBank Accession No. AF242891, dated Feb. 14, 2002.
GenBank Accession No. AF273104, dated Aug. 30, 2000.
GenBank Accession No. AF448416, dated Jan. 9, 2002.
GenBank Accession No. AY129008, dated Aug. 17, 2002.
GenBank Accession No. AY173950, dated Jan. 12, 2003.
GenBank Accession No. AY321491, dated Jul. 21, 2003.
GenBank Accession No. K01868, dated Aug. 4, 1993.
GenBank Accession No. K02202, dated Apr. 27, 1993.
GenBank Accession No. M35408, dated Apr. 27, 1993.
GenBank Accession No. U39642, dated Nov. 25, 1995.
GenBank Accession No. X01365, dated Apr. 20, 1993.
Gerlach et al., Construction of a plant disease resistance gene from the satellite RNA of tobacco ringspot virus, *Nature*, 328: 802-5 (1987).
Gindullis et al., Construction and vharacterization of A BAC library for the molecular dissection of a single wild beet centromere and sugar beet (*Beta vulfaris*), *Genome Analysis*, 44: 846-55 (2001).
Gindullis et al., The large-scale organization of the centromeric region in beta species, *Genome Res.*, 11: 253-65 (2001).
Giordano et al., Identification by denaturing high-performance liquid chromatography of numerous polymorphisms in a candidate region for multiple sclerosis susceptibility, *Genomics*, 56: 247-53 (1999).
Goding (Ed.), *Monoclonal Antibodies: Principles and Practice*, Academic Press, Orlando, Florida, 60-74 (1986).
Golic et al., The FLP recombinase of yeast catalyzes site-specific recombination in the *Drosophila* genome, *Cell*, 59: 499-509 (1989).
Goring et al., Transformation of a partial nopaline synthase gene into tobacco suppresses the expression of a resident wild-type gene, *Proc. Natl. Acad. Sci. USA*, 88, 1770-4 (1991).
Graham et al., Transformation of rat cells by DNA of human adenovirus 5, *Virology*, 54: 536-9 (1973).
Grellet et al., Organization and evolution of a higher plant alphoid-like satellite DNA sequence, *J. Mol. Biol.*, 187: 495-507(1986).
Grill et al., Construction and characterization of a yeast artificial chromosome library of *Arabidopsis* which is suitable for chromosome walking, *Mol. Gen. Genet.*, 226: 484-90 (1991).
Guerrero et al., Turgo-responsive gene transcription and RNA levels increase rapidly when pea shoots are wilted. Sequence and expression of three inducible genes, *Plant Molec. Biol.*, 15:11-26 (1990).
Gupta et al., Increased resistance to oxidative stress in transgenic plants that overexpress chloroplastic Cu/Zn superoxide dismutase, *Proc. Natl. Acad. Sci. USA*, 90: 1629-33 (1993).
Gutierrez-Marcos et al., Three members of a novel small gene-family from *Arabidopsis thaliana* able to complement functionally an *Escherichia coli* mutant defective in PAPS reducatase activity encode proteins with a thioredoxin-like domain and APS reductase activity, *Proc. Natl. Acad Sci USA*, 93: 13377-824 (1996).
Haaf et al., Integration of human satellite DNA into simian chromosomes: Centromere protein binding and disruption of normal chromosome segregation, *Cell*, 70: 681-96 (1992).
Hadlaczky et al., Centromere formation in mouse cells cotransformed with human DNA and a dominant marker gene, *Proc. Natl. Acad. Sci. USA*, 88: 8106-10 (1991).
Hall et al., Centromere satellites from *Arabidopsis* population: Maintenance of conserved and variable domains. *Genome Res.*, 13: 195-205 (2003).
Hall et al., The rapidly evolving field of plant centromeres, *Curr. Opin Plant Biol.*, 7: 108-14 (2002).
Hamilton et al., Stable transfer of intact high molecular weight DNA into plant chromosones, *Proc. Natl. Acad. Sci. USA*, 93: 9975-9(1996).
Hamilton, A binary BAC system for plant transformation with high-molecular-weight DNA, *Gene*, 4(200): 107-16 (1997).
Hammock et al., Expression and effects of the juvenile hormone esterase in a baculovirus vector, *Nature*, 344: 458-63 (1990).
Harrington et al., Formation of de novo centromeres and construction of first-generation human artificial microchromosomes, *Nat. Genet.*, 15: 345-54 (1997).
Harrison et al., Centromeric repetitive DNA sequences in the genus *Brassica, Theor. Appl. Genet.*, 90: 157-65 (1995).
Haseloff et al., Removal of a cryptic intron and subcellular localization of green fluorescent protein are required to mark transgenic *Arabidopsis* plants brightly, *Proc. Natl. Acad. Sci. USA*, 94: 2122-7 (1997).
Hauge et al., Mapping the *Arabidopsis* genome, *Symp. Society for Experimental Biology*, 45: 45-56 (1991).
Hegemann et al., The ceontromere of budding yeast, *BioEssays* 15: 451-60 (1998).
Heller et al., Mini-chromosomes derived from the human Y chromosome by telomere directed chromosome breakage, *Proc. Natl. Acad. Sci. USA*, 93: 7125-30 (1996).
Hemenway et al., Analysis of the mechanism of protection in transgenic plants expressing the potato virus X coat protein or its antisense RNA, *EMBO J.*, 7: 1273-80 (1988).
Heslop-Harrison et al., Polymorphisms and genomic organization of repetitive DNA from centromeric regions of *Arabidopsis* chromosomes, *Plant Cell*, 11:31-42 (1999).
Hilder et al., A novel mechanism of insect resistance engineered into tobacco, *Nature*, 330: 160-3 (1987).
Hinchee et al., Production of transgenic soybean plants using *Agrobacterium*-mediated DNA transfer, *BioTechnology*, 6: 915-22 (1988).
Hoess et al., P1 site-specific recombination: Nucleotide sequence of the recombining sites, *Proc. Nat. Acad. Sci. USA*, 79: 3398-402 (1982).

(56) References Cited

OTHER PUBLICATIONS

Houben et al., DNA and proteins of plant centromeres, *Curr. Opin. Plant Biol.*, 6: 554-60 (2003).
Hsiao et al., High-frequency transformation of yeast by plasmids containing the cloned yeast ARG4 gene, *Proc. Natl. Acad. Sci. USA*, 76: 3829-33 (1979).
Hudakova et al., Sequence organization of barley centromeres, *Nucl. Acids Res.*, 29: 5029-35 (2001).
Hudspeth et al., Structure and expression of the maize gene encoding the phosphoenolpyruvate carboxylase isozyme involved in $C_4$ photosynthesis, *Plant Molec. Biol.*, 12: 579-89 (1989).
Hwang et al., Identification and map position of YAC clones comprising one-third of the *Arabidopsis* genome, *Plant J.*, 1: 367-74 (1991).
Ikeda, et al., Genetic studies of avermectin biosynthesis in *Streptomyces avermitilis, J. Bacteriol.*, 16: 5615-21 (1987).
Ikeno, et al., Construction of YAC-based mammalian artificial chromosomes, *Nat. Biotechnol.*, 16: 431-9 (1998).
Ikuta et al., The alpha-amylase gene as a marker for gene cloning: Direct screening of recombinant clones, *BioTechnology*, 8: 241-2 (1990).
Inohara et al., Two genes, *atp*C1 and *atp*C2, for the subunit of *Arabidopsis thaliana* chloroplast ATP synthase, *J. Biol. Chem.*, 266: 7333-8 (1991).
Iwabuchi et al., Molecular and cytological characterization of repetitive DNA sequences in *Brassica. Theor. Appl. Genet.*, 81(3): 349-55 (1991).
Jiang et al., A conserved repetitive DNA element located in the centromeres of cereal chromosomes, *Proc. Natl. Acad. Sci. USA*, 93: 14210-3 (1996).
Jiang et al., A molecular view of plant centromeres, *Trends Plant Sci.*, 8: 570-5 (2003).
Jin et al., Maize-centromeres: Organization and functional adaptation in the genetic background of oat, department of horticulture, University of Wisconsin-Madison, Madison, Wisconsin 53706, USA, *Plant Cell*. 16:57-81 (2004).
Johnston et al., Gene gun transfection of animal cells and genetic immunization, *Meth. Cell Biol.*, 43: 353-63 (1994).
Jones et al., High level expression of introduced chimaeric genes in regenerated transformed plants, *EMBO J.* 4:2411-8 (1985).
Jones et al., T-DNA structure and gene expression in *Petunia* plants transformed by *Agrobacterium tumafaciens* C58 derivatives, *Mol. Gen. Genet.*, 207: 478-85 (1987).
Jorgensen et al., T-DNA is organized predominantly in inverted repeat structures in plants transformed with *Agrobacterium tumafaciens* C58 derivatives, *Mol. Gen. Genet.*, 207: 471-7 (1987).
Jouanin et al., Localization and restriction maps of replication origin regions of the plasmids of *Agrobacterium rhizogenes* strain $A_4$, *Mol. Gen. Genet.*, 201: 370-4 (1985).
Joyce, RNA evolution and the origins of life, *Nature*, 338: 217-24 (1989).
Kaasen et al., Molecular cloning and physical mapping of the otsBA genes, which encode the osmoregulatory trehalose pathway of *Escherichia coli*: Evidence that transcription is activated by KatF (AppR), *J. Bacteriol.*, 174: 889-98 (1992).
Karpen, Position-effect variegation and the new biology of heterochromatin, *Curr. Opin. Genet. Dev.*, 4: 281-91 (1994).
Karsten et al., Polyolcontent of bostrychia and stictosiphonia (rhodomelaceae, rhodophyta) from field and culture, *Botanica Marina*, 35:11-9 (1992).
Kaszás et al., Misdivision analysis of centromere structure in maize, *EMBO J.* 15: 5246-55 (1996).
Kato et al., Foreign DNA introduced by calcium phosphate is integrated into repetitive DNA elements of the mouse L cell genome, *Molec. Cell Biol.* 6: 1787-95 (1986).
Katz et al., Cloning and expression of the tyrosinase gene from *Streptomyces antibioticus* in *Streptomyces lividans, J. Gen. Microbiol.*, 129: 2703-14 (1983).
Kim et al., Three-dimensional model of the active site of the self-splicing rRNA precursor of tetrahymena, *Proc. Natl. Acad. Sci. USA*, 84: 8788-92 (1987).
Kishii et al., A tandem repetitive sequence located in the centromeric region of common wheat (*Triticum aestivum*) chromosomes, *Chromosome Res.*, 9:417-28 (2001).
Klee et al., Vectors for transformation of higher plants, *BioTechnology*, 3: 637-42 (1985).
Klein et al., High-velocity microprojectiles for delivering nucleic acids into living cells, *Nature*, 327: 70-3 (1987).
Klein et al., Stable genetic transformation of intact *Nicotiana* cells by the particle bombardment process, *Proc. Nat. Acad. Sci. USA*, 85: 8502-5 (1988).
Kohler et al., Continuous cultures of fused cells secreting antibody of predefined specificity, *Nature*, 256: 495-7 (1975).
Kohler et al., Derivation of specific antibody-producing tissue culture and tumor lines by cell fusion, *Eur. J. Immunol.*, 6: 511-9 (1976).
Kolchinsky et al., A major satellite DNA of soybean is a 92-base pairs tandem repeat, *Theor. Appl. Genet.*, 90: 621-6 (1995).
Konieczny et al., A procedure for mapping *Arabidopsis* mutations using co-dominant ectotype-specific PCR-based markers, *Plant J.*, 4: 403-10 (1993).
Konieczny et al., A superfamily of *Arabidopsis thaliana* retrotransposons, *Genetics*, 127: 801-9 (1991).
Koorneef et al., Trisomics in *Arabidopsis thaliana* and the location of linkage groups, *Genetica*, 61: 41-6 (1983).
Koorneef, Linkage map of *Arabidopsis thaliana, J. Heredity*, 74: 265-72 (1983).
Koorneef, The use of telotrisomics for centromere mapping in *Arabidopsis thaliana* (L.) *Heynh., Genetica*, 62: 33-40 (1983).
Koster et al., Sugars and desiccation tolerance in seeds, *Plant Physiol.*, 88: 829-32 (1988).
Kotani et al., Structural analysis and complete physical map of *Arabidopsis thaliana* chromosome 5 including centromeric telomeric regions, *DNA Res.*, 6: 381-6 (1999).
Kramer et al., Higher-accuracy method for measuring minichromosome stability in *Saccharomyces cerevisiae. Biotechniques*, 32: 1036-40 (2002).
Kuhn et al., Clustered tRNA genes in *Schizosaccharomyces pombe* centromeric DNA sequence repeats, *Proc. Natl. Acad. Sci. USA*, 88:1306-10 (1991).
Kumar et al., Plant retrotransposons. *Annu. Rev. Genet.*, 33: 479-532 (1999).
Kumekawa et al., The size and sequence organization of the centromeric region of *Arabiodpsis thaliana* chromosome 5, *DNA Res.*, 7: 315-21 (2000).
Kurata et al., Rice genome organization: The centromere and genome interactions, *Ann. Bot.*, 90: 427-35 (2002).
Kyte et al., A simple method for displaying the hydropathic character of a protein, *J. Mol. Biol.*, 157: 105-32 (1982).
Lakshmikumarin et al., Isolation and characterization of a highly repetitive DNA of *Brassica campestris, Plant Molec. Biol.*, 14: 447-8 (1990).
Lawton et al., Expression of a soybean-conclycinin gene under the control of the cauliflower mosaic virus 35S and 19S promoters in transformed *Petunia* tissues, *Plant Molec. Biol.*, 9: 315-24 (1987).
Lechner et al., A 240 kd multisubunit protein complex, CBF3, is a major component of the budding yeast centromere, *Cell*, 64: 717-25 (1991).
Lee et al., Use of cloned *mtl* genes of *Escherichia coli* to introduce *mtl* deletion mutations into the chromosome, *J. Bacteriol.*, 153: 685-92 (1983).
Levings III, The Texas cytoplasm of maize: Cytoplasmic male sterility and disease susceptibility, *Science*, 250: 942-7 (1990).
Li et al., CUE1 : A mesophyll cell-specific positive regulator of light-controlled gene expression in *Arabidopsis, Plant Cell*, 7: 1599-610(1995).
Li et al., Direct electrophoretic detection of the allelic state of single DNA molecules in human sperm by using the polymerase chain reaction, *Proc. Natl. Acad. Sci. USA*, 87: 4580-4 (1990).
Lieber et al., Selection of efficient cleavage sites in target RNAs by using a ribozyme expression library, *Molec. Cell Biol.*, 15: 540-51 (1995).

(56) References Cited

OTHER PUBLICATIONS

Lin et al., Sequence and analysis of chromosome 2 of the plant *Arabidopsis thaliana, Nature*, 402: 761-8 (1999).
Liu et al., Complementation of plant mutants with large genomic DNA fragments by a transformation-competent artificial chromosome vector accelerates positional cloning, *Proc. Natl. Acad. Sci. USA*, 96: 6535-40 (1999).
Lohe et al., Return of the H-word (heterochromatin), *Curr. Opin. Genet. Dev.*, 5: 746-55 (1995).
Loomis et al., Cyroprotective capacity of end products of anaerobic metabolism, *J. Exp. Zool.*, 252: 9-15 (1989).
Lorz et al., Gene transfer to cereal cells mediated by protoplast transformation, *Mol. Gen. Genet.*, 199: 178-82 (1985).
Louis, Corrected sequence for the right telomere of *Saccharomyces cerevisiae* chromosome III, *Yeast*, 10: 271-4 (1994).
Lu et al., High efficiency retroviral mediated gene transduction into single isolated immature and replatable $CD34^{3+}$ hemotopoietic stem/progenitor cells from human umbilical cord blood, *J. Exp. Med.*, 178: 2089-96 (1993).
Luo et al., Whole-genome fractionation rapidly purifies DNA from centromeric regions. *Nat. Methods.*, 1: 67-71 (2004).
Maeser et al., The gin recombinase of phase Mu Can catalyse site-specific recombination in plant protoplasts, *Mol. Gen. Genet.*, 230: 170-6 (1991).
Mahtani et al., Physical and genetic mapping of the human X chromosome centromere:Repression of recombination, *Genome Res.*, 8: 100-10 (1998).
Maloy, Experimental techniques in bacterial genetics , Jones and Bartlett, *Ann. N.Y. Acad. Sci.* 646 (1991).Table of Contents only.
Maluszynska et al., Localization of tandemly repeated DNA sequences in *Arabidopsis thaliana, Plant J.*, 1: 159-66 (1991).
Maluszynska et al., Molecular cytogenetics of the genus *Arabidopsis*:In situ localization of rDNA sites, chromosome numbers and diversity in centromeric heterochromatin, *Ann. Botany*, 71: 479-84 (1993).
Manuelidis et al., Novel classes of mouse repeated DNAs. *Nucl. Acids Res*,. 8: 3247-58 (1980).
Marcotte et al., Regulation of a wheat promoter by abscisic acid in rice protoplasts *Nature*, 335: 454 (1988).
Mariani et al., Induction of male sterility in plants by a chimaeric ribonuclease gene, *Nature*, 357: 737-41 (1990).
Marra et al., A map for sequence analysis of the *Arabidopsis thaliana* genome, *Nat. Genet.*, 22: 265-70 (1999).
Martinez-Zapater et al., A highly repeated DNA sequence in *Arabidopsis thaliana, Mol. Gen. Genet.*, 204: 417-23 (1986).
Matsuura et al., The *sre* gene (ORF459) encodes a site-specific recombinase responsible for integration of the R4 phage genome, *J. Baceteriol.*, 178:3374-6 (1996).
Mayer eta l., Sequence and analysis of chromosome 4 of the plant *Arabidopsis thaliana. Nature* (London), 402(6763): 769-77 (1999).
McCabe et al., Stable transformation of soybean (*Glycine max*) by particle acceleration, *BioTechnology*, 6: 924-6 (1988).
Michel et al.., Modeling of the three-dimensional architecture of group I catalytic introns based on comparative sequence analysis, *J. Mol. Biol.*, 216:585-610 (1990).
Miller et al., Retrotransposon-related DNA sequences in the centromeres of grass chromosomes, *Genetics*, 150: 1615-23 (1998).
Mortimer et al., Genetic mapping in *Saccharomyces cerevisiae*, Department of Biophysics and Medical Physics and Donner Laboratory, University of California at Berkeley:11-26 (1981).
Mozo et al., A complete BAC-based physical map of the *Arabidopsis thaliana* genome, *Nat., Genet.*, 22: 271-5 (1999).
Mozo et al., Construction and characterization of the IGF *Arabidopsis* BAC library, *Mol. Gen. Genet.*, 258: 562-70 (1998).
Mundy et al. Abscisic acid and water-stress induce the expression of a novel rice gene, *EMBO J.*, 7: 2279-86 (1988).
Murakami et al., The bialaphos biosynthetic genes of *Streptomyces hygroscopicus*:Molecular cloning and characterization of the gene cluster, *Mol. Gen. Genet.*, 205: 42-50 (1986).
Murata et al., Centromeric repetitive sequences in *Arabiidopsis thaliana, Jpn J. Genet.*, 69: 361-70 (1994).
Murata et al., Physical mapping of the 5S ribosomal RNA genes in *Arabidopsis thaliana* by multi-color fluorescence in situHybridization with Cosmid Clones, *Plant J.*, 12: 31-7 (1997).
Murdock et al., Biological effects of plant lectins on the Cowpea Weevil, *Phytochemistry*, 29: 85-9 (1990).
Murphy et al., Localization of centromere function in a *Drosophila* minichromosome, *Cell*, 82: 599-609 (1995).
Murray et al., Construction of artificial chromosomes in yeast, *Nature*, 305: 189-93(1983).
Mysore et al., An *Arabidopsis* histone H2A mutant is deficient in *Agrobacterium* T-DNA integration, *Proc. Natl. Acad. Sci. USA*, 97: 948-53 (2000).
Mysore et al., *Arabidopsis* ecotypes and mutants that are recalcritant to *Agrobacterium* root transformation are susceptible to germ-line transformation, *Plant J.*, 21: 9-16 (2000).
Nagaki et al., Molecular and cytological analysis of large tracks of centrometic DNA reveal the structure and evolutionary dynamics of maize centromeres, *Genetics*, 163: 759-70 (2003).
Nagaki et al., Sequencing of a rice centromere uncovers active genes, *Nat. Genet.*, 36: 138-45 (2004).
Nakamura et al., Construction of an 800-KB contig in the near-centromeric region of the rice blast resistance gene *Pi-ta*2 using a highly representative rice BAC library, *Mol Gen. Genet.*, 254: 611-20 (1997).
Napoli et al., Introduction of a chimeric chalcone synthase gene into *Petunia* results in reversible co-suppression of homologous genes in trans, *Plant Cell*, 2: 279-98 (1990).
Negrutiu et al. Plant protoplasts as genetic tool: Selectable markers for developmental studies, *Int. J. Dev. Biol.*, 36: 73-84 (1992).
Nester et al., Crown gall: A molecular and physiological analysis, *Ann. Rev. Plant Physiol.*, 35: 387-413 (1984).
Newman et al., Genes galore: A summary of methods for accessing results from large-scale partial sequencse of anonymous *Arabidopsis* cDNA clones. *Plant Physiol.*, 106: 1241-55 (1994).
Nicklas, The forces that move chromosomes in mitosis, *Ann. Rev. Biophys. Biophys. Chem.*, 17: 431-49 (1988).
Nonomura et al., Organization of the 1.9-KB repeat unit RCE1 in the centromeric region of rice chromosomes, *Mol. Gen. Genet.*, 261: 1-10 (1999).
Nonomura et al., The centromere composition of multiple repetitive sequences on rice, *Chromosome* 5, 110: 284-91 (2001).
Norris et al., The intron of *Arabidopsis thaliana* polyubiquitin gene is conserved in location and is a quantitative determinant of chimeric gene expression. *Plant Molec. Biol.*, 21: 895-906 (1993).
Noutoshi et al., Designing of plant artificial chromosome (PAC) by using the *Chlorella* smallest chromosome as a model system, *Nucl. Acids Symp., Ser.* 37: 143-4 (1997).
Nussbaum et al., Construction and propagation of a defective simian virus 40 genome bearing an operator from bacteriophage, *Proc. Nat. Acad. Sci. USA.*, 73: 1068-72 (1976).
Odell et al., Identification of DNA sequences required for activity of the cauliflower mosaic virus 35S promoter, *Nature*, 313: 810-2 (1985).
Ohmori et al., Nucleotide sequence of the region required for maintenance of colicin E1 plasmid, *Mol. Gen. Genet.*, 176: 161-70 (1979).
Omirulleh et al., Activity of a chimeric promoter with the doubled CaMV 35S enhancer element in protoplast-derived cells and transgenic plants in maize, *Plant Molec. Biol.*, 21: 415-28 (1993).
Ow et al., Transient and stable expression of the firefly luciferase gene in plant cells and transgenic plants, *Science*, 234: 856-9 (1986).
Page et al., Characterization of a maize chromosome 4 centromeric sequence: Evidence for an evolutionary relationship with the B chromosome centromere, *Genetics*, 159: 291-301 (2001).
Palukaitis et al., Characterization of a viroid associated with avocado sunblotch disease, *Virology*, 99: 145-51 (1979).
Peacock et al., Highly repeated DNA sequence limited to knob heterochromatin in maize, *Proc. Natl. Acad. Sci. USA*, 78: 4490-4 (1981).
Pelissier et al., Athila, a new retroelement from *Arabidopsis thaliana., Plant Mol. Biol.*, 29: 441-552 (1995).

(56) References Cited

OTHER PUBLICATIONS

Pelissier et al., DNA regions flanking the major *Arabidopsis thaliana satellite* are principally enriched in *Athila* retroelement sequences, *Genetica*, 97: 141-51 (1996).
Perkins, The detection of linkage in tetrad analysis, *Genetics*, 38: 187-97 (1953).
Perlak et al., Modification of the coding sequence enhances plant expression of insect control protein genes, *Proc. Natl. Acad. Sci USA*, 88: 3324-8 (1991).
Perriman et al., Extended target-site specificity for a hammerhead ribozyme, *Gene*, 113: 157-63 (1992).
Peterson et al., Production of transgenicmice with yeast artificial chromosomes, *TIG*, 13: 61-6 (1997).
Phi-Van et al., The chicken lysozyme 5' matrix attachment region increases transcription from a heterologous promoter in heterologous cells and dampens position effects on the expression of transfected genes, *Molec. Cell. Biol.*, 10: 2302-7 (1990).
Piatowski et al., Characterization of five abscisic acid-responsive cDNA clones isolated from the dessication-tolerant plant *Craterostigma plantagineum* and their relationship to other water-stress genes, *Plant Physiol.*, 94: 1682-8 (1990).
Potrykus et al., Direct gene transfer to cells of a graminaceous monocot, *Mol. Gen. Genet.* 199: 183-8 (1985).
Prasher et al., Cloning and expression of the cDNA coding for aequorin, a bioluminescent calcium-binding protein, *Biochem Biophys. Res. Commun.*, 126: 1259-68 (1985).
Presting et al., A *Ty3/gypsy* retrotransposon-like sequence localizes to the centromeric regions of cereal chromosomes, *Plant J.*, 16: 721-8 (1998).
Preuss et al., Tetrad analysis possible in *Arabidopsis* with mutation of the QUARTET (QRT) genes, *Science*, 264: 1458-60 (1994).
Price et al., Systematic relationships of *Arabidopsis*: A molecular and morphological perspective, in Somerville, C. and Meyerowitz, E. (eds.), *Arabidopsis*, Cold Spring Harbor Press, New York (1995) pp. 7-19.
Prody et al., Autolytic processing of dimeric plant virus satellite RNA, *Science*, 231: 1577-80 (1986).
Puechberty, Genetic and physical analyses of the centromeric and pericentromeric regions of human chromosome 5: Recombination across 5cen, *Genomics*, 56: 274-87 (1999).
Rathore et al., Use of *bar* as a selectable marker gene and for the production of herbicide-resistant rice plants from protoplasts, *Plant Molec. Biol.*, 21: 871-84 (1993).
Rattner et al., The structure of the mammalian centromere, *BioEssays*, 13: 51-6 (1991).
Ravatn et al., Int-B13, An unusual site-specific recombinase of the bacteriophage P4 integrase family, is responsible for chromosomal insertion of the 105-kilobase *clc* element of *Pseudomonas* sp. strain B13, *J. Bacteriol.* 180: 5505-14 (1998).
Reed et al., Carbohydrate accumulation and osmotic stress in cyanobacteria, *J. Gen. Microbiol.*, 130: 1-4 (1984).
Reichel et al., Enhanced green fluorescence by the expression of an *Aequorea victoria* green fluorescent protein mutant in mono- and dicotyledonous plant cells, *Proc. Nat. Acad. Sci. USA*, 93: 5888-93 (1996).
Reinhold-Hurek et al., Self-splicing introns in tRNA genes of widely divergent bacteria, *Nature*, 357: 173-6 (1990).
Rensburg et al., Proline accumulation as drought-tolerance selection criterion:Its relationship to membrane integrity and chloroplast ultrastructure in *Nicotiana tabacum* L., *J. Plant Physiol.*, 141: 188-94 (1993).
Richards et al., Isolation of a higher eukaryotic telomere from *Arabidopsis thaliana, Cell*, 53: 127-36 (1988).
Richards et al., Plant centromeres: Structure and control, *Curr. Opin. Plant Biol.*, 1: 130-5 (1998).
Richards et al., The centomere region of *Arabidopsis thaliana* chromosome 1 contains telomere-similar sequences, *Nucl. Acids Res.*, 19: 3351-7 (1991).
Rieder, The formation, structure, and composition of the mammalian kinetochore and kinetochore fiber, New York State Department of Health, Division of Laboratories and Research, *Intl. Rev. Cytol.* 79: 1-58 (1982).
Rogers et al., Improved vectors for plant transformation: Expression cassette vectors and new selectable markers, *Meth. Enzymol.*, 153: 253-77 (1987).
Rosenberg et al., RFLP subtraction: A method for making libraries of polymorphic markers, *Proc. Natl. Acad. Sci. USA*, 91: 6113-7 (1994).
Rosenfeld, Human artificial chromosomes get real, *Nat. Genet.*, 15:333-5 (1997).
Round et al., *Arabidopsis thaliana* centromere regions: Genetic map positions and repetitive DNA structure, *Genome Res.*, 7: 1045-53 (1997).
Sasnauskas et al., Molecular cloning and analysis of autonomous replicating sequence of *Candida maltosa, Yeast*, 8: 253-9 (1992).
Sauer, Functional expression of the *cre-lox* site-specific recombination system in the yeast *Saccharomyces cerevisiae, Molec. Cell Biol.*, 7: 2087-96 (1987).
Schmidt et al., Analysis of clones carrying repeated DNA sequences in two YAC libraries of *Arabidopsis thaliana* DNA, *Plant J.*, 5: 735-44 (1994).
Schmidt et al., Physical map and organization of *Arabidopsis thaliana* chromosome 4, *Science*, 270: 480-3 (1995).
Schwartz et al., New techniques for purifying large DNAs and studying their properties and packaging, Department of Human Genetics and Development, Columbia University: 189-195.
Schweizer et al., Species-specific DNA sequences for identification of somatic hybrids between *Lycopersicon esculentim* and *Solanum acaule, Theor. Appl. Genet.*, 75: 679-84 (1988).
Sears et al., Cytogenic studies in *Arabidopsis thaliana*, Department of Genetics, University of Missouri, *Can. J. Genet. Cytol.*, 12: 217-23 (1970).
Shagan et al., Nucleotide sequence of an *Arabidopsis thaliana* turgor-responsive cDNA clone encoding TMP-A, a transmembrane protein containing the major intrinsic protein motif, *Plant Physiol.*, 101: 1397-8 (1993).
Sheen et al., Green-flourescent protein as a new vital marker in plant cells, *Plant J.*, 8: 777-84 (1985).
Shizuya et al., Cloning and stable maintenance of 300-kilobase-pair fragments of human DNA in *Escherichia coli* using an F-factor-based vector. *Proc. Natl. Acad. Sci. USA*, 89: 8794-7 (1992).
Simoens et al., Characterization of highly repetitive sequences of *Arabidopsis thaliana, Nucl. Acids Res.*, 16: 6753-66 (1988).
Singh et al., Centromere mapping and orientation of the molecular linkage mao of rice (*Oryza sativa* L.), *Proc. Natl. Acad. Sci. USA*, 93: 6163-8 (1996).
Smith et al., Expression of truncated tomato polygalacturonase gene inhibits expression of the endogenous gene in transgenic plants, *Mol. Gen. Genet.*, 224: 447-81 (1990).
Smithies et al., Insertion of DNA sequences into the human chromosomal—globin locus by homologous recombination, *Nature*, 317: 230-4 (1985).
Smyth, New *Arabidopsis* mutations that result in all four products of meiosis being held together as a tetrad of fused pollen grains may facilitate genetic mapping and lead to new insights into pollen biology, *Curr. Biol.*, 4: 851-3 (1994).
Somerville et al., Plant functional genomics, *Science*, 285: 380-3 (1999).
Spielmann et al., T-DNA structure in transgenic tobacco plants with multiple independent integration sites, *Mol. Gen. Genet.*, 205: 34-43 (1986).
Stalker et al., Herbicide resistance in transgenic plants expressing a bacterial detoxification gene, *Science*, 242: 419-23 (1988).
Steif et al., A nuclear DNA attachment element mediates elevated and position-independent gene activity. *Nature*, 341: 343-5 (1989).
Steifel et al., Herbicide resistance in transgenic plants expressing a bacterial detoxification gene. *Nature*, 341: 343 (1989).
Stinchomb et al., Isolation and characterization of a yeast chromosomal replicator, *Nature*, 282: 39-43 (1979).
Stone et al., *Leafy Cotyledon2* encodes a B3 domain transcription factor that induces embryo development, *Proc. Natl. Acad. Sci. USA*, 98:11806-11 (2001).

(56) References Cited

OTHER PUBLICATIONS

Stougaard, Substrate-dependent negative selection in plants using a bacterial cytosine deaminase gene, *Plant J.*, 3: 755-61 (1993).
Sullivan et al., Isolation and characterization of a maize chlorophyll a/b binding protein gene that produces high levels of mRNA in the dark, *Mol. Gen. Genet.*, 215: 431-40 (1980).
Sun et al., A model for the evolution of polyubiquitin genes from the study of *Adabidopsis thaliana* ecotypes. *Plant Molec. Biol.*, 34(5): 745-58 (1997).
Sun et al., Human artificial episomal chromosomes for cloning large DNA fragments in human cells, *Nat. Genet.*, 8: 33-41 (1994).
Sun et al., Independent modulation of *Arabidopsis thaliana* polyubiquitin mRNAs in different organs and in response to enviromental changes. *Plant Journal*, 11(5): 1017-27 (1997).
Sun et al., Molecular structure of a functional *Drosophila* centromere, *Cell*, 91: 1007-19 (1997).
Sutcliffe, Nucleotide sequence of the ampicillin resistance gene of *Escherichia coli* plasmid pBR322, *Proc. Natl. Acad. Sci. USA*, 75: 3737-41 (1978).
Symington et al., Meiotic recombination within the centromere of a yeast chromosome, *Cell*, 52: 237-40 (1988).
Symons, Avocado sunblotch viroid: Primary sequence and proposed secondary structure, *Nucl. Acids Res.*, 9: 6527-37 (1981).
Symons, Small catalytic RNAs, *Annu. Rev. Biochem.*, 61: 641-71 (1992).
Tarczynski et al., Expression of a bacerial mtlD gene in transgenic tobacco leads to production and accumulation of mannitol, *Proc. Natl. Acad. Sci. USA*, 89: 2600-4 (1992).
Tarczynski et al., Stress protection of transgenic tobacco by production of the osmolyte mannitol, *Science*, 259: 508-10 (1993).
Tavoletti et al., Half tetrad analysis in alfalfa using multiple restriction fragment length polymorphism markers, *Proc. Natl. Acad. Sci. USA*, 93: 10918-22 (1996).
Tek eta l., Functional centromeres in soybean include two distinct tandem repeats and a retrotransposon. *Chromosome Res.*, 18: 337-47 (2010).
Thillet et al., Site-directed mutagenesis of mouse dihydrofolate reductase. Mutants with increased resistance to methotrexate and trimethoprim, *J. Biol. Chem.*, 263: 12500-8 (1988).
Thomas et al., High-frequency targeting of genes to specific sites in the mammalian genome, *Cell*, 44: 419-28 (1986).
Thomas et al., Viable molecular hybrids of bacteriophage lambda and eukaryotic DNA, *Proc. Nat. Acad. Sci. USA*, 71: 4579 (1974).
Thompson et al., A novel repetitive sequence associated with the centrometric regions of *Arabidopsis thaliana* chromosomes, *Mol. Gen. Genet.*, 253: 247-52 (1996).
Thompson et al., Decreased expression of BRCA1 accelerates growth and is often present during sporadic breast cancer progression, *Nat. Genet.*, 9: 444-50 (1995).
Thompson et al., Identification and distribution of seven classes of middle-repetitive DNA in the *Arabidopsis thaliana* genome, *Nucl. Acids Res.*, 24: 3017-22 (1996).
Tian et al., Expression of the green fluorescent protein gene in conifer tissues, *Plant Cell Reports*, 16: 267-71 (1997).
Tominaga, The site-specific recombinase encoded by pinD in *Shigella dysenteriae* is due to the presence of a defective Mu prophase, *Microbiol.*, 143: 2057-63 (1997).
Toriyama et al., Haploid and diploid plant regeneration from protoplasts of another callus in rice, *Theor Appl. Genet.*, 73: 16-9 (1986).
Tsay et al., Identification of a mobile endogenous transposon in *Arabidopsis thaliana, Science*, 260: 342-4 (1993).
Tsugeki et al., A transposon insertion in the *Arabidopsis* SSR16 gene causes an embryo-defective lethal mutation. *Plant Journal*, 10(3): 479-89 (1996).
Tugal et al., *Arabidopsis* 22-kilodalton peroxisomal membrane protein, nucleotide sequence analysis and biochemical characterization, *Plant Physiol.*, 120: 309-20 (1999).
Twell et al., Promoter analysis of genes that are coordinately expressed during pollen-specific enhancer sequences and shared regulatory elements, *Genes Dev.*, 5: 496-507 (1991).
Twell et al., Transient expression of chimeric genes delivered pollen by microprojectile bombardment, *Plant Physiol.*, 91: 1270-4 (1989).
Tyler-Smith et al., Localization of DNA sequences required for human centromere function through an analysis of rearranged Y chromosomes, *Nat. Genet.*, 5: 368-75 (1993).
Tyler-Smith et al., Mammalian chromosome structure, *Curr. Opin. Genet. Dev.*, 3: 390-7 (1993).
Uchimiya et al., Expression of a foreign gene in callus derived from DNA-treated protoplasts of rice, *Mol. Gen. Genet.*, 204: 204 (1986).
Vahedian et al., Genomic organization and evolution of the soybean SB92 satellite sequence, *Plant Molec. Biol.*, 29: 857-62 (1995).
Valvekens et al., *Agrobacterium tumefaciens*-mediated transformation of *Arabidopsis thaliana* root explants by using kanamycin selection, *Proc. Natl. Acad. Sci. USA*, 85: 5536-40 (1988).
Van Der Krol et al., Flavonoid genes in *Petunia*: Addition of a limited number of gene copies may lead to a suppression of gene expression, *Plant Cell*, 2: 291-9 (1990).
Van't Hof et al., The size and number of replicon families of chromosomal DNA of *Arabidopsis thaliana, Chromosoma*, 68: 269-285 (1978).
Vasil et al., Herbicide resistant fertile transgenic wheat plants obtained by microprojectile bombardment of regenerable embryogenic callus, *BioTechnology*, 10: 667-74 (1992).
Vasil, Progress in the regeneration and genetic manipulation of cereal crops, *BioTechnology*, 6: 397-402 (1988).
Vernon et al., A novel methyl transferase induced by osmotic stress in the faculative halophyte *Mesembryanthemum crystallinum, EMBO J.* 11: 2077-85 (1992).
Voytas et al., A copia-like transposable element family in *Arabidopsis thaliana, Nature*, 336: 242-4 (1988).
Wagner et al., Coupling of adenovirus to transferrin-polylysine/DNA complexes greatly enhances receptor-mediated gene delivery and expression of transfected genes, *Proc. Natl. Acad. Sci. USA*, 89: 6099-103(1992).
Walker et al., DNA sequences required for anaerobic expression of the maize alcohol dehydrogenase 1 gene, *Proc. Nat. Acad. Sci. USA*, 84: 6624-8 (1987).
Wang et al., Characterization of cis-acting elements regulating transcription from the promoter of a constitutively active rice actin gene, *Molec. Cell Biol.*, 3399-406 (1992).
Weide et al., Paracentromeric sequences on tomato chromosome 6 show homology to human satellite III and to the mammalian CENP-B binding box, *Mol. Gen. Genet.*, 259: 190-7 (1998).
Wensink et al., A system for mapping DNA sequences in the chromosomes of *Drosophila melanogaster, Cell*, 3: 315-25 (1974).
Wevrick et al. Partial deletion of alpha satellite DNA associated with reduced amounts of the centromere protein CENP-B in a mitotically stable human chromosome rearrangement, *Molec. Cell Biol.*, 102: 6374-80 (1990).
Whitehouse et al., Mapping chromosome centromeres by the analysis of unordered tetrads, *Nature*, 4205: 893 (1950).
Wigler et al., Transfer of purified herpes virus thymidine kinase gene to cultured mouse cells, *Cell*, 11: 223-32 (1977).
Willard, Centromeres of mammalian chromosomes, *TIG* 6(12): 410-6 (1990).
Willard, Centromeres: The missing link in the development of human artificial chromosomes, *Genet. Dev.* 8: 219-25 (1998).
Wolter et al., Chilling sensitivity of *Arabidopsis thaliana* with genetically engineered membrane lipids, *EMBO J.*, 11: 4685-92 (1992).
Wong et al., Electric field mediated gene transfer, *Biochim. Biophys. Res. Commun.*, 107: 584-7 (1982).
Wright et al., Multiple non-LTR retrotransposons in the genome of *Arabidopsis thaliana, Genet.*, 142: 569-78 (1996).
Wu et al., Composition and structure of the centromeric region of rice chromosome 8, *Plant Cell*, 16: 967-76 (2004).
Xia et al., Genomic organization of the canrepetitive DNA in *Brassica juncea, Plant Molec. Biol.*, 26: 817-32 (1994).
Xia et al., Structure and evolution of a highly repetitive DNA sequence from *Brassica napus, Plant Molec. Biol.*, 21: 213-24 (1993).

(56) References Cited

OTHER PUBLICATIONS

Xiang, et al. The Anti-*nptII* gene, *Plant Physiol.*, 102: 287-93 (1993).
Xu et al., Expression of a late embryogenesis abundant protein gene, HVA1, from barley confers tolerance to water deficit and salt stress in transgenic rice, *Plant Physiol.*, 110: 249-57 (1996).
Yamada et al., Plant regeneration from protoplast-derived callus of rice, *Plant Cell Rep.*, 4: 85 (1986).
Yamaguchi-Shinozaki et al., Molecular cloning and characterization of 9 cDNAs for genes that are responsive to a desiccation in *Arabidopsis thaliana*: Sequence analysis of one cDNA clone that encodes a putative transmembrane channel protein, *Plant Cell Physiol.*, 33: 217-24 (1992).
Yang et al., Maize sucrose synthase-1 promoter directs phloem cell-specific expression of gus gene in transgenic tobacco plants, *Proc. Natl. Acad. Sci. USA*, 87: 4144-8 (1990).
Yen et al., CENP-E, a novel human centomere-associated protein required for progression from metaphase to anaphase, *EMBO J.*, 10: 1245-54 (1991).
Young et al., A new approach for identifying and mapping structural genes in *Drosophila melanogaster*, Eukaryotic genetic systems ICNUCLA symposia on molecular and cellular biology VII: 315-31 (1977).
Yuan et al., Selection of guide sequences that direct efficient cleavage of mRNA by human ribonuclease P, *Science*, 263: 1269-73 (1994).
Yuan et al., Targeted cleavage of mRNA by human RNase P, *Proc. Natl. Acad. Sci. USA*, 89: 8006-10 (1992).
Zabel et al., Towards the construction of artificial chromosomes for tomato, 609-24.
Zatloukal et al., Transferinfection: A highly efficient way to express gene constructs in eukaryotic cells, *Ann. N.Y. Acad. Sci.*, 660: 136-153.
Zentgraf, Telomere-binding proteins of *Arabidopsis thaliana, Plant Molec. Biol.*, 27: 467-75 (1995).
Zhang et al., Molecular cloning, nucleotide sequence, and function of a site-specific recombinase encoded in the major pathogenicity island' of *Salmonella typhi, Gene*, 202: 139-46 (1997).
Zhang et al., *Zea mays* B chromosome centromere repeat sequence Zea_mays_MBsC216pMBsC216, (unpublished).
Zhong et al., Centromeric retroelements and satellites interact with maize kinetochore protein CENH3. *Plant Cell.*, 14: 2825-36 (2002).
Zukowski et al., Chromogenic identification of genetic regulatory signals in *Bacillus subtilis* based on expression of a cloned *Pseudomonas* gene, *Proc. Natl. Acad. Sci., USA*, 80: 1101-5 (1983).
Zuo et al., The *WUSCHEL* gene promotes vegetative-to-embryonic transition in *Arabidopsis, Plant J.*, 30:349-59 (2002).

*SORGHUM* CENTROMERE SEQUENCES AND MINICHROMOSOMES

CROSS-REFERENCE TO RELATED APPLICATIONS

This application is a U.S. National Phase of International Application No. PCT/US2010/043065, filed Jul. 23, 2010; which claims priority to U.S. Provisional Patent Application No. 61/228,015, filed Jul. 23, 2009, both of which are herein incorporated by reference in their entirety.

GOVERNMENT SUPPORT

Not applicable.

COMPACT DISC FOR SEQUENCE LISTINGS AND TABLES

Not applicable.

FIELD OF THE INVENTION

The present invention relates to sorghum centromere sequences that are useful, for example, in constructing artificial chromosomes comprising sorghum centromere sequences, and cells and organisms comprising such artificial chromosomes, including *Sorghum bicolor* and *Sorghum sudanese*. Methods the make and use the disclosed sorghum centromeres are also disclosed.

BACKGROUND OF THE INVENTION

Two general approaches are used for introduction of new heritable genetic information ("transformation") into cells. One approach is to introduce the new genetic information as part of another DNA molecule, referred to as an "episomal vector," or "minichromosome" (MC), which can be maintained as an independent unit (an episome) apart from the host chromosomal DNA molecule(s). Episomal vectors contain all the necessary DNA sequence elements required for DNA replication and maintenance of the vector within the cell. Many episomal vectors are available for use in bacterial cells (for example, see Maniatis et al., *Molecular Cloning: a Laboratory Manual*, Cold Spring Harbor Laboratory, Cold Spring Harbor, N.Y., 1982). However, only a few episomal vectors that function in higher eukaryotic cells have been developed. Higher eukaryotic episomal vectors were primarily based on naturally occurring viruses. In higher plant systems gemini viruses are double-stranded DNA viruses that replicate through a double-stranded intermediate upon which an episomal vector could be based, although the gemini virus is limited to an approximately 800 bp insert. Although an episomal plant vector based on the Cauliflower Mosaic Virus has been developed, its capacity to carry new genetic information also is limited (Brisson et al., *Nature,* 310:511, 1984).

The other general method of genetic transformation involves integration of introduced DNA sequences into the recipient cell's chromosomes, permitting the new information to be replicated and partitioned to the cell's progeny as a part of the natural chromosomes. The introduced DNA usually can be broken and joined together in various combinations before it is integrated at random sites into the cell's chromosome (see, for example Wigler et al., *Cell,* 11:223, 1977). Common problems with this procedure are the rearrangement of introduced DNA sequences and unpredictable levels of expression due to the location of the transgene integration site in the host genome or so called "position effect variegation" (Shingo et al., *Mol. Cell. Biol.,* 6:1787, 1986). Further, unlike episomal DNA, integrated DNA cannot normally be precisely removed. A more refined form of integrative transformation can be achieved by exploiting naturally occurring viruses that integrate into the host's chromosomes as part of their life cycle, such as retroviruses (see Chepko et al., *Cell,* 37:1053, 1984).

One common genetic transformation method used in higher plants is based on the transfer of bacterial DNA into plant chromosomes that occurs during infection by the phytopathogenic soil bacterium *Agrobacterium* (see Nester et al., *Ann. Rev. Plant Phys.,* 35:387-413, 1984). By substituting genes of interest for a portion of the naturally transferred bacterial sequences (called T-DNA), investigators have been able to introduce new DNA into plant cells. However, even this more "refined" integrative transformation system is limited in three major ways. First, DNA sequences introduced into plant cells using the *Agrobacterium* T-DNA system are frequently rearranged (see Jones et al., *Mol. Gen. Genet.,* 207:478, 1987). Second, the expression of the introduced DNA sequences varies between individual transformants (see Jones et al., *EMBO J.,* 4:2411-2418, 1985). This variability is presumably caused by rearranged sequences and the influence of surrounding sequences in the plant chromosome (i.e., position effects), as well as methylation of the transgene. Finally, insertion of extra elements into the genome can disrupt the genes, promoters or other genetic elements necessary for normal plant growth and function.

Another widely used technique to genetically transform plants involves the use of microprojectile bombardment to integrate DNA sequences into the genome. In this process, a nucleic acid containing the desired genetic elements to be introduced into the plant's native chromosome is deposited on or in small metallic particles, e.g., tungsten, platinum, or preferably gold, which are then delivered at a high velocity into the plant tissue or plant cells. However, similar problems arise as with *Agrobacterium*-mediated gene transfer, and as noted above expression of the inserted DNA can be unpredictable and insertion of extra elements into the genome can disrupt and adversely impact plant processes.

One attractive alternative to the commonly used methods of transformation is the use of an artificial chromosome. Artificial chromosomes are episomal nucleic acid molecules that exist autonomously from the native chromosomes of the host genome. They can be linear or circular DNA molecules that are comprised of cis-acting nucleic acid sequence elements that provide replication and partitioning activities (see Murray et al., *Nature,* 305:189-193, 1983). Desired elements include: (1) origin of replication, which are the sites for initiation of DNA replication, (2) centromeres (site of kinetochore assembly and responsible for proper distribution of replicated chromosomes into daughter cells at mitosis or meiosis), and (3) if the chromosome is linear, telomeres (specialized DNA structures at the ends of linear chromosomes that function to stabilize the ends and facilitate the complete replication of the extreme termini of the DNA molecule). An additional desired element is a chromatin organizing sequence. It is well documented that centromere function is crucial for stable chromosomal inheritance in almost all eukaryotic organisms (reviewed in Nicklas, *J Cell Sci.* 189: 283-5, 1988). The centromere accomplishes this by attaching, via centromere binding proteins, to the spindle fibers during mitosis and meiosis, thus ensuring proper gene segregation during cell divisions.

Artificial chromosomes have been engineered using one of two approaches. The first approach identifies and assembles the desired chromosomal elements into an artificial construct.

This is approach has been described as "bottom-up" and involves the use of a heterologous system (i.e. bacteria or fungal) to perform the various cloning steps necessary to assemble the artificial chromosome. Artificial chromosomes of this type will be referred to in this application as "minichromosomes or "MCs". The second approach derives the artificial from existing chromosomes through chromosome fragmentation and, optionally, subsequent addition of desired elements including transgenes. For example, an existing chromosome can be induced to undergo breakage events that result in chromosomal fragments. Minimal fragments that possess the elements necessary for replication and segregation during cell division (i.e. centromere, origins of replication and telomeres) can be identified. These derived artificial chromosomes can then be used as targets for further manipulation including the addition of one or more transgenes. This approach has been described as "top-down" and does not require the use of a heterologous system (i.e. bacterial or fungal) since it doesn't require in vitro-based cloning steps. Artificial chromosomes of this type will be referred to in this application as "recombinant chromosomes."

The essential chromosomal elements for construction of artificial chromosomes have been precisely characterized in lower eukaryotic species, and more recently in mouse and human Autonomous Replication Sequences (ARSs) have been isolated from unicellular fungi, including *Saccharomyces cerevisiae* (brewer's yeast) and *Schizosaccharomyces pombe* (see Stinchcomb et al., *Nature* 282:39-43, 1979 and Hsiao et al., *Proc Natl Acad Sci USA* 76:3829-33, 1979). An ARS behaves like an origin of replication allowing DNA molecules that contain the ARS to be replicated in concert with the rest of the genome after introduction into the cell nuclei of these fungi. DNA molecules containing these sequences replicate, but in the absence of a centromere they are not partitioned into daughter cells in a controlled fashion that ensures efficient chromosome inheritance.

Artificial chromosomes have been constructed in yeast using the three cloned essential chromosomal elements (see Murray et al., *Nature,* 305:189-193, 1983). None of the essential components identified in unicellular organisms, however, function in higher eukaryotic systems. For example, a yeast centromere sequence will not confer stable inheritance upon vectors transformed into higher eukaryotes.

In contrast to the detailed studies done in yeast, less is known about the molecular structure of functional centromeric DNA of higher eukaryotes. Ultrastructural studies indicate that higher eukaryotic kinetochores, which are specialized complexes of proteins that form on the centromere during late prophase, are large structures (mammalian kinetochore plates are approximately 0.3 μm in diameter) which possess multiple microtubule attachment sites (reviewed in Rieder, *Int Rev Cytol;* 79:1-58, 1982). It is therefore possible that the centromeric DNA regions of these organisms will be correspondingly large, although the minimal amount of DNA necessary for centromere function may be much smaller.

While the above studies have been useful in elucidating the structure and function of centromeres, it was not known whether information derived from lower eukaryotic or mammalian higher eukaryotic organisms would be applicable to sorghum. There exists a need for cloned centromeres from sorghum, which would represent a first step in the production of artificial chromosomes, or in the identification of recombinant chromosomes. There further exists a need for sorghum cells, plants, seeds and progeny containing functional, stable, and autonomous artificial or recombinant chromosomes capable of carrying a large number of different genes and genetic elements.

SUMMARY OF THE INVENTION

In one aspect, the present invention addresses sorghum MCs comprising a sorghum centromere having one or more repeated nucleotide sequences, described in further detail herein. In some embodiments, such MCs comprise a centromere comprising one or more selected repeated nucleotide sequences derived from sorghum, including those isolated from sorghum genomic DNA and synthetic arrays of repeat sequences. In other embodiments, the invention addresses sorghum recombinant chromosomes.

In another aspect, the invention provides modified or "adchromosomal" sorghum plants, containing functional, stable, autonomous MCs or recombinant chromosomes.

The invention provides for isolated sorghum MCs comprising a centromere, wherein the centromere comprises at least two copies of a repeated nucleotide sequences, and wherein the centromere confers the ability to segregate to daughter cells. The repeated nucleotide sequences may be short sorghum satellite sequences such as those sequences set out in SEQ ID NOs:23-176, or the consensus sorghum satellite sequence set out as SEQ ID NO:22. The repeated nucleotide sequences may be longer sequences such as the sorghum retrotransposon CRS sequence, set out as SEQ ID NO:21 or fragments thereof.

In exemplary embodiments, the invention provides for a sorghum plant cell comprising a sorghum MC comprising a sorghum centromere that comprises at least two repeat nucleotide sequences that have a sequence that hybridizes under conditions comprising hybridization at 65° C. and washing three times for 15 minutes with 0.25×SSC, 0.1% SDS at 65° C. to any one of the sorghum satellite sequence set out is SEQ ID NOs:23-176, or the consensus sorghum satellite sequence set out as SEQ ID NO:22, or the sorghum retrotransposon sequence of SEQ ID NO:21 or a fragment thereof, and wherein the centromere confers the ability to segregate to daughter cells. Alternatively, the hybridization conditions may comprise hybridization at 65° C. and washing three times for 15 minutes with 0.25×SSC, 0.1% SDS at 65° C.

In another exemplary embodiment, the invention provides for a sorghum plant cell comprising a sorghum MC comprising a sorghum centromere, wherein the centromere comprises at least two copies of a repeated nucleotide sequences that have a sequence that is at least 80% identical to any one of the sorghum satellite sequence set out in SEQ ID NOs:23-176, or the consensus sorghum satellite sequence set out as SEQ ID NO:22, or the sorghum retrotransposon sequence of SEQ ID NO:21 or a fragment thereof, and wherein the centromere confers the ability to segregate to daughter cells. The invention also provides for a sorghum plant cell comprising a sorghum MCs wherein the repeated nucleotide sequence comprise a sequence that is at least 85% identical, or 90% identical or 95% identical or 98% identical to any one of the sorghum satellite sequence set out in SEQ ID NOs:23-176, or the consensus sorghum satellite sequence set out as SEQ ID NO:22.

In another embodiment, the invention provides for a sorghum plant cell comprising a sorghum Applied MC comprising at least two copies of a repeated nucleotide sequence that is at least 80% identical to any one of the sorghum satellite sequence set out in SEQ ID NOs:23-176, or the consensus sorghum satellite sequence set out as SEQ ID NO:22, or the sorghum retrotransposon sequence of SEQ ID NO:21 or a fragment thereof or hybridizes to the nucleotide sequence of any one of the sorghum satellite sequence set out in SEQ ID NOs:23-176, or the consensus sorghum satellite sequence set out as SEQ ID NO:22, or the sorghum retrotransposon sequence of SEQ ID NO:21 or a fragment thereof under stringent conditions comprising hybridization at 65° C. and washing three times for 15 minutes with 0.25×SSC, 0.1% SDS at 65° C., and a Transgene Expression Cassette.

In a further embodiment, the invention provides for a sorghum plant cell comprising a sorghum MC comprising a sorghum centromere, wherein the centromere comprises (a) at least two copies of a sorghum satellite nucleotide sequence, and (b) at least two copies of the a sorghum CRS nucleotide sequence (SEQ ID NO:21) or fragments thereof, and wherein the centromere confers the ability to segregate to daughter sorghum cells. In another embodiment, the invention provides for a sorghum plant cell comprising a MC comprising a sorghum centromere, wherein the centromere comprises (a) at least one array of sorghum satellite nucleotide sequences, and (b) at least one array of sorghum CRS nucleotide sequence (SEQ ID NO:21) or fragments thereof, and wherein the centromere confers the ability to segregate to daughter sorghum cells. The sorghum satellite nucleotide sequence may be one of the sequences set out in SEQ ID NOs:23-176, or the consensus sorghum satellite sequence set out as SEQ ID NO:22, or a sequence that hybridizes under conditions comprising hybridization at 65° C. and washing three times for 15 minutes with 0.25×SSC, 0.1% SDS at 65° C. to any one of the sorghum satellite sequence set out in SEQ ID NOs:23-176, or to the consensus sorghum satellite sequence set out as SEQ ID NO:22, or a sequence that is al least 70% identical to any one of the sorghum satellite sequence set out in SEQ ID NOs:23-176, or to the consensus sorghum satellite sequence set out as SEQ ID NO:22.

In addition, the invention provides for a sorghum plant cell comprising a sorghum Applied MC comprising a sorghum centromere, wherein the sorghum centromere comprises (a) at least 5 copies of a repeated nucleotide sequence within 1 kb of nucleotide sequence, wherein the repeated nucleotide sequence is at least 80% identical to any one of the sorghum satellite sequence set out in SEQ ID NOs:23-176, or to the consensus sorghum satellite sequence set out as SEQ ID NO:22, or hybridizes to the nucleotide sequence of any one of the sorghum satellite sequence set out in SEQ ID NOs:23-176, or to the consensus sorghum satellite sequence set out as SEQ ID NO:22 under stringent conditions comprising hybridization at 65° C. and washing three times for 15 minutes with 0.25×SSC, 0.1% SDS at 65° C., and (b) at least 2 copies of a repeated nucleotide sequence that is at least 80% identical over its length to a fragment of the nucleotide sequence of SEQ ID NO:21 or hybridizes to a fragment of SEQ ID NO:21 under stringent conditions comprising hybridization at 65° C. and washing three times for 15 minutes with 0.25×SSC, 0.1% SDS at 65° C.

In another embodiment, the invention provides a sorghum plant cell comprising (a) a polynucleotide sequence that is transcribed as a first RNA, (b) a polynucleotide sequence that is transcribed as a second RNA, and (c) a polynucleotide sequence that is transcribed as a third RNA, wherein transcription of the polynucleotide sequences results in increased biomass of a sorghum plant.

In an additional embodiment, the invention provides for a sorghum plant cell comprising a transgene expression cassette not integrated into the plant cell genome, wherein the Transgene Expression Cassette comprises (a) a polynucleotide sequence that is transcribed as a first RNA, (b) a polynucleotide sequence that is transcribed as a second RNA, and (c) a polynucleotide sequence that is transcribed as a third RNA, wherein transcription of the polynucleotide sequences results in increased biomass of a sorghum plant.

The invention provides for a sorghum plant cell comprising a recombinant chromosome comprising at least two copies of a repeated nucleotide sequences, and wherein the centromere confers the ability to segregate to daughter cells. The repeated nucleotide sequences may be short sorghum satellite sequences such as those sequences set out in SEQ ID NOs: 23-176, or the consensus sorghum satellite sequence set out as SEQ ID NO:22. The repeated nucleotide sequences may be longer sequences such as the sorghum retrotransposon sequence CRS, set out as SEQ ID NO:21.

In exemplary embodiments, the invention provides for a sorghum plant cell comprising a recombinant chromosome comprising a sorghum centromere that comprises at least two repeat nucleotide sequences that have a sequence that hybridizes under conditions comprising hybridization at 65° C. and washing three times for 15 minutes with 0.25×SSC, 0.1% SDS at 65° C. to any one of the sorghum satellite sequence set out in SEQ ID NOs:23-176, or to the consensus sorghum satellite sequence set out as SEQ ID NO:22, or to the sorghum retrotransposon sequence of SEQ ID NO:21 or a fragment thereof, and wherein the centromere confers the ability to segregate to daughter cells. Alternatively, the hybridization conditions may comprise hybridization at 65° C. and washing three times for 15 minutes with 0.25×SSC, 0.1% SDS at 65° C.

In another exemplary embodiment, the invention provides for a sorghum plant cell comprising a recombinant chromosome comprising at least two copies of a repeated nucleotide sequences that have a sequence that is at least 80% identical to any one of the sorghum satellite sequence set out in the SEQ ID NOs:23-176, or to the consensus sorghum satellite sequence set out as SEQ ID NO:22, or to the sorghum retrotransposon sequence of SEQ ID NO:21 or a fragment thereof, and a transgene expression cassette comprising at least three exogenous nucleic acids. The invention also provides for sorghum recombinant chromosomes wherein the repeated nucleotide sequence comprise a sequence that is at least 85% identical, or 90% identical or 95% identical or 98% identical to any one of the sorghum satellite sequence set out in SEQ ID NOs:23-176, or to the consensus sorghum satellite sequence set out as SEQ ID NO:22, or the sorghum retrotransposon sequence of SEQ ID NO:21 or a fragment thereof.

In a further embodiment, the invention provides for a sorghum plant cell comprising a sorghum recombinant chromosome comprising a sorghum centromere, wherein the centromere comprises (a) at least two copies of a sorghum satellite nucleotide sequence, and (b) at least two copies of the a sorghum CRS nucleotide sequence (SEQ ID NO:21) or a fragment thereof, and wherein the centromere confers the ability to segregate to daughter cells. In another embodiment, the invention provides for a sorghum recombinant chromosome comprising a sorghum centromere, wherein the centromere comprises (a) at least one array of sorghum satellite nucleotide sequences, and (b) at least one array of sorghum CRS nucleotide sequence (SEQ ID NO:21) or a fragment thereof, and wherein the centromere confers the ability to segregate to daughter cells. The sorghum satellite nucleotide sequence may be one of the sequences set out in SEQ ID NOs:23-176, or to the consensus sorghum satellite sequence set out as SEQ ID NO:22, or to a sequence that hybridizes under conditions comprising hybridization at 65° C. and washing three times for 15 minutes with 0.25×SSC, 0.1% SDS at 65° C. to a nucleotide sequence any one of the sorghum satellite sequence set out in SEQ ID NOs:23-176, or to the consensus sorghum satellite sequence set out as SEQ ID NO:22, or to a sequence that is at least 80% identical to any one of the sorghum satellite sequence set out in SEQ ID NOs:23-176, or to the consensus sorghum satellite sequence set out as SEQ ID NO:22.

Alternatively, the invention provides for sorghum plant cells comprising a recombinant chromosome that has not been maintained in a cell of a heterologous organism.

In another embodiment, the invention provides for a sorghum plant cell comprising (a) at least two copies of a repeated nucleotide sequence that is at least 80% identical to any one of the sorghum satellite sequence set out in SEQ ID NOs:23-176, or to the consensus sorghum satellite sequence set out as SEQ ID NO:22, or to the sorghum retrotransposon sequence of SEQ ID NO:21 or a fragment thereof or hybridizes to any one of the sorghum satellite sequence set out in SEQ ID NOs:23-176, or to the consensus sorghum satellite sequence set out as SEQ ID NO:22, or to the sorghum retrotransposon sequence of SEQ ID NO:21 or a fragment thereof under stringent conditions comprising hybridization at 65° C. and washing three times for 15 minutes with 0.25× SSC, 0.1% SDS at 65° C., and (b) a Transgene Expression Cassette comprising at least three exogenous nucleic acids, wherein the nucleotide sequence and the Transgene Expression Cassette are not integrated into the genome of the sorghum plant cell.

The invention also provides for a sorghum plant cell comprising a sorghum MC comprising a sorghum centromere, wherein the centromere comprises at least two synthetic repeat sequences or a synthetic array of repeated nucleotide sequence, wherein the array comprises at least two copies of a repeated nucleotide sequence, and wherein the centromere confers the ability to segregate to daughter sorghum cells. These artificially synthesized repeated nucleotide sequences may be based on sequence information from natural sorghum centromere sequences, combinations or fragments of natural sorghum centromere sequences including a combination of repeats of different lengths, a combination of different sequences, a combination of both different repeat lengths and different sequences, a combination of different artificially synthesized sequences or a combination of natural sorghum centromere sequence(s) and artificially synthesized sorghum sequence(s). The polynucleotides comprising synthetic arrays of sorghum repeat sequences and synthetic arrays of sorghum repeat sequences may be generated using any technique known in the art including PCR from sorghum genomic DNA (or a clone thereof) or by custom oligonucleotide synthesis.

The invention provides for any of the preceding sorghum MCs or recombinant chromosomes having a centromere comprising an array of repeated nucleotide sequence that ranges from about 1 kb to about 200 kb in length, 1 kb to about 100 kb in length, about 1 kb to about 10 kb, about 2 kb to about 12 kb, about 5 kb to about 25 kb, about 10 kb to about 50 kb, about 25 kb to 100 kb.

The invention further contemplates any of the preceding sorghum MCs or recombinant chromosomes having centromeres comprising at least 300 bp, 400 bp, 500 bp, 600 bp, 700 bp, 750 bp, 1 kb, 1.5 kb, 2 kb, 2.5 kb, 3 kb, 3.5 kb, 4 kb, 4.5 kb, 5 kb, 5.5 kb, 6 kb, 6.5 kb, 7 kb, 7.5 kb, 8 kb, 8.5 kb, 9 kb, 9.5 kb, 10 kb, 10.5 kb, 11 kb, 11.5 kb, 12 kb, 12.5 kb, 13 kb, 13.5 kb, 14 kb, 14.5 kb, 15 kb, 16 kb, 17 kb, 18 kb, 19 kb, 20 kb, 25 kb, 30 kb, 35 kb, 40 kb, 45 kb, 50 kb, 60 kb, 70 kb, 80 kb, 90 kb, 100 kb, 110 kb, 120 kb, 130 kb, 140 kb, 150 kb, 160 kb, 170 kb, 180 kb, 190 kb, 200 kb, 225 kb, 250 kb, 275 kb, 300 kb, 325 kb, 350 kb or 375 kb.

In another embodiment, any of the preceding sorghum MCs or recombinant chromosomes comprise centromeres having n copies of a repeated nucleotide sequence, wherein n is less than 2000, less than 1500, less than 1000, less than 500, less than 400, less than 300, less than 250, less than 200, less than 100, less than 90, less than 80, less than 70, less than 60, less than 50, less than 40, less than 30, less than 25, less than 20, less than 15, less than 10, less than 9, less than 8, less than 7, less than 6 or less than 5. In exemplary embodiments, the centromeres of the sorghum MCs of the invention comprise n copies of a repeated nucleotide sequence, wherein n is at least 2, 3, 4, 5, 6, 7, 8, 9, 10, 15, 20, 25, 30, 35, 40, 50, 60, 70, 80, 90, 100, 110, 120, 130, 140, 150, 160, 170, 180, 190, 200, 225, 250, 275, 300, 325, 350, 375, 400, 425, 450, 475, 500, 550, 600, 650, 700, 750, 800, 850, 900 or 1000. In additional exemplary embodiments, the centromeres of the sorghum MCs or recombinant chromosomes of the invention comprise n copies of a repeated nucleotide sequence where n ranges from 2 to 10, 2 to 20, 5 to 15, 5 to 25, 5 to 50, 5 to 100, 5 to 250, 5 to 500, 5 to 1000, 15 to 25, 15 to 50, 15 to 100, 15 to 250, 15 to 500, 15 to 1000, 25 to 50, 25 to 100, 25 to 250, 25 to 500, 25 to 1000, 50 to 100, 50 to 250, 50 to 500, 50 to 1000, 100 to 250, 100 to 500, 100 to 1000, 250 to 500, 250 to 1000, or 500 to 1000.

In an embodiment of the invention, any of the preceding sorghum MCs or recombinant chromosomes comprising a centromere having at least 5 consecutive repeated nucleotide sequences in "head to tail orientation." In an embodiment of the invention, any of the preceding sorghum MCs or recombinant chromosomes comprising a centromere having at least 5 consecutive repeated nucleotide sequences in "tandem," in which one repeat sequence is immediately adjacent to another repeat sequence in any orientation, e.g. head to tail, tail to tail, or head to head. The invention also provides for any of the preceding sorghum MCs or recombinant chromosomes comprising a centromere having at least 5 repeated nucleotide sequences that are consecutive. The term "consecutive" refers to the same or similar repeated nucleotide sequences (e.g., at least 80% identical) that follow one after another without being interrupted by other significant sequence elements. Consecutive repeated nucleotide sequences may be in any orientation, e.g. head to tail, tail to tail, or head to head, and need not be directly adjacent to each other (e.g., may be 1-50 bp apart).

The invention further provides for any of the preceding sorghum MCs or recombinant chromosomes comprising a centromere having at least 5 of the consecutive repeated nucleotide sequences separated by less than n number of nucleotides, wherein n ranges from 1 to 10, or 1 to 20, or 1 to 30, or 1 to 40, or 1 to 50 or wherein n is less than 10 bp or n is less than 20 bp or n is less than 30 bp or n is less that 40 bp or n is less than 50 bp.

The invention also provide for any of the preceding sorghum MCs or recombinant chromosomes comprising a centromere having at least two arrays of consecutive repeated nucleotide sequences, wherein the array comprises at least 2, 3, 4, 5, 6, 7, 8, 9, 10, 15, 20, 25, 30, 40, 50, 60, 70, 80, 90, 100, 150, 200, 250, 300, 350, 400, 450, 500, 600, 700, 800, 900, 1000 or 2000 repeated nucleotide sequences. The repeats within an array may be in tandem in any orientation, e.g. head to tail, tail to tail, or head to head, or consecutive in any orientation, e.g. head to tail, tail to tail, or head to head. The arrays may be separated by less than n number of nucleotides, wherein n ranges from 1 to 10, or 1 to 20, or 1 to 30, or 1 to 40, or 1 to 50, or 1 to 60, or 1 to 70, or 1 to 80, or 1 to 90, or 1 to 100, or wherein n is less than 10 bp or n is less than 20 bp or n is less than 30 bp or n is less than 40 bp or n is less than 50 bp. The two arrays may comprise the same repeated nucleotide sequence or two different repeated nucleotide sequences (i.e. the first array can be comprised of repeat type 1 and the second array can be comprised of repeat type 2—here "type 1" and "type 2" are arbitrary designations).

In one embodiment, the sorghum MCs or recombinant chromosomes of the invention are 1000 kb or less in length, 900 kb or less in length, 800 kb or less in length or 700 kb or less in length. In exemplary embodiments, the sorghum MC is 600 kb or less in length, 500 kb or less in length, 250 kb or less in length, 100 kb or less in length, 50 kb or less in length, 10 kb or less in length, 5 kb or less in length, or 1 kb or less in length. For example, the sorghum MCs of the invention are 50 to 250 kb in length, 50 to 100 kb in length, 50 to 75 kb in length, 50 to 100 kb in length, 60 kb to 85 kb in length, 70 to 90 kb in length, 75 to 100 kb in length, 100 to 250 kb in length, 250 to 500 kb in length, 500 to 1000 kb in length. In an exemplary embodiment, the sorghum MC is 28 kb in length, 42 kb in length, 82 kb in length, 87 kb in length, 88 kb in length, 97 kb in length, 130 kb in length, 150 kb in length, 200 kb in length or ranges from 28-200 kb in length. The MC of the invention preferably has a segregation efficiency during mitotic division of at least 60%, at least 80%, at least 90% or at least 95% and/or a transmission efficiency during meiotic division of, e.g., at least 60%, at least 80%, at least 85%, at least 90% or at least 95%.

The sorghum MC or recombinant chromosomes of the invention preferably has a segregation efficiency during mitotic division of at least 60%, at least 80%, at least 90% or at least 95% and/or a transmission efficiency during meiotic division of, e.g., at least 60%, at least 80%, at least 85%, at least 90% or at least 95%.

In another embodiment, the sorghum MCs or recombinant chromosomes of the invention comprise a site for site-specific recombination.

The invention also provides for a sorghum MC, wherein the MC is derived from a donor clone or a centromere clone and has substitutions, deletions, insertions, duplications or arrangements of one or more nucleotides in the MC compared to the nucleotide sequence of the donor clone or centromere clone. In one embodiment, the sorghum MC is obtained by passage of the sorghum MC through one or more hosts. In another embodiment, the MC is obtained by passage of the MC through two or more different hosts. The host may be selected from the group consisting of viruses, bacteria, yeasts. In another embodiment, the sorghum MC is obtained from a donor clone by in vitro methods that introduce sequence variation during template-based replication of the donor clone, or its complementary sequence. In one embodiment this variation may be introduced by a DNA-dependent DNA polymerase. In a further embodiment a sorghum MC derived by an in vitro method may be further modified by passage of the MC through one or more hosts.

The invention also provides for a sorghum MC or recombinant chromosome, wherein the MC comprises at least one exogenous nucleic acid. In further exemplary embodiments, the sorghum MC or recombinant chromosome comprises at least two or more, at least three or more, at least four or more, at least five or more, at least ten or more, at least 20 or more, at least 30 or more, at least 40 or more, at least 50 or more exogenous nucleic acids.

In one embodiment, at least one exogenous nucleic acid of any of the preceding sorghum MCs or recombinant chromosome is operably linked to a heterologous regulatory sequence functional in plant cells, including but not limited to a plant regulatory sequence. The invention also provides for exogenous nucleic acids linked to a non-plant regulatory sequence, such as an arthropod, viral, bacterial, vertebrate or yeast regulatory sequence. The invention also provides for exogenous nucleic acids linked to a regulatory sequence from sorghum.

The invention also provides for a MC or recombinant chromosome comprising a gene or group of genes that act to improve the total recoverable sugar from sorghum. Such genes may act to increase the sugar concentration of the stem juice, increase the amount of juice, or increase the stem strength to improve yield, increase total bomass of the plant. Such genes may be derived from bacterial sequences such as a sucrose isomerase or from animal, plant fungal, or protist sequences. Such genes from plants may include genes involved in sugar metabolism or transport or genes of unknown function that have been shown to quantitatively increase total recoverable sugar. Such genes may also include genes that affect plant height, stem diameter, water metabolism or total biomass. Such genes may also include those that regulate the equilibrium between starch and sugar. Several genes have been shown to improve sugar accumulation. For example, expression of a bacterial sucrose isomerase can increase sugarcane sugar content by as much as two-fold (Birch, R. G., and Wu, L. (2007). Doubled sugar content in sugarcane plants modified to produce a sucrose isomer. Plant Biotechnology Journal 5: 109-117. The lignin-deficient "brown midrib" mutations improve sorghum sugar content via their effects on lignin; this phenotype is caused by mutations in cinnamyl alcohol dehydrogenase (CAD), and 14 CAD-like genes are present in the sorghum genome (Saballos, A et al. *Genetics* 181:783-95, 2009).

In another embodiment, the sorghum MC or recombinant chromosome comprises an exogenous nucleic acid comprises a QTL that confers a desirable trait. QTLs that affect total recoverable sugars have been mapped in sugarcane (Murray, S. C., et al. Crop Sci. 48:2165-2179, 2008).

In another embodiment, the sorghum MC or recombinant chromosome comprises an exogenous nucleic acid that confers herbicide resistance, insect resistance, disease resistance, or stress resistance on the sorghum plant. The invention provides for sorghum MCs or recombinant chromosomes comprising an exogenous nucleic acid that confers resistance to phosphinothricin or glyphosate herbicide. Nonlimiting examples include an exogenous nucleic acid that encodes a phosphinothricin acetyltransferase, glyphosate acetyltransferase, acetohydroxyadic synthase or a mutant enoylpyruvylshikimate phosphate (EPSP) synthase. Nonlimiting examples of exogenous nucleic acids that confer insect resistance include a *Bacillus thuringiensis* toxin gene or *Bacillus cereus* toxin gene. In related embodiments, the sorghum MC or recombinant chromosome comprises an exogenous nucleic acid conferring herbicide resistance, an exogenous nucleic acid conferring insect resistance, and at least one additional exogenous nucleic acid.

The invention further provides for sorghum MCs or recombinant chromosomes comprising additional copies of genes already found in the sorghum genome. The invention also provides for the additional copies of sorghum genes carried on the sorghum MC or recombinant chromosomes to be operably linked to either their native regulatory sequences or to heterologous regulatory sequences.

The invention further provides for sorghum MCs or recombinant chromosome comprising an exogenous nucleic acid that confers resistance to drought, heat, chilling, freezing, excessive moisture, ultraviolet light, ionizing radiation, toxins, pollution, mechanical stress or salt stress. The invention also provides for a sorghum MC that comprises an exogenous nucleic acid that confers resistance to a virus, bacteria, fungi or nematode.

The invention provides for sorghum MCs or recombinant chromosome comprising an exogenous nucleic acid selected from the group consisting of a nitrogen fixation gene, a plant stress-induced gene, a nutrient utilization gene, a gene that affects plant pigmentation, a gene that encodes an antisense or ribozyme molecule, a gene encoding a secretable antigen, a toxin gene, a receptor gene, a ligand gene, a seed storage gene, a hormone gene, an enzyme gene, an interleukin gene, a clotting factor gene, a cytokine gene, an antibody gene, a growth factor gene, a transcription factor gene, a transcriptional repressor gene, a DNA-binding protein gene, a recombination gene, a DNA replication gene, a programmed cell death gene, a kinase gene, a phosphatase gene, a G protein gene, a cyclin gene, a cell cycle control gene, a gene involved in transcription, a gene involved in translation, a gene involved in RNA processing, a gene involved in RNAi, an organellar gene, a intracellular trafficking gene, an integral membrane protein gene, a transporter gene, a membrane channel protein gene, a cell wall gene, a gene involved in protein processing, a gene involved in protein modification, a gene involved in protein degradation, a gene involved in metabolism, a gene involved in biosynthesis, a gene involved in assimilation of nitrogen or other elements or nutrients, a gene involved in controlling carbon flux, gene involved in respiration, a gene involved in photosynthesis, a gene involved in light sensing, a gene involved in organogenesis, a gene involved in embryogenesis, a gene involved in differentiation, a gene involved in meiotic drive, a gene involved in self incompatibility, a gene involved in development, a gene involved in nutrient, metabolite or mineral transport, a gene involved in nutrient, metabolite or mineral storage, a calcium-binding protein gene, or a lipid-binding protein gene.

The invention also provides for a sorghum MC or recombinant chromosome comprising an exogenous enzyme gene selected from the group consisting of a gene that encodes an enzyme involved in metabolizing biochemical wastes for use in bioremediation, a gene that encodes an enzyme for modifying pathways that produce secondary plant metabolites, a gene that encodes an enzyme that produces a pharmaceutical, a gene that encodes an enzyme that improves changes the nutritional content of a plant, a gene that encodes an enzyme involved in vitamin synthesis, a gene that encodes an enzyme involved in carbohydrate, polysaccharide or starch synthesis, a gene that encodes an enzyme involved in mineral accumulation or availability, a gene that encodes a phytase, a gene that encodes an enzyme involved in fatty acid, fat or oil synthesis, a gene that encodes an enzyme involved in synthesis of chemicals or plastics, a gene that encodes an enzyme involved in synthesis of a fuel and a gene that encodes an enzyme involved in synthesis of a fragrance, a gene that encodes an enzyme involved in synthesis of a flavor, a gene that encodes an enzyme involved in synthesis of a pigment or dye, a gene that encodes an enzyme involved in synthesis of a hydrocarbon, a gene that encodes an enzyme involved in synthesis of a structural or fibrous compound, a gene that encodes an enzyme involved in synthesis of a food additive, a gene that encodes an enzyme involved in synthesis of a chemical insecticide, a gene that encodes an enzyme involved in synthesis of an insect repellent, or a gene controlling carbon flux in a plant.

In another embodiment of the invention, any of the preceding sorghum MCs or recombinant chromosomes comprises a telomere.

The invention also provides embodiments wherein any of the preceding sorghum MCs or recombinant chromosomes is linear or circular.

In one embodiment, the invention provides for sorghum plants or plant cells comprising any of the preceding sorghum MCs or recombinant chromosomes. The invention also provides for sorghum plant tissue and sorghum seed obtained from the sorghum plants of the invention.

In another embodiment, the invention provides for sorghum plants comprising any of the preceding sorghum MCs or recombinant chromosomes, which may be referred to herein as "adchromosomal" sorghum plants. In addition, the invention provides for sorghum plant cells, tissues and seeds obtained from these modified plants.

In one embodiment, the invention provides for a sorghum plant cell comprising any of the preceding sorghum MCs or recombinant chromosomes that (i) is not integrated into the sorghum plant cell genome and (ii) confers an altered phenotype on the sorghum plant cell associated with at least one structural gene within the sorghum MC. The altered phenotype comprises increased expression of a native gene, decreased expression of a native gene, or expression of an exogenous gene. In a further embodiment, these sorghum plant cells also comprise one or more integrated exogenous structural gene(s).

Another embodiment of the invention is a part of any of the preceding sorghum plants. Exemplary sorghum plant parts of the invention include a pod, root, sett root, shoot root, root primordial, shoot, primary shoot, secondary shoot, tassle, panicle, arrow, midrib, blade, ligule, auricle, dewlap, blade joint, sheath, node, internode, bud furrow, leaf scar, cutting, tuber, stem, stalk, fruit, berry, nut, flower, leaf, bark, wood, epidermis, vascular tissue, organ, protoplast, crown, callus culture, petiole, petal, sepal, stamen, stigma, style, bud, meristem, cambium, cortex, pith, sheath, silk, ovule or embryo. Other exemplary sorghum plant parts are a meiocyte or gamete or ovule or pollen or endosperm of any of the preceding plants. Other exemplary plant parts are a seed, seed-piece, embryo, protoplast, cell culture, any group of plant cells organized into a structural and functional unit, ratoon, or propagule of any of the preceding sorghum plants.

An embodiment of the invention is a progeny of any of the preceding sorghum plants of the invention. These progeny of the invention may be the result of self-breeding, cross-breeding, apomyxis or clonal propagation. In exemplary embodiments, the invention also provides for progeny that comprise a sorghum MC or recombinant chromosome that is descended from a parental sorghum MC or recombinant chromosome that contained a centromere less than about 1000 kilobases in length, less than about 750 kilobases in length, less than about 600 kilobases in length, less than about 500 kilobases in length, less than about 400 kilobases in length, less than about 300 kilobases in length, less than about 250 kilobases in length, less than about 200 kilobases in length, less than about 150 kilobases, less than about 100 kilobases, less than about 90 kilobases in length, less than about 85 kilobases in length, less than about 80 kilobases in length, less than about 75 kilobases in length, less than about 70 kilobases in length, less than about 65 kilobases in length, less than about 60 kilobases in length, less than about 55 kilobases in length, less than about 50 kilobases in length, less than about 45 kilobases in length, less than about 40 kilobases in length, less than about 35 kilobases in length, less than about 30 kb in length, less than about 25 kilobases in length, less than about 20 kb in length, less than about 15 kilobases in length, less than about 12 kilobases in length, less than about 10 kb in length, less than about 7 kb in length, less than about 5 kb in length, or less than about 2 kb in length.

In another aspect, the invention provides for methods of making a sorghum MC for use in any of the preceding sorghum plants of the invention. These methods comprise identifying a centromere nucleotide sequence in a sorghum genomic DNA library using a multiplicity of diverse probes, and constructing a sorghum MC comprising the centromere nucleotide sequence. These methods may further comprise determining hybridization scores for hybridization of the multiplicity of diverse probes to genomic clones within the sorghum genomic nucleic acid library, determining a classification for genomic clones within the sorghum genomic nucleic acid library according to the hybridization scores for at least two of the diverse probes, and selecting one or more genomic clones within one or more classifications for constructing the sorghum MC.

The invention also contemplates methods of using any of the preceding sorghum plants to produce a recombinant protein, by growing a sorghum plant comprising a sorghum MC or recombinant chromosome that comprises an exogenous nucleic acid encoding the desired recombinant protein. Optionally the sorghum plant is harvested and the desired protein product is isolated from the plant. Exemplary protein products include industrial enzymes such as those useful for biofuel production.

The invention also contemplates methods of using any of the preceding sorghum plants to produce a chemical product, by growing a sorghum plant comprising a sorghum MC or recombinant chromosome that comprises an exogenous nucleic acid encoding and enzyme involved in the synthesis of the chemical product. Optionally the sorghum plant is harvested and the desired chemical product is isolated from the plant. Exemplary chemical products include sugars, lipids and carbohydrates useful in the production of biofuels.

Another aspect of the invention provides for methods of using any of the preceding sorghum plants comprising a sorghum MCs or recombinant chromosome for a food product, a pharmaceutical product or chemical product, according to which a suitable exogenous nucleic acid is expressed in sorghum plants or plant cells and the plant or plant cells are grown. The plant may secrete the product into its growth environment or the product may be contained within the plant, in which case the plant is harvested and desirable products are extracted.

Thus, the invention contemplates methods of using any of the preceding sorghum plants comprising a sorghum MC or recombinant chromosome to produce a modified food product, for example, by growing a plant that expresses a exogenous nucleic acid that alters the nutritional content of the plant, and harvesting or processing the sorghum plant.

The invention also provides for methods of constructing a synthetic array of repeated nucleotide sequence having sorghum centromere function comprising the steps of: (a) PCR amplifying a sorghum satellite sequence, (b) cloning the PCR amplified satellite sequence into a cloning vector, (c) sequencing the cloned satellite DNA, (d) use a restriction enzyme with an asymmetric recognition sequence to excise the cloned satellite sequence from the cloning vector, (e) ligate the satellite sequence to one another forming a synthetic tandem array, (f) ligate the synthetic array into a sorghum MC backbone vector. The invention also provides for an isolated sorghum MC comprising a synthetic array of repeated nucleotide sequence constructed according to the method of the invention, and sorghum plant cells and plants comprising these MCs.

In another embodiment, the invention provides for methods of contacting a sorghum cell with a sorghum MC comprising the steps of (a) delivering the MC to immature differentiated leaves of the apical region of the stem of a sorghum plant, wherein the MC comprises a selectable marker gene, and (b) selecting the sorghum cells expressing the marker gene, wherein expression of the marker gene indicates transformation with the MC. The leaves used in this method are immature but are fully differentiated, such as the inner immature leaves of the sorghum stem. In an exemplary embodiment, the MC may be delivered by bombarding the immature leaves with micro-particles comprising the sorghum MC.

The invention also provides for methods of regenerating a sorghum plant transformed with a sorghum MC comprising the steps of (a) obtaining a callus comprising a sorghum cell that is transformed by any of the methods of the invention, and (b) growing the callus in media that may comprise 1%-3% polyvinylpyrrolidone to form a plantlet, wherein the cells of the plantlet are transformed with the sorghum MC. In a further embodiment, the methods of culturing the callus comprise growing the cells in liquid media for a time period and subsequently culturing the cells in a solid culture media. In an exemplary embodiment, the sorghum MC comprises a growth regulating gene such as a gene in the auxin biosynthesis or perception pathways. Such genes may include iaaM (Trp mono-oxygenase), iaaH (Indole-3-acetamide hydrolase), and ipt (AMP iso-pentenyl transferase). When these three genes are expressed on a MC, IaaM converts Trp into indole-3-acetamide, which IaaH converts into auxin. Ipt converts AMP into a cytokinin. The expression of all three genes allows a cultured cell to grow in the absence of exogenously supplied hormones.

SEQUENCES OF THE INVENTION

The following list indicates the identity of the SEQ ID NOs in the sequence listing:

SEQ ID NOs:1-20—promoter sequences

SEQ ID NO:21—sorghum CRS sequence

SEQ ID NO:22—sorghum consensus satellite repeat sequence

SEQ ID NOs:23-177—sorghum satellite repeat sequences

SEQ ID NO:178—previously identified sorghum CRS sequence

SEQ ID NOs:179-180—forward and reverse primers for amplifying SEQ ID NO:21 of the invention SEQ ID NOs:181-182—forward and reverse primers for making sorghum satellite repeat-specific probes for FISH analysis SEQ ID NOs:183-275—sorghum centromere sequence contigs from BAC 42NM (identified as CRS-positive)

SEQ ID NOs:276-326—sorghum centromere sequence contigs from BAC 89F4 (identified as satellite-positive)

DETAILED DESCRIPTION OF THE INVENTION

While this invention is susceptible of embodiment in many different forms, and will be described herein in detail, specific embodiments thereof with the understanding that the present disclosure is to be considered as an exemplification of the principles of the invention and is not intended to limit the invention to the specific embodiments illustrated.

The invention provides novel, isolated functional, stable, autonomous MCs and recombinant chromosomes comprising centromere comprising sorghum repeat sequences including synthetic sequences. The invention also provides for "adchromosomal sorghum plants," described in further detail herein.

One aspect of the invention is related to plants containing functional, stable, autonomous MCs or recombinant chromosomes, preferably carrying one or more exogenous nucleic acids or carrying extra copies of a nucleic acid that already exists in the plant's genome. Such plants carrying MCs or recombinant chromosomes are contrasted to transgenic plants whose genome has been altered by integrating exogenous nucleic acid transgenes into the native plant chromosomes. Preferably, expression of the exogenous nucleic acid, either constitutively or in response to a signal (which may be induced by challenge or a stimulus), e.g. or tissue specific expression, or time specific expression, results in an altered phenotype of the plant.

The invention provides for MCs or recombinant chromosomes comprising at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 60, 70, 80, 90, 100, 110, 120, 130, 140, 150, 250, 500, 1000 or more exogenous nucleic acids.

The invention contemplates that sorghum plants may be used to cary the autonomous MCs as described herein. A related aspect of the invention is a plant part or plant tissue, including a pod, root, sett root, shoot root, root primordial, shoot, primary shoot, secondary shoot, tassle, panicle, arrow, midrib, blade, ligule, auricle, dewlap, blade joint, sheath, node, internode, bud furrow, leaf scar, cutting, tuber, stem, stalk, fruit, berry, nut, flower, leaf, bark, wood, epidermis, vascular tissue, organ, protoplast, crown, callus culture, petiole, petal, sepal, stamen, stigma, style, bud, meristem, cambium, cortex, pith, sheath, silk, ovule or embryo. Other exemplary plant parts are a meiocyte or gamete or ovule or pollen or endosperm of any of the preceding plants. Other exemplary plant parts are a seed, seed-piece, embryo, protoplast, cell culture, any group of plant cells organized into a structural and functional unit, ratoon or propagule of any of the preceding plants.

In one preferred embodiment, the exogenous nucleic acid is primarily expressed in a specific location or tissue of a plant, for example, stem, epidermis, vascular tissue, meristem, cambium, cortex, pith, leaf, sheath, flower, root or seed. Tissue-specific expression can be accomplished with, for example, localized presence of the MC or recombinant chromosome, selective maintenance of the MC or recombinant chromosomes, or with promoters that drive tissue-specific expression.

Another related aspect of the invention is meiocytes, pollen, ovules, endosperm, seed, somatic embryos, apomyctic embryos, embryos derived from fertilization, vegetative propagules and progeny of the originally adchromosomal plant and of its filial generations that retain the functional, stable, autonomous MC or recombinant chromosome. Such progeny include clonally propagated plants, embryos and plant parts as well as filial progeny from self- and cross-breeding, and from apomyxis.

Preferably the MC or recombinant chromosome is transmitted to subsequent generations of viable daughter cells during mitotic cell division with a transmission efficiency of at least 60%, 70%, 80%, 85%, 90%, 95%, 96%, 97%, 98%, or 99%.

During meiotic division, the MC or recombinant chromosome is preferably transmitted to viable gametes with a transmission efficiency of at least 60%, 70%, 80%, 85%, 90%, 95%, 96%, 97%, 98%, or 99% when more than one copy of the MC recombinant chromosome is present in the gamete mother cells of the plant. Preferably, the MC or recombinant chromosome is transmitted to viable gametes during meiotic cell division with a transmission frequency of at least 1%, 10%, 20%, 30%, 40%, 45%, 46%, 47%, 48%, or 49% when one copy of the MC or recombinant chromosome is present in the gamete mother cells of the plant. For production of seeds via sexual reproduction or by apomyxis the MC or recombinant chromosome is preferably transferred into at least 60%, 70%, 80%, 85%, 90%, 95%, 96%, 97%, 98%, or 99% of viable embryos when cells of the plant contain more than one copy of the MC or recombinant chromosome. For production of seeds via sexual reproduction or by apomyxis from plants with one MC or recombinant chromosome per cell, the MC or recombinant chromosome is preferably transferred into at least 1%, 10%, 20%, 30%, 40%, 45%, 46%, 47%, 48%, or 49% of viable embryos.

Preferably, a MC or recombinant chromosome that comprises an exogenous selectable trait or exogenous selectable marker can be employed to increase the frequency in subsequent generations of adchromosomal cells, tissues, gametes, embryos, endosperm, seeds, plants or progeny that comprise the MC or recombinant chromosome. More preferably, the frequency of transmission of MCs or recombinant chromosomes into viable cells, tissues, gametes, embryos, endosperm, seeds, plants or progeny can be at least 95%, 96%, 97%, 98%, 99% or 99.5% after mitosis or meiosis by applying at least one selection that favors the survival of adchromosomal cells, tissues, gametes, embryos, endosperm, seeds, plants or progeny over such cells, tissues, gametes, embryos, endosperm, seeds, plants or progeny lacking the MC or recombinant chromosome.

Transmission efficiency may be measured as the percentage of progeny cells or plants that carry the MC or recombinant chromosome as measured by one of several assays taught herein including detection of reporter gene fluorescence, PCR detection of a sequence that is carried by the MC or recombinant chromosome, RT-PCR detection of a gene transcript for a gene carried on the MC or recombinant, Western analysis of a protein produced by a gene carried on the MC or recombinant chromosome, Southern analysis of the DNA (either in total or a portion thereof) carried by the MC or recombinant chromosome, fluorescence in situ hybridization (FISH) or in situ localization by repressor binding, to name a few. Any assay used to detect the presence of the MC (or a portion of the MC) or recombinant chromosome may be used to measure the efficiency that a parental cell or plant transmits the MC or recombinant chromosome to its progeny. Efficient transmission as measured by some benchmark percentage should indicate the degree to which the MC or recombinant chromosome is stable through the mitotic and meiotic cycles.

Plants of the invention may also contain chromosomally integrated exogenous nucleic acid in addition to the autonomous MCs or recombinant chromosome. The modified plants or plant parts, including plant tissues of the invention may include plants that have chromosomal integration of some portion of the MC (e.g. exogenous nucleic acid or centromere sequences) or recombinant chromosome in some or all cells the plant. In one aspect of the invention, the autonomous MC or recombinant chromosome can be isolated from integrated exogenous nucleic acid by crossing the modified plant containing the integrated exogenous nucleic acid with plants producing some gametes lacking the integrated exogenous nucleic acid and subsequently isolating offspring of the cross, or subsequent crosses, that are modified but lack the integrated exogenous nucleic acid. This independent segregation of the MC or recombinant chromosome is one measure of the autonomous nature of the MC.

Another aspect of the invention relates to methods for producing and isolating such modified plants containing functional, stable, autonomous MCs.

In one embodiment, the invention contemplates improved methods for isolating native centromere sequences. In another embodiment, the invention contemplates methods for generating variants of native or artificial centromere sequences by passage through other host cells such are bacterial or fungal hosts.

In a further embodiment, the invention contemplates methods for delivering the MC into plant cells or tissues to transform the cells or tissues, optionally detecting MC presence or assessing MC performance, and optionally generating a plant from such cells or tissues.

Exemplary assays for assessing MC performance include lineage-based inheritance assays, use of chromosome loss agents to demonstrate autonomy, exonuclease digestion, global mitotic MC inheritance assays (sectoring assays) with or without the use of agents inducing chromosomal loss, assays measuring expression levels of genes (including marker genes) carried by the MC over time and space in a plant, physical assays for separation of autonomous MCs or recombinant chromosomes from endogenous nuclear chromosomes of plants, molecular assays demonstrating conserved MC structure, such as PCR, Southern blots, MC rescue, cloning and characterization of MC sequences present in the plant, cytological assays detecting MC presence in the cell's genome (e.g. FISH) and meiotic MC inheritance assays, which measure the levels of MC inheritance into a subsequent generation of plants via meiosis and gametes, embryos, endosperm or seeds.

Another aspect of the invention relates to methods for using such plants containing a MC or recombinant chromosome for producing food products, pharmaceutical products, biofuels and chemical products by appropriate expression of exogenous nucleic acid(s) contained within the MC(s) or recombinant chromosome(s).

Yet another aspect of the invention provides novel autonomous MCs with novel compositions and structures which are used to transform plant cells which are in turn used to generate a plant (or multiple plants). Exemplary MCs of the invention are contemplated to be of a size 2000 kb or less in length. Other exemplary sizes of MCs include less than or equal to, e.g., 1500 kb, 1000 kb, 900 kb, 800 kb, 700 kb, 600 kb, 500 kb, 450 kb, 400 kb, 350 kb, 300 kb, 250 kb, 200 kb, 150 kb, 100 kb, 80 kb, 60 kb, 40 kb, 35 kb in length. In an exemplary embodiment, the MC is about 28 kb in length, 42 kb in length, 82 kb in length, 87 kb in length, 88 kb in length, 97 kb in length, 130 kb in length, 150 kb in length, 200 kb in length or ranges from 28 kb to 200 kb in length.

In a related aspect, novel centromere compositions as characterized by sequence content, size or other parameters are provided. Preferably, the minimal size of centromeric sequence is utilized in MC construction. Exemplary sizes include a centromeric nucleic acid segment derived from a portion of plant genomic DNA or a synthesized based on a plant satellite repeat sequence, that is less than or equal to 1000 kb, 900 kb, 800 kb, 700 kb, 600 kb, 500 kb, 400 kb, 300 kb, 200 kb, 190 kb, 150 kb, 100 kb, 95 kb, 90 kb, 85 kb, 80 kb, 75 kb, 70 kb, 65 kb, 60 kb, 55 kb, 50 kb, 45 kb, 40 kb, 35 kb, 30 kb, 28 kb, 25 kb, 20 kb, 17 kb, 15 kb, 12 kb, 10 kb, 7, kb, 6.4 kb, 5 kb, or 2 kb in length. Exemplary inserts may range in size 80 kb to 100 kb, 7 kb to 190 kb, 7 kb to 12 kb, 5 kb to 10 kb, 3 kb to 10 kb, 3 kb to 7 kb, 5 kb to 7 kb, 10 to 30 kb, 15 to 30 kb, and 15 to 28 kb. Another related aspect is the novel structure of the MC, particularly structures lacking bacterial sequences, e.g., required for bacterial propagation, referred to as backbone-free MCs.

In other exemplary embodiments, the invention contemplates MCs or other vectors comprising centromeric nucleotide sequence that when hybridized to 1, 2, 3, 4, 5, 6, 7, 8 or more of the probes described in the examples herein, under hybridization conditions described herein, e.g. low, medium or high stringency, provides relative hybridization scores. Exemplary stringent hybridization conditions comprise hybridization at 65° C. and washing three times for 15 minutes with 0.25×SSC, 0.1% SDS at 65° C. Additional exemplary stringent hybridization conditions comprise hybridization in 0.02 M to 0.15 M NaCl at temperatures of about 50° C. to 70° C. or 0.5×SSC 0.25% SDS at 65° for 15 minutes, followed by a wash at 65° C. for a half hour or hybridization at 65° C. for 14 hours followed by 3 washings with 0.5×SSC, 1% SDS at 65° C. Probe hybridization can be scored visually to determine a binary (positive versus negative) value, or more preferably the probes can be assigned a score based on the relative strength of their hybridization on a 10 point scale. For example, relative hybridization scores of 5 may be used to select clones that hybridize well to the probe. Alternatively, a hybridization signal greater than background for one or more of these probes can be used to select clones. Modified or adchromosomal plants or plant parts containing such MCs are contemplated.

The advantages of the present invention include: provision of an autonomous, independent genetic linkage group for accelerating breeding; lack of disruption of host genome; multiple gene "stacking" of large and potentially unlimited numbers of genes; uniform genetic composition exogenous DNA sequences in plant cells and plants containing autonomous MCs; defined genetic context for predictable gene expression; higher frequency occurrence and recovery of plant cells and plants containing stably maintained exogenous DNA due to elimination of inefficient integration step. In addition, MCs that increase total recoverable sugars, or enhance the utility of modified plants for use in biofuel production are specifically envisioned.

I. Composition of MCs and MC Construction

The MC vector of the present invention may contain a variety of elements, including (1) sequences that function as plant centromeres, (2) one or more exogenous nucleic acids, including, for example, plant-expressed genes, or genes for non-coding RNAs, (3) sequences that function as an origin of replication, which may be included in the region that functions as plant centromere, (4) optionally, a bacterial plasmid backbone for propagation of the plasmid in bacteria, (5) optionally, sequences that function as plant telomeres, (6) optionally, additional "stuffer DNA" sequences that serve to physically separate the various components on the MC from each other, (7) optionally "buffer" sequences such as MARs or SARs, (8) optionally marker sequences of any origin, including but not limited to plant and bacterial origin, (9) optionally, sequences that serve as recombination sites, and (10) "chromatin packaging sequences" such as cohesion and condensing binding sites.

The MCs of the present invention may be constructed to include various components which are novel, which include, but are not limited to, the centromere comprising novel repeating centromeric sequences, as described in further detail below.

Novel Centromere Compositions

The centromere in the MC of the present invention may comprise novel repeating centromeric sequences.

Vectors comprising one, two, three, four, five, six, seven, eight, nine, ten, 15 or 20 or more of the elements contained in any of the exemplary vectors described in the examples below are also contemplated.

The invention specifically contemplates the alternative use of fragments or variants (mutants) of any of the nucleic acids described herein that retain the desired activity, including nucleic acids that function as centromeres, nucleic acids that function as promoters or other regulatory control sequences, or exogenous nucleic acids. Variants may have one or more additions, substitutions or deletions of nucleotides within the original nucleotide sequence or consensus sequence. Variants include nucleic acid sequences that are at least 50%, 55%, 60, 65, 70, 75, 80, 81, 82, 83, 84, 85, 86, 87, 88, 89, 90, 91, 92, 93, 94, 95, 96, 97, 98, 99, or 100% identical to the original nucleic acid sequence. Variants also include nucleic acid sequences that hybridize under low, medium, high or very high stringency conditions to the original nucleic acid sequence. Similarly, the specification also contemplates the alternative use of fragments or variants of any of the polypeptides described herein.

The comparison of sequences and determination of percent identity between two nucleotide sequences can be accomplished using a mathematical algorithm. In a preferred embodiment, the percent identity between two amino acid sequences is determined using the Needleman and Wunsch (1970) J. Mol. Biol. 48:444-453 algorithm which has been incorporated into the GAP program in the GCG software package, using either a Blossum 62 matrix or a PAM250 matrix. Preferably parameters are set so as to maximize the percent identity.

As used herein, the term "hybridizes under low stringency, medium stringency, and high stringency conditions" describes conditions for hybridization and washing. Guidance for performing hybridization reactions can be found in Current Protocols in Molecular Biology (1989) John Wiley & Sons, N.Y., 6.3.1-6.3.6, which is incorporated by reference. Aqueous and non-aqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.5× SSC, 0.1% SDS, at least at 50° C.; 2) medium stringency hybridization conditions in 6×SSC at about 45° C., followed by one or more washes in 0.2×SSC, 0.1% SDS at 55° C.; 3) high stringency hybridization conditions are hybridization at 65° C. for 12-18 hours and washing three times for 15-90 minutes with 0.25×SSC, 0.1% SDS at 65° C. Additional exemplary stringent hybridization conditions comprise 6×SSC at about 45° C., followed by one or more washes in 0.2×SSC, 0.1% SDS at 65° C. Other exemplary highly selective or stringent hybridization conditions comprise 0.02 M to 0.15 M NaCl at temperatures of about 50° C. to 70° C. or 0.5×SSC 0.25% SDS at 65° for 12-15 hours, followed by three washes at 65° C. for 15-90 minutes each.

MC Sequence Content and Structure

Plant-expressed genes from non-plant sources may be modified to accommodate plant codon usage, to insert preferred motifs near the translation initiation ATG codon, to remove sequences recognized in plants as 5' or 3' splice sites, or to better reflect plant GC/AT content. Plant genes typically have a GC content of more than 35%, and coding sequences which are rich in A and T nucleotides can be problematic. For example, ATTTA motifs may destabilize mRNA; plant polyadenylation signals such as AATAAA at inappropriate positions within the message may cause premature truncation of transcription; and monocotyledons, such as sorghum, may recognize AT-rich sequences as splice sites.

Each exogenous nucleic acid or plant-expressed gene may include a promoter, a coding region and a terminator sequence, which may be separated from each other by restriction endonuclease sites or recombination sites or both. Genes may also include introns, which may be present in any number and at any position within the transcribed portion of the gene, including the 5' untranslated sequence, the coding region and the 3' untranslated sequence. Introns may be natural plant introns derived from any plant, or artificial introns based on the splice site consensus that has been defined for plant species. Some intron sequences have been shown to enhance expression in plants. Optionally the exogenous nucleic acid may include a plant transcriptional terminator, non-translated leader sequences derived from viruses that enhance expression, a minimal promoter, or a signal sequence controlling the targeting of gene products to plant compartments or organelles.

The coding regions of the genes can encode any protein, including but not limited to visible marker genes (for example, fluorescent protein genes, other genes conferring a visible phenotype to the plant) or other screenable or selectable marker genes (for example, conferring resistance to antibiotics, herbicides or other toxic compounds or encoding a protein that confers a growth advantage to the cell expressing the protein) or genes which confer some commercial or agronomic value to the modified or adchromosomal plant. Multiple genes can be placed on the same MC vector. The genes may be separated from each other by restriction endonuclease sites, homing endonuclease sites, recombination sites or any combinations thereof. Alternatively, the cloning process can be executed in a manner that destroys the intervening restriction sites. Any number of genes can be present.

The MC vector may also contain a bacterial plasmid backbone for propagation of the plasmid in bacteria such as *E. coli*, *A. tumefaciens*, or *A. rhizogenes*. The plasmid backbone may be that of a low-copy vector or in other embodiments it may be desirable to use a mid to high level copy backbone. In one embodiment of the invention, this backbone contains the replicon of the F' plasmid of *E. coli*. However, other plasmid replicons, such as the bacteriophage P1 replicon, or other low-copy plasmid systems such as the RK2 replication origin, may also be used. The backbone may include one or several antibiotic-resistance genes conferring resistance to a specific antibiotic to the bacterial cell in which the plasmid is present. Bacterial antibiotic-resistance genes include but are not limited to kanamycin-, ampicillin-, chloramphenicol-, streptomycin-, spectinomycin-, tetracycline- and gentamycin-resistance genes.

The MC vector may also contain plant telomeres. An exemplary telomere sequence is TTTAGGG or its complement. Telomeres are specialized DNA structures at the ends of linear chromosomes that function to stabilize the ends and facilitate the complete replication of the extreme termini of the DNA molecule (Richards et al., *Cell*, 53:127-36, 1988; Ausubel et al., *Current Protocols in Molecular Biology*, Wiley & Sons, 1997).

Additionally, the MC vector may contain "stuffer DNA" sequences that serve to separate the various components on the MC (centromere, genes, telomeres) from each other. The stuffer DNA may be of any origin, prokaryotic or eukaryotic, and from any genome or species, plant, animal, microbe or organelle, or may be of synthetic origin. The stuffer DNA can range from 100 bp to 10 Mb in length and can be repetitive in sequence, with unit repeats from 10 to 1,000,000 bp.

Examples of repetitive sequences that can be used as stuffer DNAs include but are not limited to: rDNA, satellite repeats, retroelements, transposons, pseudogenes, transcribed genes, microsatellites, tDNA genes, short sequence repeats and combinations thereof. Alternatively, the stuffer DNA can consist of unique, non-repetitive DNA of any origin or sequence. The stuffer sequences may also include DNA with the ability to form boundary domains, such as but not limited to scaffold attachment regions (SARs) or matrix attachment regions (MARs). The stuffer DNA may be entirely synthetic, composed of random sequence. In this case, the stuffer DNA may have any base composition, or any A/T or G/C content. For example, the G/C content of the stuffer DNA could resemble that of the plant (~30-40%), or could be much lower (0-30%) or much higher (40-100%). Alternatively, the stuffer sequences could be synthesized to contain an excess of any given nucleotide such as A, C, G or T. Different synthetic stuffers of different compositions may also be combined with each other. For example a fragment with low G/C content may be flanked or abutted by a fragment of medium or high G/C content, or vice versa.

In one embodiment of the invention, the MC has a circular structure without telomeres. In another embodiment, the MC has a circular structure with telomeres. In a third embodiment, the MC has a linear structure with telomeres, as would result if a "linear" structure were to be cut with a unique endonuclease, exposing the telomeres at the ends of a DNA molecule that contains all of the sequence contained in the original, closed construct with the exception of an antibiotic-resistance gene. In a fourth embodiment of the invention, the telomeres could be placed in such a manner that the bacterial replicon, backbone sequences, antibiotic-resistance genes and any other sequences of bacterial origin and present for the purposes of propagation of the MC in bacteria, can be removed from the plant-expressed genes, the centromere, telomeres, and other sequences by cutting the structure with, for example, an unique endonuclease. This results in a MC from which much of, or preferably all, bacterial sequences have been removed. In this embodiment, bacterial sequence present between or among the plant-expressed genes or other MC sequences would be excised prior to removal of the remaining bacterial sequences by cutting the MC with an endonuclease and re-ligating the structure such that the antibiotic-resistance gene has been lost. The unique endonuclease site may be the recognition sequence of any of a number of endonucleases including but not limited to restriction endonucleases, meganucleases, or homing endonuclease. Alternatively, the endonucleases and their sites can be replaced with any specific DNA cutting mechanism and its specific recognition site such as rare-cutting endonuclease or recombinase and its specific recognition site, as long as that site is present in the MCs only at the indicated positions.

Various structural configurations are possible by which MC elements can be oriented with respect to each other. A centromere can be placed on a MC either between genes or outside a cluster of genes next to one telomere or next to the other telomere. Stuffer DNAs can be combined with these configurations to place the stuffer sequences inside the telomeres, around the centromere between genes or any combination thereof. Thus, a large number of alternative MC structures are possible, depending on the relative placement of centromere DNA, genes, stuffer DNAs, bacterial sequences, telomeres, and other sequences. The sequence content of each of these variants is the same, but their structure may be different depending on how the sequences are placed. These variations in architecture are possible both for linear and for circular MCs.

Exemplary Centromere Components

Centromere components may be isolated or derived from native plant genome, for example, modified through recombinant techniques or through the cell-based techniques described below. Alternatively, wholly artificial centromere components may be constructed using as a general guide the sequence of native centromeres such as native sorghum satellite repeat sequences. Combinations of centromere components derived from natural sources and/or combinations of naturally derived and artificial components are also contemplated. As noted above, centromere sequences from one taxonomic plant species may be functional in another taxonomic plant species, genus and family.

In one embodiment, the centromere contains n copies of a repeated nucleotide sequence obtained by the methods disclosed herein; wherein n is at least 2. In another embodiment, the centromere contains n copies of interdigitated repeats. An interdigitated repeat is a DNA sequence that consists of two distinct repetitive elements that combine to create a unique permutation. Potentially any number of repeat copies capable of physically being placed on the recombinant construct could be included on the construct, including about 5, 10, 15, 20, 30, 50, 75, 100, 150, 200, 300, 400, 500, 750, 1,000, 1,500, 2,000, 3,000, 5,000, 7,500, 10,000, 20,000, 30,000, 40,000, 50,000, 60,000, 70,000, 80,000, 90,000 and about 100,000, including all ranges in-between such copy numbers. Moreover, the copies, while largely identical, can vary from each other. Such repeat variation is commonly observed in naturally occurring centromeres. The length of the repeat may vary, but will preferably range from about 20 bp to about 360 bp, from about 20 bp to about 250 bp, from about 50 bp to about 225 bp, from 20 bp to 137 bp, from about 75 bp to about 210 bp, such as a 92 bp repeat, a 97 bp repeat and a 100 bp repeat, from about 100 bp to about 205 bp, from about 125 bp to about 200 bp, from about 150 bp to about 195 bp, from about 160 bp to about 190 and from about 170 bp to about 185 bp including about 180 bp. Larger repeats including those up to 3,465 bp or 3,500 bp or 3,600 bp or 3,700 bp are also anticipated by the current invention.

The invention contemplates that two or more of these repeated nucleotide sequences, or similar repeated nucleotide sequences, may be oriented head to tail within the centromere. The term "head to tail" refers to multiple consecutive copies of the same or similar repeated nucleotide sequence (e.g., at least 70% identical) that are in the same 5'-3' orientation. The invention also contemplates that two or more of these repeated nucleotide sequences may be consecutive within the centromere. The term "consecutive" refers to the same or similar repeated nucleotide sequences (e.g., at least 70% identical) that follow one after another without being interrupted by other significant sequence elements. Such consecutive repeated nucleotide sequences may be in any orientation, e.g. head to tail, tail to tail, or head to head, and may be separated by n number of nucleotides, wherein n ranges from 1 to 10, or 1 to 20, or 1 to 30, or 1 to 40, or 1 to 50. Exemplary repeated nucleotide sequences derived from sorghum are set out in SEQ ID NOs:23-176, the consensus sorghum satellite sequence (SEQ ID NO:22, and the sorghum retrotransoposon sequence (SEQ ID NO:21) or a fragment thereof.

Modification of Centromeres Isolated from Native Plant Genome

Modification and changes may be made in the centromeric DNA segments of the current invention and still obtain a functional molecule with desirable characteristics. The following is a discussion based upon changing the nucleic acids of a centromere to create an equivalent, or even an improved, second generation molecule.

In particular embodiments of the invention, mutated centromeric sequences are contemplated to be useful for increasing the utility of the centromere. It is specifically contemplated that the function of the centromeres of the current invention may be based in part or in whole upon the secondary structure of the DNA sequences of the centromere, modification of the DNA with methyl groups or other adducts, and/or the proteins which interact with the centromere. By changing the DNA sequence of the centromere, one may alter the affinity of one or more centromere-associated protein(s) for the centromere and/or the secondary structure or modification of the centromeric sequences, thereby changing the activity of the centromere. Alternatively, changes may be made in the centromeres of the invention which do not affect the activity of the centromere. Changes in the centromeric sequences which reduce the size of the DNA segment needed to confer centromere activity are contemplated to be particularly useful in the current invention, as would changes which increased the fidelity with which the centromere was transmitted during mitosis or meiosis.

Modification of Centromeres by Passage Through Bacteria, Plant or Other Hosts or Processes In the methods of the present invention, the resulting MC DNA sequence may also be a derivative of the parental clone or centromere clone having substitutions, deletions, insertions, duplications and/or rearrangements of one or more nucleotides in the nucleic acid sequence. Such nucleotide mutations may occur individually or consecutively in stretches of 1, 2, 3, 4, 5, 6, 7, 8, 9 10, 15, 20, 25, 30, 35, 40, 50, 60, 70, 80, 90, 100, 125, 150, 175, 200, 250, 300, 350, 400, 450, 500, 600, 700, 800, 900, 1000, 2000, 4000, 8000, 10000, 50000, 100000, and about 200000, including all ranges in-between.

Variations of MCs may arise through passage of MCs through various hosts including virus, bacteria, yeast, plant or other prokaryotic or eukaryotic organism and may occur through passage of multiple hosts or individual host. Variations may also occur by replicating the MC in vitro.

Derivatives may be identified through sequence analysis, or variations in MC molecular weight through electrophoresis such as, but not limited to, CHEF gel analysis, column or gradient separation, or any other methods used in the field to determine and/or analyze DNA molecular weight or sequence content. Alternately, derivatives may be identified by the altered activity of a derivative in conferring centromere function to a MC.

Production or Synthesis of Synthetic Centromere Repeat Sequences

These artificially synthesized repeated nucleotide sequences of the invention may be derived from natural centromere sequences, combinations or fragments of natural centromere sequences including a combination of repeats of different lengths, a combination of different sequences, a combination of both different repeat lengths and different sequences, a combination of different artificially synthesized sequences or a combination of natural centromere sequence(s) and artificially synthesized sequence(s). The synthetic nucleotide sequences and arrays of these synthetic repeat sequences may be generated using any technique known in the art including PCR from genomic DNA, e.g. the methods described in Example 1, or by custom polynucleotide synthesis.

Polynucleotide synthesis is the non-biological, chemical synthesis of defined sequences of nucleic acids using automated synthesizers. Oligonucleotides may be chemically synthesized, purified and then these oligonucleotides are connected by specific annealing and standard ligation or polymerase reactions. Exemplary ligation methods include ligation of phosphorylated overlapping oligonucleotides (Gupta et al. *PNAS USA,* 60, 1338-1344, 1993, Fuhrmann et al. *Plant J.* 19:353-61, 1999), the FokI method (Mandecki et al. *Gene,* 68, 101-107) and a modified form of ligase chain reaction for gene synthesis. In addition, PCR assembly approaches may be used which generally employ oligonucleotides of 40-50 nt long that overlap each other. These oligonucleotides are designed to cover most of the sequence of both strands, and the full-length molecule is generated progressively by overlap extension PCR (Stemmer et al. *Gene,* 164, 49-53), thermodynamically balanced inside-out PCR (Gao et al. *Nucleic Acids Res.* 15; 31(22):e143, 2003) or combined approaches (Young et al. *Nucleic Acids Res.* 15; 32(7):e59, 2004).

Exemplary Exogenous Nucleic Acids Including Plant-Expressed Genes

Of particular interest in the present invention are exogenous nucleic acids which when introduced into plants will alter the phenotype of the plant, a plant organ, plant tissue, or a portion of the plant. Exemplary exogenous nucleic acids encode polypeptides. Other exemplary exogenous nucleic acids alter expression of exogenous or endogenous genes, either increasing or decreasing expression, optionally in response to a specific signal or stimulus.

As used herein, the term "trait" can refer either to the altered phenotype of interest or the nucleic acid which causes the altered phenotype of interest.

One of the major purposes of transformation of crop plants is to add some commercially desirable, agronomically important traits to the plant. Such traits include, but are not limited to, enhanced production of total recoverable sugars; utility for production of biofuels; herbicide resistance or tolerance; insect (pest) resistance or tolerance; disease resistance or tolerance (viral, bacterial, fungal, nematode or other pathogens); stress tolerance and/or resistance, as exemplified by resistance or tolerance to drought, heat, chilling, freezing, excessive moisture, salt stress, mechanical stress, extreme acidity, alkalinity, toxins, UV light, ionizing radiation or oxidative stress; increased yields, increased biomass, whether in quantity or quality; enhanced or altered nutrient acquisition and enhanced or altered metabolic efficiency; enhanced or altered nutritional content and makeup of plant tissues used for food, feed, fiber or processing; physical appearance; male sterility; drydown; standability; prolificacy; starch quantity and quality; oil quantity and quality; protein quality and quantity; amino acid composition; modified chemical production; altered pharmaceutical or nutraceutical properties; altered bioremediation properties; increased biomass; altered growth rate; altered fitness; altered biodegradability; altered $CO_2$ fixation; presence of bioindicator activity; altered digestibility by humans or animals; altered allergenicity; altered mating characteristics; altered pollen dispersal; improved environmental impact; altered nitrogen fixation capability; the production of a pharmaceutically active protein; the production of a small molecule with medicinal properties; the production of a chemical including those with industrial utility; the production of nutraceuticals, food additives, carbohydrates, RNAs, lipids, fuels, dyes, pigments, vitamins, scents, flavors, vaccines, antibodies, hormones, and the like; and alterations in plant architecture or development, including changes in developmental timing, photosynthesis, signal transduction, cell growth, reproduction, or differentiation. Additionally one could create a library of an entire genome from any organism or organelle including mammals, plants, microbes, fungi, or bacteria, represented on MCs.

In one embodiment, the sorghum plant comprising a sorghum MC or recombinant chromosome may exhibit increased or decreased expression or accumulation of a product of the plant, which may be a natural product of the plant or a new or altered product of the plant. Exemplary products include an enzyme, an RNA molecule, a nutritional protein, a structural protein, an amino acid, a lipid, a fatty acid, a polysaccharide, a sugar, an alcohol, an alkaloid, a carotenoid, a propanoid, a phenylpropanoid, or terpenoid, a steroid, a flavonoid, a phenolic compound, an anthocyanin, a pigment, a vitamin or a plant hormone. In another embodiment, the sorghum plant comprising a sorghum MC or recombinant chromosome has enhanced or diminished requirements for light, water, nitrogen, or trace elements. In another embodiment the sorghum plant comprising a sorghum MC or recombinant chromosome has an enhanced ability to capture or fix nitrogen from its environment. In yet another embodiment, the sorghum plant comprising a sorghum MC or recombinant chromosome is enriched for an essential amino acid as a proportion of a protein fraction of the plant. The protein fraction may be, for example, total seed protein, soluble protein, insoluble protein, water-extractable protein, and lipid-associated protein. The sorghum plant comprising a sorghum MC or recombinant chromosome may include genes that cause the overexpression, underexpression, antisense modulation, sense suppression, inducible expression, inducible repression, or inducible modulation of another gene.

A brief summary of exemplary improved properties and polypeptides of interest for either increased or decreased expression is provided below.

(i) Herbicide Resistance

A herbicide resistance (or tolerance) trait is a characteristic of a sorghum plant comprising a sorghum MC or recombinant chromosome that is resistant to dosages of an herbicide that is typically lethal to a wild type plant. Exemplary herbicides for which resistance is useful in a plant include glyphosate herbicides, phosphinothricin herbicides, oxynil herbicides, imidazolinone herbicides, dinitroaniline herbicides, pyridine herbicides, sulfonylurea herbicides, bialaphos herbicides, sulfonamide herbicides and glufosinate herbicides. Other herbicides would be useful as would combinations of herbicide genes on the same MC or recombinant chromosome.

The genes encoding phosphinothricin acetyltransferase (bar), glyphosate tolerant EPSP synthase genes, glyphosate acetyltransferase, the glyphosate degradative enzyme gene gox encoding glyphosate oxidoreductase, deh (encoding a dehalogenase enzyme that inactivates dalapon), herbicide resistant (e.g., sulfonylurea and imidazolinone) acetolactate synthase, and bxn genes (encoding a nitrilase enzyme that degrades bromoxynil) are good examples of herbicide resistant genes for use in transformation. The bar gene codes for an enzyme, phosphinothricin acetyltransferase (PAT), which inactivates the herbicide phosphinothricin and prevents this compound from inhibiting glutamine synthetase enzymes. The enzyme 5 enolpyruvylshikimate 3 phosphate synthase (EPSP Synthase), is normally inhibited by the herbicide N (phosphonomethyl)glycine (glyphosate). However, genes are known that encode glyphosate resistant EPSP synthase enzymes. These genes are particularly contemplated for use in plant transformation. The deh gene encodes the enzyme dalapon dehalogenase and confers resistance to the herbicide dalapon. The bxn gene codes for a specific nitrilase enzyme that converts bromoxynil to a non herbicidal degradation product. The glyphosate acetyl transferase gene inactivates the herbicide glyphosate and prevents this compound from inhibiting EPSP synthase.

Polypeptides that may produce plants having tolerance to plant herbicides include polypeptides involved in the shikimate pathway, which are of interest for providing glyphosate tolerant plants. Such polypeptides include polypeptides involved in biosynthesis of chorismate, phenylalanine, tyrosine and tryptophan.

(ii) Insect Resistance

Potential insect resistance (or tolerance) genes that can be introduced include *Bacillus thuringiensis* toxin genes or Bt genes (Watrud et al., In: Engineered Organisms and the Environment, 1985). Bt genes may provide resistance to lepidopteran or coleopteran pests such as European Corn Borer (ECB). Preferred Bt toxin genes for use in such embodiments include the CrylA(b) and CrylA(c) genes. Endotoxin genes from other species of *B. thuringiensis* which affect insect growth or development also may be employed in this regard.

It is contemplated that preferred Bt genes for use in the MCs or recombinant chromosomes disclosed herein will be those in which the coding sequence has been modified to effect increased expression in plants, and for example, in monocot plants including sorghum. Means for preparing synthetic genes are well known in the art and are disclosed in, for example, U.S. Pat. No. 5,500,365 and U.S. Pat. No. 5,689,052, each of the disclosures of which are specifically incorporated herein by reference in their entirety. Examples of such modified Bt toxin genes include a synthetic Bt CrylA(b) gene (Perlak et al., *PNAS USA,* 88:3324-3328, 1991), and the synthetic CrylA(c) gene termed 1800b (PCT Application WO 95/06128). Some examples of other Bt toxin genes known to those of skill in the art are given in Table 1 below.

TABLE 1

*Bacillus thuringiensis* Endotoxin Genes[a]

| New Nomenclature | Old Nomenclature | GenBank Accession |
|---|---|---|
| Cry1Aa | CryIA(a) | M11250 |
| Cry1Ab | CryIA(b) | M13898 |
| Cry1Ac | CryIA(c) | M11068 |
| Cry1Ad | CryIA(d) | M73250 |
| Cry1Ae | CryIA(e) | M65252 |
| Cry1Ba | CryIB | X06711 |
| Cry1Bb | ET5 | L32020 |
| Cry1Bc | PEG5 | Z46442 |
| Cry1Bd | CryE1 | U70726 |
| Cry1Ca | CryIC | X07518 |
| Cry1Cb | CryIC(b) | M97880 |
| Cry1Da | CryID | X54160 |
| Cry1Db | PrtB | Z22511 |
| Cry1Ea | CryIE | X53985 |
| Cry1Eb | CryIE(b) | M73253 |
| Cry1Fa | CryIF | M63897 |
| Cry1Fb | PrtD | Z22512 |
| Cry1Ga | PrtA | Z22510 |
| Cry1Gb | CryH2 | U70725 |
| Cry1Ha | PrtC | Z22513 |
| Cry1Hb | | U35780 |
| Cry1Ia | CryV | X62821 |
| Cry1Ib | CryV | U07642 |
| Cry1Ja | ET4 | L32019 |
| Cry1Jb | ET1 | U31527 |
| Cry1K | | U28801 |
| Cry2Aa | CryIIA | M31738 |
| Cry2Ab | CryIIB | M23724 |
| Cry2Ac | CryIIC | X57252 |
| Cry3A | CryIIIA | M22472 |
| Cry3Ba | CryIIIB | X17123 |
| Cry3Bb | CryIIIB2 | M89794 |
| Cry3C | CryIIID | X59797 |
| Cry4A | CryIVA | Y00423 |
| Cry4B | CryIVB | X07423 |
| Cry5Aa | CryVA(a) | L07025 |
| Cry5Ab | CryVA(b) | L07026 |
| Cry6A | CryVIA | L07022 |
| Cry6B | CryVIB | L07024 |
| Cry7Aa | CryIIIC | M64478 |

TABLE 1-continued

*Bacillus thuringiensis* Endotoxin Genes[a]

| New Nomenclature | Old Nomenclature | GenBank Accession |
|---|---|---|
| Cry7Ab | CryIIICb | U04367 |
| Cry8A | CryIIIE | U04364 |
| Cry8B | CryIIIG | U04365 |
| Cry8C | CryIIIF | U04366 |
| Cry9A | CryIG | X58120 |
| Cry9B | CryIX | X75019 |
| Cry9C | CryIH | Z37527 |
| Cry10A | CryIVC | M12662 |
| Cry11A | CryIVD | M31737 |
| Cry11B | Jeg80 | X86902 |
| Cry12A | CryVB | L07027 |
| Cry13A | CryVC | L07023 |
| Cry14A | CryVD | U13955 |
| Cry15A | 34kDa | M76442 |
| Cry16A | cbm71 | X94146 |
| Cry17A | cbm71 | X99478 |
| Cry18A | CryBP1 | X99049 |
| Cry19A | Jeg65 | Y08920 |
| Cyt1Aa | CytA | X03182 |
| Cyt1Ab | CytM | X98793 |
| Cyt2A | CytB | Z14147 |
| Cyt2B | CytB | U52043 |

[a]Adapted from Crickmore, N, Zeigler, DR, Feitelson, J. et aL. Microbiol. Molec. Biol. Rev. 62:807-813, 1998.

Protease inhibitors also may provide insect resistance (Johnson et al., *PNAS USA* 86): 9871-9875, 1989), and will thus have utility in plant transformation. The use of a pinII gene in combination with a Bt toxin gene, the combined effect of which has been discovered to produce synergistic insecticidal activity is envisioned to be particularly useful. Other genes which encode inhibitors of the insect's digestive system, or those that encode enzymes or co factors that facilitate the production of inhibitors, also may be useful. This group may be exemplified by oryzacystatin and amylase inhibitors such as those from wheat and barley.

Amylase inhibitors are found in various plant species and are used to ward off insect predation via inhibition of the digestive amylases of attacking insects. Several amylase inhibitor genes have been isolated from plants and some have been introduced as exogenous nucleic acids, conferring an insect resistant phenotype that is potentially useful (Chrispeels, M J and D E Sadava, *Plants, Genes, and Crop Biotechnology* Jones and Bartlett Press, 2003).

Genes encoding lectins may confer additional or alternative insecticide properties. Lectins are multivalent carbohydrate binding proteins which have the ability to agglutinate red blood cells from a range of species. Lectins have been identified recently as insecticidal agents with activity against weevils, ECB and rootworm (Murdock et al., *Phytochemistry,* 29:85-89, 1990, Czapla & Lang, *J. Econ. Entomol.,* 83:2480-2485, 1990). Lectin genes contemplated to be useful include, for example, barley and wheat germ agglutinin (WGA) and rice lectins (Gatehouse et al., *J. Sci. Food. Agric.,* 35:373-380, 1984), with WGA being preferred.

Genes controlling the production of large or small polypeptides active against insects when introduced into the insect pests, such as, e.g., lytic peptides, peptide hormones and toxins and venoms, form another aspect of the invention. For example, it is contemplated that the expression of juvenile hormone esterase, directed towards specific insect pests, also may result in insecticidal activity, or perhaps cause cessation of metamorphosis (Hammock et al., *Nature,* 344:458-461, 1990).

Genes that encode enzymes that affect the integrity of the insect cuticle form yet another aspect of the invention. Such genes include those encoding, e.g., chitinase, proteases, lipases and also genes for the production of nikkomycin, a compound that inhibits chitin synthesis, the introduction of any of which is contemplated to produce insect resistant plants. Genes that code for activities that affect insect molting, such as those affecting the production of ecdysteroid UDP glucosyl transferase, also fall within the scope of the useful exogenous nucleic acids of the present invention.

Genes that code for enzymes that facilitate the production of compounds that reduce the nutritional quality of the host plant to insect pests also are encompassed by the present invention. It may be possible, for instance, to confer insecticidal activity on a plant by altering its sterol composition. Sterols are obtained by insects from their diet and are used for hormone synthesis and membrane stability. Therefore alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti nutritional effects on insects and to reduce the nutritional quality of their diet. Therefore, further embodiments of the invention concern modified plants with enhanced lipoxygenase activity which may be resistant to insect feeding.

*Tripsacum dactyloides* is a species of grass that is resistant to certain insects, including root worm. It is anticipated that genes encoding proteins that are toxic to insects or are involved in the biosynthesis of compounds toxic to insects will be isolated from *Tripsacum* and that these novel genes will be useful in conferring resistance to insects. It is known that the basis of insect resistance in *Tripsacum* is genetic, because said resistance has been transferred to *Zea mays* via sexual crosses (Branson and Guss, Proceedings North Central Branch Entomological Society of America, 27:91-95, 1972). It is further anticipated that other cereal, monocot or dicot plant species may have genes encoding proteins that are toxic to insects which would be useful for producing insect resistant plants.

Further genes encoding proteins characterized as having potential insecticidal activity also may be used as exogenous nucleic acids in accordance herewith. Such genes include, for example, the cowpea trypsin inhibitor (CpTI; Hilder et al., *Nature,* 330:160-163, 1987) which may be used as a rootworm deterrent; genes encoding avermectin (Avermectin and Abamectin; Campbell, W. C., Ed., 1989; Ikeda et al., *J. Bacteriol.,* 169:5615-5621, 1987) which may prove particularly useful as a corn rootworm deterrent; ribosome inactivating protein genes; and even genes that regulate plant structures. *Sorghum* plant comprising a sorghum MC or recombinant chromosome comprising anti insect antibody genes and genes that code for enzymes that can convert a non toxic insecticide (pro insecticide) applied to the outside of the plant into an insecticide inside the plant also are contemplated.

Polypeptides that may improve plant tolerance to the effects of plant pests or pathogens include proteases, polypeptides involved in anthocyanin biosynthesis, polypeptides involved in cell wall metabolism, including cellulases, glucosidases, pectin methylesterase, pectinase, polygalacturonase, chitinase, chitosanase, and cellulose synthase, and polypeptides involved in biosynthesis of terpenoids or indole for production of bioactive metabolites to provide defense against herbivorous insects. It is also anticipated that combinations of different insect resistance genes on the same MC or recombinant chromosomes will be particularly useful.

Vegetative Insecticidal Proteins (VIP) are another class of proteins originally found to be produced in the vegetative growth phase of the bacterium, *Bacillus cereus*, but do have a spectrum of insect lethality similar to the insecticidal genes found in strains of *Bacillus thuriengensis*. Both the vip1a and vip3A genes have been isolated and have demonstrated insect toxicity. It is anticipated that such genes may be used in modified plants to confer insect resistance ("Plants, Genes, and Crop Biotechnology" by Maarten J. Chrispeels and David E. Sadava (2003) Jones and Bartlett Press).

(iii) Environment or Stress Resistance

Improvement of a plant's ability to tolerate various environmental stresses such as, but not limited to, drought, excess moisture, chilling, freezing, high temperature, salt, and oxidative stress, also can be affected through expression of novel genes. It is proposed that benefits may be realized in terms of increased resistance to freezing temperatures through the introduction of an "antifreeze" protein such as that of the Winter Flounder (Cutler et al., *J. Plant Physiol.,* 135:351-354, 1989) or synthetic gene derivatives thereof. Improved chilling tolerance also may be conferred through increased expression of glycerol 3 phosphate acetyltransferase in chloroplasts (Wolter et al., *EMBO J.,* 4685-4692, 1992). Resistance to oxidative stress (often exacerbated by conditions such as chilling temperatures in combination with high light intensities) can be conferred by expression of superoxide dismutase (Gupta et al., 1993), and may be improved by glutathione reductase (Bowler et al., *Ann Rev. Plant Physiol.,* 43:83-116, 1992). Such strategies may allow for tolerance to freezing in newly emerged fields as well as extending later maturity higher yielding varieties to earlier relative maturity zones. Many sorghum genes are known to be modulated by various stresses including drought stress, salt stress and the application of stress response hormones (Buchanan C D, et al. *Plant Mol. Biol.* 58:699-720, 2005) and (Srinivas G, et al. *Theor Appl Genet.* 118:703-17, 2009).

It is contemplated that the expression of novel genes that favorably affect plant water content, total water potential, osmotic potential, or turgor will enhance the ability of the plant to tolerate drought. As used herein, the terms "drought resistance" and "drought tolerance" are used to refer to a plant's increased resistance or tolerance to stress induced by a reduction in water availability, as compared to normal circumstances, and the ability of the plant to function and survive in lower water environments. In this aspect of the invention it is proposed, for example, that the expression of genes encoding for the biosynthesis of osmotically active solutes, such as polyol compounds, may impart protection against drought. Within this class are genes encoding for mannitol L phosphate dehydrogenase (Lee and Saier, *PNAS USA* 78:7336-7340, 1981) and trehalose 6 phosphate synthase (Kaasen et al., *J. Bacteriology,* 174:889-898, 1992). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski et al., Science, 259:508-510, 1993, Tarczynski et al. *PNAS USA,* 89:1-5, 1993).

Similarly, the efficacy of other metabolites in protecting either enzyme function (e.g., alanopine or propionic acid) or membrane integrity (e.g., alanopine) has been documented (Loomis et al., *J. Expt. Zoology* 252:9-15, 1989), and therefore expression of genes encoding for the biosynthesis of these compounds might confer drought resistance in a manner similar to or complimentary to mannitol. Other examples of naturally occurring metabolites that are osmotically active and/or provide some direct protective effect during drought and/or desiccation include fructose, erythritol (Coxson et al., *Biotropica* 24:121-133, 1992), sorbitol, dulcitol (Karsten et al., *Botanica Marina* 35:11-19, 1992), glucosylglycerol (Reed et al., *J. Gen. Microbiol.* 130:1-4, 1984; Erdmann et al., *J. Gen. Microbiol.* 138:363-368, 1992), sucrose, stachyose (Koster and Leopold, *Plant Physiol.* 88:829-832, 1988; Blackman et al., *Plant Physiol.* 100:225-230, 1992), raffinose (Lugo and Leopold, *Plant Physiol.* 98:1207-1210, 1992), proline (Rensburg et al., *J. Plant Physiol.* 141:188-194, 1993), glycine betaine, ononitol and pinitol (Vernon and Bohnert, *EMBO J.* 11:2077-2085, 1992). Continued growth and increased reproductive fitness during times of stress may be augmented by introduction and expression of genes such as those controlling the osmotically active compounds discussed above and other such compounds. Currently preferred genes which promote the synthesis of an osmotically active polyol compound are genes which encode the enzymes mannitol 1 phosphate dehydrogenase, trehalose 6 phosphate synthase and myoinositol 0 methyltransferase.

It is contemplated that the expression of specific proteins also may increase drought tolerance. Three classes of Late Embryogenic Abundant (LEA) Proteins have been assigned based on structural similarities (see Dure et al., *Plant Molec. Biol.* 12:475-486, 1989). All three classes of LEAs have been demonstrated in maturing (e.g. desiccating) seeds. Within these 3 types of LEA proteins, the Type II (dehydrin type) have generally been implicated in drought and/or desiccation tolerance in vegetative plant parts (e.g. Mundy and Chua, *EMBO J.,* 7:2279-2286, 1988; Piatkowski et al., *Plant Physiol.* 94:1682-1688, 1990; Yamaguchi Shinozaki et al., *Plant Cell Physiol.* 33:217-224, 1992). Expression of a Type III LEA (HVA 1) in tobacco was found to influence plant height, maturity and drought tolerance (Fitzpatrick, *Gen. Engineering News* 22:7, 1993). In rice, expression of the HVA 1 gene influenced tolerance to water deficit and salinity (Xu et al., *Plant Physiol.* 110:249-257, 1996). Expression of structural genes from any of the three LEA groups may therefore confer drought tolerance. Other types of proteins induced during water stress include thiol proteases, aldolases or transmembrane transporters (Guerrero et al., *Plant Molecul. Biol.* 15:11-26, 1990), which may confer various protective and/or repair type functions during drought stress. It also is contemplated that genes that effect lipid biosynthesis and hence membrane composition might also be useful in conferring drought resistance on the plant.

Many of these genes for improving drought resistance have complementary modes of action. Thus, it is envisaged that combinations of these genes might have additive and/or synergistic effects in improving drought resistance in plants. Many of these genes also improve freezing tolerance (or resistance); the physical stresses incurred during freezing and drought are similar in nature and may be mitigated in similar fashion. Benefits may be conferred via constitutive expression of these genes, but the preferred means of expressing these novel genes may be through the use of a turgor induced promoter (such as the promoters for the turgor induced genes described in Guerrero et al., *Plant Molecul. Biol.* 15:11-26, 1990 and Shagan et al., *Plant Physiol.* 101:1397-1398, 1993 which are incorporated herein by reference). Spatial and temporal expression patterns of these genes may enable plants to better withstand stress.

It is proposed that expression of genes that are involved with specific morphological traits that allow for increased water extractions from drying soil would be of benefit. For example, introduction and expression of genes that alter root characteristics may enhance water uptake. It also is contemplated that expression of genes that enhance reproductive fitness during times of stress would be of significant value. For example, expression of genes that improve the synchrony of pollen shed and receptiveness of the female flower parts, e.g., silks, would be of benefit. In addition it is proposed that expression of genes that minimize kernel abortion during times of stress would increase the amount of grain to be harvested and hence be of value.

Given the overall role of water in determining yield, it is contemplated that enabling plants to utilize water more efficiently, through the introduction and expression of novel genes, will improve overall performance even when soil water availability is not limiting. By introducing genes that improve the ability of plants to maximize water usage across a full range of stresses relating to water availability, yield stability or consistency of yield performance may be realized.

Polypeptides that may improve stress tolerance under a variety of stress conditions include polypeptides involved in gene regulation, such as serine/threonine-protein kinases, MAP kinases, MAP kinase kinases, and MAP kinase kinase kinases; polypeptides that act as receptors for signal transduction and regulation, such as receptor protein kinases; intracellular signaling proteins, such as protein phosphatases, GTP binding proteins, and phospholipid signaling proteins; polypeptides involved in arginine biosynthesis; polypeptides involved in ATP metabolism, including for example ATPase, adenylate transporters, and polypeptides involved in ATP synthesis and transport; polypeptides involved in glycine betaine, jasmonic acid, flavonoid or steroid biosynthesis; and hemoglobin. Enhanced or reduced activity of such polypeptides in modified plants will provide changes in the ability of a plant to respond to a variety of environmental stresses, such as chemical stress, drought stress and pest stress.

Other polypeptides that may improve plant tolerance to cold or freezing temperatures include polypeptides involved in biosynthesis of trehalose or raffinose, polypeptides encoded by cold induced genes, fatty acyl desaturases and other polypeptides involved in glycerolipid or membrane lipid biosynthesis, which find use in modification of membrane fatty acid composition, alternative oxidase, calcium-dependent protein kinases, LEA proteins or uncoupling protein.

Other polypeptides that may improve plant tolerance to heat include polypeptides involved in biosynthesis of trehalose, polypeptides involved in glycerolipid biosynthesis or membrane lipid metabolism (for altering membrane fatty acid composition), heat shock proteins or mitochondrial NDK.

Other polypeptides that may improve tolerance to extreme osmotic conditions include polypeptides involved in proline biosynthesis.

Other polypeptides that may improve plant tolerance to drought conditions include aquaporins, polypeptides involved in biosynthesis of trehalose or wax, LEA proteins or invertase.

(iv) Disease Resistance

It is proposed that increased resistance (or tolerance) to diseases may be realized through introduction of genes into plants, for example, into monocotyledonous plants such as sorghum. It is possible to produce resistance to diseases caused by viruses, viroids, bacteria, fungi and nematodes. It also is contemplated that control of mycotoxin producing organisms may be realized through expression of introduced genes. Resistance can be affected through suppression of endogenous factors that encourage disease-causing interactions, expression of exogenous factors that are toxic to or otherwise provide protection from pathogens, or expression of factors that enhance the plant's own defense responses.

Resistance to viruses may be produced through expression of novel genes. For example, it has been demonstrated that expression of a viral coat protein in a modified plant can impart resistance to infection of the plant by that virus and perhaps other closely related viruses (Hemenway et al., *EMBO J.* 7:1273-1280, 1988, Abel et al., *Science* 232:738-743, 1986). It is contemplated that expression of antisense genes targeted at essential viral functions may also impart resistance to viruses. For example, an antisense gene targeted at the gene responsible for replication of viral nucleic acid may inhibit replication and lead to resistance to the virus. It is believed that interference with other viral functions through the use of antisense genes also may increase resistance to viruses. Further, it is proposed that it may be possible to achieve resistance to viruses through other approaches, including, but not limited to the use of satellite viruses.

It is proposed that increased resistance to diseases caused by bacteria and fungi may be realized through introduction of novel genes. It is contemplated that genes encoding so called "peptide antibiotics," pathogenesis related (PR) proteins, toxin resistance, or proteins affecting host pathogen interactions such as morphological characteristics will be useful. Peptide antibiotics are polypeptide sequences which are inhibitory to growth of bacteria and other microorganisms. For example, the classes of peptides referred to as cecropins and magainins inhibit growth of many species of bacteria and fungi. It is proposed that expression of PR proteins in plants, for example, monocots such as sorghum, may be useful in conferring resistance to bacterial disease. These genes are induced following pathogen attack on a host plant and have been divided into at least five classes of proteins (Bol et al. *Annu. Rev. Pytopathol.* 28:113-138, 1990). Included amongst the PR proteins are beta 1, 3 glucanases, chitinases, and osmotin and other proteins that are believed to function in plant resistance to disease organisms. Other genes have been identified that have antifungal properties, e.g., UDA (stinging nettle lectin), or hevein (Broakaert et al., *PNAS USA* 87:7633-7, 1989; Barkai Golan et al., *Arch. Microbiol.* 116:119-121, 1978). It is known that certain plant diseases are caused by the production of phytotoxins. It is proposed that resistance to these diseases would be achieved through expression of a novel gene that encodes an enzyme capable of degrading or otherwise inactivating the phytotoxin. It also is contemplated that expression of novel genes that alter the interactions between the host plant and pathogen may be useful in reducing the ability of the disease organism to invade the tissues of the host plant, e.g., an increase in the waxiness of the leaf cuticle or other morphological characteristics.

Polypeptides useful for imparting improved disease responses to plants include polypeptides encoded by cercosporin-induced genes, antifungal proteins and proteins encoded by R-genes or SAR genes.

Agronomically important diseases in sorghum include but are not limited to *Exserohilum turcicum, Colletotrichum graminicola* (*Glomerella graminicola*), *Cercospora sorghi, Gloeocercospora soghi, Ascochyta sorghi, Pseudomonas syringae* p.v. *syringae, Xanthomonas campestris* p.v. *holcicola, Pseudomonas andropogonis, Puccinia purpurea, Mac-*

*rophomina phaseolina, Periconia circinata, FUSArium moniliforme, Alternaria alternate, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari Sporisorium relianum* (*Sphacelotheca reliana*), *Sphacelotheca cruenta, Sporisorium sorghi*, Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, FUSArium graminearum, FUSArium Oxysporum, Pythium arrhenomanes*, and *Pythium graminicola.*

(v) Plant Agronomic Characteristics

Temperature also influences where crop plants can be grown. Within the areas where it is possible to grow a particular crop, there are varying limitations on the maximal time it is allowed to grow to maturity and be harvested. For example, a variety to be grown in a particular area is selected for its ability to mature within the required period of time with maximum possible yield. It is considered that genes that influence maturity can be identified and introduced into plant lines to create new varieties adapted to different growing locations or the same growing location, but having improved yield at harvest. Expression of genes that are involved in regulation of plant development may be especially useful.

It is contemplated that genes may be introduced into plants that would improve standability and other plant growth characteristics. Expression of novel genes in plants which confer stronger stalks, improved root systems, or prevent or reduce ear droppage or shattering would be of great value to the farmer. It is proposed that introduction and expression of genes that increase the total amount of photoassimilate available by, for example, increasing light distribution and/or interception would be advantageous. In addition, the expression of genes that increase the efficiency of photosynthesis and/or the leaf canopy would further increase gains in productivity. It is contemplated that expression of a phytochrome gene in crop plants may be advantageous. Expression of such a gene may reduce apical dominance, confer semidwarfism on a plant, or increase shade tolerance (U.S. Pat. No. 5,268,526). Such approaches would allow for increased plant populations in the field.

(vi) Nutrient Utilization

The ability to utilize available nutrients may be a limiting factor in growth of crop plants. It is proposed that it would be possible to alter nutrient uptake, tolerate pH extremes, mobilization through the plant, storage pools, and availability for metabolic activities by the introduction of novel genes. These modifications would allow a plant, for example, sorghum to more efficiently utilize available nutrients. It is contemplated that an increase in the activity of, for example, an enzyme that is normally present in the plant and involved in nutrient utilization would increase the availability of a nutrient or decrease the availability of an antinutritive factor. An example of such an enzyme would be phytase. It is further contemplated that enhanced nitrogen utilization by a plant is desirable. Expression of a glutamate dehydrogenase gene in plants, e.g., *E. coli* gdhA genes, may lead to increased fixation of nitrogen in organic compounds. Furthermore, expression of gdhA in plants may lead to enhanced resistance to the herbicide glufosinate by incorporation of excess ammonia into glutamate, thereby detoxifying the ammonia. It also is contemplated that expression of a novel gene may make a nutrient source available that was previously not accessible, e.g., an enzyme that releases a component of nutrient value from a more complex molecule, perhaps a macromolecule.

Polypeptides useful for improving nitrogen flow, sensing, uptake, storage and/or transport include those involved in aspartate, glutamine or glutamate biosynthesis, polypeptides involved in aspartate, glutamine or glutamate transport, polypeptides associated with the TOR (Target of Rapamycin) pathway, nitrate transporters, nitrate reductases, amino transferases, ammonium transporters, chlorate transporters or polypeptides involved in tetrapyrrole biosynthesis.

Polypeptides useful for increasing the rate of photosynthesis include phytochrome, ribulose bisphosphate carboxylase-oxygenase, Rubisco activase, photosystem I and II proteins, electron carriers, ATP synthase, NADH dehydrogenase or cytochrome oxidase.

Polypeptides useful for increasing phosphorus uptake, transport or utilization include phosphatases or phosphate transporters.

(vii) Male Sterility

Male sterility is useful in the production of hybrid varieties of sorghum. It is proposed that male sterility may be produced through expression of novel genes. For example, it has been shown that expression of genes that encode proteins, RNAs, or peptides that interfere with development of the male inflorescence and/or gametophyte result in male sterility. Chimeric ribonuclease genes that express in the anthers of transgenic tobacco and oilseed rape have been demonstrated to lead to male sterility (Mariani et al., *Nature,* 347:737-741, 1990).

A number of mutations were discovered in maize that confer cytoplasmic male sterility. One mutation in particular, referred to as T cytoplasm, also correlates with sensitivity to Southern corn leaf blight. A DNA sequence, designated TURF 13 (Levings, *Science,* 250:942-947, 1990), was identified that correlates with T cytoplasm. It is proposed that it would be possible through the introduction of TURF 13 via transformation, to separate male sterility from disease sensitivity. As it is necessary to be able to restore male fertility for breeding purposes and for grain production, it is proposed that genes encoding restoration of male fertility also may be introduced.

Male sterility systems have also been described in sorghum. These include cytoplasmic male sterility (Van Tang H, et al. *Curr Genet.* 29:265-74, 1996), gametophytic male sterility (Pring D R, et al. *J. Hered.* 90:386-93, 1999), and nuclear male sterility (J. F. Pedersen and J. J. Toy, *Crop Science* 41:607, 2001).

(viii) Altered Nutritional Content

Genes can be introduced into plants to improve or alter the nutrient quality or content. Introduction of genes that alter the nutrient composition of a crop can greatly enhance the feed, food or forage value. Limiting essential amino acids can include lysine, methionine, tryptophan, threonine, valine, arginine, and histidine. The levels of these essential amino acids can be elevated by mechanisms which include, but are not limited to, the introduction of genes to increase the biosynthesis of the amino acids, decrease the degradation of the amino acids, increase the storage of the amino acids in proteins, or increase transport of the amino acids to particular tissues.

Polypeptides useful for providing increased protein quantity and/or quality include polypeptides involved in the metabolism of amino acids in plants, particularly polypeptides involved in biosynthesis of methionine/cysteine and lysine, amino acid transporters, amino acid efflux carriers, seed storage proteins, proteases, or polypeptides involved in phytic acid metabolism.

The protein composition of a crop can be altered to improve the balance of amino acids in a variety of ways including elevating expression of native proteins, decreasing expression of those with poor composition, changing the composition of native proteins, or introducing genes encoding entirely new proteins possessing superior composition.

The introduction of genes that alter the oil content of a crop plant can also be of value. Increases in oil content can result in increases in metabolizable-energy-content. The introduced genes can encode enzymes that remove or reduce rate-limitations or regulated steps in fatty acid or lipid biosynthesis. Such genes can include, but are not limited to, those that encode acetyl-CoA carboxylase, ACP-acyltransferase, alpha-ketoacyl-ACP synthase, or other well known fatty acid biosynthetic activities. Other possibilities are genes that encode proteins that do not possess enzymatic activity such as acyl carrier protein. Genes can be introduced that alter the balance of fatty acids present in the oil providing a more healthful or nutritive feedstuff. The introduced DNA also can encode sequences that block expression of enzymes involved in fatty acid biosynthesis, altering the proportions of fatty acids present in crops.

Genes can be introduced that enhance the nutritive value of crops, or of foods derived from crops by increasing the level of naturally occurring phytosterols, or by encoding for proteins to enable the synthesis of phytosterols in crops. The phytosterols from these crops can be processed directly into foods, or extracted and used to manufacture food products.

Genes can be introduced that enhance the nutritive value or energy value of the starch component of crops, for example by altering increasing the degree of branching of starch molecules, resulting in improved utilization of the starch in biofuel feedstock applications. Additionally, other major constituents of a crop can be altered, including genes that affect a variety of other nutritive, processing, or other quality aspects. For example, pigmentation can be increased or decreased.

Carbohydrate metabolism can be altered, for example by increased sucrose production and/or transport. Polypeptides useful for affecting on carbohydrate metabolism include polypeptides involved in sucrose or starch metabolism, carbon assimilation or carbohydrate transport, including, for example sucrose transporters or glucose/hexose transporters, enzymes involved in glycolysis/gluconeogenesis, the pentose phosphate cycle, or raffinose biosynthesis, or polypeptides involved in glucose signaling, such as SNF1 complex proteins.

Feed or food crops can also possess sub-optimal quantities of vitamins, antioxidants or other nutraceuticals, requiring supplementation to provide adequate nutritive value and ideal health value. Introduction of genes that enhance vitamin biosynthesis can be envisioned including, for example, vitamins A, E, B12, choline, or the like. Mineral content can also be sub-optimal. Thus genes that affect the accumulation or availability of compounds containing phosphorus, sulfur, calcium, manganese, zinc, or iron among others would be valuable.

Numerous other examples of improvements of crops can be used with the invention. Introduction of DNA to accomplish this might include sequences that alter lignin production such as those that result in the "brown midrib" phenotype associated with superior feed value for cattle. Other genes can encode for enzymes that alter the structure of extracellular carbohydrates, or that facilitate the degradation of the carbohydrates so that it can be efficiently fermented into ethanol or other useful carbohydrates.

It can be desirable to modify the nutritional content of plants by reducing undesirable components such as fats, starches, etc. This can be done, for example, by the use of exogenous nucleic acids that encode enzymes which increase plant use or metabolism of such components so that they are present at lower quantities. Alternatively, it can be done by use of exogenous nucleic acids that reduce expression levels or activity of native plant enzymes that synthesize such components.

Likewise the elimination of certain undesirable traits can improve the food or feed value of the crop. Many undesirable traits must currently be eliminated by special post-harvest processing steps and the degree to which these can be engineered into the plant prior to harvest and processing would provide significant value. Examples of such traits are the elimination of anti-nutritionals such as phytates and phenolic compounds which are commonly found in many crop species. Also, the reduction of fats, carbohydrates and certain phytohormones can be valuable for the food and feed industries as they can allow a more efficient mechanism to meet specific dietary requirements.

In addition to direct improvements in feed or food value, genes also can be introduced which improve the processing of crops and improve the value of the products resulting from the processing. Novel genes that increase the efficiency and reduce the cost of such processing, for example by decreasing the time required at a particular step, can also find use. Improving the value of products derived from processed plants, such as sorghum, can include altering the quantity or quality of sugar, starch, oil, fiber, gluten, or the components. Elevation of sugar or starch can be achieved through the identification and elimination of rate limiting steps in sugar and starch and sugar biosynthesis by expressing increased amounts of enzymes involved in biosynthesis or by decreasing levels of the other components of crops resulting in proportional increases in sugar or starch. In addition, plants can be modified by introducing or expressing a gene or genes that produce novel products, such as secondary plant metabolites or pharmaceutical products, which can be purified during the processing step. Using MCs or recombinant chromosomes to both introduce genes for new products and optionally for improving processing steps could provide a cost effective option to produce these novel products.

Oil is another product of processing, the value of which can be improved by introduction and expression of genes. Oil properties can be altered to improve its performance in the production and use of cooking oil, shortenings, lubricants or other oil-derived products or improvement of its health attributes when used in the food-related applications. Novel fatty acids also can be synthesized which upon extraction can serve as starting materials for chemical syntheses. The changes in oil properties can be achieved by altering the type, level, or lipid arrangement of the fatty acids present in the oil. This in turn can be accomplished by the addition of genes that encode enzymes that catalyze the synthesis of novel fatty acids (e.g. fatty acid elongases, desaturases) and the lipids possessing them or by increasing levels of native fatty acids while possibly reducing levels of precursors or breakdown products. Alternatively, DNA sequences can be introduced which slow or block steps in fatty acid biosynthesis resulting in the increase in precursor fatty acid intermediates. Genes that might be added include desaturases, epoxidases, hydratases, dehydratases, or other enzymes that catalyze reactions involving fatty acid intermediates. Representative examples of catalytic steps that might be blocked include the desaturations from stearic to oleic acid or oleic to linolenic acid resulting in the respective accumulations of stearic and oleic acids. Another example is the blockage of elongation steps resulting in the accumulation of C8 to C12 saturated fatty acids.

Polypeptides useful for providing increased oil quantity and/or quality include polypeptides involved in fatty acid and glycerolipid biosynthesis, beta-oxidation enzymes, enzymes involved in biosynthesis of nutritional compounds, such as carotenoids and tocopherols.

Polypeptides involved in production of galactomannans or arabinogalactans are of interest for providing plants having increased and/or modified reserve polysaccharides for use in food, pharmaceutical, cosmetic, paper and paint industries.

Polypeptides involved in modification of flavonoid/isoflavonoid metabolism in plants include cinnamate-4-hydroxylase, chalcone synthase or flavones synthase. Enhanced or reduced activity of such polypeptides in modified plants will provide changes in the quantity and/or speed of flavonoid metabolism in plants and can improve disease resistance by enhancing synthesis of protective secondary metabolites or improving signaling pathways governing disease resistance.

Polypeptides involved in lignin biosynthesis are of interest for increasing plants' resistance to lodging and for increasing the usefulness of plant materials as biofuels.

(ix) Production or Assimilation of Chemicals or Biologicals

It may further be considered that a sorghum plant comprising a sorghum MC or recombinant chromosome prepared in accordance with the invention may be used for the production or manufacturing of useful biological compounds that were either not produced at all, or not produced at the same level, in the plant previously. Alternatively, plants produced in accordance with the invention may be made to metabolize or absorb and concentrate certain compounds, such as hazardous wastes, thereby allowing bioremediation of these compounds.

The novel plants producing these compounds are made possible by the introduction and expression of one or potentially many genes with the constructs provided by the invention. The vast array of possibilities include but are not limited to any biological compound which is presently produced by any organism such as proteins, nucleic acids, primary and intermediary metabolites, carbohydrate polymers, enzymes for uses in bioremediation, enzymes for modifying pathways that produce secondary plant metabolites such as falconoid or vitamins, enzymes that could produce pharmaceuticals, and for introducing enzymes that could produce compounds of interest to the manufacturing industry such as specialty chemicals and plastics. The compounds may be produced by the plant, extracted upon harvest and/or processing, and used for any presently recognized useful purpose such as pharmaceuticals, fragrances, and industrial enzymes to name a few.

(x) Other Characteristics

Cell cycle modification: Polypeptides encoding cell cycle enzymes and regulators of the cell cycle pathway are useful for manipulating growth rate in plants to provide early vigor and accelerated maturation. Improvements in quality traits, such as seed oil content, may also be obtained by expression of cell cycle enzymes and cell cycle regulators. Polypeptides of interest for modification of cell cycle pathway include cycling and EIF5$\alpha$ pathway proteins, polypeptides involved in polyamine metabolism, polypeptides which act as regulators of the cell cycle pathway, including cyclin-dependent kinases (CDKs), CDK-activating kinases, cell cycle-dependent phosphatases, CDK-inhibitors, Rb and Rb-binding proteins, or transcription factors that activate genes involved in cell proliferation and division, such as the E2F family of transcription factors, proteins involved in degradation of cyclins, such as cullins, and plant homologs of tumor suppressor polypeptides.

Plant growth regulators: Polypeptides involved in production of substances that regulate the growth of various plant tissues are of interest in the present invention and may be used to provide modified plants having altered morphologies and improved plant growth and development profiles leading to improvements in yield and stress response. Of particular interest are polypeptides involved in the biosynthesis, or degradation of plant growth hormones, such as gibberellins, brassinosteroids, cytokinins, auxins, ethylene or abscisic acid, and other proteins involved in the activity, uptake and/or transport of such polypeptides, including for example, cytokinin oxidase, cytokinin/purine permeases, F-box proteins, G-proteins or phytosulfokines.

Transcription factors in plants: Transcription factors play a key role in plant growth and development by controlling the expression of one or more genes in temporal, spatial and physiological specific patterns. Enhanced or reduced activity of such polypeptides in modified plants will provide significant changes in gene transcription patterns and provide a variety of beneficial effects in plant growth, development and response to environmental conditions. Transcription factors of interest include, but are not limited to myb transcription factors, including helix-turn-helix proteins, homeodomain transcription factors, leucine zipper transcription factors, MADS transcription factors, transcription factors having AP2 domains, zinc finger transcription factors, CCAAT binding transcription factors, ethylene responsive transcription factors, transcription initiation factors or UV damaged DNA binding proteins.

Homologous recombination: Increasing the rate of homologous recombination in plants is useful for accelerating the introgression of transgenes into breeding varieties by backcrossing, and to enhance the conventional breeding process by allowing rare recombinants between closely linked genes in phase repulsion to be identified more easily. Polypeptides useful for expression in plants to provide increased homologous recombination include polypeptides involved in mitosis and/or meiosis, DNA replication, nucleic acid metabolism, DNA repair pathways or homologous recombination pathways including for example, recombinases, nucleases, proteins binding to DNA double-strand breaks, single-strand DNA binding proteins, strand-exchange proteins, resolvases, ligases, helicases and polypeptide members of the RAD52 epistasis group.

Enhanced Biofuel Conversion

Biofuels can be produced from the conversion of biomass into liquid or gaseous fuels by converting the biomass into sugars, or by direct extract of sugars, that can be fermented or chemically converted to form a biofuel. Biofuels can also be generated by extracting oils from the biomass. Exemplary biofuels are ethanol, propanol, butanol, methanol, methane, 2,5-dimethylfurqan, dimethyl ether, biodiesel (short chain acid alkyl esters), biogasoline, syngas, parrafins (alkanes), other hydrocarbons or co-products of hydrogen.

The invention provides for MCs or recombinant chromosomes expressing at least one gene that enhance or increase sugar production or extractability, enhance or increase biomass, enhance the conversion of biomass to sugars or enhance sugar fermentation to biofuels. It may further be considered that a modified plant prepared in accordance with the invention may be used as biomass for the production of biofuels or the plant may facilitate conversion of biomass to sugars or facilitate fermentation of sugars to biofuels.

Enzymes that may be useful for biofuel production include those that break down glucans. In some embodiments, the enzymes are selected from the group consisting of: endo-β(1,4)-glucanase, cellobiohydrolase, β-glucosidase, α/β-glucosidase, mixed-linked glucanase, endo-β(1,3)-glucanase, exo-β

(1,3)-glucanse and β-(1,6)-glucanase. In other embodiments the enzymes break down xyloglucans, xylans, mannans or lignins.

The enzyme genes may be controlled by inducible promoters that may be inactive until a desired time, such as at harvest or when the plant is added to the biofuels process (e.g. inactive at physiological conditions, then activated by heat or pH), or sequestered by subcellular localization. The enzymes may also be controlled by a tissue-specific promoter which may be active only in specific tissues (e.g seeds or leaves).

Non-Protein-Expressing Exogenous Nucleic Acids

Plants with decreased expression of a gene of interest can also be achieved, for example, by expression of antisense nucleic acids, dsRNA or RNAi, acatalytic RNA such as ribozymes, sense expression constructs that exhibit cosuppression effects, aptamers or zinc finger proteins.

Antisense RNA reduces production of the polypeptide product of the target messenger RNA, for example by blocking translation through formation of RNA:RNA duplexes or by inducing degradation of the target mRNA. Antisense approaches are a way of preventing or reducing gene function by targeting the genetic material as disclosed in U.S. Pat. Nos. 4,801,540, 5,107,065, 5,759,829, 5,910,444, 6,184,439, and 6,198,026, all of which are incorporated herein by reference. In one approach, an antisense gene sequence is introduced that is transcribed into antisense RNA that is complementary to the target mRNA. For example, part or all of the normal gene sequences are placed under a promoter in inverted orientation so that the complementary strand is transcribed into a non-protein expressing antisense RNA. The promoter used for the antisense gene may influence the level, timing, tissue, specificity, or inducibility of the antisense inhibition.

Autonomous MCs or recombinant chromosome may comprise exogenous DNA flanked by recombination sites, for example lox-P sites, that can be recognized by a recombinase, e.g. Cre, and removed from the MC or recombinant chromosome. In cases where there is a homologous recombination site or sites in the host genomic DNA, the exogenous DNA excised the MC or recombinant chromosome may be integrated into the genome at one of the specific recombination sites and the DNA flanked by the recombination sites will become integrated into the host DNA. The use of a MC or recombinant chromosome as a platform for DNA excision or for launching such DNA integration into the host genome may include in vivo induction of the expression of a recombinase encoded in the genomic DNA of a transgenic host, or in a MC or recombinant chromosome.

RNAi gene suppression in plants by transcription of a dsRNA is described in U.S. Pat. No. 6,506,559, US patent application Publication No. 2002/0168707, WO 98/53083, WO 99/53050 and WO 99/61631, all of which are incorporated herein by reference. The double-stranded RNA or RNAi constructs can trigger the sequence-specific degradation of the target messenger RNA. Suppression of a gene by RNAi can be achieved using a recombinant DNA construct having a promoter operably linked to a DNA element comprising a sense and anti-sense element of a segment of genomic DNA of the gene, e.g., a segment of at least about 23 nucleotides, more preferably about 50 to 200 nucleotides where the sense and anti-sense DNA components can be directly linked or joined by an intron or artificial DNA segment that can form a loop when the transcribed RNA hybridizes to form a hairpin structure.

Catalytic RNA molecules or ribozymes can also be used to inhibit expression of the target gene or genes or facilitate molecular reactions. Ribozymes are targeted to a given sequence by hybridization of sequences within the ribozyme to the target mRNA. Two stretches of homology are required for this targeting, and these stretches of homologous sequences flank the catalytic ribozyme structure. It is possible to design ribozymes that specifically pair with virtually any target mRNA and cleave the target mRNA at a specific location, thereby inactivating it. A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include Tobacco Ringspot Virus (Prody et al., *Science,* 231:1577-1580, 1986), Avocado Sun blotch Viroid (Palukaitis et al., *Virology,* 99:145-151, 1979; Symons, *Nucl. Acids Res.,* 9:6527-6537, 1981), and Lucerne Transient Streak Virus (Forster and Symons, *Cell,* 49:211-220, 1987), and the satellite RNAs from velvet tobacco mottle virus, Solanum nodiflorum mottle virus and subterranean clover mottle virus. The design and use of target RNA-specific ribozymes is described in Haseloff, et al., *Nature* 334:585-591 (1988). Several different ribozyme motifs have been described with RNA cleavage activity (Symons, *Annu. Rev. Biochem.,* 61:641-671, 1992). Other suitable ribozymes include sequences from RNase P with RNA cleavage activity (Yuan et al., *PNAS USA,* 89:8006-8010, 1992; Yuan and Altman, *Science,* 263:1269-1273, 1994; U.S. Pat. Nos. 5,168,053 and 5,624,824), hairpin ribozyme structures (Berzal-Herranz et al., *Genes and Devel.,* 6:129-134, 1992; Chowrira et al., *J. Biol. Chem.,* 269:25856-25864, 1994) and Hepatitis Delta virus based ribozymes (U.S. Pat. No. 5,625,047). The general design and optimization of ribozyme directed RNA cleavage activity has been discussed in detail (Haseloff and Gerlach, *Nature* 334:585-91, 1988; Chowrira et al., *J. Biol. Chem.,* 269:25856-25864, 1994).

Another method of reducing protein expression utilizes the phenomenon of cosuppression or gene silencing (for example, U.S. Pat. Nos. 6,063,947, 5,686,649, or 5,283,184; each of which is incorporated herein by reference). Cosuppression of an endogenous gene using a full-length cDNA sequence as well as a partial cDNA sequence are known (for example, Napoli et al., *Plant Cell* 2:279-289, 1990; van der Krol et al., *Plant Cell* 2:291-299, 1990; Smith et al., *Mol. Gen. Genetics* 224:477-481, 1990). The phenomenon of cosuppression has also been used to inhibit plant target genes in a tissue-specific manner.

In some embodiments, nucleic acids from one species of plant are expressed in another species of plant to effect cosuppression of a homologous gene. The introduced sequence generally will be substantially identical to the endogenous sequence intended to be repressed, for example, about 65%, 80%, 85%, 90%, or preferably 95% or greater identical. Higher identity may result in a more effective repression of expression of the endogenous sequence. A higher identity in a shorter than full length sequence compensates for a longer, less identical sequence. Furthermore, the introduced sequence need not have the same intron or exon pattern, and identity of non-coding segments will be equally effective. Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence.

Yet another method of reducing protein activity is by expressing nucleic acid ligands, so-called aptamers, which specifically bind to the protein. Aptamers may be obtained by the SELEX (Systematic Evolution of Ligands by EXponential Enrichment) method. See U.S. Pat. No. 5,270,163, incorporated herein by reference. In the SELEX method, a candidate mixture of single stranded nucleic acids having regions of randomized sequence is contacted with the protein and those nucleic acids having an increased affinity to the target are selected and amplified. After several iterations a nucleic acid with optimal affinity to the polypeptide is obtained and is used for expression in modified plants.

A zinc finger protein that binds a polypeptide-encoding sequence or its regulatory region is also used to alter expression of the nucleotide sequence. Transcription of the nucleotide sequence may be reduced or increased. Zinc finger proteins are, for example, described in Beerli et al. (1998) *PNAS USA* 95:14628-14633, or in WO 95/19431, WO 98/54311, or WO 96/06166, all incorporated herein by reference.

Other examples of non-protein expressing sequences specifically envisioned for use with the invention include: tRNA sequences, for example, to alter codon usage; rRNA variants, for example, which may confer resistance to various agents such as antibiotics.

It is contemplated that unexpressed DNA sequences, including novel synthetic sequences, could be introduced into cells as proprietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a plant and this DNA element would identify all cells, plants, and progeny of these cells as having arisen from that labeled source. It is proposed that inclusion of label DNAs would enable one to distinguish proprietary germplasm or germplasm derived from such, from unlabelled germplasm.

Exemplary Plant Promoters, Regulatory Sequences and Targeting Sequences

Exemplary classes of plant promoters are described below.

Constitutive Expression promoters: Exemplary constitutive expression promoters include the ubiquitin promoter (e.g., sunflower—Binet et al. *Plant Science* 79: 87-94, 1991; maize—Christensen et al. *Plant Molec. Biol.* 12: 619-632, 1989; and *Arabidopsis*—Callis et al., *J. Biol. Chem.* 265: 12486-12493, 1990; and Norris et al., *Plant Mol. Biol.* 21: 895-906, 1993); the CaMV 35S promoter (U.S. Pat. Nos. 5,858,742 and 5,322,938); or the actin promoter (e.g., rice—U.S. Pat. No. 5,641,876; McElroy et al. *Plant Cell* 2: 163-171, 1990; McElroy et al. *Mol. Gen. Genet.* 231: 150-160, 1991, and Chibbar et al. *Plant Cell Rep.* 12: 506-509, 1993. Exemplary promoters for use in sorghum include the seed-specific SBEIIb promoter (Mutisya J, et al. *J Plant Physiol.* 163:770-80, 2005). Other promoters that may be useful in sorghum include the maize polyubiquitin 1 (Mubi-1) and the Sugarcane polyubiquitin 9 (SCubi9) promoters (Wang M L, et al. *Transgenic Res.* 14:167-78, 2005); and the Sugarcane polyubiquitin 4 (ubi4) promoter (Wei H, et al. J Plant Physiol. 160:1241-51, 2003).

Inducible Expression promoters: Exemplary inducible expression promoters include the chemically regulatable tobacco PR-1 promoter (e.g., tobacco—U.S. Pat. No. 5,614,395; *Arabidopsis*—Lebel et al., *Plant J.* 16: 223-233, 1998; maize—U.S. Pat. No. 6,429,362). Various chemical regulators may be employed to induce expression, including the benzothiadiazole, isonicotinic acid, and salicylic acid compounds disclosed in U.S. Pat. Nos. 5,523,311 and 5,614,395. Other promoters inducible by certain alcohols or ketones, such as ethanol, include, for example, the alcA gene promoter from *Aspergillus nidulans* (Caddick et al. *Nat. Biotechnol* 16:177-180, 1998). A glucocorticoid-mediated induction system is described in Aoyama and Chua (*Plant Journal* 11: 605-612, 1997) wherein gene expression is induced by application of a glucocorticoid, for example a dexamethasone. Another class of useful promoters is water-deficit-inducible promoters, e.g. promoters which are derived from the 5' regulatory region of genes identified as a heat shock protein 17.5 gene (HSP 17.5), an HVA22 gene (HVA22), and a cinnamic acid 4-hydroxylase (CA4H) gene of *Zea mays*. Another water-deficit-inducible promoter is derived from the rab-17 promoter as disclosed by Vilardell et al. (*Plant Molec. Biol,* 17:985-993, 1990). See also U.S. Pat. No. 6,084,089 which discloses cold inducible promoters, U.S. Pat. No. 6,294,714 which discloses light inducible promoters, U.S. Pat. No. 6,140,078 which discloses salt inducible promoters, U.S. Pat. No. 6,252,138 which discloses pathogen inducible promoters, and U.S. Pat. No. 6,175,060 which discloses phosphorus deficiency inducible promoters.

As another example, numerous wound-inducible promoters have been described (e.g. Xu et al. *Plant Molec. Biol.* 22: 573-588, 1993; Logemann et al., *Plant Cell* 1: 151-158, 1989; Rohrmeier & Lehle, *Plant Molec. Biol.* 22: 783-792, 1993; Firek et al. *Plant Molec. Biol.* 22: 129-142, 1993; Warner et al. *Plant J.* 3: 191-201, 1993)). Logemann describe 5' upstream sequences of the potato wunl gene. Xu et al. show that a wound-inducible promoter from the dicotyledon potato (pin2) is active in the monocotyledon rice. Rohrmeier & Lehle describe maize Wipl cDNA which is wound induced and which can be used to isolate the cognate promoter. Firek et al. and Warner et al. have described a wound-induced gene from the monocotyledon *Asparagus officinalis*, which is expressed at local wound and pathogen invasion sites.

Tissue-Specific Promoters: Exemplary promoters that express genes only in certain tissues are useful according to the present invention. For example root specific expression may be attained using the promoter of the maize metallothionein-like (MTL) gene described by de Framond (*FEBS* 290: 103-106, 1991) and also in U.S. Pat. No. 5,466,785, incorporated herein by reference. U.S. Pat. No. 5,837,848 discloses a root specific promoter. Another exemplary promoter confers pith-preferred expression (see WO 93/07278, herein incorporated by reference, which describes the maize trpA gene and promoter that is preferentially expressed in pith cells). Leaf-specific expression may be attained, for example, by using the promoter for a maize gene encoding phosphoenol carboxylase (PEPC) (see Hudspeth & Grula, *Plant Molec Biol* 12: 579-589 (1989)). Pollen-specific expression may be conferred by the promoter for the maize calcium-dependent protein kinase (CDPK) gene which is expressed in pollen cells (WO 93/07278). US Pat. Appl. Pub. No. 20040016025 describes tissue-specific promoters. Pollen-specific expression may be conferred by the tomato LAT52 pollen-specific promoter (Bate et al., *Plant Mol. Biol.* 37:859-69, 1998).

See also U.S. Pat. No. 6,437,217 which discloses a root-specific maize RS81 promoter, U.S. Pat. No. 6,426,446 which discloses a root specific maize RS324 promoter, U.S. Pat. No. 6,232,526 which discloses a constitutive maize A3 promoter, U.S. Pat. No. 6,177,611 which discloses constitutive maize promoters, U.S. Pat. No. 6,433,252 which discloses a maize L3 oleosin promoter that are aleurone and seed coat-specific promoters, U.S. Pat. No. 6,429,357 which discloses a constitutive rice actin 2 promoter and intron, US patent application Pub. No. 20040216189 which discloses an inducible constitutive leaf specific maize chloroplast aldolase promoter.

Optionally a plant transcriptional terminator can be used in place of the plant-expressed gene native transcriptional terminator. Exemplary transcriptional terminators are those that are known to function in plants and include the CaMV 35S terminator, the tml terminator, the nopaline synthase terminator and the pea rbcS E9 terminator. These can be used in both monocotyledons and dicotyledons.

Various intron sequences have been shown to enhance expression, particularly in monocotyledonous cells. For example, the introns of the maize Adhl gene have been found to significantly enhance expression. Intron 1 was found to be particularly effective and enhanced expression in fusion constructs with the chloramphenicol acetyltransferase gene (Callis et al., *Genes Develop.* 1: 1183-1200, 1987). The intron from the maize bronze1 gene also enhances expression. Intron sequences have been routinely incorporated into plant transformation vectors, typically within the non-translated leader. US Patent Application Publication 2002/0192813 discloses 5', 3' and intron elements useful in the design of effective plant expression vectors.

A number of non-translated leader sequences derived from viruses are also known to enhance expression, and these are particularly effective in dicotyledonous cells. Specifically, leader sequences from Tobacco Mosaic Virus (TMV, the "omega-sequence"), Maize Chlorotic Mottle Virus (MCMV), and Alfalfa Mosaic Virus (AMV) have been shown to be effective in enhancing expression (e.g. Gallie et al. *Nucl. Acids Res.* 15: 8693-8711, 1987; Skuzeski et al. *Plant Molec. Biol.* 15: 65-79, 1990). Other leader sequences known in the art include but are not limited to: picornavirus leaders, for example, EMCV leader (Encephalomyocarditis 5' noncoding region) (Elroy-Stein, O, et al. *PNAS USA* 86:6126-6130, 1989); potyvirus leaders, for example, TEV leader (Tobacco Etch Virus) (Allison et al., *Virology* 154:9-20, 1986); MDMV leader (Maize Dwarf Mosaic Virus); *Virology* 154:9-20); human immunoglobulin heavy-chain binding protein (BiP) leader, (Macejak, D. G., and Sarnow, P., *Nature* 353: 90-94, 1991; untranslated leader from the coat protein mRNA of alfalfa mosaic virus (AMV RNA 4), (Jobling, S. A., and Gehrke, L., *Nature* 325:622-625, 1987); tobacco mosaic virus leader (TMV), (Gallie et al., *Molecular Biology of RNA, pages* 237-256, 1989); or Maize Chlorotic Mottle Virus leader (MCMV) (Lommel et al., *Virology* 81:382-385, 1991). See also, Della-Cioppa et al., *Plant Physiology* 84:965-968 (1987).

A minimal promoter may also be incorporated. Such a promoter has low background activity in plants when there is no transactivator present or when enhancer or response element binding sites are absent. One exemplary minimal promoter is the Bz1 minimal promoter, which is obtained from the bronze1 gene of maize. Roth et al., *Plant Cell* 3: 317 (1991). A minimal promoter may also be created by use of a synthetic TATA element. The TATA element allows recognition of the promoter by RNA polymerase factors and confers a basal level of gene expression in the absence of activation (see generally, Mukumoto, *Plant Mol Biol* 23: 995-1003, 1993; Green, *Trends Biochem Sci* 25: 59-63, 2000).

Sequences controlling the targeting of gene products also may be included. For example, the targeting of gene products to the chloroplast is controlled by a signal sequence found at the amino terminal end of various proteins which is cleaved during chloroplast import to yield the mature protein (e.g. Comai et al., *J. Biol. Chem.* 263: 15104-15109, 1988). These signal sequences can be fused to heterologous gene products to affect the import of heterologous products into the chloroplast (van den Broeck, et al. *Nature* 313: 358-363, 1985). DNA encoding for appropriate signal sequences can be isolated from the 5' end of the cDNAs encoding the RUBISCO protein, the CAB protein, the EPSP synthase enzyme, the GS2 protein or many other proteins which are known to be chloroplast localized. Other gene products are localized to other organelles such as the mitochondrion and the peroxisome (e.g. Unger et al. *Plant Molec. Biol.* 13: 411-418, 1989). Examples of sequences that target to such organelles are the nuclear-encoded ATPases or specific aspartate amino transferase isoforms for mitochondria. Targeting cellular protein bodies has been described by Rogers et al. (*PNAS USA* 82: 6512-6516, 1985). In addition, amino terminal and carboxy-terminal sequences are responsible for targeting to the ER, the apoplast, and extracellular secretion from aleurone cells (Koehler & Ho, *Plant Cell* 2: 769-783, 1990). Additionally, amino terminal sequences in conjunction with carboxy terminal sequences are responsible for vacuolar targeting of gene products (Shinshi et al. *Plant Molec. Biol.* 14: 357-368, 1990).

Another possible element which may be introduced is a matrix attachment region element (MAR), such as the chicken lysozyme A element (Stief et al. *Nature* 34:343-5, 1989), which can be positioned around an expressible gene of interest to effect an increase in overall expression of the gene and diminish position dependent effects upon incorporation into the plant genome (Stief et al., *Nature,* 341:343, 1989; Phi-Van et al., *Mol. Cell. Biol.,* 10:2302-230, 1990).

Use of Non-Plant Promoter Regions Isolated from *Drosophila melanogaster* and *Saccharomyces cerevisiae* to Express Genes in Plants The promoter in the sorghum MC or recombinant chromosome of the present invention can be derived from plant or non-plant species. In one embodiment, the nucleotide sequence of the promoter is derived from non-plant species for the expression of genes in plant cells, including but not limited to dicotyledon plant cells such as tobacco, tomato, potato, soybean, canola, sunflower, alfalfa, cotton and *Arabidopsis*, or monocotyledonous plant cell, such as wheat, maize, rye, rice, turf grass, oat, barley, sorghum, sugarcane and millet. In one embodiment, the non-plant promoters are constitutive or inducible promoters derived from insect, e.g., *Drosophila melanogaster* or yeast, e.g., *Saccharomyces cerevisiae*. Table 2 lists the promoters from *Drosophila melanogaster* and *Saccharomyces cerevisiae* that are used to derive the examples of non-plant promoters in the present invention. Promoters derived from any animal, protist, or fungi are also contemplated. SEQ ID NOs:1-20, or fragments, mutants, hybrid or tandem promoters thereof, are examples of promoter sequences derived from *Drosophila melanogaster* or *Saccharomyces cerevisiae*. These non-plant promoters can be operably linked to nucleic acid sequences encoding polypeptides or non-protein-expressing sequences including, but not limited to, antisense RNA and ribozymes, to form nucleic acid constructs, vectors, and host cells (prokaryotic or eukaryotic), comprising the promoters.

TABLE 2

Exemplary Promoters from *D. melanogaster* and *S. cerevisiae*

*Drosophila melanogaster* promoters (adapted from the *Drosophila* FlyBase, referenced in Grumbling, G. and Strelets, *Nucl. Acids Rsrch.* 34:D484-8, 2006

| SEQ ID NO: | Symbol | Flybase ID | Standard promoter gene name | Gene product | Chromosome |
|---|---|---|---|---|---|
| 1 | Pgd | FBgn0004654 | Phosphogluconate dehydrogenase | 6-phosphogluconate dehydrogenase | X |
| 2 | Grim | FBgn0015946 | grim | grim-P138 | 3 |
| 3 | Uro | FBgn0003961 | Urate oxidase | Uro-P1 | 2 |
| 4 | Sna | FBgn0003448 | Snail | sna-P1 | 2 |
| 5 | Rh3 | FBgn0003249 | Rhodopsin 3 | Rh3 | 3 |
| 6 | Lsp-1 γ | FBgn0002564 | Larval serum protein 1 | Lsp1γ-P1 | 3 |

*Saccharomyces cerevisiae* Promoters (adapted from information available from the *Saccharomyces* Genome Database, referenced in Dwight SS et al. *Brief Bioinform.* 5:9-22, 2004).

| SEQ ID NO: | Symbol | Systematic Name | Standard promoter gene name | Gene product | Chromosome |
|---|---|---|---|---|---|
| 7 | Tef-2 | YBR118W | TEF2 (Translation elongation factor promtoer) | Translation elongation factor EF-1 alpha | 2 |
| 8 | Leu-1 | YGL009C | LEU1 (LEUcine biosynthesis) | isopropylmalate isomerase | 7 |
| 9 | Met16 | YPR167C | METhionine requiring | 3'phosphoadenylyl-sulfate reductase | 16 |
| 10 | Leu-2 | YCL018W | LEU2 (leucine biosynthesis) | beta-IPM (isopropylmalate) dehydrogenase | 3 |
| 11 | His-4 | YCL030C | HIS4 (HIStidine requiring) | histidinol dehydrogenase | 3 |
| 12 | Met-2 | YNL277W | MET2 (methionine requiring) | L-homoserine-O-acetyltransferase | 14 |
| 13 | Ste-3 | YKL178C | STE3 (alias DAF2 Sterile) | a-factor receptor | 11 |
| 14 | Arg-1 | YOL058W | ARG1(alias ARG10 ARGinine requiring) | arginosuccinate synthetase | 15 |
| 15 | Pgk-1 | YCR012W | PGK1 (phosphoglycerate kinase ) | phosphoglycerate kinase | 3 |
| 16 | GPD-1 | YDL022W | GPD1 (alias DAR1/HOR1/OSG1/OSR 5:glycerol-3-phosphate dehydrogenase activity | glycerol-3-phosphate dehydrogenase | 4 |
| 17 | ADH1 | YOL086C | ADH1 (alias ADC1) | alcohol dehydrogenase | 15 |
| 18 | GPD-2 | YOL059W | GPD2 (alias GPD3: glycerol-3-phosphate dehydrogenase activity | glycerol-3-phosphate dehydrogenase | 15 |
| 19 | Arg-4 | YHR018C | ARGinine requiring | argininosuccinate lyase | 8 |
| 20 | Yat-1 | YAR035W | YAT-1(carnitine acetyltransferase) | carnitine acetyltransferase | 1 |

In the MCs or recombinant chromosome of the present invention, the promoter may be a mutant of the promoters having a substitution, deletion, and/or insertion of one or more nucleotides in the nucleic acid sequence of SEQ ID NOs:1 to 20, hybrid or tandem promoters.

The techniques used to isolate or clone a nucleic acid sequence comprising a promoter of interest are known in the art and include isolation from genomic DNA. The cloning procedures may involve excision or amplification, for example by polymerase chain reaction, and isolation of a desired nucleic acid fragment comprising the nucleic acid sequence encoding the promoter, insertion of the fragment into a vector molecule, and incorporation of the recombinant vector into the plant cell.

DEFINITIONS

The term “adchromosomal” plant or plant part means a plant or plant part that contains functional, stable and autonomous MCs. Adchromosomal plants or plant parts may be chimeric or not chimeric (chimeric meaning that MCs are only in certain portions of the plant, and are not uniformly distributed throughout the plant). An adchromosomal plant cell contains at least one functional, stable and autonomous MC.

The term “autonomous” means that when delivered to plant cells, at least some MCs are transmitted through mitotic division to daughter cells and are episomal in the daughter plant cells, i.e. are not chromosomally integrated in the daughter plant cells. Daughter plant cells that contain autonomous MCs can be selected for further replication using, for example, selectable or screenable markers. During the introduction into a cell of a MC, or during subsequent stages of the cell cycle, there may be chromosomal integration of some portion or all of the DNA derived from a MC in some cells. The MC is still characterized as autonomous despite the occurrence of such events if a plant may be regenerated that contains episomal descendants of the MC distributed throughout its parts, or if gametes or progeny can be derived from the plant that contain episomal descendants of the MC distributed through its parts.

A "centromere" is any DNA sequence that confers an ability to segregate to daughter cells through cell division. In one context, this sequence may produce a transmission efficiency to daughter cells ranging from about 1% to about 100%, including to about 5%, 10%, 20%, 30%, 40%, 50%, 60%, 70%, 80%, 90% or about 95% of daughter cells. Variations in transmission efficiency may find important applications within the scope of the invention; for example, MCs carrying centromeres that confer 100% stability could be maintained in all daughter cells without selection, while those that confer 1% stability could be temporarily introduced into a transgenic organism, but be eliminated when desired. In particular embodiments of the invention, the centromere may confer stable transmission to daughter cells of a nucleic acid sequence, including a recombinant construct comprising the centromere, through mitotic or meiotic divisions, including through both meiotic and meiotic divisions. A plant centromere is not necessarily derived from plants, but has the ability to promote DNA transmission to daughter plant cells.

The term "circular permutations" refer to variants of a sequence that begin at base n within the sequence, proceed to the end of the sequence, resume with base number one of the sequence, and proceed to base n−1. For this analysis, n may be any number less than or equal to the length of the sequence. For example, circular permutations of the sequence ABCD are: ABCD, BCDA, CDAB, and DABC.

The term "co-delivery" refers to the delivery of two nucleic acid segments to a cell. In co-delivery of plant growth inducing genes and MCs, the two nucleic acid segments are delivered simultaneously using the same delivery method. Alternatively, the nucleic acid segment containing the growth inducing gene, optionally as part of an episomal vector, such as a viral vector or a plasmid vector, may be delivered to the plant cells before or after delivery of the MC, and the MC may carry an exogenous nucleic acid that induces expression of the earlier-delivered growth inducing gene. In this embodiment, the two nucleic acid segments may be delivered separately at different times provided the encoded growth inducing factors are functional during the appropriate time period.

The term "coding sequence" is defined herein as a nucleic acid sequence that is transcribed into mRNA which is translated into a polypeptide when placed under the control of promoter sequences. The boundaries of the coding sequence are generally determined by the ATG start codon located at the start of the open reading frame, near the 5' end of the mRNA, and TAG, TGA or TAA stop codons at the end of the coding sequence, near the 3' end of the mRNA, and in some cases, a transcription terminator sequence located just downstream of the open reading frame at the 3' end of the mRNA. A coding sequence can include, but is not limited to, genomic DNA, cDNA, semisynthetic, synthetic, or recombinant nucleic acid sequences.

The term "consensus" refers to a nucleic acid sequence derived by comparing two or more related sequences. A consensus sequence defines both the conserved and variable sites between the sequences being compared. Any one of the sequences used to derive the consensus or any permutation defined by the consensus may be useful in construction of MCs.

The term "exogenous" when used in reference to a nucleic acid, for example, is intended to refer to any nucleic acid that has been introduced into a recipient cell, regardless of whether the same or similar nucleic acid is already present in such a cell. Thus, as an example, "exogenous DNA" can include an additional copy of DNA that is already present in the plant cell, DNA from another plant, DNA from a different organism, or a DNA generated externally, such as a DNA sequence containing an antisense message of a gene, or a DNA sequence encoding a synthetic or modified version of a gene. An "exogenous gene" can be a gene not normally found in the host genome in an identical context, or an extra copy of a host gene. The gene may be isolated from a different species than that of the host genome, or alternatively, isolated from the host genome but operably linked to one or more regulatory regions which differ from those found in the unaltered, native gene.

The term "functional" to describe a MC means that when an exogenous nucleic acid is present within the MC the exogenous nucleic acid can function in a detectable manner when the MC is within a plant cell; exemplary functions of the exogenous nucleic acid include transcription of the exogenous nucleic acid, expression of the exogenous nucleic acid, regulatory control of expression of other exogenous nucleic acids, recognition by a restriction enzyme or other endonuclease, ribozyme or recombinase; providing a substrate for DNA methylation, DNA glycolation or other DNA chemical modification; binding to proteins such as histones, helix-loop-helix proteins, zinc binding proteins, leucine zipper proteins, MADS box proteins, topoisomerases, helicases, transposases, TATA box binding proteins, viral protein, reverse transcriptases, or cohesins; providing an integration site for homologous recombination; providing an integration site for a transposon, T-DNA or retrovirus; providing a substrate for RNAi synthesis; priming of DNA replication; aptamer binding; or kinetochore binding. If multiple exogenous nucleic acids are present within the MC, the function of one or preferably more of the exogenous nucleic acids can be detected under suitable conditions permitting function thereof.

"Library" is a pool of cloned DNA fragments that represents some or all DNA sequences collected, prepared or purified from a specific source. Each library may contain the DNA of a given organism inserted as discrete restriction enzyme generated fragments or as randomly sheared fragments into many thoUSAnds of plasmid vectors. For purposes of the present invention, *E. coli*, yeast, and *Salmonella* plasmids are particularly useful for propagating the genome inserts from other organisms. In principle, any gene or sequence present in the starting DNA preparation can be isolated by screening the library with a specific hybridization probe (see, for example, Young et al., In: Eukaryotic Genetic Systems ICN-UCLA Symposia on Molecular and Cellular Biology, VII, 315-331, 1977).

The term "linker" refers to a DNA molecule, generally up to 50 or 60 nucleotides long and composed of two or more complementary oligonucleotides that have been synthesized chemically, or excised or amplified from existing plasmids or vectors. In a preferred embodiment, this fragment contains one, or preferably more than one, restriction enzyme site for a blunt cutting enzyme and/or a staggered cutting enzyme, such as BamHI. One end of the linker is designed to be ligatable to one end of a linear DNA molecule and the other end is designed to be ligatable to the other end of the linear molecule, or both ends may be designed to be ligatable to both ends of the linear DNA molecule.

A "MC" is a recombinant DNA construct including a centromere that is capable of transmission to daughter cells. A MC may remain separate from the host genome (as episomes) or may integrate into host chromosomes. The stability of this construct through cell division could range between from about 1% to about 100%, including about 5%, 10%, 20%, 30%, 40%, 50%, 60%, 70%, 80%, 90% and about 95%. The MC construct may be a circular or linear molecule. It may include elements such as one or more telomeres, origin of replication sequences, stuffer sequences, buffer sequences, chromatin packaging sequences, linkers and genes. The number of such sequences included is only limited by the physical size limitations of the construct itself. It could contain DNA derived from a natural centromere, although it may be preferable to limit the amount of DNA to the minimal amount required to obtain a transmission efficiency in the range of 1-100%. The MC could also contain a synthetic centromere composed of tandem arrays of repeats of any sequence, either derived from a natural centromere, or of synthetic DNA. The MC could also contain DNA derived from multiple natural centromeres. The MC may be inherited through mitosis or meiosis, or through both meiosis and mitosis, the term MC specifically encompasses and includes the terms "plant artificial chromosome" or "PLAC," or engineered chromosomes or microchromosomes and all teachings relevant to a PLAC or plant artificial chromosome specifically apply to constructs within the meaning of the term MC.

The term "non-protein expressing sequence" or "non-protein coding sequence" is defined herein as a nucleic acid sequence that is not eventually translated into protein. The nucleic acid may or may not be transcribed into RNA. Exemplary sequences include ribozymes or antisense RNA.

The term "operably linked" is defined herein as a configuration in which a control sequence, e.g., a promoter sequence, directs transcription or translation of another sequence, for example a coding sequence. For example, a promoter sequence could be appropriately placed at a position relative to a coding sequence such that the control sequence directs the production of a polypeptide encoded by the coding sequence.

"Phenotype" or "phenotypic trait(s)", refers to an observable property or set of properties resulting from the expression of a gene. The set of properties may be observed visually or after biological or biochemical testing, and may be constantly present or may only manifest upon challenge with the appropriate stimulus or activation with the appropriate signal.

The term "plant" refers to any type of plant. Modified plants of the invention include, for example, dicots, gymnosperm, monocots, mosses, ferns, horsetails, club mosses, liver worts, hornworts, red algae, brown algae, gametophytes and sporophytes of pteridophytes, and green algae.

One modified crop plant of particular interest in the present invention is *Sorghum*, including but not limited to *Sorghum bicolor* (primary cultivated species), *Sorghum almum, Sorghum amplum, Sorghum angustum, Sorghum rundinaceum, Sorghum brachypodum, Sorghum bulbosum, Sorghum burmahicum, Sorghum controversum, Sorghum drummondii, Sorghum carinatum, Sorghum exstans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum nigrum, Sorghum nitidum, Sorghum plumosum, Sorghum propinquum, Sorghum purpureosericeum, Sorghum stipoideum, Sorghum timorense, Sorghum trichodadum, Sorghum versicolor, Sorghum virgatum*, and *Sorghum vulgare* (including but not limited to the variety *Sorghum vulgare* var. *sudanens* also known as sudangrass). Hybrids of these species are also of interest in the present invention as are hybrids with other members of the Family Poaceae.

The term "plant part" includes a pod, root, sett root, shoot root, root primordial, shoot, primary shoot, secondary shoot, tassle, panicle, arrow, midrib, blade, ligule, auricle, dewlap, blade joint, sheath, node, internode, bud furrow, leaf scar, cutting, tuber, stem, stalk, fruit, berry, nut, flower, leaf, bark, wood, epidermis, vascular tissue, organ, protoplast, crown, callus culture, petiole, petal, sepal, stamen, stigma, style, bud, meristem, cambium, cortex, pith, sheath, silk, ovule or embryo. Other exemplary sorghum plant parts are a meiocyte or gamete or ovule or pollen or endosperm of any of the preceding plants. Other exemplary plant parts are a seed, seed-piece, embryo, protoplast, cell culture, any group of plant cells organized into a structural and functional unit, ratoon or propagule.

The term "promoter" is a DNA sequence that allows the binding of RNA polymerase (including but not limited to RNA polymerase I, RNA polymerase II and RNA polymerase III from eukaryotes) and directs the polymerase to a downstream transcriptional start site of a nucleic acid sequence encoding a polypeptide to initiate transcription. RNA polymerase effectively catalyzes the assembly of messenger RNA complementary to the appropriate DNA strand of the coding region.

A "promoter operably linked to a heterologous gene" is a promoter that is operably linked to a gene that is different from the gene to which the promoter is normally operably linked in its native state. Similarly, an "exogenous nucleic acid operably linked to a heterologous regulatory sequence" is a nucleic acid that is operably linked to a regulatory control sequence to which it is not normally linked in its native state.

The term "recombinant chromosome" refers to an engineered or artificial chromosome that has been constructed by fragmenting a natural chromosome and identifying fragmentation products that are capable of segregation through mitotic and/or meiotic cell divisions. Recombinant chromosomes are distinct from MCs in that they are not constructed in vitro from constituent parts and have not been passaged through an heterologous cell such as a bacteria or fungus (as is commonly used in standard cloning techniques). Recombinant chromosomes may the used as targets for addition of transgene expression cassettes.

The term "Basic MC" is defined as a recombinant DNA construct that when present within a cell is capable of mitotic and/or meiotic transmission to daughter cells under appropriate conditions and comprises a Assembled Centromere and, optionally, one or more of the following: (a) one or more telomeres; (b) one or more sequences for regulating, maintaining, or imparting topological or chromatin structure, molecular integrity, or stability of gene expression or inheritance in a cell; (c) the required vector DNA that allows for propagation of MC in and DNA that facilitates the selective removal of unwanted portions of MC prior to or after transformation; or (d) a Transgene Expression Cassette, wherein the Transgene Expression Cassette serves only to regulate, maintain, or impart function or stability to a MC in a cell.

A "Basic MC" does not include a Transgene Expression Cassette that imparts one or more functions other than those expressly set forth in subsection (d), above.

An "Assembled Centromere" means a polynucleotide sequence having the properties of a Centromere that is assembled from one or more fragments of native Centromere(s) and/or other polynucleotide sequence, which are (i) isolated from a plant cell, and/or based on plant Centromere sequence motifs, (ii) inserted into a plasmid vector that is propagated and maintained in a cell of a heterologous organism, and (iii) delivered back into a plant cell as part of a Basic or Applied MC. An Assembled Centromere may possibly be modified by an endogenous in vivo process after it is delivered into a plant cell such that its sequence now differs from that contained in the parental Basic or Applied MC as propagated in a cell of a heterologous organism. For the avoidance of doubt an Assembled Centromere does not include derivatives or deletions of native Centromeres that are constructed within the plant cell, and are never maintained in their entirety in a cell of a heterologous organism.

An "Applied MC" means a genetic construct formed by integrating one or more Transgene Expression Cassettes into a Basic MC, wherein said Transgene Expression Cassettes impart one or more functions other than to regulate, maintain, or impart function or stability to a MC.

The term "hybrid promoter" is defined herein as parts of two or more promoters that are fused together to generate a sequence that is a fusion of the two or more promoters, which is operably linked to a coding sequence and mediates the transcription of the coding sequence into mRNA.

The term "tandem promoter" is defined herein as two or more promoter sequences each of which is operably linked to a coding sequence and mediates the transcription of the coding sequence into mRNA.

The term "constitutive active promoter" is defined herein as a promoter that allows permanent stable expression of the gene of interest.

The term "Inducible promoter" is defined herein as a promoter induced by the presence or absence of biotic or an abiotic factor.

The term "polypeptide" does not refer to a specific length of the encoded product and, therefore, encompasses peptides, oligopeptides, and proteins. The term "exogenous polypeptide" is defined as a polypeptide which is not native to the plant cell, a native polypeptide in which modifications have been made to alter the native sequence, or a native polypeptide whose expression is quantitatively altered as a result of a manipulation of the plant cell by recombinant DNA techniques.

The term "pseudogene" refers to a non-functional copy of a protein-coding gene; pseudogenes found in the genomes of eukaryotic organisms are often inactivated by mutations and are thus presumed to be non-essential to that organism; pseudogenes of reverse transcriptase and other open reading frames found in retroelements are abundant in the centromeric regions of *Arabidopsis* and other organisms and are often present in complex clusters of related sequences.

The term "regulatory sequence" refers to any DNA sequence that influences the efficiency of transcription or translation of any gene. The term includes, but is not limited to, sequences comprising promoters, enhancers and terminators.

The term "repeated nucleotide sequence" refers to any nucleic acid sequence of at least 25 bp present in a genome or a recombinant molecule, other than a telomere repeat, that occurs at least two or more times and that are preferably at least 80% identical either in head to tail or head to head orientation either with or without intervening sequence between repeat units.

The term "retroelement" or "retrotransposon" refers to a genetic element related to retroviruses that disperse through an RNA stage; the abundant retroelements present in plant genomes contain long terminal repeats (LTR retrotransposons) and encode a polyprotein gene that is processed into several proteins including a reverse transcriptase. Specific retroelements (complete or partial sequences) can be found in and around plant centromeres and can be present as dispersed copies or complex repeat clusters. Individual copies of retroelements may be truncated or contain mutations; intact retroelements are rarely encountered.

The term "satellite DNA" refers to short DNA sequences (typically <1000 bp) present in a genome as multiple repeats, mostly arranged in a tandemly repeated fashion, as opposed to a dispersed fashion. Repetitive arrays of specific satellite repeats are abundant in the centromeres of many higher eukaryotic organisms.

A "screenable marker" is a gene whose presence results in an identifiable phenotype. This phenotype may be observable under standard conditions, altered conditions such as elevated temperature, or in the presence of certain chemicals used to detect the phenotype. The use of a screenable marker allows for the use of lower, sub-killing antibiotic concentrations and the use of a visible marker gene to identify clusters of transformed cells, and then manipulation of these cells to homogeneity. Preferred screenable markers of the present include genes that encode fluorescent proteins that are detectable by a visual microscope such as the fluorescent reporter genes DsRed, ZsGreen, ZsYellow, AmCyan, Green Fluorescent Protein (GFP) and modifications of these reporter genes to excite or emit at altered wavelengths. An additional preferred screenable marker gene is lac.

Alternative methods of screening for modified plant cells may involve use of relatively low, sub-killing concentrations of a selection agent (e.g. sub-killing antibiotic concentrations), and also involve use of a screenable marker (e.g., a visible marker gene) to identify clusters of modified cells carrying the screenable marker, after which these screenable cells are manipulated to homogeneity, a "selectable marker" is a gene whose presence results in a clear phenotype, and most often a growth advantage for cells that contain the marker. This growth advantage may be present under standard conditions, altered conditions such as elevated temperature, specialized media compositions, or in the presence of certain chemicals such as herbicides or antibiotics. Use of selectable markers is described, for example, in Broach et al. (*Gene,* 8:121-133, 1979). Examples of selectable markers include the thymidine kinase gene, the cellular adenine phosphoribosyltransferase gene and the dihydrylfolate reductase gene, hygromycin phosphotransferase genes, the bar gene, neomycin phosphotransferase genes and phosphomannose isomerase, among others. Preferred selectable markers in the present invention include genes whose expression confer antibiotic or herbicide resistance to the host cell, or proteins allowing utilization of a carbon source not normally utilized by plant cells. Expression of one of these markers should be sufficient to enable the survival of those cells that comprise a vector within the host cell, and facilitate the manipulation of the plasmid into new host cells. Of particular interest in the present invention are proteins conferring cellular resistance to kanamycin, G418, paramomycin, hygromycin, bialaphos, and glyphosate for example, or proteins allowing utilization of a carbon source, such as mannose, not normally utilized by plant cells.

The term "stable" means that the MC can be transmitted to daughter cells over at least 8 mitotic generations. Some embodiments of MCs may be transmitted as functional, autonomous units for less than 8 mitotic generations, e.g. 1, 2, 3, 4, 5, 6, or 7. Preferred MCs can be transmitted over at least 8, 9, 10, 11, 12, 13, 14, 15, 16, 17, 18, 18, 19, 20, 21, 22, 23, 24, 25, 26, 27, 28, 29 or 30 generations, for example, through the regeneration or differentiation of an entire plant, and preferably are transmitted through meiotic division to gametes. Other preferred MCs can be further maintained in the zygote derived from such a gamete or in an embryo or endosperm derived from one or more such gametes. A "functional and stable" MC is one in which functional MCs can be detected after transmission of the MCs over at least 8 mitotic generations, or after inheritance through a meiotic division. During mitotic division, as occurs occasionally with native chromosomes, there may be some non-transmission of MCs;

the MC may still be characterized as stable despite the occurrence of such events if an adchromosomal plant that contains descendants of the MC distributed throughout its parts may be regenerated from cells, cuttings, propagules, or cell cultures containing the MC, or if an adchromosomal plant can be identified in progeny of the plant containing the MC.

A "structural gene" is a sequence which codes for a polypeptide or RNA and includes 5' and 3' ends. The structural gene may be from the host into which the structural gene is transformed or from another species. A structural gene will preferably but not necessarily include one or more regulatory sequences which modulate the expression of the structural gene, such as a promoter, terminator or enhancer. A structural gene will preferably but not necessarily confer some useful phenotype upon an organism comprising the structural gene, for example, herbicide resistance. In one embodiment of the invention, a structural gene may encode an RNA sequence which is not translated into a protein, for example a tRNA or rRNA gene.

The term "telomere" or "telomere DNA" refers to a sequence capable of capping the ends of a chromosome, thereby preventing degradation of the chromosome end, ensuring replication and preventing fusion to other chromosome sequences. Telomeres can include naturally occurring telomere sequences or synthetic sequences. Telomeres from one species may confer telomere activity in another species. An exemplary telomere DNA is a heptanucleotide telomere repeat TTTAGGG (and its complement) found in the majority of plants.

"Transformed," "transgenic," "modified," and "recombinant" refer to a host organism such as a plant into which an exogenous or heterologous nucleic acid molecule has been introduced, and includes meiocytes, seeds, zygotes, embryos, endosperm, or progeny of such plant that retain the exogenous or heterologous nucleic acid molecule but which have not themselves been subjected to the transformation process.

When the phrase "transmission efficiency" of a certain percent is used, transmission percent efficiency is calculated by measuring MC presence through one or more mitotic or meiotic generations. It is directly measured as the ratio (expressed as a percentage) of the daughter cells or plants demonstrating presence of the MC to parental cells or plants demonstrating presence of the MC. Presence of the MC in parental and daughter cells is demonstrated with assays that detect the presence of an exogenous nucleic acid carried on the MC. Exemplary assays can be the detection of a screenable marker (e.g. presence of a fluorescent protein or any gene whose expression results in an observable phenotype), a selectable marker, or PCR amplification of any exogenous nucleic acid carried on the MC.

I. Constructing MCs by Site-Specific Recombination

Plant MCs may be constructed using site-specific recombination sequences (for example those recognized by the bacteriophage P1 Cre recombinase, or the bacteriophage lambda integrase, or similar recombination enzymes). A compatible recombination site, or a pair of such sites, is present on both the centromere containing DNA clones and the donor DNA clones. Incubation of the donor clone and the centromere clone in the presence of the recombinase enzyme causes strand exchange to occur between the recombination sites in the two plasmids; the resulting MCs contain centromere sequences as well as MC vector sequences. The DNA molecules formed in such recombination reactions is introduced into *E. coli*, other bacteria, yeast or plant cells by common methods in the field including, but not limited to, heat shock, chemical transformation, electroporation, particle bombardment, whiskers, or other transformation methods followed by selection for marker genes including chemical, enzymatic, color, or other marker present on either parental plasmid, allowing for the selection of transformants harboring MCs.

II. Methods of Detecting and Characterizing MCs in Plant Cells or of Scoring MC Performance in Plant Cells Identification of Candidate Centromere Fragments by Probing BAC Libraries Centromere clones are identified from a large genomic insert library such as a Bacterial Artificial Chromosome library. Probes are labeled using nick-translation in the presence of radioactively labeled dCTP, dATP, dGTP or dTTP as in, for example, the commercially available REDIPRIME™ kit (GE Healthcare; Piscataway, N.J.; USA) as per the manufacturer's instructions. Other labeling methods familiar to those skilled in the art could be substituted. The libraries are screened and deconvoluted. Genomic clones are screened by probing with small centromere-specific clones. Other embodiments of this procedure would involve hybridizing a library with other centromere sequences. Of the BAC clones identified using this procedure, a representative set are identified as having high hybridization signals to some probes, and optionally low hybridization signals to other probes. These are selected, the bacterial clones grown up in cultures and DNA prepared by methods familiar to those skilled in the art such as alkaline lysis. The DNA composition of purified clones is surveyed using for example fingerprinting by digesting with restriction enzymes such as, but not limited to, HinfI or HindIII. In a preferred embodiment the restriction enzyme cuts within the tandem centromere satellite repeat (see below). A variety of clones showing different fingerprints are selected for conversion into MCs and inheritance testing. It can also be informative to use multiple restriction enzymes for fingerprinting or other enzymes which can cleave DNA.

Fingerprinting Analysis of BACs and MCs

Centromere function may be associated with large tandem arrays of satellite repeats. To assess the composition and architecture of the centromere BACs, the candidate BACs are digested with a restriction enzyme, such as HindIII, which cuts with known frequency within the consensus sequence of the unit repeat of the tandemly repeated centromere satellite. Digestion products are then separated by agarose gel electrophoresis. Large insert clones containing a large array of tandem repeats will produce a strong band of the unit repeat size, as well as less intense bands at 2× and 3× the unit repeat size, and further multiples of the repeat size. These methods are well-known and there are many possible variations known to those skilled in the art.

Determining Sequence Composition of MCs by Shotgun Cloning/Sequencing, Sequence Analysis To determine the sequence composition of the MC, the centromeric region of the MC is sequenced. To generate DNA suitable for sequencing MCs are fragmented, for example by using a random shearing method (such as sonication, nebulization, etc). Other fragmentation techniques may also be used such as enzymatic digestion. These fragments are then cloned into a plasmid vector and sequenced. The resulting DNA sequence is trimmed of poor-quality sequence and of sequence corresponding to the plasmid vector. The sequence is then compared to known DNA sequences using an algorithm such as BLAST to search a sequence database such as GenBank.

To determine the consensus of the satellite repeat in the MC, the sequences containing satellite repeat are aligned using a DNA sequence alignment program such as CONTIGEXPRESS® from Vector NTI®. The sequences may also be aligned to previously determined repeats for that species.

The sequences are trimmed to unit repeat length using the consensus as a template. Sequences trimmed from the ends of the alignment are realigned with the consensus and further trimmed until all sequences are at or below the consensus length. The sequences are then aligned with each other. The consensus is determined by the frequency of a specific nucleotide at each position; if the most frequent base is three times more frequent than the next most frequent base, it was considered the consensus.

Methods for determining consensus sequence are well known in the art, see, e.g., US Pat. App. Pub. No. 20030124561; Hall et al. *Plant Physiol.* 129:1439-1447, 2002. These methods, including DNA sequencing, assembly, and analysis, are well-known and there are many possible variations known to those skilled in the art. Other alignment parameters may also be useful such as using more or less stringent definitions of consensus.

Non-Selective MC Mitotic Inheritance Assays

The following list of assays and potential outcomes illustrates how various assays can be used to distinguish autonomous events from integrated events.

Assay #1: Transient Assay

MCs are tested for their ability to become established as chromosomes and their ability to be inherited in mitotic cell divisions. In this assay, MCs are delivered to plant cells, for example suspension cells in liquid culture. The cells used can be at various stages of growth. In this example, a population in which some cells were undergoing division was used. The MC is then assessed over the course of several cell divisions, by tracking the presence of a screenable marker, e.g. a visible marker gene such as a fluorescent protein. MCs that are established and inherited well may show an initial delivery into many single cells; after several cell divisions, these single cells divide to form clusters of MC-containing cells. Other exemplary embodiments of this method include delivering MCs to other mitotic cell types, including roots and shoot meristems.

Assay #2: Non-Lineage Based Inheritance Assays on Modified Transformed Cells and Plants MC inheritance is assessed on modified cell lines and plants by following the presence of the MC over the course of multiple cell divisions. An initial population of MC containing cells is assayed for the presence of the MC, by the presence of a marker gene, including but not limited to a fluorescent protein, a colored protein, a protein assayable by histochemical assay, and a gene affecting cell morphology. In the use of a DNA-specific dye, all nuclei are stained with a dye including but not limited to DAPI, Hoechst 33258, OliGreen, Giemsa YOYO, or TOTO, allowing a determination of the number of cells that do not contain the MC. After the initial determination of the percent of cells carrying the MC, the cells are allowed to divide over the course of several cell divisions. The number of cell divisions, n, is determined by a method including but not limited to monitoring the change in total weight of cells, and monitoring the change in volume of the cells or by directly counting cells in an aliquot of the culture. After a number of cell divisions, the population of cells is again assayed for the presence of the MC. The loss rate per generation is calculated by the equation (1):

$$\text{Loss rate per generation} = 1-(F/I)^{1/n} \quad (1)$$

The population of MC-containing cells may include suspension cells, callus, roots, leaves, meristems, flowers, or any other tissue of modified plants, or any other cell type containing a MC.

These methods are well-known and there are many possible variations known to those skilled in the art; they have been used before with human cells and yeast cells.

Assay #3: Lineage Based Inheritance Assays on Modified Cells and Plants

MC inheritance is assessed on cell lines and plants comprising the MCs by following the presence of the MC over the course of multiple cell divisions. In cell types that allow for tracking of cell lineage, including but not limited to root or leaf cell files, trichomes, and leaf stomata guard cells, MC loss per generation does not need to be determined statistically over a population, it can be discerned directly through successive cell divisions. In other manifestations of this method, cell lineage can be discerned from cell position, or methods including but not limited to the use of histological lineage tracing dyes, and the induction of genetic mosaics in dividing cells.

In one simple example, the two guard cells of the stomata are daughters of a single precursor cell. To assay MC inheritance in this cell type, the epidermis of the leaf of a plant containing a MC is examined for the presence of the MC by the presence of a marker gene, including but not limited to a fluorescent protein, a colored protein, a protein assayable by histochemical assay, and a gene affecting cell morphology. The number of loss events in which one guard cell contains the MC (L) and the number of cell divisions in which both guard cells contain the MC (B) are counted. The loss rate per cell division is determined as L/(L+B). Other lineage-based cell types are assayed in similar fashion. These methods are well-known and there are many possible variations known to those skilled in the art; they have been used before with yeast cells (though, instead of observing the marker in stomates, a color marker was observed in yeast colonies).

Linear MC inheritance may also be assessed by examining leaf or root files or clustered cells in callus over time. Changes in the percent of cells carrying the MC will indicate the mitotic inheritance.

Assay #4: Inheritance Assays on Modified Cells and Plants in the Presence of Chromosome Loss Agents Any of the above three assays can be done in the presence of chromosome loss agents (including but not limited to colchicine, colcemid, caffeine, etopocide, nocodazole, oryzalin, trifluran). It is likely that an autonomous MC will prove more susceptible to loss induced by chromosome loss agents; therefore, autonomous MCs should show a lower rate of inheritance in the presence of chromosome loss agents. These methods have been used to study chromosome loss in fruit flies and yeast; there are many possible variations known to those skilled in the art.

III. Transformation of Plant Cells and Plant Regeneration

Various methods may be used to deliver DNA into plant cells. These include biological methods, such as *Agrobacterium, E. coli*, and viruses, physical methods such as biolistic particle bombardment, nanocopoea device, the Stein beam gun, silicon carbide whiskers and microinjection, electrical methods such as electroporation, and chemical methods such as the use of poly-ethylene glycol and other compounds known to stimulate DNA uptake into cells. Examples of these techniques have been described (Paszkowski et al., *EMBO J.* 3:2717-2722, 1984); Potrykus et al., *Mol. Gen. Genet.* 199: 169-177. 1985; Reich et al., *Biotechnol.* 4:1001-1004; 1986; and Klein et al., *Nature* 327:70-73, 1987). Transformation using silicon carbide whiskers, e.g. in maize, is described in Brisibe (*J. Exp. Bot.* 51:187-196, 2000) and Dunwell (*Methods Mol. Biol.* 111:375-82, 1999) and U.S. Pat. No. 5,464,765.

*Agrobacterium*-Mediated Delivery

*Agrobacterium*-mediated transformation is one method for introducing a desired genetic element into a plant. Several *Agrobacterium* species mediate the transfer of a specific DNA known as "T-DNA" that can be genetically engineered to carry a desired piece of DNA into many plant species. Plasmids used for delivery contain the T-DNA flanking the nucleic acid to be inserted into the plant. The major events marking the process of T-DNA mediated pathogenesis are induction of virulence genes, processing and transfer of T-DNA.

There are three common methods to transform plant cells with *Agrobacterium*. The first method is co-cultivation of *Agrobacterium* with cultured isolated protoplasts. This method requires an established culture system that allows culturing protoplasts and plant regeneration from cultured protoplasts. The second method is transformation of cells or tissues with *Agrobacterium*. This method requires (a) that the plant cells or tissues can be modified by *Agrobacterium* and (b) that the modified cells or tissues can be induced to regenerate into whole plants. The third method is transformation of seeds, immature or mature embryos, apices or meristems with *Agrobacterium*. This method requires exposure of the meristematic cells of these tissues to *Agrobacterium* and micropropagation of the shoots or plan organs arising from these meristematic cells.

Those of skill in the art are familiar with procedures for growth and suitable culture conditions for *Agrobacterium* as well as subsequent inoculation procedures. Liquid, solid or semi-solid culture media can be used. The density of the *Agrobacterium* culture used for inoculation and the ratio of *Agrobacterium* cells to explant can vary from one system to the next, as can media, growth procedures, timing and lighting conditions.

Transformation of dicotyledons using *Agrobacterium* has long been known in the art, and transformation of monocotyledons using *Agrobacterium* has also been described. See, WO 94/00977 and U.S. Pat. No. 5,591,616, both of which are incorporated herein by reference. See also, Negrotto et al. (*Plant Cell Rep.* 19:798-803, 2000, incorporated herein by reference).

A number of wild-type and disarmed strains of *Agrobacterium tumefaciens* and *Agrobacterium rhizogenes* harboring Ti or Ri plasmids can be used for gene transfer into plants. Preferably, the *Agrobacterium* hosts contain disarmed Ti and Ri plasmids that do not contain the oncogenes that cause tumorigenesis or rhizogenesis. Exemplary strains include *Agrobacterium tumefaciens* strain C58, a nopaline-type strain that is used to mediate the transfer of DNA into a plant cell, octopine-type strains such as LBA4404 or succinamopine-type strains, e.g., EHA101 or EHA105. The use of these strains for plant transformation has been reported and the methods are familiar to those of skill in the art.

US Application No. 20040244075 published Dec. 2, 2004 describes improved methods of *Agrobacterium*-mediated transformation. The efficiency of transformation by *Agrobacterium* may be enhanced by using a number of methods known in the art. For example, the inclusion of a natural wound response molecule such as acetosyringone (AS) to the *Agrobacterium* culture has been shown to enhance transformation efficiency with *Agrobacterium tumefaciens* (Shahla et al., (1987) *Plant Molec. Biol.* 8:291-298). Alternatively, transformation efficiency may be enhanced by wounding the target tissue to be modified or transformed. Wounding of plant tissue may be achieved, for example, by punching, maceration, bombardment with microprojectiles, etc. (See e.g., Bidney et al., *Plant Molec. Biol.* 18:301-313, 1992).

In addition, another recent method described by Broothaerts, et al. (*Nature* 433:629-633, 2005) expands the bacterial genera that can be used to transfer genes into plants. This work involved the transfer of a disarmed Ti plasmid without T-DNA and another vector with T-DNA containing the marker enzyme beta-glucuronidase, into three different bacteria. Gene transfer was successful and this method significantly expands the tools available for gene delivery into plants.

Microprojectile Bombardment Delivery

Another widely used technique to genetically transform plants involves the use of microprojectile bombardment. In this process, a nucleic acid containing the desired genetic elements to be introduced into the plant is deposited on or in small dense particles, e.g., tungsten, platinum, or preferably 0.5 to 1.0 micron gold particles, which are then delivered at a high velocity into the plant tissue or plant cells using a specialized biolistics device. Many such devices have been designed and constructed; one in particular, the PDS1000/He sold by Bio-Rad Laboratories (Hercules, Calif.; USA), is the instrument most commonly used for biolistics of plant cells. The advantage of this method is that no specialized sequences need to be present on the nucleic acid molecule to be delivered into plant cells; delivery of any nucleic acid sequence is theoretically possible.

For the bombardment, cells in suspension are concentrated on filters, petri dishes or solid culture medium. Alternatively, immature embryos, seedling explants, or any plant tissue or target cells may be arranged on filters, petri dishes or solid culture medium. The cells to be bombarded are positioned at an appropriate distance below the microprojectile stopping plate.

Various biolistics protocols have been described that differ in the type of particle or the manner in which DNA is coated onto the particle. Any technique for coating microprojectiles that allows for delivery of transforming DNA to the target cells may be used. For example, particles may be prepared by functionalizing the surface of a gold particle by providing free amine groups. DNA, having a strong negative charge, will then bind to the functionalized particles.

Parameters such as the concentration of DNA used to coat microprojectiles may influence the recovery of transformants containing a single copy of the transgene. For example, a lower concentration of DNA may not necessarily change the efficiency of the transformation but may instead increase the proportion of single copy insertion events. In this regard, ranges of approximately 1 ng to approximately 10 μg (10,000 ng), approximately 5 ng to 8 μg or approximately 20 ng, 50 ng, 100 ng, 200 ng, 500 ng, 1 μg, 2 μg, 5 μg, or 7 μg of transforming DNA may be used per each 1.0-2.0 mg of starting gold particles (in the 0.5 to 1.0 micron range).

Other physical and biological parameters may be varied, such as manipulation of the DNA/microprojectile precipitate, factors that affect the flight and velocity of the projectiles, manipulation of the cells before and immediately after bombardment (including osmotic state, tissue hydration and the subculture stage or cell cycle of the recipient cells), the orientation of an immature embryo or other target tissue relative to the particle trajectory, and also the nature of the transforming DNA, such as linearized DNA or intact supercoiled plasmids. One may also want to use agents to protect the DNA during delivery. One may particularly wish to adjust physical parameters such as DNA concentration, gap distance, flight distance, tissue distance, and helium pressure.

The particles delivered via biolistics can be "dry" or "wet." In the "dry" method, the MC DNA-coated particles such as gold are applied onto a macrocarrier (such as a metal plate, or a carrier sheet made of a fragile material such as mylar) and dried. The gas discharge then accelerates the macrocarrier into a stopping screen, which halts the macrocarrier but allows the particles to pass through; the particles then continue their trajectory until they impact the tissue being bombarded. For the "wet" method, the droplet containing the MC DNA-coated particles is applied to the bottom part of a filter holder, which is attached to a base which is itself attached to a rupture disk holder used to hold the rupture disk to the helium egress tube for bombardment. The gas discharge directly displaces the DNA/gold droplet from the filter holder and accelerates the particles and their DNA cargo into the tissue being bombarded. The wet biolistics method has been described in detail elsewhere but has not previously been applied in the context of plants (Mialhe et al., Mol Mar Biol Biotechnol. 4(4):275-83, 1995). The concentrations of the various components for coating particles and the physical parameters for delivery can be optimized using procedures known in the art.

A variety of plant cells/tissues are suitable for transformation, including immature embryos, scutellar tissue, suspension cell cultures, immature inflorescence, shoot meristem, epithelial peels, nodal explants, callus tissue, hypocotyl tissue, cotyledons, roots, leaves, meristem cells, and gametic cells such as microspores, pollen, sperm and egg cells. It is contemplated that any cell from which a fertile plant may be regenerated is useful as a recipient cell. Callus may be initiated from tissue sources including, but not limited to, immature embryos, seedling apical meristems, microspore-derived embryos, roots, hypocotyls, cotyledons and the like. Those cells which are capable of proliferating as callus also are recipient cells for genetic transformation.

Any suitable plant culture medium can be used. Examples of suitable media would include but are not limited to MS-based media (Murashige and Skoog, *Physiol. Plant,* 15:473-497, 1962) or N6-based media (Chu et al., *Scientia Sinica* 18:659, 1975) supplemented with additional plant growth regulators including but not limited to auxins such as picloram (4-amino-3,5,6-trichloropicolinic acid), 2,4-D (2,4-dichlorophenoxyacetic acid), naphalene-acetic acid (NAA) and dicamba (3,6-dichloroanisic acid), cytokinins such as BAP (6-benzylaminopurine) and kinetin, and gibberellins. Other media additives can include but are not limited to amino acids, macroelements, iron, microelements, vitamins and organics, carbohydrates, undefined media components such as casein hydrolysates, an appropriate gelling agent such as a form of agar, a low melting point agarose or Gelrite if desired. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Examples of such media would include but are not limited to Murashige and Skoog, N6, Linsmaier and Skoog (*Physio. Plant,* 18:100, 1965), Uchimiya and Murashige (*Plant Physiol.* 15:473, 1962), Gamborg's B5 media (*Exp. Cell Res.,* 50:151, 1968), D medium (Duncan et al., *Planta,* 165:322-332, 1985), McCown's Woody plant media (McCown and Lloyd, *HortScience* 6:453, 1981), Nitsch and Nitsch (*Science* 163:85-87, 1969), and Schenk and Hildebrandt (*Can. J. Bot.* 50:199-204, 1972) or derivations of these media supplemented accordingly. Those of skill in the art are aware that media and media supplements such as nutrients and growth regulators for use in transformation and regeneration and other culture conditions such as light intensity during incubation, pH, and incubation temperatures can be varied.

Those of skill in the art are aware of the numerous modifications in selective regimes, media, and growth conditions that can be varied depending on the plant system and the selective agent. Typical selective agents include but are not limited to antibiotics such as geneticin (G418), kanamycin, paromomycin or other chemicals such as glyphosate or other herbicides. Consequently, such media and culture conditions disclosed in the present invention can be modified or substituted with nutritionally equivalent components, or similar processes for selection and recovery of transgenic events, and still fall within the scope of the present invention.

MC Delivery without Selection

The MC is delivered to plant cells or tissues, e.g., plant cells in suspension to obtain stably modified callus clones for inheritance assay. Suspension cells are maintained in a growth media, for example MS liquid medium containing an auxin such as 2,4-dichlorophenoxyacetic acid (2,4-D). Cells are bombarded using a particle bombardment process, such as the helium-driven PDS-1000/He system, and propagated in the same liquid medium to permit the growth of modified and non-modified cells. Portions of each bombardment are monitored for formation of fluorescent clusters, which are isolated by micromanipulation and cultured on solid medium. Clones modified with the MC are expanded and homogenous clones are used in inheritance assays, or assays measuring MC structure or autonomy.

MC Transformation with Selectable Marker Gene

Isolation of MC-modified cells in bombarded calluses or explants can be facilitated by the use of a selectable marker gene. The bombarded tissues are transferred to a medium containing an appropriate selective agent for a particular selectable marker gene. Such a transfer usually occurs between 0 and about 7 days after bombardment. The transfer could also take place any number of days after bombardment. The amount of selective agent and timing of incorporation of such an agent in selection medium can be optimized by using procedures known in the art. Selection inhibits the growth of non-modified cells, thus providing an advantage to the growth of modified cells, which can be further monitored by tracking the presence of a fluorescent marker gene or by the appearance of modified explants (modified cells or explants may be green under light in selection medium, while surrounding non-modified cells are weakly pigmented). In plants that develop through shoot organogenesis, the modified cells can form shoots directly, or alternatively, can be isolated and expanded for regeneration of multiple shoots transgenic for the MC. In plants that develop through embryogenesis, additional culturing steps may be necessary. *Sorghum* can be regenerated through embryogenesis (Wernicke & Brettell, *Nature* 287:138-139, 1990; and Bhaskaran and Smith, *In Vitro Cell. Devel. Biol. Plant* 24:65-70, 1987) and can also be regenerated by shoot organogenesis (Nirwan and Kothari, *J. Plant Biochem. Biotech.,* 13:149-152, 2004).

Useful selectable marker genes are well known in the art and include, for example, herbicide and antibiotic resistance genes including but not limited to neomycin phosphotransferase II (conferring resistance to kanamycin, paramomycin and G418), hygromycin phosphotransferase (conferring resistance to hygromycin), 5-enolpyruvylshikimate-3-phosphate synthase (EPSPS, conferring resistance to glyphosate), phosphinothricin acetyltransferase (conferring resistance to phosphinothricin/bialophos), MerA (conferring resistance to mercuric ions). Selectable marker genes may be transformed using standard methods in the art.

The first step in the production of plants containing novel genes involves delivery of DNA into a suitable plant tissue (described in the previous section) and selection of the tissue under conditions that allow preferential growth of any cells containing the novel genes. Selection is typically achieved with a selectable marker gene present in the delivered DNA, which may be a gene conferring resistance to an antibiotic, herbicide or other killing agent, or a gene allowing utilization of a carbon source not normally metabolized by plant cells. For selection to be effective, the plant cells or tissue need to be grown on selective medium containing the appropriate concentration of antibiotic or killing agent, and the cells need to be plated at a defined and constant density. The concentration of selective agent and cell density are generally chosen to cause complete growth inhibition of wild type plant tissue that does not express the selectable marker gene; but allowing cells containing the introduced DNA to grow and expand into adchromosomal clones. This critical concentration of selective agent typically is the lowest concentration at which there is complete growth inhibition of wild type cells, at the cell density used in the experiments. However, in some cases, sub-killing concentrations of the selective agent may be equally or more effective for the isolation of plant cells containing MC DNA, especially in cases where the identification of such cells is assisted by a visible marker gene (e.g., fluorescent protein gene) present on the MC. Such sub-killing concentrations of the selective agent may be administered during part or all of the selection timing.

In some species (e.g., tobacco or tomato), a homogenous clone of modified cells can also arise spontaneously when bombarded cells are placed under the appropriate selection. An exemplary selective agent is the neomycin phosphotransferase II (nptII) marker gene, which is commonly used in plant biotechnology and confers resistance to the antibiotics kanamycin, G418 (geneticin) and paramomycin. In other species, or in certain plant tissues or when using particular selectable markers, homogeneous clones may not arise spontaneously under selection; in this case the clusters of modified cells can be manipulated to homogeneity using the visible marker genes present on the MCs as an indication of which cells contain MC DNA.

Regeneration of Modified Plants from Explants to Mature, Rooted Plants

In instances where shoot organogenesis is less efficient or for other reasons undesirable, an embryogenic step is necessary for regeneration. In these cases explant tissue is cultured on an appropriate media for embryogenesis, and the embryo is cultured until shoots form. The regenerated shoots are cultured in a rooting medium to obtain intact whole plants with a fully developed root system. These plants are potted in soil and grown to maturity in a greenhouse.

Generally, regeneration and tissue culture of sorghum plant parts and whole plants is challenging as sorghum produces phenolic compounds while in culture. The present invention provides for methods of culturing sorghum cells and tissues in media containing polyvinylpyrrolidone (PVP), see Examples, below. The PVP acts as a sink for the phenolic compounds produced by sorghum and enhances callus growth during selection as well as facilitating callus and plantlet regeneration. Furthermore, generation of sorghum callus can be facilitated by delivering to the plant cells and/or tissues MCs of the invention that contain auxin genes. The presence of the auxin genes will facilitate callus induction of the transformed tissue. The invention also provides for tissue culture methods which cycle between the liquid culture media and solid culture media in order to promote the frequency and the morphogenic competence of the regenerable sorghum callus.

For plants that develop through shoot organogenesis, regeneration of a whole plant involves culturing of regenerable explant tissues taken from sterile organogenic callus tissue, seedlings or mature plants on a shoot regeneration medium for shoot organogenesis, and rooting of the regenerated shoots in a rooting medium to obtain intact whole plants with a fully developed root system. These plants are potted in soil and grown to maturity in a greenhouse.

Explants are obtained from any tissues of a plant suitable for regeneration. Exemplary tissues include hypocotyls, internodes, roots, cotyledons, petioles, cotyledonary petioles, leaves and peduncles, prepared from sterile seedlings or mature plants.

Explants are wounded (for example with a scalpel or razor blade) and cultured on a shoot regeneration medium (SRM) containing Murashige and Skoog (MS) medium as well as a cytokinin, e.g., 6-benzylaminopurine (BA), and an auxin, e.g., α-naphthaleneacetic acid (NAA), and an anti-ethylene agent, e.g., silver nitrate ($AgNO_3$). For example, 2 mg/L of BA, 0.05 mg/L of NAA, and 2 mg/L of $AgNO_3$ can be added to MS medium for shoot organogenesis. The most efficient shoot regeneration is obtained from longitudinal sections of internode explants.

Shoots regenerated via organogenesis are rooted in a MS medium. Plants are potted and grown in a greenhouse to sexual maturity for seed harvest.

To regenerate a whole plant with a MC, explants are pre-incubated for 1 to 7 days (or longer) on the shoot regeneration medium prior to bombardment with MC (see below). Following bombardment, explants are incubated on the same shoot regeneration medium for a recovery period up to 7 days (or longer), followed by selection for transformed shoots or clusters on the same medium but with a selective agent appropriate for a particular selectable marker gene (see below).

Method of Co-Delivering Growth Inducing Genes to Facilitate Isolation of Modified Plant Cell Clones Another method used in the generation of cell clones containing MCs involves the co-delivery of DNA containing genes that are capable of activating growth of plant cells, or that promote the formation of a specific organ, embryo or plant structure that is capable of self-sustaining growth. In one embodiment, the recipient cell receives simultaneously the MC, and a separate DNA molecule encoding one or more growth promoting, organogenesis-promoting, embryogenesis-promoting or regeneration-promoting genes. Following DNA delivery, expression of the plant growth regulator genes stimulates the plant cells to divide, or to initiate differentiation into a specific organ, embryo, or other cell types or tissues capable of regeneration. Multiple plant growth regulator genes can be combined on the same molecule, or co-bombarded on separate molecules. Use of these genes can also be combined with application of plant growth regulator molecules into the medium used to culture the plant cells, or of precursors to such molecules that are converted to functional plant growth regulators by the plant cell's biosynthetic machinery, or by the genes delivered into the plant cell.

The co-bombardment strategy of MCs with separate DNA molecules encoding plant growth regulators transiently supplies the plant growth regulator genes for several generations of plant cells following DNA delivery. During this time, the MC may be stabilized by virtue of its centromere, but the DNA molecules encoding plant growth regulator genes, or organogenesis-promoting, embryogenesis-promoting or regeneration-promoting genes will tend to be lost. The transient expression of these genes, prior to their loss, may give the cells containing MC DNA a sufficient growth advantage, or sufficient tendency to develop into plant organs, embryos or a regenerable cell cluster, to outgrow the non-modified cells in their vicinity, or to form a readily identifiable structure that is not formed by non-modified cells. Loss of the DNA molecule encoding these genes will prevent phenotypes from manifesting themselves that may be caused by these genes if present through the remainder of plant regeneration. In rare cases, the DNA molecules encoding plant growth regulator genes will integrate into the host plant's genome or into the MC.

Alternatively the genes promoting plant cell growth may be genes promoting shoot formation or embryogenesis, or giving rise to any identifiable organ, tissue or structure that can be regenerated into a plant. In this case, it may be possible to obtain embryos or shoots harboring MCs directly after DNA delivery, without the need to induce shoot formation with growth activators supplied into the medium, or lowering the growth activator treatment necessary to regenerate plants. The advantages of this method are more rapid regeneration, higher transformation efficiency, lower background growth of non-modified tissue, and lower rates of morphologic abnormalities in the regenerated plants (due to shorter and less intense treatments of the tissue with chemical plant growth activators added to the growth medium).

Determination of MC Structure and Autonomy in Adchromosomal Plants and Tissues

The structure and autonomy of the MC in adchromosomal plants and tissues can be determined by methods including but not limited to: conventional and pulsed-field Southern blot hybridization to genomic DNA from modified tissue subjected or not subjected to restriction endonuclease digestion, dot blot hybridization of genomic DNA from modified tissue hybridized with different MC specific sequences, MC rescue, exonucleas activity, PCR on DNA from modified tissues with probes specific to the MC, or Fluorescence Hybridization (FISH) to nuclei of modified cells. Table 3 below summarizes these methods.

TABLE 3

Examples of methods to determin MC structure and autonomy

| Assay | Assay details | Potential outcome | Interpretation |
|---|---|---|---|
| Southern blot | Restriction digest of genomic DNA* compared to purified MC | 1. Native sizes and pattern of bands | 1. Autonomous or integrated via CEN fragment |
| | | 2. Altered sizes or pattern of bands | 2. Integrated or rearranged |
| CHEF gel Southern blot | Restriction digest of genomic DNA compared to purified MC | 1. Native sizes and pattern of bands | 1. Autonomous or integrated via CEN fragment |
| | | 2. Altered sizes or pattern of bands | 2. Integrated or rearranged |
| | Native genomic DNA (no digest) | 1. MC band migrating ahead of genomic DNA | 1. Autonomous circles or linears present in plant |
| | | 2. MC band co-migrating with genomic DNA | 2. Integrated |
| | | 3. >1 MC bands observed | 3. Various possibilities |
| Exonuclease assay | Exonuclease digestion of genomic DNA followed by detection of circular MC by PCR, dot blot, or restriction digest (optional), electrophoresis and southern blot (useful for circular MCs) | 1. Signal strength close to that w/o exonuclease | 1. Autonomous circles present |
| | | 2. No signal or signal strength lower that w/o exonuclease | 2. Integrated |
| MC rescue | Transformation of plant genomic DNA into *E. coli* followed by selection for antibiotic resistance genes on MC | 1. Colonies isolated only from MC plants with MCs, not from controls; MC structure matches that of the parental MC | 1. Autonomous circles present, native MC structure |
| | | 2. Colonies isolated only from MC plants with MCs, not from controls; MC structure different from parental MC | 2. Autonomous circles present, rearranged MC structure OR MCs integrated via centromere fragment |
| | | 3. Colonies observed both in MC-modified plants and in controls | 3. Various possibilities |
| PCR | PCR amplification of various parts of the MC | 1. All MC parts detected by PCR | 1. Complete MC sequences present in plant |
| | | 2. Subset of MC parts detected by PCR | 2. Partial MC sequences present in plant |
| FISH | Detection of MC sequences in mitotic or meiotic nuclei by fluorescence in situ hybridization | 1. MC sequences detected, free of genome | 1. Autonomous |
| | | 2. MC sequences detected, associated with genome | 2. Integrated |
| | | 3. MC sequences detected, both free and associated with genome | 3. Both autonomous and integrated MC sequences present |
| | | 4. No MC sequences detected | 4. MC DNA not visible by FISH |

*Genomic DNA refers to total DNA extracted from plants containing a MC

Furthermore, MC structure can be examined by characterizing MCs 'rescued' from adchromosomal cells. Circular MCs that contain bacterial sequences for their selection and propagation in bacteria can be rescued from an adchromosomal plant or plant cell and re-introduced into bacteria. If no loss of sequences has occurred during replication of the MC in plant cells, the MC is able to replicate in bacteria and confer antibiotic resistance. Total genomic DNA is isolated from the adchromosomal plant cells by any method for DNA isolation known to those skilled in the art, including but not limited to a standard cetyltrimethylammonium bromide (CTAB) based method (*Current Protocols in Molecular Biology*. John Wiley & Sons, NY, 1994 et seq.) The purified genomic DNA is introduced into bacteria (e.g., *E. coli*) using methods familiar to one skilled in the art (for example heat shock or electroporation). The transformed bacteria are plated on solid medium containing antibiotics to select bacterial clones modified with MC DNA. Modified bacterial clones are grown up, the plasmid DNA purified (by alkaline lysis for example), and DNA analyzed by restriction enzyme digestion and gel electrophoresis or by sequencing. Because plant-methylated DNA containing methylcytosine residues will be degraded by wild-type strains of *E. coli*, bacterial strains (e.g. DH10B) deficient in the genes encoding methylation restriction nucleases (e.g. the mcr and mrr gene loci in *E. coli*) are best suited for this type of analysis. MC rescue can be performed on any plant tissue or clone of plant cells comprising a MC.

MC Autonomy Demonstration by In Situ Hybridization (ISH)

To assess whether the MC is autonomous from the native plant chromosomes, or has integrated into the plant genome, In Situ Hybridization is carried out (Fluorescent In Situ Hybridization or FISH is particularly well suited to this purpose). In this assay, mitotic or meiotic tissue, such as root tips or meiocytes from the anther, possibly treated with metaphase arrest agents such as colchicines or nitrous oxide is obtained, and standard FISH methods are used to label both the centromere and sequences specific to the MC. For example, a sorghum centromere is labeled using a probe from a sequence that labels all sorghum centromeres, attached to one fluorescent tag (Molecular Probes Alexafluor 568, for example), and sequences specific to the MC are labeled with another fluorescent tag (Alexafluor 488, for example). All centromere sequences are detected with the first tag; only MCs are detected with both the first and second tag. Chromosomes are stained with a DNA-specific dye including but not limited to DAPI, Hoechst 33258, OliGreen, Giemsa YOYO, and TOTO. An autonomous MC is visualized as a body that shows hybridization signal with both centromere probes and MC specific probes and is separate from the native chromosomes.

Determination of Gene Expression Levels

The expression level of any gene present on the MC can be determined by methods including but not limited to one of the following. The mRNA level of the gene can be determined by Northern Blot hybridization, Reverse Transcriptase-Polymerase Chain Reaction, binding levels of a specific RNA-binding protein, in situ hybridization, or dot blot hybridization.

The protein level of the gene product can be determined by Western blot hybridization, Enzyme-Linked Immunosorbant Assay (ELISA), fluorescent quantitation of a fluorescent gene product, enzymatic quantitation of an enzymatic gene product, immunohistochemical quantitation, or spectroscopic quantitation of a gene product that absorbs a specific wavelength of light.

Use of Exonuclease to Isolate Circular MC DNA from Genomic DNA

Exonucleases may be used to obtain pure MC DNA, suitable for isolation of MCs from *E. coli* or from plant cells. The method assumes a circular structure of the MC. A DNA preparation containing MC DNA and genomic DNA from the source organism is treated with exonuclease, for example lambda exonuclease combined with *E. coli* exonuclease I, or the ATP-dependent exonuclease (Qiagen Inc.; Valencia, Calif.; USA). Because the exonuclease is only active on DNA ends, it will specifically degrade the linear genomic DNA fragments, but will not affect the circular MC DNA. The result is MC DNA in pure form. The resultant MC DNA can be detected by a number of methods for DNA detection known to those skilled in the art, including but not limited to PCR, dot blot followed by hybridization analysis, and southern blot followed by hybridization analysis. Exonuclease treatment followed by detection of resultant circular MC may be used as a method to determine MC autonomy.

Structural Analysis of MCs by BAC-End Sequencing

BAC-end sequencing procedures, known to those skilled in the art, can be applied to characterize MC clones for a variety of purposes, such as structural characterization, determination of sequence content, and determination of the precise sequence at a unique site on the chromosome (for example the specific sequence signature found at the junction between a centromere fragment and the vector sequences). In particular, this method is useful to prove the relationship between a parental MC and the MCs descended from it and isolated from plant cells by MC rescue, described above. This method also fosters identification of specific sorghum MCs if more than one unique sorghum MC is present in a plant cell simultaneously.

Methods for Scoring Meiotic MC Inheritance

A variety of methods can be used to assess the efficiency of meiotic MC transmission. In one embodiment of the method, gene expression of genes encoded by the MC (marker genes or non-marker genes) can be scored by any method for detection of gene expression known to those skilled in the art, including but not limited to visible methods (e.g. fluorescence of fluorescent protein markers, scoring of visible phenotypes of the plant), scoring resistance of the plant or plant tissues to antibiotics, herbicides or other selective agents, by measuring enzyme activity of proteins encoded by the MC, or measuring non-visible plant phenotypes, or directly measuring the RNA and protein products of gene expression using microarray, northern blots, in situ hybridization, dot blot hybridization, RT-PCR, western blots, immunoprecipitation, Enzyme-Linked Immunosorbant Assay (ELISA), immunofluorescence and radio-immunoassays (RIA). Gene expression can be scored in the post-meiotic stages of microspore, pollen, pollen tube or female gametophyte, or the post-zygotic stages such as embryo, seed, or progeny seedlings and plants. In another embodiment of the method, the MC can de directly detected or visualized in post-meiotic, zygotic, embryonal or other cells in by a number of methods for DNA detection known to those skilled in the art, including but not limited to fluorescence in situ hybridization, in situ PCR, PCR, southern blot, or by MC rescue described above.

FISH Analysis of MC Copy Number in Meiocytes, Roots or Other Tissues of Adchromosomal Plants The copy number of the MC can be assessed in any cell or plant tissue by FISH is particularly well suited to this purpose). In an exemplary assay, standard FISH methods are used to label the centromere, using a probe which labels all chromosomes with one fluorescent tag (e.g., ALEXA FLUOR® 568; Invitrogen Corp.; Carlsbad, Calif.; USA), and to label sequences specific to the MC with another fluorescent tag (ALEXA FLUOR® 488, for example). All centromere sequences are detected with the first tag; only MCs are detected with both the first and second tag. Nuclei are stained with a DNA-specific dye including but not limited to DAPI, Hoechst 33258, OliGreen, Giemsa YOYO, and TOTO. MC copy number is determined by counting the number of fluorescent foci per cell that label with both tags.

Induction of Callus and Roots from Adchromosomal Plants Tissues for Inheritance Assays MC inheritance is assessed using callus and roots induced from transformed plants. To induce roots and callus, tissues such as leaf pieces are prepared from adchromosomal plants and cultured on a MS or N6 medium that may contain a cytokinin, e.g., 6-benzylaminopurine (BA), and an auxin, e.g., α-naphthaleneacetic acid (NAA). Any tissue of an adchromosomal plant can be used for callus and root induction, and the medium recipe for tissue culture can be optimized using procedures known in the art.

Clonal Propagation of Adchromosomal Plants

To produce multiple clones of plants from a MC-transformed plant, any tissue of the plant can be tissue-cultured for shoot organogenesis using regeneration procedures described under the section regeneration of plants from explants to mature, rooted plants (see above). Alternatively, multiple auxiliary buds can induced from a MC-modified plant by excising the shoot tip, which can be rooted and subsequently be grown into a whole plant; each auxiliary bud can be rooted and produce a whole plant. Additionally, multiple shoots that result from one plant can be subdivided in culture to produce multiple individual plants.

Scoring of Antibiotic- or Herbicide Resistance in Seedlings and Plants (Progeny of Self- and Out-Crossed Transformants)

Progeny seeds harvested from MC-modified plants can be scored for antibiotic- or herbicide resistance by seed germination under sterile conditions on a growth media (for example MS medium) containing an appropriate selective agent for a particular selectable marker gene. Only seeds containing the MC can germinate on the medium and further grow and develop into whole plants. Alternatively, seeds can be germinated in soil, and the germinating seedlings can then be sprayed with a selective agent appropriate for a selectable marker gene. Seedlings that do not contain MC do not survive; only seedlings containing MC can survive and develop into mature plants.

Genetic Methods for Analyzing MC Performance

Though sorghum is typically propagated vegitatively, it is possible to use sexual propagation techniques as well. In addition to direct transformation of a plant with a MC, plants containing a MChromsome can be prepared by crossing a first plant containing the functional, stable, autonomous MC with a second plant lacking the MC.

Fertile plants modified with MCs can be crossed to other plant lines to study MC performance and inheritance. In the first embodiment of this method, pollen from an adchromosomal plant can be used to fertilize the stigma of a non-adchromosomal plant. MC presence is scored in the progeny of this cross using the methods outlined in the preceding section. In the second embodiment, the reciprocal cross is performed by using pollen from a non-adchromosomal plant to fertilize the flowers of an adchromosomal plant. The rate of MC inheritance in both crosses can be used to establish the frequencies of meiotic inheritance in male and female meiosis. In a third embodiment of this method, pollen for an adchromosomal plant is used to fertilize another or the same adchromosomal plant (e.g. self or sibling pollination). In the fourth embodiment of this method, the progeny of one of the crosses just described are back-crossed to a non-adchromosomal parental line, and the progeny of this second cross are scored for the presence of genetic markers in the plant's natural chromosomes as well as the MC. Scoring of a sufficient marker set against a sufficiently large set of progeny allows the determination of linkage or co-segregation of the MC to specific chromosomes or chromosomal loci in the plant's genome. Genetic crosses performed for testing genetic linkage can be done with a variety of combinations of parental lines; such variations of the methods described are known to those skilled in the art.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

EXAMPLES

Example 1

*Sorghum* Centromere Discovery

Identification of Sorghum Satellite Repeat Sequences

The investigators compiled *Sorghum* repetitive genomic DNA as candidate probes for hybridization with the BAC libraries. *Sorghum* sequence was extracted from GenBank and analyzed the sequence by homology to a known *Sorghum* satellite sequence (Zwick, M S, et al. *Am J Bot* 87: 1757-1764, 2000), set out in SEQ ID NO:177:

```
tacgtaagct tcgtttcgtc tgtttggaca tagtgctaat ctttatgcaa gatagatgca   60
cggtttacgt ggaacatatg atatgctcag aagcaattta ggacgcacct aatataactc  120
cttgatgatg tgtgtcacat ggaatcttgc ttcggtttct ttagagacag tgttagtttt  180
ggtagaagat atgtgcacag tgtacgccta atgcaccata ggctaaagaa accattttag  240
acgcacccga tggtactcgt agttgaagag gctcaactgg aggctcgatt tggtctgttc  300
ggatatagtg ctaatcttga tgcaagatag ttgcacaatt tgcaggcaac gtaccatatg  360
ttaagaaatc aatttggacg cacccaatgg aactcctaga tgacgtgtgt catatggaac  420
tcgcttcggt ctgtttggtg accatattag tttcactgca ggaaaggtgc atagtttgtg  480
cctaatgcac catagtctaa gaaaaccatt tttgatgcac ctgtttgtac ttctatgaag  540
aggctcaagt ggaagctcgg ttcggtctgt ttggagatag tgctaatctt gatgcaagat  600
aggtgtacgg tttgtatgga acataccata tgcttggaaa tcaatttgga tgcacccgtt  660
```

-continued

```
ggaactcctt gagaagtgtg tcttatgtac cctcgctttg gtctgtttag aaatagtgtt  720

agtttcagtg caagatatga gcatggtttg cgcctaacgc accatagtct aagaaaccat  780

tttggaagca cctgttggta cttcggtgaa gaagctcaag tggaagctcg gtttgacctg  840

tttggagata gtgctaatct tgatgcaaga tagtgcatga tttgcaagga acataccata  900

tgcttagaaa tcaacttgga cgcacgcccc gcaactccta catcacgtgt gtcatatgga  960

atcttacttc ggtccatttg taacattgta agttttagtg caag                  1004
```

The investigators identified the sequences listed in Table 4 (SEQ ID NOs:23-176). Each sequence represents a different repetitive DNA sequence from *S. bicolor*.

TABLE 4

Sorghum satellite sequences

| SEQ ID NO: | Nucleic acid sequence | |
|---|---|---|
| 23 | aaactgagct tccacttgag ccccttttacc caggagtatc atcgggtgca tccaaaatgg | 60 |
| | tttcttagcc aatgatgcat taggcacaaa ttgtgtacct atcttgtacc aaaactaact | 120 |
| | ctgtctccaa aca | 133 |
| 24 | aaactgagct tccacttgag ccccttttaca caggagtatc atcgggtgca tccaaaatgg | 60 |
| | tttcttagcc aatgatgcat taggcgcaaa ttgtgtacct atcttgtacc aaaactaact | 120 |
| | ctgtctccaa aca | 133 |
| 25 | caaactgagc ttccacttga gcccctttac ctaggagtat gatcaggtgc atccaaaatg | 60 |
| | gtttcttagc ctatgatgca ttaggcgcaa actgtgtacc tatcttgtac caaaactaac | 120 |
| | tctgtctcca aac | 133 |
| 26 | caaactgagc ttccacttga gcccctttac ccaggagtat cttcaggtgc atccaaaatt | 60 |
| | gtttcttagc ctatgatgca ttaggcgcaa actgtgtatc tatcttgcac caaaactaac | 120 |
| | tctgtctcca aac | 133 |
| 27 | caaactgagc ttccacttga gcacctttac ccacgagtat catcgggctc atccaaaatg | 60 |
| | gtttcttagc ccatgatgca ttaggcgcaa actgtgtacc tatcttgcac caaaactaac | 120 |
| | tctgtctcca aac | 133 |
| 28 | caaactgagc ttccacttga gcccctgtac ccaggagtat catcgggtgc atccaaaatg | 60 |
| | gtttcttagc ctatgatgca ttaggcgcaa actgtgtacc tatcttgcac taaaactacc | 120 |
| | tttgtctcca aac | 133 |
| 29 | gaaccgacct tccacttgag cctctccacc taggattatc atcgggtgct tgcataatgg | 60 |
| | tttctgagcc tatggtgcat tatgcgcaaa ccatgcacca atcctgcacc taaactaaca | 120 |
| | ctgtctccaa aca | 133 |
| 30 | caaactgagc ttccacatga gcccctttac ccaggagtat attcgggtgc atccaaaatg | 60 |
| | gtttcttagc ctatgatgca ttaggcgcaa agtatgtacc gatcttgcac caaaactaac | 120 |
| | tctgtctcca aac | 133 |
| 31 | caaactgaga ttccacttga gcccctttac cggggagtat catcgtgtgc atccaaaatg | 60 |
| | gtttcttagc ctatgatgca ttaggcgcaa actatgtacc tatcttacac caaaactaac | 120 |
| | tctgtctcca aac | 133 |
| 32 | caaactgagc ttccacttga gcccctttac ctaggagtat catcgggtgc atccaaaatg | 60 |
| | gtttcttagc ctgtgatgca ttaggagaaa actgtgtacc tatcttgcac caaaactaac | 120 |
| | tctgtctcca aac | 133 |
| 33 | aaactgagct tccacttgag ccccttttacc caggagtgtt atcgagtgca tccaaaatag | 60 |
| | tttcttagcc tatgatgcat taggcgcaaa ctgtgtacct atcttgcacc aaaactatct | 120 |
| | ctgtctccaa aca | 133 |
| 34 | aaactgagct tccacttgag ccccttttact caggagtatc atcgggttca tccaaaatgg | 60 |
| | tttcttagcc aatgatgcat ttggcgcaaa ctgtgtacct atctcgcacc aaaactaact | 120 |
| | ttgtctccaa aca | 133 |
| 35 | caaactgagc ttccacttga gcccctttac ccaggagtat catcgagtgc atccaaaata | 60 |
| | gtttcttagc ctatgatgca ttaggcgcaa actgtgtacc tatcttgcac caaaactgcc | 120 |
| | tctgtctcca aac | 133 |
| 36 | caaactgagc ttccacttga gcccctttac ccaggagtat catcaggttc atccaaaatt | 60 |
| | gtttcttagc ctatgatgca ttaggcgtaa actgtgtacc tatcttgcac caaaactaac | 120 |
| | tctgtctcca aac | 133 |

TABLE 4-continued

Sorghum satellite sequences

| SEQ ID NO: | Nucleic acid sequence | |
|---|---|---|
| 37 | caaactgagc ttccacttga gcccctttgc ccaggagtat catcaggttc atccaaaatt | 60 |
| | gtttcttagc ctttgatgca ttaggcgtaa actgtgtacc tatcttgcac caaaactaac | 120 |
| | tctgtctcca aac | 133 |
| 38 | aaactgagct tccacttgag ccccttacc caggagtatc gtcgggtgca tccaaaatgg | 60 |
| | tttcttaccc tatgatgcat taggcgcaaa atgtgtacct atcttgaacc aaaactaact | 120 |
| | ctgtctccaa aca | 133 |
| 39 | caaactgagc ttccacttga gccccttac ccaggagtat gatcgggtgc atctaaaatg | 60 |
| | gtttcttagc ctatgatgca ttaggcgaaa actgtgtacc tattttgcac caaaactaac | 120 |
| | tctgtctcca aac | 133 |
| 40 | caaactgagc ttccacttga gccccttac ccaggagtat catcgggtgc atccaaaatg | 60 |
| | gtttcttagg ctatgatgca ttaggcgcaa actgtgcacc tatcctgtac ctaaactaac | 120 |
| | actgtctcca aac | 133 |
| 41 | caaactgagc ttccacttga gccccattac ctaggagtat gttcgggtgg attcaaaatg | 60 |
| | gtttcttagc ctatgatgca ttatgcgcaa actgtgtacc tatcttgcac caaaactaac | 120 |
| | tctgtctcca aac | 133 |
| 42 | aaactgagct tccacttgag cccctatacc tagtagtatc atcgggtgca tccaaaatga | 60 |
| | tttcttatcc tatgatgcat taggcgcaaa ctgtgtacct atcttgcacc aaaactaact | 120 |
| | ctgtctccaa aca | 133 |
| 43 | caaactgagc ttccacttga gccccttac ctaggagtat catcgggtgc atccaaaatg | 60 |
| | gtttcttagc ctatgatgca ttaggcacag actatgtacc tatcttgcac caaaactaac | 120 |
| | tccgtctcca aac | 133 |
| 44 | caaaccgacc ttccacttca gcctctttac ctaggattat catcgggtgc ttccataatg | 60 |
| | gtttttgagc ctatggtgca tattgcgcaa accatgcacc aatcttgcat ctaaactaac | 120 |
| | actgtctcca aac | 133 |
| 45 | aaactgagct tccaattgag ccccttacc caggagtatc atcgggtgca aacaaaatgg | 60 |
| | tttcttagcc tatgatgcat taggcgcaaa ctgtgtacct atcttgcacc aaaaataact | 120 |
| | ctgtctccaa aca | 133 |
| 46 | caaactgagc ttccacttga gccccttac ctaggagtgt catcgggtgc attcaaaatg | 60 |
| | gtttcttagc ctatgatgca ttaggcgcaa actgtgtacc tatcttgcac caaaactaac | 120 |
| | tttgtctcta aac | 133 |
| 47 | caaactgagc ttccatttga gccccttac ccacgagtat aattgggtgc atccaaaatg | 60 |
| | gtttcttagc ctatgatgca ttaggcgcaa actgtatacc tatattgcac caaaactacc | 120 |
| | tctgtctcca aac | 133 |
| 48 | caaactgagc ttccacttga gcccctatac cgaggagtat catcgggtgc attcaaaatg | 60 |
| | gtttcttagc ctatgatgca ttaggcgcaa actgtgtacc tatcttgcac tgaaactaac | 120 |
| | tctgtctcca aac | 133 |
| 49 | caaactgagc tttcacttga gccccttac ctaggagtat gaacgggtgc atccaaaatg | 60 |
| | gtttcttagc ctatgatgca ttaggcgcaa actgtgtacc tatcttgcac caaaactaac | 120 |
| | tctgtctcta aac | 133 |
| 50 | aaactgagct tccacttgag ccccttaca caggagtatc atcgggtgca tccaaaatgg | 60 |
| | tttcttagcc tatgatacat aaggcgcaaa ctgtgtatgt atcttgcacc aaatctaact | 120 |
| | ctatctccaa aca | 133 |
| 51 | caaactgagc ttccacttga gcccttttac ccaggagtat catcgagtgc atccaaaatg | 60 |
| | gtttcttagc ctatgatgca ttaggcgcaa actgtgtacc tatcttgcac caaaactacc | 120 |
| | tccgtctcca aac | 133 |
| 52 | caaactgagc ttccacttga gccccttac ctaggagtat catcgggtgc atccaaaatg | 60 |
| | gtttcttcgc ctatgatgca ttaggcgcaa actatgtacc tatcttgcac caaaactaac | 120 |
| | tttgtctcca aac | 133 |
| 53 | aaactgagct tccacttgag ccccttacc caggtgtatc atcgggtgca tccaaactgg | 60 |
| | tttcttagcc tatgacgcat taggcgcaaa ctgtgtacct atcttgcacc aaaactacct | 120 |
| | ctgtctccaa aca | 133 |
| 54 | caaactgagc ttccacttga gccccttac ccaggagtat attcgggtgc atccaaaatg | 60 |
| | gtttcttagc ctatgatgcc ttaggcgcaa agtgtgtacc tatcttgcac caaaactaac | 120 |
| | tctgtctcca aac | 133 |

TABLE 4-continued

| SEQ ID NO: | Sorghum satellite sequences<br>Nucleic acid sequence | |
|---|---|---|
| 55 | caaactgagc ctccacttga gcccctttac ccaggagtat catcaggtgc atccaaaatg | 60 |
| | gtttcttagc atatgatgca ttaggcgtaa actgtgtacc tatcttgcac caaaactaac | 120 |
| | tctgtctcca aac | 133 |
| 56 | caaactgagc ttccacttga gcccctttac ccaggagaat caacagatgc atccaaaata | 60 |
| | gtttcttagc ctttgatgca ttaggtgcaa actgtgtagc tatcttgcac caatactaac | 120 |
| | tctgtctcca aac | 133 |
| 57 | gaactgacct tccacttgag cctctttacc taggattatc atcgggtgct tccataatgg | 60 |
| | tttctgagcc tatggtgcat tatgcgcaaa ccatgcacca atcttgcacc taaactaaca | 120 |
| | ctgtctccaa aca | 133 |
| 58 | aaactgagct tccacttgag ccctttttacc caggagtatc atcgagtgca tccaaaatga | 60 |
| | tttcttaccc tatgatgcat taggcgcaaa ctgtgaacct atcttgcacc aaaactacct | 120 |
| | ctgtctccaa aca | 133 |
| 59 | caaactgagt ttccacttga gcccctttac ccaggagtat catcgggtgc atccaaaatg | 60 |
| | gtttcttagc ctatgatgca ttcggcgcaa attgtgtacc taacttgcac caaaactaac | 120 |
| | tctgtctcca aac | 133 |
| 60 | aaactgagct tccacttgag cccctttacc taggattatc atcgggtgca tccaaaatgg | 60 |
| | tttcttagcc tattatgcat taggcgtaaa ctgtgtacca atcttgcacc aaaactaact | 120 |
| | ctctctccaa ac | 132 |
| 61 | aaactgagct tccatttgag cccctttacc caggattatc atcgggtgcg tccaaaatgg | 60 |
| | tttctgagcc tatgatgcat taggtggaaa ctgtgtacct attttgcacc aaaactaact | 120 |
| | ctgtctccaa aca | 133 |
| 62 | accaaactgt gcttccactt aagcctcttc acctaggatt accatcaagt gcatccaaaa | 60 |
| | tggtttctta gactatggtg aattaggcaa aaactgtgca cctatcttgc accaaaacta | 120 |
| | acactatgtc caa | 133 |
| 63 | caaactgagc ttctgcttga gcccctttac ctaggagtat catcgggtgc atccaaaatg | 60 |
| | gtttctcagc ctttgatgca ttaggcgtaa actgtgtacc tatgttgcac caaaactaac | 120 |
| | tctatctcca aac | 133 |
| 64 | gatcaaacca agcttccact tgagcccctt ttcctaggag taccattagg tgtgtccaaa | 60 |
| | aaggttctta gcctatggtg cattaggcgc aaaccattca cctatcttgc acagaaacta | 120 |
| | atactgtctc aaa | 133 |
| 65 | cgaaccgacc ttccacatga gactcttcac ctaggattat catcgggtgc ttccataatg | 60 |
| | gtttctgtgc ctatggtgca ttatgcgcaa accatgcacc aatcttgcac ctaaactaac | 120 |
| | actctctcca aac | 133 |
| 66 | caaactgagc tttcccttga gccccttgag ccaggagtat catcgggtgc atccaaaatg | 60 |
| | gtttcttagc tgtatgaagc attaggcgca aactgtgtac ttatcttgca ccaaaactaa | 120 |
| | ctctgtctcc aaa | 133 |
| 67 | caaactgagc ttccacttga gcccctttac cttggagtat caacgggtgc atccaaaatg | 60 |
| | ttttcttagc ctatgatgca ttaggcgcaa actgtgtacc tatcttgcac caaaactaac | 120 |
| | tttgtctcca aac | 133 |
| 68 | aaactgagct tccacttgag cccctttacc caggagtatc atcgggtgca tccaaaatgg | 60 |
| | attcttagcc tatgatgcat taggcgtaaa ctgtgtacct ttcttgtacc aaaactaact | 120 |
| | ctgtctccaa aca | 133 |
| 69 | caaactgagc ttccacttga gcccctttac ctaggagtat catcggctcc atccaaaatg | 60 |
| | gtttcttagc ctatgatgca ttaggcgcaa actgtgtacc tatcttgcac caaaactaac | 120 |
| | tctgtctcct aac | 133 |
| 70 | caaactgagc ttccgcttga gcccctttac ctaggagtat catcgggtgc atccaaaatg | 60 |
| | gtttctcagc ctatgatgcc ttaggagcaa actgtgtacc tatcttgcac caaaactaag | 120 |
| | tctgtctcca aac | 133 |
| 71 | aaactgagct tccacttgag ccccttttgcc caggagtatc atcaggttca tccaaaatgg | 60 |
| | tttcttagcc tttgatgcat taggcgtagc ctgtgtacct atcttgcacc ataactaact | 120 |
| | ctgtctccaa aca | 133 |
| 72 | accaaactgt gcttccactt gagcctcttc atctaggatt accatcaagt gcatccaaaa | 60 |
| | tggtttctta gactacggtg aattaggcta aaattgtgca cctatcttgc accaaaacta | 120 |
| | acactatgtc caa | 133 |

TABLE 4-continued

Sorghum satellite sequences

| SEQ ID NO: | Nucleic acid sequence | |
|---|---|---|
| 73 | caaactgagc ttccacttga gccccgttac ctaggagtat cttcgggtgc atccaaaatg | 60 |
| | gtttcttagc ctatgatgca ttaggcacaa actatgtacc tatcttacac taaaactaac | 120 |
| | tctgtctcca aac | 133 |
| 74 | aaactgagct tccacctgag ccccttttacc caggagtatc atcgggtgca tccaaaatgg | 60 |
| | tttcttagcc tatgatgctt taggcgcaaa ctgtgtacct atctagcacc aaaactagct | 120 |
| | ctgtctccaa aca | 133 |
| 75 | cgaaccgacc tttcaattga gcctcttcac ctaggattat catcgggtgt ttccataatg | 60 |
| | gtttctgagc ctatggtgca ttatgcgcaa accatgcacc aatcttgcac ctaaactaac | 120 |
| | actgtctcca aac | 133 |
| 76 | caaactgagc ttccacttga gccccttac ctaggagtat catcgggtgc atccaaaatg | 60 |
| | gtttcttagc ctatgatgca ttaggagaaa actgtgtccc tatcttgcac caaaactaac | 120 |
| | tctgtctcca aac | 133 |
| 77 | aaactgagct tccacttgag cccctttacc caggagtatc attgggtgca tccaaactgg | 60 |
| | tttcttagcc tatgatgcat ttggcgcaaa ctgtgtacct atcttgcacc aaaactgact | 120 |
| | ctgtctccaa aca | 133 |
| 78 | aaactgagat tccacttgag cccctttacc caacagtata atcgggtgca tccaaaatgg | 60 |
| | tttcttagcc tatgatgcat taggcgcaaa ctgtgtaccg atcttgcacc aaaactaact | 120 |
| | ctgtctccaa aca | 133 |
| 79 | caaactgagc ttccacttgg gcccctttac ccaggagtat caacagatgc atccaaaata | 60 |
| | gtttcttagc ctttgatgca ttaggtgcaa actgtgtagc tatcttgcac caatactaac | 120 |
| | tctgtctcca aac | 133 |
| 80 | caaactgagc ttccacttga gcccctttac ctaggagtat catcgggtgc atacaaaatg | 60 |
| | gttccttagc ctatgatgca ttaggcgcaa actgtgtact tatcttgcac caaaactaac | 120 |
| | tctgtctcca aac | 133 |
| 81 | aaactgagct tccacttgag cccctttacc taggagtatc atcgggtgca tccaaaatgg | 60 |
| | tttcttagcc tatgatgcat ttggcacaaa ctgtgtacct atcctgcacc aaaactaact | 120 |
| | ctgtctccaa aca | 133 |
| 82 | aaactgagct tccagttgag cccctttacc gaggagtatc atcaggtgca tccaaaatgg | 60 |
| | tttcttagcc tatgatgcat taggcgcaac ctgtgtacct atcttgcacc aaaactacct | 120 |
| | ctgtatccaa aca | 133 |
| 83 | caaactgagc ttccacttga gcccctttac ccaggagtat caacagattc atccaaaata | 60 |
| | gtttcttagc ctttgatgca ttaggtgcaa actgtgtagc tatcttgcac caatactaac | 120 |
| | tctgtctcca aac | 133 |
| 84 | aaacctacct tccacttgag cctctccacc taggagtatt atcgggtgct tccataatgg | 60 |
| | tttccgagcc tatggtgcat tatgcgcaaa ccatgcacca atcttgcacc taaactaaca | 120 |
| | ctgtctccaa aca | 133 |
| 85 | caaactgacc ttccacttga cactcttcac ctaggagtat tatccggtgc ttccataatg | 60 |
| | gtttctgagc ctatggtgca ttatgcgcaa accatgcacc aatcttgcac ctaaactaac | 120 |
| | actatctcca aac | 133 |
| 86 | caaactgagc ttccacttga gcccctttac cctggagtat cttcaggtgc atccaaaatt | 60 |
| | gtttcttagc ctatgatgca ttaggcgcaa actgtgtacc tatcttgcac caaaactaac | 120 |
| | tctgtctcca aac | 133 |
| 87 | caaactgagc ttccacttga gcccctttac ccaggagtat catcaggtgc atcagaaatg | 60 |
| | gtttcttagc ctatgatgca ttaggtgcaa actgtgtacc tatcttgcac caaaactaac | 120 |
| | tctgtctcca aac | 133 |
| 88 | caaactgagc ttccacttga gcccctttac ccaagagtat catcgggtgc atccaaaatg | 60 |
| | gtttcttagc ctatgacgca ttaggcacaa actgtgtacc tatgttgcac caaaactaac | 120 |
| | tctgtctcca aac | 133 |
| 89 | caaactgagc ttcctcttga gcccctttac ctaggagtat catcggttgc atccaaaatg | 60 |
| | gtttcttagc ctatgatgca ttaggcgtaa actgtgtacc tatcttgcac caaaacttac | 120 |
| | tctgtctcca aac | 133 |
| 90 | caaactgagc ttccacttga gcccctttac ccaggagtat catcgggtgc atacaaaatg | 60 |
| | gattcttagc ctatgacgca ttaggcgcaa actatgtacc tatcttgcac caaaactaac | 120 |
| | tctgtctcca aac | 133 |

TABLE 4-continued

Sorghum satellite sequences

| SEQ ID NO: | Nucleic acid sequence | |
|---|---|---|
| 91 | aaactgagtt tccacatgag cacctttacc ctggagtatc atcaggtgca tccaaaatgg | 60 |
| | tttcttagcc tatgatgcat taggcgcaaa ctgtgtacct atattgcacc aaaactaact | 120 |
| | ctttctccaa aca | 133 |
| 92 | caaactgagc ttccacttga gcccctttac ctaggagtat catcgggcgc atccaaaatg | 60 |
| | gtttcttagc ctatgatgca ttaggcacaa actatgtacc tatcttgcac caaaactaac | 120 |
| | tctgtctcca aac | 133 |
| 93 | aaactgagct tccagttgag ccccttttacc cagcagtatc atcgggtgga tccaaaatgg | 60 |
| | tttcttcacc tatgatgcat taggcgcaaa ctgtgtacct atcttgcacc aaaactaact | 120 |
| | ctatctcgaa aca | 133 |
| 94 | aactgagctt ccacttgagc ccctttagcc aggagtatca tcgggtgcat ccaaaatggt | 60 |
| | ttcttagcct atgaaatcat taggcgcaaa ctgtgtacct atcttgcacc aaaactaact | 120 |
| | ctgtctctaa aca | 133 |
| 95 | caaactgagc ttccacttga gcccctttac ctaggagtat catcgggagc atccaaaatg | 60 |
| | gtttcttagc ctatgatgca taaggagcaa actgtgtacc tatcttgcac caaaactaac | 120 |
| | tctgtctcca aac | 133 |
| 96 | caaactgagc ttccacttaa gcccctttac ctaggagtat catcgggtgc atccaaaatg | 60 |
| | gtttcttagc ctatgatgca ttacgcgcaa actgtgtacc tatcttgcac caaaactaac | 120 |
| | tttgtctcca aac | 133 |
| 97 | caaactgagc ttccacttga gcccctttac ctaggagtat aatcgggtgc atccaaaatg | 60 |
| | gtttcttagc ctatgatgca ttagacgtaa actatgtacc tatcttgcac caaaactaac | 120 |
| | tctgtctccg aac | 133 |
| 98 | aaactgagct tccacttgag ccccttttacc taggagtatc atcgggtgta tccaaaattg | 60 |
| | tttcttagcc tacgatgcat taggcgcaaa ctgtgtacct atcttgcacc aaaactaact | 120 |
| | ctgtctccaa aca | 133 |
| 99 | caaactgagc ttccacttga gcccctttac ctaggagtat cattgggtgc atccaaaatg | 60 |
| | ctttcttagc ctatgatgca ttaggtgcaa actgtgtagc tatcttgcac caaaactatc | 120 |
| | tctatctcca aac | 133 |
| 100 | aaactgagct tccacttgag cccgtttacc gaggagtatc atcgagtgca tctaaaatga | 60 |
| | tttcttagcc tatgatgcat taggcacaaa ctgtgtacct atctagcacc aaaactaact | 120 |
| | ttctctccaa aca | 133 |
| 101 | accgaccttc cacttgagac tcttcaccta ggattatcat cgggtgcttc cataatggtt | 60 |
| | tctgagccta tggtgcatta tgcacaaacc atgcaccaat attgcaccga aactaacact | 120 |
| | gtctccaaac a | 131 |
| 102 | caaactgagc ttccacttga gcccctttac ctaggagtat catcgggtgc atccaaaatg | 60 |
| | gtttcttagc caatgatgca ttaggagaaa actgtgtacc aatcttgcac caaaactaac | 120 |
| | tctgtctcca aac | 133 |
| 103 | caaactgagc ttccacttga gcccctttac ctaggagtat catcgggtgc atccaaaaag | 60 |
| | gtctcttagc ctatgatgcc ttaggagaaa actatgtacc tgtcttgcac cataactaac | 120 |
| | tctgtctcca aac | 133 |
| 104 | aaactgtgct tgcacttgag ccccttttacc caggagtatc atcgggtgca tccaaaatgg | 60 |
| | tttcttagcc tatgatgcat taggcgcata ctgtgtacct atcttgcagt aaaactaact | 120 |
| | ctgtctccaa aca | 133 |
| 105 | aaactgagct tccacttgag gcccttttatc taggagtatc atcgggtgca tccaaaatgg | 60 |
| | tttcttagcc tatgatgcgt taggcgcaaa ctatgtacct atcttgcacc aaaactaact | 120 |
| | ctgtctccaa aca | 133 |
| 106 | aaactgagct tccacttgag ccccttttacc taggagtatc ttcgggtgca tcagaaatgg | 60 |
| | tttcttagcc tatcatgcat taggcacaaa ctgtgcacct atcttacatc aaaattaact | 120 |
| | ctgtctccaa aca | 133 |
| 107 | caaactgagc ttccacttga gcccctttac ccaggagtat attcgggtgc atccaaaatg | 60 |
| | gtttcttagc ctatgatgcg ttaggcgcaa actgtgtacc tatcttgcac cacaactaaa | 120 |
| | tctgtctcca aac | 133 |
| 108 | caaactgagc ttccacttga gcccctttac ccaggagtat caacagatgc atccaaaata | 60 |
| | gtttcttagc ctttgatgca ttaggtgcaa actgtgtagc tatcttgcac caatactaac | 120 |
| | tctgtctgca aac | 133 |

TABLE 4-continued

Sorghum satellite sequences

| SEQ ID NO: | Nucleic acid sequence | |
|---|---|---|
| 109 | caaactgagg ttccgcttga gcccctttac ctaggagtat catcgggttc atccaaaatg | 60 |
| | gtttctcagc ctatgatgcc ttaggcgcaa actgtgtacc tatcttgcac caaaactaac | 120 |
| | tctgtctcca aac | 133 |
| 110 | aaactgagct tccacttgag cccctttacc caggagtatc atcgggtgca tccaaaatgg | 60 |
| | attcttcgcc tatgatgcat taggcgcaaa ctgtgtacct atcttgcacg aaaactaact | 120 |
| | ctatctccaa aca | 133 |
| 111 | cgaaccgacc ttccacttga gccccttcac ctaggattat catcgggtgc ttccataatg | 60 |
| | gtttttgagc ctatggtgca ttatgcacaa accatgcacc aatcttgcac ctaaactaac | 120 |
| | actgtctcca aac | 133 |
| 112 | caaactgagc ttccacttga gcccctttac ctaggagtat catcgggtgc atccaaaatg | 60 |
| | gttaattagc ctatgatgca ttaggcgcta actgtgtacc tatcttgcac caaaactaac | 120 |
| | tctgtctcca aac | 133 |
| 113 | caaactgagc ttccacttaa gcccctttac ccaggagtat cttcaggtgc atccaaaatg | 60 |
| | gtttcttagc ctatgatgca ttaggcacaa actatgtacc tatcttacac caaaactaac | 120 |
| | tctgtctcca aac | 133 |
| 114 | aaccgagacc tccacttgag gcctcttcac ctaggagata ccatcggatg cgtctaagat | 60 |
| | ggtttcttat cctatggtgc attatgcgta acccgtgcac atatcttgct ccaaaactaa | 120 |
| | tgctgtctct aaa | 133 |
| 115 | caaactgagc ttccacttga gcccctttac ccagtagtat catcgggtgc atccaaaatg | 60 |
| | gtttcttagc ctatgatgca ttatgcgaaa attgtgtacc tatattgcac caaaactaac | 120 |
| | tctgtctcca aac | 133 |
| 116 | caaactgagc atccacttga gcccctttac ctaggagtat catcgggtgc atacaaaatg | 60 |
| | gtttcttaac ctatgatgca ttagacgcaa actgtgtacc tatattgcac caaaactaac | 120 |
| | tctgtctcca aac | 133 |
| 117 | caaactgagc ttccacttga gcccctttac cttggagtat catcgggtgc atccaaaatg | 60 |
| | gtttcttagc ctatgatgca ttaggcacaa actgtgtacc tatcttgaac caaaactaac | 120 |
| | tctgtctcca aac | 133 |
| 118 | aaactgagct tccacttgag cccctttacc caggagtatc ttcaggtgca tccaaaattg | 60 |
| | tttcttagcc tatgatgcat taggcgcaaa ctgtgtacct atctttcacc aaaactaaca | 120 |
| | ctgtctccaa aca | 133 |
| 119 | caaactgagc ttccacttga gcccctttac ctagaagtat catcgggtgc atccaaaagg | 60 |
| | gtttcttagc ctatgatgta ctaggcgtaa actgtgtacc tatcttgcac caaaactaac | 120 |
| | tctgtctcca aac | 133 |
| 120 | caaactgagc taccacttga gcccctttac ctaggagtat catcaggttc atccaaaatt | 60 |
| | gtttcttagc ctatgatgcg ttaggcgtaa actgtttacc tatcttgcac caaaactaac | 120 |
| | tctgtctcca aac | 133 |
| 121 | caaactgagc ttccatttga gcccctttgc ctaggagtat catcgggtgc atccaaaatg | 60 |
| | gttccttagc ctatgatgca ttaggtgcaa actgtgtacc tatcttgcac caaaactaac | 120 |
| | tttgtctcca aac | 133 |
| 122 | caaactgagc ttccacctga gccactttaa ccaggagtat catcgggtgc atccaaaatg | 60 |
| | ttttcttagc ctatgatgct ttaggcgcaa attgtgtacc tatcttgcac caaaactaac | 120 |
| | tctgcctcca aac | 133 |
| 123 | caaactgagc ttccacttga gcatctttac ccaggagtat catcaggtgc atccaaaata | 60 |
| | gtttcttagc ctatgatgca ttaggcacaa actgtgtacc tatcttgcaa caaaactaac | 120 |
| | tctgtctcca tac | 133 |
| 124 | caaactgagc ttccacttga gcccctttac ctaggggtaa catcgggtgc atccaaaatg | 60 |
| | gtttcttagc ctatgatgca ttaggcacaa actgtgtacc tatcttgcac caaaactaac | 120 |
| | tctgtctcca aac | 133 |
| 125 | caaactgagc ttccacctga gcccctttac ctaggagtat catcgtgtgc atctaaaatg | 60 |
| | gtttcttagc ctatgatgca ttaggcgcaa actgtgtacc tatcttgcac caaaactaac | 120 |
| | tctgtctcca aac | 133 |
| 126 | caaactgagc ttccacttga gcccctttac ctaggagtat catcgtgtgc atcaaaaatg | 60 |
| | gtttcttagc ctatgaagca ttaggcgcaa actgtgtacc tatcttgcac caaaactaac | 120 |
| | tctgtctcca aac | 133 |

TABLE 4-continued

Sorghum satellite sequences

| SEQ ID NO: | Nucleic acid sequence | |
|---|---|---|
| 127 | caaactgagc ttccacatga gcccctttac ctaggagtat catcgggtgc atccaaaatg | 60 |
| | gtttcttagc ctatgatgca ttaggcacaa actgtgtacc tatcttgcac caaaactaac | 120 |
| | tctgtatcca aac | 133 |
| 128 | caaactgagc ttccacttga gcccctttac ccaggagtat catcgagtgc atctaaaaag | 60 |
| | gtttcttagc ctatgatgca ttaggcgcaa actgtgtacc tatcttgcac caaagctacc | 120 |
| | tctgtctcca aac | 133 |
| 129 | caaactgagc ttccacttga gcccctttac ccaggagtat caacagatgc atccaaaata | 60 |
| | gtttcttagc ctttcatgca ttaggtgcaa actgtgtagc tatcttgcac caatactaac | 120 |
| | tctgtctcca aac | 133 |
| 130 | aaactgagct tccacttgag cccctttacc ctggaatatc atcgggtgca tcccaaatgg | 60 |
| | tttcttagcc tatgatgcat taggcgcaaa gtgtgtacct atcttgcacc aaaactaact | 120 |
| | ttgtctccaa aca | 133 |
| 131 | aaactgagct tcaacttgag cccctttacc taggagtatc atcgggtgca tccaaaatgg | 60 |
| | tttcttagcc tatgatgcat taggcgcaaa ctgtgtacct gtcttgcacc aaaactaacc | 120 |
| | ctgtctccaa aca | 133 |
| 132 | caaactgagc ttccacttga gcccctttac ccaggagtat caacagatgc ttccaaaata | 60 |
| | gtttcttagc ctttgatgca ttaggtgcaa actgtgtagc tatcttgcac caatactaac | 120 |
| | tctgtctcca aac | 133 |
| 133 | caaactgagc ttccacttga gcccctttac ccaggagtat caacagatgc atccaaaata | 60 |
| | gtttcttagt ctttgatgca ttaggtgcaa actgtgtagc tatcttgccc caatactaac | 120 |
| | tctgtctcca aac | 133 |
| 134 | aaactgagct tccacgtgag cccctttacc caggagtata atcgggtgca tccaaaatgg | 60 |
| | tttcttagcc tatgatgcat taggcgcaaa ctgtgtacct atcttgcacc aaagctatct | 120 |
| | ctgtctccaa aca | 133 |
| 135 | caaactgagc ttccacttga gcccctttac ctaggagtat catcgggtgc attcaaaatg | 60 |
| | gtttcatagc ctatgatgca ttaggcgcaa actatgtacc tatcttgcac caaaactacc | 120 |
| | tccgtctcca aac | 133 |
| 136 | caaactgagc ttccacttga gcccctttac ctaggagtat catcgggtgt atccaaaatg | 60 |
| | gtttcttagc ctatgatgca ttaggcatag actgtgtacc tatattgcac caaaactaac | 120 |
| | tccgtctcca aac | 133 |
| 137 | caaactgagc ttccacttga gcccctttac ccaggagtat catcgggtgc atccaaaatt | 60 |
| | gtttcttagc ttatgatgca ttaggtgtaa actgtgtacc tatcttgcat caaaactcac | 120 |
| | tctgtctcca aac | 133 |
| 138 | caaactgagc ttccacttga gcccctttac ccaggagtat cttcaggtgc atccaaaatt | 60 |
| | gtttcttagc ctatgatgca ttaggcgcaa actgtgtacc tttcttgcac caaaactaac | 120 |
| | tctgtctcca aac | 133 |
| 139 | aaactgagct tccacttgag cccctttacc caagagtacc atcgggtgca tccaaaatgg | 60 |
| | tttcttagcc aatgatgcat taggcgcaaa ttgtgtacct atcttgtacc aaaactaact | 120 |
| | ttgtctccaa aca | 133 |
| 140 | caaactgagc ttccacttga gcccctttac ctagcagtat aatcgggtgc atccaaaatg | 60 |
| | gtttcttagc ctatgatgca ttaggcacaa actatgtact tatcttgcac caaaactaac | 120 |
| | tctgtctcca aac | 133 |
| 141 | aaactgagct tccacttgag cccctttacc gaggagtatc atcgggtgca ttcaaaatgg | 60 |
| | tttcttagcc tatgatgcat taggcgcaaa ctgtgtacct atcttgcaca aaaactagct | 120 |
| | ctgtctccaa aca | 133 |
| 142 | caaactgagc ttccacttga gcccctttac ccaggagtat catcaggttc atccaaaatt | 60 |
| | gtttcttagc ctttgatgca ttaggcgtaa actgtgtacc tatcttgcac caaaactaac | 120 |
| | tctgtctcca aac | 133 |
| 143 | aaactgagtt tccacatgag cacctttacc caggagtatc atcaggtgca tccaaaatgg | 60 |
| | tttcttagcc tatgatgcat taggcgcaaa ctgtgtacct atcttgcacc aaaactaact | 120 |
| | ctgtctccaa aca | 133 |
| 144 | aaactgagct tccacttgag cccctttttct caggagtatc attgggttca tccaaaatgg | 60 |
| | tttcttagcc tatgatgcat taggcgcaaa ctgtgtacct atcttgtacc aaaactaact | 120 |
| | ctgtctccaa aca | 133 |

TABLE 4-continued

Sorghum satellite sequences

| SEQ ID NO: | Nucleic acid sequence | |
|---|---|---|
| 145 | caaactgagc ttccacttga gcccctttac ccaggagtat catcgggtgc atccaaaatg | 60 |
| | gtttctttgc ctatgatgca ttaggcggaa actgtgtacc tgttttgcac caaaactaac | 120 |
| | tctatctcca aac | 133 |
| 146 | aaactgtgct tccacttgag ccccttttacc taggagtatc atcagggtgc atccacaatg | 60 |
| | gtttcttagc ctatgatgca ttaggcgcaa actgtgtacc tatcttgcac caaaactaac | 120 |
| | tctgtctcca aac | 133 |
| 147 | caaactgagc ttccacttgg gcccctttac ccaggagtat cttcaggtgc atccaaaatt | 60 |
| | gtttcttagc ctatgatgca ttaggcgcaa actgtgtacc tatcttgcac caaaactaac | 120 |
| | tctgtctcca aac | 133 |
| 148 | aaactgagct tccgcttgtg cccctttacc caagagtatc gacgggtgca tccaaaatgg | 60 |
| | tttcttagcc tacgatgcat taggcgcaaa cagtgtagct atcttgcacc aaaactaact | 120 |
| | ttgtctccaa aca | 133 |
| 149 | caaactgagc ttccacttga gcccctttac ctaggagtat catcaggtgc atccaaaatg | 60 |
| | gtttcttagc ctatgatgca ttaggagaaa actgtgtacc tatcttgcac caaaactaac | 120 |
| | tctgtctcca aac | 133 |
| 150 | caaactgagc ttccacttga gcccctttac ctaggagtat catcgtgtgc atccaaaatg | 60 |
| | gtttcttagc ctatgatgca ttaggcacaa actgtgtacc tatcttgcac caaaagtaac | 120 |
| | tctgtctcca aac | 133 |
| 151 | caaactgagc ttccacttga gcccctttac caaggagtat catcgggtgc atccaaaatg | 60 |
| | gtttcttagc ctctggtgca ttaggcacaa gctaggtacc tatcttgcac caaaactaac | 120 |
| | tctgtctcca aac | 133 |
| 152 | aaactgagct tccacttgag cccctttact caggagtatc atcgtgtgcc tccaaaatgg | 60 |
| | tttcttagcc tatgatgcat taggcgcata ctgtgtacct atcttgcacc aaaactacct | 120 |
| | ctatctccaa aca | 133 |
| 153 | aaactgagct tccacttgag cccctttaca cacgagtatc atcgggtgca tccaaaatgg | 60 |
| | tttcttagcc tatgatgcat taggcgcaaa ctgtgtacct atcttgtacc aaaactaact | 120 |
| | ctggctctaa aca | 133 |
| 154 | caaactgagc ttccacttga gtccctttac ccaggagtat catagggtgc atccaaaatg | 60 |
| | ttttcttagc ctatgatgca ttaggcgtaa actgtgtacc tatcttgcac caaaactaac | 120 |
| | tctgtctcca aac | 133 |
| 155 | caaactgagc ttccacttga gcccctttac ctaggagtat catcgggtgc atccaagatg | 60 |
| | gtttcttagc ctatgatgca ttagacgcaa actgtgtacc tatcttgcac caaaactaac | 120 |
| | tttgtctcca aac | 133 |
| 156 | aaactgagct tccacttgag cccctttaca caggagtatc atcgggtgca tccaaaatgg | 60 |
| | tttcttagca tatgatgcat tagtcgcaaa ctgtgtacct atcttgtacc aaaactaact | 120 |
| | ctgtctccaa aca | 133 |
| 157 | caaacggagc ttccgcttga gcccctttac ctaagagtat catcgggtgc atccaaaatg | 60 |
| | gtttgtcagc ctatgatgca ttaggtgcaa actgtgtacc tatcttgccc caaaactaac | 120 |
| | tctgtctcca aac | 133 |
| 158 | caaactgagc ttccacttga gcccctttac ctaggagtat catcgggtgc atccaaaaag | 60 |
| | gtttcttagc ctatgatgct ctaggagaaa actgtgtacc tatcttgcac caaaactaac | 120 |
| | tctgtctcta aac | 133 |
| 159 | caaactgagc ttccacttga gcccctttac ccaggagtat catcgggtgc atctaaagtg | 60 |
| | gtttcttagc ctacgatgca gtaggcgcaa actgtgtaca tatcttgcac caaaactaac | 120 |
| | tctgtctcca aac | 133 |
| 160 | tgaaacggag ctttcacttg agccccttga cctaggagta ccatcgggtg catccaaaat | 60 |
| | ggtttcttat cctatggtgc attaggtgta aaccgtgcac ctatcttgca ccgaaactaa | 120 |
| | cgttgtctct aaa | 133 |
| 161 | caaactgagc ttccacttga gcccctttac ccgggagtat catcgggtgc atccaaaatg | 60 |
| | gtttcttatc caatgatgcg ttaggcgcaa actatgtacc tatcttgcac caaaactaac | 120 |
| | tctgtctcca aac | 133 |
| 162 | caaactgagc ttccagttga gcctctttac ccaggagtat catcgggtgg atccaaaatg | 60 |
| | gtttgttagc ctatgatgca ttaggagcaa actatgtacc tatcttgcac caaaactaat | 120 |
| | tctgtctcca aac | 133 |

TABLE 4-continued

Sorghum satellite sequences

| SEQ ID NO: | Nucleic acid sequence | |
|---|---|---|
| 163 | caaactgagc ttccacttga gcccctttac ccaggaggat cttcgggtgc atccaaaatg | 60 |
| | gtttcttagc ctatgatgca ttaggcgcaa actgtgtacc tttcatgcac caaaactaac | 120 |
| | tctgtctcca aac | 133 |
| 164 | caaaccgagc tttcacttta gccccttgac ctaggagtac catcgggtgc gttcaaaacg | 60 |
| | gtttcttatc ctatggtgca ttaggtgcaa accgtgcacc tatcttgcac tgaaactaac | 120 |
| | actgtctcta aac | 133 |
| 165 | aaactgagct tcgacttgag cccctttacc caggagtatc atcgggtgca tccaaaaggg | 60 |
| | tttcttagcc tatgatgcat taggcgcaaa ctgtgtacgt atcttgcacc aaaactacct | 120 |
| | ctgtctctaa aca | 133 |
| 166 | aaactgagct tccacttgag cccctttacc caggagtatc atcgggtgca tccaaaagag | 60 |
| | tttcttagcc tatgatgcat taggcgcaaa ctgtgtacgt atcttgcacc aaaactacct | 120 |
| | ctgtctccaa aca | 133 |
| 167 | caaactgagc ttccacttca gcccctttaa tcaggaatat catcgggtgc atccaaagta | 60 |
| | gtttcttagc ctatgatgca ttaggcgcaa actgtgtacc tatcttgcac caaaactaac | 120 |
| | tctgtctcca aac | 133 |
| 168 | caaactgagc ttccacttga gcccctttac ccaggagtat catcgggtgc atccaaaata | 60 |
| | gtttcttagc ctacgatgca gtaagcgcaa actgtgtacc tatcttgcac caaaactaac | 120 |
| | tcggtctcca aac | 133 |
| 169 | caaactgagc ttccacttga gcccctttac ctaggagtat gatcaggtgc atccaaaatg | 60 |
| | gtttcttagc ctatgatgca ttaggcacaa actgtgtacc tatcttgcac caaaactaac | 120 |
| | tctgtctcca aac | 133 |
| 170 | aaactgagct tccacttgag caccttta cc caggagtatc atcaggtgca tccaaaatgg | 60 |
| | gttcttagcc tatgatgcat taggcgcaaa ctgtgtacct atcttgaacc aaaactaact | 120 |
| | ctatctccaa aca | 133 |
| 171 | caaactgagc ttccacttga gcccctttac ccaggagtat cttcaggtgc atccaaaatt | 60 |
| | gtttcttagc ctatgatgca ttaggcgcaa actgtgtacc tatcttgcac caaaactaac | 120 |
| | tttgtctcca aac | 133 |
| 172 | caaactgagc ttccacttga gcccctttac ctaggagtat aatcgggtgc atccaaaatg | 60 |
| | gtttcttagc ctatgatgca ttaggtgcaa actatgtacc tatcttgcac caaaactaac | 120 |
| | tttgtctccg aac | 133 |
| 173 | caaacagagc ttccaattga gacccttta c tcaggagtat catcgggttc atccaaaatg | 60 |
| | gtttcttagc ctatgatgca ttaggcgcaa actgtgtacc tattttgcac caaaactaac | 120 |
| | tctgtctcca aac | 133 |
| 174 | caaactgagc ttccacttga gcccctttac ccacgagtat catcgggctc atccaaaatg | 60 |
| | atttcttagc ctatgatgca ttaggcgcaa actgtgtacc tatcttgcac caaaactaac | 120 |
| | tctgtctcca aac | 133 |
| 175 | actgcgcttc cacttgagcc ccattaccca ggagtatcat cgggtgcatc caaaatagtt | 60 |
| | tcatagccga tgatgcatta ggtgtaaact gtgtacctat cttgcaccaa aactaactct | 120 |
| | gtctccaaac a | 131 |
| 176 | aactgagctt gcacttgagc ccctttaccc aggagtatca tcgagtgcat ccaaaattgt | 60 |
| | ttcttagcct gtgatgcatt aggcgcaaac tgtgtacctg tcttgcacca aaactaactc | 120 |
| | tgtctccaaa c | 131 |

To identify the consensus sorghum satellite sequence from the sequences of SEQ ID NOs:23-176, these sequences were aligned using ALIGN (publicly available software; Altschul, S F, et al., *J Mol. Biol.* 215:403-10, 1990). The sequences were trimmed to unit repeat length using the consensus as a template. Sequences trimmed from the ends of the alignment were realigned with the consensus and further trimmed until all sequences were at or below the consensus length. The consensus was determined by the frequency of a specific nucleotide at each position; if the most frequent base was three times more frequent than the next most frequent base, it was considered the consensus. An exemplary consensus sorghum satellite sequence is set out as SEQ ID NO:22:

```
aaactgagct tccacttgag cccctttacc aggagtatca tcgggtgcat ccaaaatggt    60

ttcttagcct atgatgcatt aggcgcaaac tgtgtaccta tcttgcacca aaactaactc   120

tgtctccaaa cc                                                        132
```

The sorghum centromere specific retrotransposon sequence (CRS) was amplified using PCR and sequenced using primers designed from published sequence (set forth in SEQ ID NO:178; Presting, G G, et al., *Plant J* 16: 721-728, 1998 and Miller, J T, et al. *Genetics* 150: 1615-1623, 1998) and are set forth in SEQ ID NOs:179 and 180. The sequence for sorghum CRS is set out as SEQ ID NO:21:

```
tggattcgga ctggaaaata actctaactt gtatggatca ccacgacgtc atatggactc   60
caactgggac gttcctatac ttgttggaaa gctcatgaag tctactttcc aatgggtcca  120
accacatatc tatgcggctt atgagtcggg cgcagtcctt gttttcgtgc cgacaccttt  180
ttctgttttg gtgctgcgtc actctatttt ggaccaatgg cccatgtatc aagttgagtc  240
cattagggac gcatcctagg gttggaggac gactctagca cccctttggt cgtcctcccc  300
tctatttatt tacatctaga gccgccatga acaactggat tttgtttaga tcaagtttag  360
ccttcgctac ttgcttgtag gcgcgcgtgc aggatcagcc gcccgcctcc ttgtcttcgg  420
aaccccattg ttgattaaga ttcagtttaa aaccttcaat tcatcttgca aattcagtgc  480
ttgtttcctc gttcttgcta gttcttcgat tgcttgcagg acgggagccc taggggctgg  540
ttgtcgcgct ccacaagatc gtgacggttg ttggacgtgg tgtatcggtt gctaaggcgc  600
ggtcttgagg gctgtagtcg ggccgtgaac gtcatctcca tccactaatc gagttatcca  660
gcgcctctca tcgaaagatc aggccaaaaa ccctagcggg ctcgcatcag ttggtaatca  720
gagcaaggtt cttcggtgag agacttctaa tcctttgctg tttttaatta atttcctata  780
gtccagaaaa gccaaaaaaa tatagtagat tagtttttcc ataatcctat taaacctttg  840
tgccttggct agtaccgttt tagttagggc ttgttgaatt tgcgttgctt cggtttgtgt  900
cgagttgctg gtcttagtgt ctagtccttt agagtttcga gttcttgtca ccatctatac  960
acagccgagt attaccatat cttctctctg tcgaatctgt tgcgaagtct gaattgaact 1020
gtggtcatgg tccggatcga gtagagttcc aatctgagtt caaaaagaaa gataactcta 1080
cttgttcggc cttactctag agagagagag agagtgtgga gcgaaaaaag tgtgtggagc 1140
gaattgctct tttgtattct tttgttcata taatcagttt tggaggttgc ccacaaaaaa 1200
agaaaaaaaa gaaaagagaa aagattcaaa aaaaagaggc tgtttttcat attgatttta 1260
ggtttgtccc accttgtttt cgggggtgtg ctgtggtttt cctttgtgtc caggctcgcg 1320
tctctagcac ggtctagcct aggaccagca cagtaccatc gtcgaacgct tattcagctc 1380
gcttttataa ctaacgtggt gctagttcgt tccttgtttc agcccaccta tagctccaca 1440
tactctacag cttgacaggt cttgtgctgc agcaccgata cacttcgtcc attgctatac 1500
acttgttggc agacgacccc tcctgtcaag caagataaga attggtaaga acttgtgtta 1560
caggttgagt gtgagcgact tgctatagct acatcctagt agttgtaggg attttatttc 1620
ttcacttgct ttttgttgtc tttgtctttg aaccatgcca ggggcagatg atggtaacga 1680
aacaccactt acacctcgca ctatgggcat catacaatat tttgaaagga aagtgaagct 1740
gcacacagag ggacttgata acgacttgca ggtgacgaat gaaaagctgg ggcagttgga 1800
ggctacgcag attgccacaa acaacaagct cacaagtttg gaggaatccg ttgctagtgt 1860
ggacaaaagc cttgctgctc tcctaaggcg atttgatgct ttccacaccg aagataaaga 1920
gaagcataaa gaagaaaagg agggagatcg agagcacggt agtcatgaag atgactacac 1980
tggtgatact gaacatgatg atcaagacac tcgtgatcga cgtcgccttc gtcacaaccg 2040
tagaggtatg ggtggcaacc gccgacgcga ggtacacaat aatgatgatg ctttcagtaa 2100
gattaaattt aagataccccc tttttgatgg taaatatgac cctgatgctt acatcacttg 2160
```

-continued

```
ggagattgct gttgatcaaa agtttgcatg tcatgaattt cctgagacta cacgtgttag 2220
ggctgctact agtgagttta cagattttgc ttctgtttgg tggatagaat atggaaagaa 2280
aaatcataat aacttaccta gaacttggga tgcgctgaaa agggccatga gagctagatt 2340
tgttccatct tactatgcgc gtgatatgat aaataagttg cagcagttaa gacaaggtgc 2400
taaaagtgta gaagaatatt atcaggaatt acaaacgggt atgttgcgtt gtaacctaga 2460
ggaggatgag gaaccggcta tggctagatt tttgggtggg ttaaatcggg aaattcagga 2520
catcctcgct tacaaagaat acaataatgt aacccgtttg tttcatcttg cttgtaaagc 2580
tgaaagggaa gtgcagagac gacgtgctag cacaaggagt aatatttctg cagggaaggc 2640
taattcatgg cagcaacgcg tggcttcaac tccatctaca cgtatttcta ctccatcatc 2700
tagtgacaag actcgagctg cccccaccaa ttcagttgcg aagacgatgc aaaagcctgc 2760
tgcgagtact tcatccgtgg catcgacggg tagaacaagc aacatacaat gtcaccggtg 2820
caagggatat gggcacatga tgcgtgactg tccaaacaag cgagttatga ttgtcaggga 2880
tgatggtgag tactcatctg ctagtgattt tgatgaggat acacttgcac tgcttgcgac 2940
tgaccatgca ggtaatgaag atcaaataga agaatatatt aatgcaggtg aagcggacca 3000
ctatgagagc ttgatcgtgc agcgagtgct tagtgcacaa atggagatgg cggaacaaaa 3060
tcagcgacac attttattcc aaacaaagtg tgtcatcaaa gagcgttctt gtcgcatgat 3120
cattgatgga ggtagctgca acaacttggc aagcagcgat atggtgcaga agcttgccct 3180
caacaccaaa ccacacccgc atccctacta catccaatgg ctgaacaaca gtggtaaggc 3240
aaaggtaact agacttgtga gaattaattt ttccatcgga tcctacaaag atattgttga 3300
atgtgatgtt gtgcctatgc aagcttgtaa cattctgcta ggtagacctt ggcaatttga 3360
tagagattct atgcatcatg gtagatcaaa tcagtattct tttctatacc atgatcgcaa 3420
aattgtgttg catcctatat cccctgaaac tattatgcaa actgatgttg ctagggctac 3480
taaagcaaag agcaagagca ataaaaatga taaatctgta attggtaaca aagatgagat 3540
aaaactgaaa ggacattgta tgatagctac caaatcagat attaatgagt tcaatgcatc 3600
cacttctgtt gcttatgctt tgatatgcaa ggatgctttg atttcagttg aggatatgca 3660
atgttctttg ccccctgctg ttgctaacgt tttgcaggag tattctgatg tgtttccaag 3720
tgatgtacca gcggggctgc ctccactacg cgggattgag caccaaattg atcttattcc 3780
tggatcagtt ttgccaaatc gtgcaccata caggacaaac ccggaggaaa caaaggaaat 3840
tcagcgacaa gtgcaagaac tactagacaa aggttatgtc cgagaatctc ttagtccttg 3900
tgctgttcca gtaattttag tgcctaagaa agatggaaca tggcgtatgt gtgttgattg 3960
tagagctatt aataatatca ccattcgata ttgacaccct attccacgat tagatgatat 4020
gctagatgaa ctgagtggtg ctgttgtgtt ttcaaaagtt gatttacgta gtgggtacca 4080
ccagattcgt atgaaattgg gagatgaatg gaaaactgct ttcaaaacta agttcggttt 4140
gtatgagtgg ttagtcatgc cttttgggtt aactaatgca cctagtactt tcatgagatt 4200
aatgaacgag gtcttgcgtg ctttcattgg gaaatttgtt gtcgtatatt ttgatgacat 4260
attgatttac agcaaatcat tggatgaaca tcttgatcat ttacgtgctg tttttaatgc 4320
actacgcgag gcacgtttat ttggtaacct tgagaagtgc accttttgca ccgatcgagt 4380
gtcttttctt ggttatgttg tgactccaca gggaattgag gttgatcaag ccaaggtgga 4440
agctatacag ggatggcctg tcccaaatac tatcacccag gtgcggagtt tcctaggact 4500
tgctagattc tatcgccgtt ttgtgaagga tttcagcacc attgctgcac cattgaatga 4560
gcttacaaag aagggggtgc cttttgattg ggcaaagca caagagaatt cattcaacat 4620
```

-continued

```
gttgaaagat aagttaactc atgcacctct cctacaactt cctgatttta ataagacttt 4680

tgagcttgaa tgtgatgcta gtggaattgg tttgggaggt gttttattac aagagggaaa 4740

acctattgca tattttagtg agaaattgag tgggcctgtt ctcaaattca acttatgata 4800

aagaactcta tgctcttgtt agaacattag agacatggca gcattatttg tggcccaaag 4860

agtttattat ccattttgat catgaatctt tgaaacatat tcgtagtcaa ggaaaactga 4920

atcgtaggca tgcaaagttg gttgaattta ttgaatcttt tccttatatt attaagcaca 4980

agaaagggaa ggaaaatatt attgctgatg ctttatcacg gagatatact ttgctgaatc 5040

aacttgatta caagatattt gggttagaaa caattaaaga ccaatatgtt catgatgctg 5100

attttagaga cgtgttgctg cattgtaaag atggaaaagg gtggaataaa ttcatcgtta 5160

gtgatgggtt tgtgtttaga gctaacaagc tatgcattcc agctagctct gttcgtttgt 5220

tgttgttgca ggaagcgcat ggaggtggct tgatgggaca ttttggagca aagaagaccg 5280

aggacatact tgctggtcat ttcttttggc ccaggatgaa gagagatgtg gagaggtttg 5340

ttgctcgttg cacaacatgt caaaaggcaa agtcacggtt aaatccccac ggtttgtatt 5400

tacctcttcc tgttcctaat gctccttggg aggatatatc tatggatttt gtgttgggac 5460

taccaaggac taggagggga cgtgatagtg tgtttgtggt tgttgataga ttttctaaga 5520

tggcacattt cataccatgt cataaaactg atgatgctac aaatattgct gatttgtttt 5580

ttcgagaaat tgttcgctta catggtgtgc ccaacacaat tgtttctgat cgtgatgcta 5640

aatttcttag tcatttttgg aagactttgt ggttcaaatt ggggactaag cttttatttt 5700

ccaccacctg tcatccccaa actgatggtc aaactgaagt tgttaataga actttatcca 5760

ctatgttaag ggctgtttta aagaagaata ttaagatgtg ggaagaatgt ttgcctcatg 5820

ttgagttcgc ctataatcgt tcattgcatt ctactacaaa aatgtgtcct tttgagattg 5880

tctatggctt cttgccacgt gctcctattg atttaatgcc tttgccaagt tctgaaaaaa 5940

taaattttga tgctaagcaa catgctgaat tgatgttaaa attgcatgaa gccactaaac 6000

aaaacataga gcgcatgaat gctaagtaca aatgcactgg agataaaggt agaaagcaat 6060

tgattctgga acctggggat ttggtttggt tgcatttgcg aaaagataga tttccagaac 6120

tgataaaatc caaattgatg cctagagctg atggtccttt taaagtgctg caacgaatta 6180

atgagaatgc atataagctt gatcttcctg cagattttgg ggttagtccc acatttaaca 6240

ttgcagattt gaagccttat ttgggtgagg aagatgagct tgagtcgagg acgactcaaa 6300

tgcaagaaag ggaggatgat gaggacatca acac                             6334

SEQ ID NO: 179 (forward primer): gggaagtaca gggacgaaga gc         22

SEQ ID NO: 180 (reverse primer): tgcaaccaaa ccaaatcacc ag         22
```

BAC Library Construction

A Bacterial Artificial Chromosome (BAC) library was constructed from sorghum genomic DNA. The sorghum genomic DNA was isolated from *Sorghum bicolor*, and digested with a restriction enzyme that was methylation insensitive to enrich BAC libraries for centromere DNA sequences.

Probe Identification and Selection

Groups of sorghum repetitive genomic DNA, including specific centromere-localized sequences, were initially compiled as candidate probes for hybridization with the BAC libraries. The satellite sequences set out in SEQ ID NOs:22-176 were used as probes for interrogating BAC libraries. These probes were prepared and labeled with standard molecular methods.

Library Interrogation and Data Analysis

The BAC clones from the libraries were spotted onto filters for further analysis. The filters were hybridized with the probes to identify specific BAC clones that contained DNA from the group of sequences represented by probes to identify those BAC clones that were positive for satellite sequence (the probe being amplified from sorghum genomic DNA using for a forward primer gtcacccagc agttccatcg ggtgc (SEQ ID NO:181) and for the reverse primer, actgctgggt gacgtggctc aagt (SEQ ID NO:182). Hybridization was at 65° C. for 12-15 hours and washing three times for 15-90 minutes with 0.25× SSC, 0.1% SDS at 65° C. Other exemplary stringent hybridization conditions comprise 0.5×SSC 0.25% SDS at 65° C. for 15 minutes, followed by a wash at 65° C. for a half hour.

Unique clones that hybridized with one or more of the probes were isolated. Probe hybridization was scored visually to determine a binary (positive versus negative) value, and the signal was assigned a score based on the relative strength of hybridization on a 10 point scale.

From this experiment, 211 BACs were CRS-positive and 624 BACs were 137 bp satellite positive, providing at least 624 BACs as centromere candidates for MC construction. Exemplary BACs are shown in Table 5.

TABLE 5

Sorghum centromere sequence-containing BACs

| Satellite-positive BACs | CRS-positive BACs |
|---|---|
| 81J23 | 41A11 |
| 82O22 | 41D7 |
| 84B23 | 42D9 |
| 85K22 | 42N11 |
| 89A3 | 43C3 |
| 89E2 | 43D8 |
| 89F4 | 43E5 |
| 89H10 | 44B3 |
| 89H10 | 44K3 |
| 89H8 | 44N12 |
| 89I6 | 45C3 |
| 89J10 | 45M8 |
| 89J9 | 45P2 |
| 89N4 | 46F1 |
| 89N6 | 46F4 |
| 89P4 | 46P12 |
| 90C2 | 47F1 |
| 90I3 | 47H1 |
| 90L2 | 48D6 |
| 90L3 | 48F2 |

Of the BACs shown in Table, 42N11 and 89F4 were sequenced. BAC 42N11, identified for containing the CRS sequence, assembled into 90 contigs (set forth in SEQ ID NOs:183-275), yielding about 65 kb, of which 104 bp aligned to the consensus satellite sequence (SEQ ID NO:22), and 3325 bp aligned with the CRS sequence (SEQ ID NO:21). Further analysis showed that this BAC also aligned 2852 bp with CRM2, a corn centromere retroelement sequence related to CRS. BAC 89F4, identified for containing the CRS sequence, assembled into 50 contigs (set forth in SEQ ID NOs:276-326), yielding a total of about 47 kb, of which 857 bp aligned with the CRS sequence (SEQ ID NO:21), another 6314 aligned with CRM2, and 1632 aligned with the consensus satellite sequence of SEQ ID NO:22. These results also demonstrate that BAC clones containing centromere sequence as identified by SEQ ID NO:21 or SEQ ID NO:22 contain both sequences.

Example 2

Construction of Sorghum MCs Containing Genomic DNA (Prophetic)

A subset of BAC clones, identified as described in Example 1, are grown up and DNA is extracted for MC construction using NUCLOBOND™ Purification Kit (Clontech). To determine the molecular weight of centromere fragments in the BAC libraries, a frozen sample of bacteria harboring a BAC clone is grown in selective liquid media, and the BAC DNA harvested using standard alkaline lysis. The recovered BAC DNA is restriction digested and resolved on an agarose gel. Centromere fragment size is determined by comparing to a molecular weight standard.

The components of a exemplary sorghum MCs are described in Table 6. The UBQ10 promoter is used to express DsRed in MCs constructed with the backbone vector CHROM-SB.

TABLE 6

Donor components of CHROM-SB

| Element | Size (bp) | Location (bp) | Details |
|---|---|---|---|
| YAT1 yeast Promoter | 2000 | 7110-9109 | PCR amplified YAT1 promoter from chromosome I of *S. cerevisiae* for expression of NptII in sorghum |
| A. UBQ10 Intron | 360 | 9123-9482 | PCR amplified *A. thaliana* intron from UBQ10 gene (At4g05320) for stabilization of NptII gene transcript and increase protein expression level |
| NPTII | 795 | 9510-10304 | Neomycin phosphotransferase II plant selectable marker |
| Rps16A terminator | 489 | 10368-10856 | Amplified from *A. thaliana* 40S ribosomal protein S16 (At2g09990) for termination of NptII gene |
| Bacterial Kanamycin | 817 | 11039-11855 | Bacterial kanamycin selectable marker |
| Terminator 6 | 332 | 12000-12331 | Terminator 6 |
| DsRed2 + NLS | 780 | 12466-13245 | Nuclear localized red fluorescent protein from *Discosoma* sp. |
| UBQ10 Promoter | 2038 | 13282-15319 | PCR amplified *A. thaliana* promoter from UBQ10 gene (At4g05320) for stabilization of DsRedI gene transcript and increase protein expression level |
| LoxP | 34 | 7057-7090 and 15335-15368 | Recombination site for Cre mediated recombination |

The MCs are constructed by following a two-step procedure: Step 1: Preparation of donor DNA for retrofitting with BAC centromere vectors and Step 2: Cre-Lox Recombination-BAC and Donor DNA to generate the MC. The resulting MChromsomes are subsequently tested in several different sorghum cell line.

Preparation of Donor DNA for Retrofitting

Cre recombinase-mediated exchange is used to construct MCs by combining the centromere fragments cloned in pBeloBAC11 with a donor plasmid (i.e. CHROM-SB Table 5). The recipient BAC vector carrying the sorghum centromere fragment contained a loxP recombination site; the donor plasmid contained two such sites, flanking the sequences to be inserted into the recipient BAC.

*Sorghum* MCs are constructed using a two-step method. First, the donor plasmid is linearized to allow free contact between the two loxP sites; eliminating the backbone of the donor plasmid. Second, the donor molecules are combined with sorghum centromere BACs and treated with Cre recombinase, generating circular sorghum MCs with all the components of the donor and recipient DNA. The MCs are delivered into *E. coli* and selected on medium containing kanamycin and chloramphenicol. Only vectors that successfully cre-recombined and contain both selectable markers survive in the medium. The MCs are extracted and restriction digested to verify DNA composition and calculate sorghum centromere insert size.

To determine the molecular weight of the sorghum centromere fragments in the sorghum MCs, three bacterial colonies from each transformation event are independently grown in selective liquid media, and the MC DNA harvested using alkaline lysis methods. The recovered MC is restriction digested and resolved on an agarose gel. *Sorghum* centromere fragment size is determined by comparing to a molecular weight standard. If variation in sorghum centromere size is noted, the MC with the largest sorghum centromere insert is used for further experimentation.

Functional Testing of Sorghum MCs Using Transient Assays

The MCs are tested, for example, in several sorghum cell lines, and the procedure optimized for antibiotic selection, cell pre-treatments, and bombardment conditions. All assays are transient and fluorescent cells are counted at several time points.

Example 3

Construction of Sorghum MCs Containing Synthetic Arrays of Repeat Sequence (Prophetic)

A synthetic array of the sorghum satellite repeat sequences is generated using PCR and directional cloning. A block of sorghum satellite repeats are PCR amplified and sequenced, and this sequence used as the basis for building the synthetic array.

For example, MCs containing synthetic arrays of sorghum satellite repeats may also contained either 5 or 8 stacked exogenous genes. The five-gene stack may include the genes NptII, DsRed, Anthocyanin, ZsGreen, and ZsYellow. The eight-gene stack may include those of the five-gene stack plus three additional genes from the *A. tumefaciens* tumor-inducing (Ti) pathway. These include iaaM (Trp mono-oxygenase), iaaH (Indole-3-acetamide hydrolase), and ipt (AMP iso-pentenyl transferase).

In order to investigate whether the MCs can carry a large number of genes, MCs containing a gene stack, a synthetic array of sorghum repeat nucleotide sequence and about 20 kb of peace lily (*Spathiphyllum* spp.) DNA is constructed. The total size of these MCs ranges between 82 kb and 87 kb.

In addition, MCs with a gene stack with two genes in addition to a synthetic sorghum centromere repeat array and an approximately 50 kb insertion of peace lily DNA may be constructed using the methods described above. The functionality of this MC demonstrates that the MCs of the invention can accommodate a large payload of genes, as 50 kb of the peace lily DNA includes a wide variety of genes.

Example 4

MC Delivery into Sorghum Cells and Regeneration (Prophetic)

To enhance the efficiency with which sorghum cells transformed with MCs can be regenerated into sorghum plants, where the MCs contain the auxin gene pathway and are delivered into fully differentiated leaf rolls rather than undifferentiated tissue, e.g. embryos. In addition, growth conditions are modified to enable development and propagation of transformed sorghum callus.

*Sorghum* is grown in the greenhouse for up to 6 months without floral initiation due to the growth time as well as the daylength settings on greenhouse supplemental lighting for those varieties that are day-length-sensitive. Stalks from several (clonal) plants are used to generate leaf rolls that do not include any developing meristematic tissue.

The MCs with a synthetic sorghum centromere are delivered to leaf rolls. For example, the MC may contain an eight-gene stack ("eight-gene MC"), or the MC may contain a five-gene stack ("five-gene MC"). In addition, a control plasmid (lacking a centromere) containing eight genes is also delivered, in which the eight-gene stack is identical to that delivered on the eight-gene MC.

The eight-gene MC includes *A. tumefaciens* tumor inducing (Ti) pathway genes (iaaM, iaaH, and ipt). The inclusion of these genes minimizes the time the transformed cells are in culture. IaaM converts Trp into indole-3-acetamide, which IaaH converts into auxin. Isopentenyl transferase (Ipt) converts 3',5'-adenosine monophosphate (AMP) into a cytokinin. Auxin is used in cell culture to stimulate plant cells to form callus. Media with auxin promotes callus growth from plant cells whereas plant cells cultured on media lacking auxin either germinate (for embryogenic material) or are unable to grow (non-embryogenic or meristematic tissue such as leaf tissue). Thus, the eight-gene MC induces callus formation without supplementing the media with auxin.

A biolistic delivery method using dry gold particles is used to deliver MCs to the sorghum leaf rolls. MC DNA (in 1×TE) is precipitated onto 2.1 mg of sterilized and washed 0.6μ gold particles. The DNA-containing gold particles are resuspended in 2.5 M $CaCl_2$ solution. 0.1 M spermidine (free base) are added to the mixture. The mixture is incubated on ice for 1.5 hours, with gentle finger vortexing (3×) for 45 minutes. The precipitated DNA is then washed with 100% ethanol, resuspended in 100% ethanol, and then the ethanol evaporated prior to bombardment.

The apical region of the sorghum stem is collected (20-30 cm long), after removing the outermost mature leaves, and the remaining leaves are sterilized by submersion in a solution of 50 ml bleach in 1 liter of water for 10 minutes. The remaining mature leaves are aseptically removed, and the young inner immature leaves are sliced into sections/discs approximately 2-3 mm thick. The leaf rolls are placed in *Sorghum* Osmotic Medium (SCOM; 4.3 g/l MS salts and vitamins, supplemented with 20 g/l sucrose, 0.5 g/l casein, 3 mg/l 2,4-D, 0.2 M mannitol, 0.2 M sorbitol pH to 5.8 and solidify with 2 g/L Gelrite) at 28° C. for 4-5 hours before the bombardment.

The three constructs are each initially tested by delivery into the leaf rolls. For delivery, the leaf rolls are bombarded with the MC DNA using the BioRad PDS-1000/He with a rupture disk rating of 900-1800 psi (1350 psi is preferred with one shot per plate). The gap distance (distance from rupture disk to macrocarrier) is 6 mm. Target shelf for tissue is L2-L4; L2 or L3 is preferred. The vacuum pressure of 25-29 in Hg; 27.5 in Hg is preferred. The bombarded leaf rolls are stored at 28° C. (dark) for an additional 16-18 hours on SCOM.

Subsequently, the bombarded leaf rolls are transferred to MSO (4.3 g/l MS salts and vitamins, supplemented with 20 g/l sucrose, 0.5 g/l casein, with NO 2,4-D. pH to 5.8 and solidify with 2 g/L Gelrite) and stored at 28° C., in the dark, for 2 weeks. The leaf rolls are visually assessed for callus production two and four weeks after bombardment.

Callus arising from the bombarded tissue is phenotypically evaluated for DsRed expression using a fluorescent dissecting microscope. If DsRed is observed in the tissue, then the callus is transferred to Regeneration *Sorghum* Medium (RSCM; 4.3 g/l MS salts and vitamins supplemented with 20 g/l sucrose, 0.5 g/l casein, 0.5 mg/l kinetin. pH to 5.8 and solidify with 2 g/L Gelrite) in low light (e.g., 16 hour day length, 26° C.) to initiate regeneration. This media does not contain auxin. If after a couple of additional weeks of culture, callus has also started to differentiate into root (primarily) and shoot material, which is not expected in the presence of auxin, then this result suggests either silencing or loss of the 3 genes from the *A. tumefaciens* tumor-inducing (Ti) pathway. After 2 additional weeks on media, PCR evaluation of this material or presence of the DsRed gene is carried out. If PCR results are negative, further suggesting loss of the entire MC and verifies that the genes are not silenced.

The advantages of including the genes of the Ti pathway on a MC are that the non-meristematic tissues are transformed and the need for callus initiation prior to DNA delivery is eliminated. In addition, the time in culture is reduced and as a result somaclonal variation, endogenous chromosome number changes and the like are also reduced. Furthermore, the inclusion of the Ti pathway genes eliminated the need for selectable marker genes.

In a separate experiment, five-gene (NptII, DsRed, Anthocyanin, ZsGreen, and ZsYellow) MCs are delivered into sorghum callus. These MCs are delivered to the callus cells using the wet biolistic method as described above.

Following delivery, Callus from the tissue is phenotypically evaluated for DsRed expression using a fluorescent dissecting microscope. If DsRed is observed in the tissue, the calluses are transferred to Selection *Sorghum* Medium MS3-50 (4.3 g/l MS salts and vitamins supplemented with 20 g/l sucrose, 0.5 g/l casein, 3.0 mg/l 2,4-D, 0.5 g/l polyvinylpyrrolidone (PVP). pH to 5.8 with 2 g/l Gelrite; further supplemented with 50 mg/l G418) for initial selection for 2 weeks. All calluses are subsequently transferred to additional selection on Selection *Sorghum* Medium MS3-75 (4.3 g/l MS salts and vitamins supplemented with 20 g/l sucrose, 0.5 g/l casein, 3.0 mg/l 2,4-D, 0.5 g/l polyvinylpyrrolidone (PVP) pH to 5.8 with 2 g/l Gelrite; further supplemented with 75 mg/l G418) for 4 additional weeks. Tissue is then visually assessed for sorghum callus tissue that is able to grow. Those identified events are transferred to Regeneration *Sorghum* Medium RSCM-25 (4.3 g/l MS salts and vitamins supplemented with 20 g/l sucrose, 0.5 g/l casein, 0.5 mg/l kinetin. pH to 5.8 and solidify with 2 g/L Gelrite; further supplemented with 25 mg/l G418 after autoclaving) in low light (16 hour day length, 26° C.) to initiate regeneration. Simultaneous with initiating regeneration, this callus tissue is evaluated by PCR for presence of the genes on the MC.

After an additional 4-6 weeks on regeneration, plantlets (with and without initial root initiation) are transferred to Rooting Medium RtSC-25 (2.15 g MS salts and vitamins supplemented with 20 g/l sucrose, 0.5 g/l casein, 0.5 mg/l kinetin. pH to 5.8 and solidify with 2 g/L Gelrite; further supplemented with 25 mg/l G418 after autoclaving). Rooting occurs in 2 to 6 additional weeks of culture with 16 hour day length at 26° C. Rooting occurs in sundae cups (Solo Cup Co.; Joliet, Ill.; USA) for additional plantlet growth and root development. Plantlets with well established root systems are transferred into pre-moistened soil-less mix (LC1, BFG Supply Co.; Burton, Ohio; USA) under a humidome in an 18 well flat in a growth chamber (28° C., 16 hour day length). The dome is opened slightly 3-4 days after transplanting to slowly reduce humidity. The dome is removed completely 2 days later and the plantlets are then transferred to a greenhouse (28° C., 16 hour day length). The plants are watered from trays beneath the pots when soil began to dry. The plants are subsequently transplanted and grown to maturity in 1.6 gallon pots with Soil:Peat:Perlite (1:1:1) supplemented with Osmocote fertilizer (Scotts Co.; Marysville, Ohio; USA).

*Sorghum* callus and tissues produce phenolic compounds while in tissue culture, and these phenolic compounds reduce or inhibit callus growth and plantlet regeneration. In order to promote sorghum plantlet regeneration in culture, the media described above (MS0, MS3 and variants thereof, and RSCM) are supplemented with PVP at a concentrations of 1% to 3% w/v according to the intensity of the exudation of the phenolic compounds. The PVP acts as a sink for phenolic compounds and enhances subsequent callus growth and plantlet regeneration.

In order to promote the frequency and the morphogenetic competence of regenerable sorghum callus, the cells are cycled from a liquid culture to a solid culture. The apical region of the sorghum stem (20-30 cm long) is collected and the mature leaves are removed. The stem is surface sterilize by submerging the tissue in a solution of 50 ml bleach in 1 liter of water for 10 minutes. The remaining outermost mature leaves are aseptically removed and the young inner immature leaves are sliced into sections/discs approximately 2-3 mm thick.

The resulting leaf roll discs are placed on sorghum MS3 Medium (MS3; 3 g/l MS salts and vitamins with 20 g/l sucrose, 0.5 g/l casein, 3 mg/l 2,4-D. pH to 5.8 and solidified with 2 g/L Gelrite) at 28° C. for 2 weeks in the dark. The resulting regenerable sorghum callus (white nodular embryogenic pieces) is then removed and placed into liquid sorghum MS1 Medium (MS1; 4.3 g/l MS salts and vitamins with 20 g/l sucrose, 0.5 g/l casein, 1 mg/l 2,4-D. pH to 5.8) at 28° C. for 2 weeks on a rotating orbital shaker (100-150 rpm) in the dark. After the 2 weeks, the regenerable sorghum callus (white nodular embryogenic pieces) is removed and subcultured back onto sorghum MS3 Medium (MS3) at 28° C. for 2 additional weeks in the dark. *Sorghum* callus can be subcultured in 2-week intervals between solid MS medium containing 3 mg/l 2,4-D and liquid MS medium containing 1 mg/l 2,4-D to maintain embryogenic callus.

Example 5

Evaluation of Autonomous MCs (Prophetic)

To evaluate whether the candidate MCs are maintained autonomously, FISH can be performed on mitotic metaphase chromosome spreads from root tips. FISH can be performed essentially as described in Kato et al. (*PNAS USA*. 101: 13554-13559, 2004).

For FISH, root tips can be collected approximately 10 days after transplanting regenerated T0 plants to soil or after germination (T1-T4 plants). Sampled roots (3-6 per plant) are moistened and exposed to nitrous oxide at 150 psi for 3 hours to arrest chromosomes in metaphase as described in Kato (*Biotech. Histochem* 74: 160-166, 1999). Roots are fixed in 90% acetic acid, and spread onto poly-lysine coated glass slides by squashing thin cross sections. Following hybridization with ALEXA FLUOR® 488 and ALEXA FLUOR® 568-labeled probes, slides are counter-stained with DAPI (0.04 mg/ml) and ≥15 metaphase cells are evaluated per plant using a Zeiss Axio-Imager equipped with rhodamine, FITC, and DAPI filter sets (excitation BP 550/24, emission BP 605/70; excitation BP 470/40, emission: BP 525/50; and excitation G 365, emission BP 445/50, respectively).

Extra-chromosomal signals are only considered to indicate autonomous MCs if ≥70% of the images (n≥15 cells analyzed) show co-localization of the ALEXA FLUOR® 488 and ALEXA FLUOR® 568 signals within 1 nuclear diameter of the endogenous metaphase maize chromosomes. Grayscale images can be captured in each panel, merged and adjusted with pseudo-color using Zeiss AxioVision software (Zeiss; Thornwood, N.Y.; USA); fluorescent signals from doubly labeled MCs can be detected in both the red and green channels.

Integrated constructs result in two FISH signals, each on a replicated metaphase chromatid. The MCs can be considered autonomous when (i)≥70% of the cells examined (n≥15)

contained signals that are clearly distinct from the DAPI-stained host chromosomes, (ii) integrated signals are not detected, and (iii) the fluorescent probe corresponding to the MC-encoded genes co-localize with the probe to repetitive centromeric DNA, suggesting an intact construct and making it unlikely that the signal is due to noise.

We claim:

1. A sorghum plant cell comprising a sorghum mini-chromosome comprising at least one exogenous nucleic acid and a sorghum centromere, wherein the sorghum centromere comprises at least five copies of a first repeated nucleotide sequence that (i) is at least 80% identical to the nucleotide sequence of any one of SEQ ID NOs: 22-176, or (ii) hybridizes to a nucleotide sequence of any one of SEQ ID NOs: 22-176 under stringent conditions comprising hybridization at 65° C. and washing three times for 15 minutes with 0.25×SSC, 0.1% SDS at 65° C., wherein the centromere confers the ability to segregate to daughter cells.

2. The sorghum plant cell of claim 1, further comprising a transgene expression cassette comprises at least one exogenous nucleic acid.

3. The sorghum plant cell of claim 1, further comprising at least two copies of a second repeated nucleotide sequence that is at least 80% identical over its length to a fragment of a sorghum retrotransposon sequence of SEQ ID NO: 21 or hybridizes to a fragment of the sorghum retrotransposon sequence of SEQ ID NO: 21 under stringent conditions comprising hybridization at 65° C. and washing three times for 15 minutes with 0.25×SSC, 0.1% SDS at 65° C.

4. A sorghum plant cell of claim 3, wherein the sorghum centromere comprises:

(a) at least 5 copies of the first repeat within 1 kb of nucleotide sequence and (b) a transgene expression cassette comprising at least one exogenous nucleic acid.

5. The sorghum plant cell of claim 1, wherein the sorghum mini-chromosome exhibits a mitotic segregation efficiency in sorghum cells of at least 90%.

6. The sorghum plant cell of claim 2, wherein at least one of the exogenous nucleic acids is operably linked to a heterologous regulatory sequence functional in sorghum cells.

7. The sorghum plant cell according to claim 6, wherein the exogenous nucleic acid is selected from the group consisting of a herbicide resistance gene, a nitrogen fixation gene, an insect resistance gene, a disease resistance gene, a plant stress-induced gene, a nutrient utilization gene, a gene that affects plant pigmentation, a gene that encodes an antisense or ribozyme molecule, a gene encoding a secretable antigen, a toxin gene, a receptor gene, a ligand gene, a seed storage gene, a hormone gene, an enzyme gene, an antibody gene, a growth factor gene, a drought resistance gene, a heat resistance gene, a chilling resistance gene, a freezing resistance gene, an excessive moisture resistance gene, or a salt stress resistance gene or a biofuel gene.

8. The sorghum plant cell according to claim 1 wherein:

(a) a polynucleotide sequence is transcribed as a first RNA;

(b) a polynucleotide sequence is transcribed as a second RNA; and (c) a polynucleotide sequence is transcribed as a third RNA, and wherein transcription of the polynucleotide sequences results in increased biomass of a sorghum plant compared to the biomass of a wild type sorghum plant.

9. A sorghum plant cell comprising a transgene expression cassette comprising at least one exogenous nucleic acid not integrated into the plant cell genome, wherein the transgene expression cassette comprises (a) a polynucleotide sequence that is transcribed as a first RNA;

(b) a polynucleotide sequence that is transcribed as a second RNA; and (c) a polynucleotide sequence that is transcribed as a third RNA; wherein transcription of the polynucleotide sequences results in increased biomass of a sorghum plant compared to the biomass of a wild type sorghum plant.

10. The sorghum plant cell of claim 1, wherein the recombinant chromosome has not been maintained in a cell of a heterologous organism.

11. The sorghum plant cell of claim 1, wherein the transgene expression cassette comprises at least three exogenous nucleic acids, and wherein the first repeated nucleotide sequence and the transgene expression cassette are not integrated into the genome of the sorghum plant cell.

12. The sorghum plant cell of claim 2 that exhibits an altered phenotype associated with at least one exogenous nucleic acid within the sorghum mini-chromosome.

13. The sorghum plant cell of claim 12, wherein the altered phenotype comprises altered expression of a native active gene or the expression of an exogenous gene.

14. A sorghum plant, plant tissue or sorghum plant part comprising the plant cell of claim 1.

15. A sorghum seed obtained from the plant of claim 14, wherein the seed comprises a sorghum mini-chromosome comprising at least one exogenous nucleic acid and a sorghum centromere, wherein the sorghum centromere comprises at least five copies of a first repeated nucleotide sequence that (i) is at least 80% identical to a nucleotide sequence of any one of SEQ ID NOs: 22-176, or (ii) hybridizes to a nucleotide sequence of any one of SEQ ID NOs: 22-176 under stringent conditions comprising hybridization at 65° C. and washing three times for 15 minutes with 0.25×SSC, 0.1% SDS at 65° C. and wherein the centromere confers the ability to segregation to daughter cells.

16. A sorghum plant progeny comprising a sorghum mini-chromosome, wherein the plant progeny is the result of breeding a plant of claim 14.

17. A method of using a sorghum plant of claim 14, the method comprising growing the plant to produce a recombinant protein encoded by an exogenous nucleic acid of the mini-chromosome, and alternatively, further comprising a step of harvesting or processing the sorghum plant.

18. The sorghum plant cell of claim 4, wherein at least one exogenous nucleic acid is operably linked to a heterologous regulatory sequence functional in sorghum cells.

19. A sorghum plant of claim 4 that exhibits an altered phenotype associated with at least one exogenous nucleic acid within the sorghum mini-chromosome.

* * * * *

SEQUENCE LISTING

<160> NUMBER OF SEQ ID NOS: 326

<210> SEQ ID NO 1
<211> LENGTH: 2139
<212> TYPE: DNA
<213> ORGANISM: Drosophila melanogaster

<400> SEQUENCE: 1

```
gttgtccgca gcggagatgc aactgatgca acccacattt cagatcaccg acaacgtgca     60
gcgcggcaac tacgccactc tgaccgacaa ggatgtggcg catttcgagc agctcctggg    120
caagaacttc gtgctcactg aggacctgga gggatacaac atctgcttcc ttaagaggat    180
tcgaggtagg ttgtgtaacc aaattcattc acattcgtgt gccctttaat gaatttctcc    240
gatgaattgc ttcaaccagg caacagcaag ttggtgctta agcccggaag cacggcggag    300
gtggccgcca tcctgaagta ctgcaacgag cgtcgtttgg cggtggtgcc gcagggcggg    360
aacacaggtc tagtgggcgg atccgtgccg atctgcgacg agattgtcct ttctctagcg    420
cgcctgaaca aggtgttatc cgtggacgag gtcaccggca ttgctgtcgt ggaggcgggc    480
tgcatcctgg agaacttcga tcagagggcc agagaggtgg gcttgacggt gccactggac    540
ctgggcgcca aggccagttg ccacatcggg ggcaatgtgt ccacaaacgc gggcggagtg    600
cgggtggtgc gttacggcaa tctgcacggc tctgttttgg gcgtggaggc ggtgctggcc    660
accggtcagg tgctggacct tatgtccaac ttcaagaagg acaacaccgg ctaccacatg    720
aagcacttgt tcataggatc cgagggcact ctgggcgtgg tcacgaagct ttcgatgctc    780
tgccccccatt cctcgcgagc ggtgaacgtg gccttcatcg gcctgaactc cttcgacgat    840
gtgctgaaga cttttgtcag tgccaagcgt aatctgggcg agattctaag ctcctgcgag    900
ctgattgacg agcgggcctt gaacaccgcc ctcgagcagt tcaagttcct gaagtgagtt    960
gcgccacctt tgtcttctct gagcgttacc aatcctgttc acaaacttat ttcccatagc   1020
tcccccattt cgggatttcc cttctacatg ctcatcgaga cctcgggcag caacggtgac   1080
cacgacgagg agaagatcaa ccagttcatt ggggacggta tggagcgtgg cgagatccag   1140
gatggcaccg taaccggtga tcccggcaag gtgcaggaga tctggaagat ccgcgaaatg   1200
gtgccgctgg gtctgatcga gaagagcttc tgcttcaagt acgacatctc gctgcctctg   1260
cgggacttct acaacattgt ggacgtgatg cgagagaggt gcggtcccct ggccacagtt   1320
gtctgcggat acggccatct gggggactct aatctgcacc tgaacgtctc ctgcgaggag   1380
tttaacggcg agatctacaa gcgggtcgaa cccttcgtct acgagtacac ctccaagctg   1440
aagggcagca ttagtgcgga gcacggcatt ggcttcctga agaaggacta cctgcactac   1500
tccaaggacc cggtggccat tggctacatg cgcgagatga agaagctgct ggaccccaac   1560
agcatcctca atccctataa ggtgcttaac tgaaggcttc tacctaatag attctatttt   1620
ttttgtttgt gtgtaatttt cataacctta taatacagaa atggcattag aagtgaattt   1680
tgttaacttg tgaagttaaa aaggaccatc atatttggca cgaaaccaat gggcaaaact   1740
tacttataaa atagtccgaa aaaatagtat ataccagttt ttacagtacc acattatagg   1800
tactcggagg taataataga aaaaacacta tctttgcatt tactgttaca ctacgaagca   1860
ctatatttag tagcagtact cattagagtc cactcacaaa attagcacca accggcagta   1920
```

```
attggtcaag gatcggcgat agcttcaaac tccgaagttc aaagtcaaac tgccgccctg   1980

cgaaagcttc gcgagtggag cttttctgca cttatcgata gctaacattg tggcgcgact   2040

atcgatcgac gagctgccgc ttaacagtgc catatataga ttgtaacatt agaagctcaa   2100

atcattgttg gagcacaaac cacaaagaac acacgaaac                          2139
```

<210> SEQ ID NO 2
<211> LENGTH: 2191
<212> TYPE: DNA
<213> ORGANISM: Drosophila melanogaster

<400> SEQUENCE: 2

```
aaaatatttc acctcatttt ccgcacacca tttataagca aagttacccc caacccataa     60

cttttatggt aagtaataca gaccctccaa gttcggcaaa tcgataccca gcgaccttga    120

gcttgacatt tatatatatg ccagaatata acgaccacgt gctgtcaact gtgtcaggaa    180

aagctcaccc acactttctt tggaggagct gtgctcccta aacgaatttc attgtcaagg    240

tcgcacgcac aaaaatgaag aggaaaagct gaatgtgggt ggaaatgccg gccggcacga    300

ccttgaagcc agttgggtga gaaataaaaa gcttttgccg gtaggagact tgtggaacat    360

cacccacaag tggcggactt ggccttggcg atggccttgt tggagctccc tcagcaaaaa    420

tgttacatag gggqaggaaa taagctcaat tggctttatg ctttccgctc cctggaagtc    480

cttttctgga atgttaaagt gttaaatgac atttattgaa catttgggac agaggaggag    540

ataatacaat atacttgtct aattaaaaaa aatcgttatt atgatttatt ccatatgtaa    600

gattttaatt catcatgatt gtaaataaat tatataaaac aaattcaata aatttacatt    660

attgataaaa tttattttt catgaaatta tacccaaaaa ttattctcaa tttttcttat    720

aatcagtttt gcataagtat actttcttca taccccctcta ccacagccac tgctttcttg    780

actttgcaac tatccgggaa cagcttatca taatggatga gctgcagcta acggaaaatg    840

ggggagctgg gatcaaacat tttccaaggt tgaaattgtc gtcagcataa tgtttgaggg    900

agctggattc gcgttagctt gaaggtcaat ccatttgggt gccctttgtt atggtcaagt    960

ttaaggctgc aatagggga atcttcaagg accattacgc aaggttttcg catcaaagat   1020

ttgccgtgca agctttttga gttgaaggat gcttaacttg aaagcgggtt agtggttcca   1080

agagatttta ggtgaaggag actccgctgt tttgaaatat attaagtatg taaagaagta   1140

tactataaat aacccaaagt gatacaatgt aagaaaagat ctcgttggtc cctggtataa   1200

atttgtttgc cattaatgaa tattgaaaat aataattata ctaataatag gtacaataag   1260

caagattaaa ttgcatttaa tcaccaaaaa tcagtttcta tgcgaaccaa aatgtcataa   1320

caaacaattg ttgattcatc cgtagtgaaa tccaagttcg aaattcgaaa tgagcatacg   1380

acgaccaaac ttcccctcaa aattgctaga ctcagctaga gcaagtacgc ccaagttaac   1440

ccctgaaatt cgaaatgaat tcgatgccgc gcttcgaaca acgaaatccc aaagagctta   1500

cgttttattt gacgtagcac tcttacgtga aatgattttc cccaattccg ctctcatttc   1560

ccgagtctct caccgcttct cagccacttt cccacccct ttctagttcc gaagtaaagg   1620

taacaaaggc agccgtgtct ttggggtggt aaactggcgg tggtggtggc acattgtcag   1680

tggtgtgggt tcctgtggtt ggtggttcaa ttggttggtt gttggcataa acaaagcaca   1740

cacacaatac acacaaactc ccgggggtg gtggaaattg ggagggtgac attcactgcg   1800

agagaggaac tcgcttccta taggaaagta caaagagagc tattttataa atgtgactgc   1860

agcaaggata tttacagtca gtccactctg aaacctcgac gagagaacat tgaataacaa   1920
```

```
gcggaagcga aaagcgcagt tgaaagttcg tcaaaaagcg acaagtttcc tcgttcgttt   1980

tcccgccaaa tgagtcagaa aaattttcca agtgctcgat acgaaacata aagacttaca   2040

agacttaaag tgcaagcagt gaatggaata tattattcct cagcgatatt gaaatcaaac   2100

attaaaaata tatgctacac taaagttata tattttttta aagattcata cgttttgtaa   2160

aatcacattt tgtattaaat taaataccgc c                                  2191
```

<210> SEQ ID NO 3
<211> LENGTH: 2035
<212> TYPE: DNA
<213> ORGANISM: Drosophila melanogaster

<400> SEQUENCE: 3

```
tgggtgcgtc gcaggtttca ctggaaaaca atttgcactt ttgtttgtgg agtcgacaac     60

aaaagcattc acttgtctaa gactctctca ttcataactc gcactttagt tcactgaacc    120

gcacgcaaaa ctttggggcg gacaacatgt tttcgaggtg ccaaaagctt cataaaacta    180

ccaatccatt agattaaatt ccaggcggta catcttttgg ggatgattca tgtggcaggg    240

gttctctact cgtttacaat catatcatca tcttcaagat catatagttt atcatatcag    300

tagagtacta caatataatg cataaactaa gccaaataac tttatgacgc gtgcttatgc    360

gaaagtaaac tttattatca aatttactta accgtgaaat caaaaccttt atataaacac    420

gaatattatt atctttgcta aataaaactc tcgcttaaca aacaatgaca cttcaattcc    480

aacatagagt ttatcttaag ccaataacca aaaacggaac ttacataact tgccaacaaa    540

catatgaata tagctatttc ggatcgtggg agaccattat gcatacaagg cacgctccta    600

aaaaccgtgt taaacaaata tatgtcaaat gtatatctta aaaaagcgcg cacatatctt    660

ttgaaatatc ttcacccaga gtatgtatga gattaaactg gattagcact aagccacagc    720

ttctgtagat agaaatttta tgcagagagt agattatttg gctgctgagc aatttgacca    780

ccacaagata gcagagaaca tctgacattt tctatatcca tataataaaa ctgacttaac    840

actaagctga agtggtatgt ttaaatcctc cagctaataa atcgagacta aacgccctat    900

cttatagtga tatataatag tatctatatg tgtattgtca tttactgttt atgagtattt    960

gaaaaaacca ttctatattt tataggttag ttaataaata ttttgatata catatgtaga   1020

ttggctcaca cgtacttatg acccactaca taataaaatt gttttgtttt ttaatagaat   1080

aatggtttat aaaaagttta gactcacacg gaaatgataa actctttgca aatacagctt   1140

tcattttatt acaaattgca ctctttcaga tctgcagttg ctatgccaac cttttattcc   1200

ctttactaaa agggtatact aggcttactg aacagtatgt aactggtaaa gtaaagcgtt   1260

tccgattcta taaattatat atctaaactt ttgatcagtc gaatccatct gaacacattc   1320

tgtcacatta gattattcca gaaactcaac ttaaacatgt gtattttttta agaccattat   1380

caaggatatt aaaaatggtc tcctaaaatt taataaacaa aagtgtcaca tcaaatttaa   1440

gacgtaaatt aatatttttt ttctatggtg aaataattgt tattttccaa tgttgtgaaa   1500

taataaatgt atcttttcaa cgcacacatt ttcaaggttt taataataat agtgactcgt   1560

gcgtgaataa gagagaaatt aagattttaa aaaagaataa aattcagaga tgtgatctgt   1620

aaaaattatt taccaatttt catttacccc cgaaagtgat gctaatggtt aaaacggcat   1680

ttgcgactta tctcctacgt aatattgcaa aaataaggat ttggttagat gagtgtgaag   1740

taaacaagat gcaaagtttt ggagatagaa aacatagcct tgagtcttgg tcatgtttac   1800
```

```
ttggcaccag gccgcgatta tcagcgctac tagtcgtaat ttgagttaga cctttaatac   1860

tctaagtgag agtgatgata tacgatttcc cagccacttg ctttctacga aatgcgctaa   1920

aaaaaatccc taactacaca aagatttgtg ttgttatcca ggtgttctga tataaaaggc   1980

ggcaaggaaa ttgatggcat catcagtatc aaagtgagag tgattgcagt cacac        2035
```

<210> SEQ ID NO 4
<211> LENGTH: 2136
<212> TYPE: DNA
<213> ORGANISM: Drosophila melanogaster

<400> SEQUENCE: 4

```
atgggacggt cctattctca gcaaaaattg acaagaacaa caacaatgtc tatggaaaat     60

cgaacttcat cccagcacct gcagaaatcc cgagcgagtc ggggaaaaag tatttaaccc    120

ccgaaagggt tttccccaaa ataatgaagt aatgaatgaa gcggaaaaca ctggccgcca    180

atctacctaa tactaatgag cgggccaacc cgaccaggaa tttttgcaag tcaggtactt    240

caacggatat atgggttcga caagtgcgga ttttcccgcg acatcaatga ggacttggcc    300

gggttatccg cggtgctcat cgggcaattc cgcggccgag gacttcatcg tagtgatcat    360

taggtagata tgtgcatgga tgtgacatgg cgatcattgc gcggaataac acacgtaata    420

accgagatat ccgggatgac ccaccaggta ggatgtgagg acatatagaa aaccccccagc    480

cagtttttcc actcgtcgtg gcttgttttg cttgagtttc gctgactgcg taattggata    540

agatgggaaa ttactttaaa tccttcgctg atccacatcc ggacattcgt cgaaggaaaa    600

tccattgcag ggaaatacga aatggaaatg cggctgggtt attggctcga catttcccat    660

cttccctcac gccattggtt gcaggatcgc ggggaattgg aattccgcgc tggaattttt    720

tgtcacctct tgggtttatc aaaactttg ggtttgctat ggattttttc caattttacc    780

accgcgcctg gttttttttt tttgacgacg cggaaaatcg gacttggcta tgcgggcttg    840

tctgtttttc cgggtacaaa gtctgcatgt cagcctccat gcgggagtgg gagttgggaa    900

agtttcccat cgatagttgg aggggtggct tgaaagtctg gaggtgctag ctgggaaagt    960

tgtgtgtgcg cgatgaggca aggagtcaaa gatcagggga gttggaaagc gagaattgtg   1020

ggaatcgtcc aggactcagc tggatgctga ggggcagtat gatttttttt acgttatcaa   1080

tcgaattgat tttaagacag cagaacttca catactaata agatgaccat gggattagtt   1140

aaaatgtgta actcgtattc gaatcgtcat tctttcacgg accaatcgtg ggaacaggag   1200

atctcttcga tccaagctca caggagactt gacactcttc gtctattcct tgtcaagttt   1260

ttaatgacat ctcctatgcc ctgagctatg ttttcctagc tctcatcgat cgctgccaat   1320

gagccactgg agatgatcca taagtcagcg tagagtgcac cccagagttg acacttggtg   1380

tctcggaatt cggctcatta tcagtgctat ttttggaaca cctctctgcg aaggtgtcat   1440

ttttgtcagt gcgtatcgct caggttcaac tccccaccaa aaaccgaatt tagagcatcg   1500

gcagatgtac ttgaagcact caatctaagt gaggaaacca ccccatgaac gaagagtact   1560

aggagtccta tttgactcgt gcttaaaaat agaaaattac ttagggtgat ccataggtag   1620

ggaggcgata ttgtaacttg catttcggac ccggacctgc acgagttatt acgggtgggt   1680

tgtgagcgta tcgggaaatt ggagagccac cagatctgtc ataacttata cgggggatcc   1740

ttattcctgg gagggtgcgc ctgcgtctgc tcttccgaga gagaggtggg aaatggagga   1800

agagagagag agagagagtg agagagcagg tagagggaag tgagggaaat acgcaataag   1860

ggtatgggaa aagtgctgtt gttgttgcta ggtagcgacg cacacgtgcg agtgtttttc   1920
```

```
tgttttgaag aagaaccacc accaaatggc gacagcggcg tcggcagagg cgcagagttc   1980

cgggtataaa agagcgtgct cgactgttga cctgtcacag ccacctcagc tctcgttgag   2040

aacgcaacca ccgctctata ctcgatcccg aactatataa ctcgcctctc gatcgccgat   2100

ctcccgattt acccatctcg atcagtaccg gaaacc                             2136


<210> SEQ ID NO 5
<211> LENGTH: 2015
<212> TYPE: DNA
<213> ORGANISM: Drosophila melanogaster

<400> SEQUENCE: 5

atttggctcc ccatcgccat cggttgctcc aatgacacta gggaattgtg ggccgccgac     60

agctgtcctt aattacatgg aaatccacac tagattcgtg cccctcgccc cgtactcgca    120

gccgaagtcc ccacagagtc attcaccttg ccaccaccaa aaaaaaaacg aaagcaactg    180

aaggaaaagt tcgattcgaa ggctgaggga tacccttaaa ggcccatttc ccggcttcgt    240

aaatcacatt tagttagcca tttagactac agcaagtctt ttaagataca ctgcaaaata    300

aataccatta cattaataga agtgtcatgt catcggtctg tatttttgtt accacagaat    360

agacttacat atatgataaa aaaatgttca acaataagtt acatcggtag ccaattctat    420

agatttaatt ccttacgaat atagtttcgt tggaatactc aatttgtaat tgtaattaat    480

tataattatt ataattttaa gaatttatat aagtaactaa aagacacggc agacacagaa    540

tgaaaacact ctatgttagg gaatgcaaaa aaacgtggcg gaagccaaaa ggcgcaagca    600

aaaatcgaaa ccaagtgaat ataacatatt atttcaacag gcaactcatt cagcatataa    660

tattaccacc catggagctt tatgtagttg atgtacgtag tctatgatgt ggagcccacg    720

ttggcggaac tgggaatggg gattggggtt tgagagctgt ggtaaattgg ggggttgaag    780

tatcaagggt ttgggttctg tagacctgcg gaatcgaggt gaataagcga agaacacatt    840

cacacacact aaaaggcaaa caaagggaaa tcaatctttg tacatacttt tagcatatgc    900

acacgtatga tctccaccca cttttccctc ccaatgaaac aaacacacac acacatgcaa    960

ggccgtacgt ttgtatatgt gtgcggttgt cggctttgcc gggaattggg gaatatttgc   1020

atgcctttgt gtactttttc catatgattt atgacctaaa ttgttgctgc tcgcgcacat   1080

ataattacac acacatcgct gtggccatgt gtgtgtgtgt cgtcttggga cgcgcgccaa   1140

agtatgctac actttttgtt ttatgagtta ataagtaggc gtggccccag cccaattgct   1200

acactctgat tatggcaccg gatacccaga tagacgccca tccaccccac tgtaagatgg   1260

gggaatttcc aaacctatat gtatgtgcag atcagatagg atagcacaga actttttaaa   1320

gtacactttt ggggcacgca atttagaaaa tgtacctcgg tgtcggagaa attattttaa   1380

aagtcgactg aaccacctcg ttccatatgg agaagtctac gagttcaagt ttaatggagc   1440

agctgactgc actgaatttt gtagtttaat acacaaatcc gcaaattgca tctcacttca   1500

aatagcctgg tacatagtat ctactaacat aactcatatt aaaataaagc aaccaaccag   1560

agggccgaag ttctattaat aaaactaata tttaactatt atatatacat tttatttact   1620

tggtacgctt atgataacct tcgaaagaga accaacacaa tacgctttgt catttgaaaa   1680

ataaatatgc tgtaactact ttacaaggtg aaactcttgt cagaagataa gaggctaggt   1740

aagttgatta ttcaatcagt ttacttactg caacccaaaa tggtcactgc actaaccttc   1800

agatgagctg cactacaccc tcaatcgaga atcaatgcaa acgcagtgcc agcgaaaatg   1860
```

```
tcagcaaggg attaggccaa tcccaaacgg gtaatcccgc tgcgacaatg ctaatccaat   1920

tccgatgggc cgtataaaag ccccaagctg ggctggctgt gatttcgtct tggcccgcag   1980

accggagcat ggagtccggt aacgtgtcgt cgagc                              2015


<210> SEQ ID NO 6
<211> LENGTH: 2082
<212> TYPE: DNA
<213> ORGANISM: Drosophila melanogaster

<400> SEQUENCE: 6

atcgatgacg gcatcggctt gacctctcgg agtacgtttg attttataga acaagttttc     60

tcctttctta tactataagg aaaaattata aaaattgctg aaaatgaaac atggctagaa    120

ttcgtttttt aacatttttt caatctgaga aaaaatttcc gattagtctt aaaataacta    180

aaccaattcg tatacccgtt aatcgtagaa gaaaaatgaa attcatataa taagtagatg    240

gatttgctga cccggtgagg tatatatgta ttcctgaaca tgatcagtaa acgagtcgat    300

ctggccttat ccgtatgaac gtcgagatct cgggaaatac aaaagctaga aggttgagat    360

taagtatgca gattctagaa gaagacgcag cgcaagtttg cgactacgct gaatctactg    420

ctaaaaactg ccacgcccac acttcttaag aatttgattt attttcacaa gctgaggaac    480

ggtagggtcg aggaactcga ctacaacgtt ctgccttgtt tatttcttaa caaaaactta    540

gtagccgttt gggttggaaa ccacctgacc ttaggtctgg tagcagttat ttaatttatt    600

tttttatttt tatacaactt gctcgctgtt tgttcccccct agccctgaaa cacaagctgt    660

caaacggtgg aggtgataag tctaatgaat gcgataagct ttatttcaat tcgcaatttt    720

cgtgtggcat tttggcaaaa aaaaaaactc gtcggacata catgttgcca caaacataaa    780

gtgaatacat aatgttgggt gaacgactca tacacgattg tggcaaatca aattctttta    840

acacgggacg gggaaaggcg agtgaagata ttttagcata tatttagcac atctgttaaa    900

tccatttttt tactctccgt tttcggccag atatggttag aaaagaaaaa aattagtaca    960

taccccccata tataataaga aaaaaagaga gagtcagcag aagtacgggg agcttaagtg   1020

tagcaatcag aacatcacaa atagtaaata aattaataat aataataatc atatccaaaa   1080

atatttttat tcctaaccta tcgcattgtt acatcgaggg tgaaattcaa aatagacaaa   1140

aagttgggga ataaaatgtg aaaaaagtgg taaaatgttt aatagtgtgg gcgttactgt   1200

tttgtcggtg tgaggtgcgt ggccaccaaa gtgtttttgg tataacgata gaaattggta   1260

agacaaacaa tattgcgaag aaaacccgaa gcatttttaa aaagtgcgaa cgtggcagtt   1320

ttaagggttt gtgggcgtgg caataatttt tggcaattcg ataaaaaatgt acaggaccaa   1380

atatatgaag aaatataaaa tatttttcaa aatgacagcc agcaaccata catatatata   1440

aataaatgtc ggagaccctt ccttctacct gtaacatact tttccacgaa tctagtattg   1500

gttgatatat aattatgctg tgtataagac caaaatcagt gtacatttcc attggattca   1560

ccaaccggat ggttccggat ggtaatgcaa aatattcatc taagaaacga aaacacctag   1620

aattaaacct gaactgatat gacttatgca catatcagtg aggtgggcag ttcaaagcaa   1680

tcacgatgct ccaagttatt atcgcagtgc agtgaaaaat tcacagtcac cgtcgccaat   1740

tgccaataaa gatcggccat tatacaacag aaccgcgttg aagacgatcg acgaggtcgt   1800

gggtcttatc ttatcaccac ctgaattgag gcatgcctcc agaatgacga gggcatccga   1860

agataatgtg gcccgctatt ttcggccggg actggaccta tgcgacgacc tatgctgatg   1920

acgggagtct gccgctgata tggtgcaatg caaggctcca gtcgggggta taaaagaccc   1980
```

agtttcggtg cagtcaagac aacagacttt aggtgttggt cgttgagcga accaaagccg 2040
gagcagttga ggaaccaaag aatagcagcg agaggaccaa gg 2082

<210> SEQ ID NO 7
<211> LENGTH: 1999
<212> TYPE: DNA
<213> ORGANISM: Saccharomyces cerevisiae

<400> SEQUENCE: 7
tgtagggacc caaatccaat tgtagtagtt accttgatta tggttggctt gtccttcgat 60
agttttgcct tttccaaagc gctagaaatg gattccatat cgtcgtctcc tttatcgact 120
tccatgactt cccaaccata tgcctcgtat cgcttcaaaa catcttcgtc gaacgagtac 180
gaggttttac cgtcaatgga aatgctatta ctgtcataaa acgtaatcaa gttacccaat 240
tgcagatgtc ccgctaagga agaggtctcc gaagaaacac cctcttgtaa gcaaccatcc 300
cctacaatag caaacgtata tgagtcggaa atgggaaagc catcctcgtt ataagtggcg 360
gcaaagttgg cctgcgctat tgccatacca acagcatttg agataccctg gcctagcgga 420
ccggaagtga tttccactcc cgctgagtgg aattctggat gacccggtgt ccttgagttt 480
acttgtctaa attgtctcaa gtcctcgata gagtaatcgt atcctaatag atggagcatt 540
gagtacagaa gagcgcatga gtgaccgttc gacagaacaa acctgtctct attgatccaa 600
tgttcattgt tagggttaca gcgcagttgc ttgaaaatta catgggcaac tggtgccaat 660
cctagtggtg cacctgggtg gccagattgt gcgctttcca cctggtcaac ggaaagtaat 720
cttaaagtgg aaaccgcaag tttatcaatg tcggagaact gtgccatttt tttgttcttt 780
ttttgattag taaggtataa tcgtctacgt agaggttaca aatcgaagac tacagtaaga 840
ggggacaagc caattgaata tacgactgaa ataaatggaa taattctgca ttattacact 900
cgtttatata tccaaacagg tgatctggta ttctcttgac aacgaatgaa gctccctata 960
ttcgacactc cttattcagg actcctccca acaaggagaa gtaggtgttc cttgagctac 1020
cctttaaagc tggggagatg agcttgccct tcctgtcatc gccattatga cgagaaaagt 1080
aaaacatgta gaataaggtc cacccaaaca tgtccgagca atgacgttat atatcgtgtt 1140
ccctgttcaa agcatggcat atgtgccatt aaaggcgaat tttgtccct agcaaaggag 1200 agacagcgag ccaccattaa gaagtgactt gaaagcaagc gaaaatagct acacatatat 1260
atcaatatat tgacctataa acccaaaatg tgaaagaaat ttgataggtc aagatcaatg 1320
taaacaatta ctttgttatg tagagttttt ttagctacct atattccacc ataacatcaa 1380
tcatgcggtt gctggtgtat ttaccaataa tgtttaatgt atatatatat atatatatat 1440
ggggccgtat acttacatat agtagatgtc aagcgtaggc gcttcccctg ccggctgtga 1500
gggcgccata accaaggtat ctatagaccg ccaatcagca aactacctcc gtacattcat 1560
gttgcaccca cacatttata cacccagacc gcgacaaatt acccataagg ttgtttgtga 1620
cggcgtcgta caagagaacg tgggaacttt ttaggctcac caaaaaagaa agaaaaaata 1680
cgagttgctg acagaagcct caagaaaaaa aaaattcttc ttcgactatg ctggaggcag 1740
agatgatcga gccggtagtt aactatatat agctaaattg gttccatcac cttcttttct 1800
ggtgtcgctc cttctagtgc tatttctggc ttttcctatt ttttttttc catttttctt 1860 tctctctttc taatatataa attctcttgc attttctatt tttctctcta tctattctac 1920
ttgtttattc ccttcaaggt ttttttttaa ggagtacttg tttttagaat atacggtcaa 1980

```
cgaactataa ttaactaaa                                                1999


<210> SEQ ID NO 8
<211> LENGTH: 2001
<212> TYPE: DNA
<213> ORGANISM: Saccharomyces cerevisiae

<400> SEQUENCE: 8

tctgctatta ttgatgcttt gaagacctcc agacaaattt ttcacagaat gtactcttac      60

gttgtttacc gtattgcttt gtctctacat ttggaaatct tcttgggtct atggattgct     120

attttggata actctttgga cattgatttg attgttttca tcgctatttt cgctgatgtt     180

gctactttgg ctattgctta cgataatgct ccttactctc caaagcccgt taaatggaac     240

ctaccaagat tatggggtat gtctattatt ttgggcatag ttttagctat aggttcttgg     300

attaccttga ctactatgtt cttaccaaag ggtggtatta tccaaaactt cggtgctatg     360

aacggtatta tgttcttgca aatttccttg actgaaaact ggttgatttt cattaccaga     420

gctgctggtc cattctggtc ttctatccca tcctggcaat tggctggtgc cgtcttcgct     480

gtcgacatca tcgctaccat gtttacctta ttcggttggt ggtctgaaaa ctggactgat     540

attgttactg tcgtccgtgt ctggatctgg tctatcggta tcttctgtgt tttgggtggt     600

ttctactacg aaatgtccac ttctgaagcc tttgacagat tgatgaacgg taagccaatg     660

aaggaaaaga agtctaccag aagtgtcgaa gacttcatgg ctgctatgca aagagtctct     720

actcaacacg aaaaggaaac ctaatcctgt tgaagtagca tttaatcata atttttgtca     780

cattttaatc aacttgattt ttctggttta atttttctaa ttttaatttt aatttttta     840

tcaatgggaa ctgatacact aaaaagaatt aggagccaac aagaataagc cgcttatttc     900

ctactagagt ttgcttaaaa tttcatctcg aattgtcatt ctaatatttt atccacacac     960

acaccttaaa atttttagat taaatggcat caactcttag cttcacacac acacacacac    1020

cgaagctggt tgttttattt gatttgatat aattggtttc tctggatggt actttttctt    1080

tcttggttat ttcctatttt aaaatatgaa acgcacacaa gtcataatta ttctaataga    1140

gcacaattca caacacgcac atttcaactt taatattttt ttagaaacac tttatttagt    1200

ctaattctta atttttaata tatataatgc acacacacta atttattcat taattttta    1260

ttgagtagga tttgaaaata tttggtatct ttgcaagatg tttgtataga gggacaaaga    1320

atcgtcttta ttatggtcaa ggctttacgt cataatagtt cctgcccagc tcttctataa    1380

tactttaaag atctcttctc gtttgctcca tttggaagtc tcgcttacgt ttatgcgccc    1440

atacagacac tcaagataca cacttacatg aacgtataca aatttactaa cactacttga    1500

aaatatgaac cacagtacat catattaaga cgtagtattc gatgattgaa ggccgcctcc    1560

gcgaaatacc tttactgatt ttgccggtta atcgcatcga aatttcttca tcacaagaaa    1620

gcaaacaaat cgccaggcca ttctacaagt ttccttttct tatgaagatg taaaagctac    1680

taaggcgtca ttactctaga tgactcagtt tagtctgacc ttctatagta tactaccctg    1740

gcgctatgat gatgagcggt tcttttattg cggaaacgaa aattccggga ccggcgaaat    1800

ttgcccggtt ttgtccgtaa ccggcttcat gagtcggctt caatagtagt tgaatactta    1860

tttaaacagc agaacttaac tcactcatca cgctgtttcc gctgaatttt ctcaaaatat    1920

ctaagcagtc aacaaatata aagaatattg aaattgacag tttttgtcgc tatcgatttt    1980

tattatttgc tgttttaaat c                                              2001
```

<210> SEQ ID NO 9
<211> LENGTH: 2000
<212> TYPE: DNA
<213> ORGANISM: Saccharomyces cerevisiae

<400> SEQUENCE: 9

```
ccaaatcatt cttattcggt ttccagacgg taacaatacc ctcgcccatc ccacacaaaa     60

gggtatctgc tacttcggga tcgacgaaac aaccacaaag aacttcgtcc tcctgatcat    120

cgctgatcaa aattttacca tcctcgtttc cagctacgtt cggtttggca tctttgtcgc    180

gaacgtcaaa ataagctaac gttgtctggc ccaaagaaat gaatttatat gcagatcttt    240

tatcaaagtg gaaaatatcg ttgatagagt cgccaaaatg tatcgaacga atggaatttg    300

ataatgccaa gttttccgag tttattacgt gtatattacc ggattcatcg cctattaaaa    360

tgaatgggtg agtttgagag gcgcataatt tcgtaaattt atcatttttt ttctcttcag    420

aattaaacag tgagcttaag tttacctttt tgacgacttt gccggtcata gtattggcct    480

tttttaaaac attatccgat ccaacagaaa aaatattgtc acctttagaa tcaaagcaca    540

tggcacggac actaccttta tgtcttttag tcttccaaag tgtttttacg cccaagtctt    600

catcttttcc tgtttgcttt tgttgctgtt gttcttcaat atcaacaaat ttcaaatctc    660

cagtttctag gtctatatct aatctaatcc aagggcatac acctttcttt gcatccttgc    720

ctgtagttgc agtgtcaatt ctacgtctac gatctaggtg cgattgcaac ttagcggggt    780

cataacgatg gcacacaata tgtcctgtac caaagccagt tattataatg ggcagttcag    840

gatgtaaaag agactggaaa atgggagctt ttaatgatag taattctaga atgggcaggt    900

ttgttgaatc gacaacatct gttttttttt tgctctttgc catagctgat gcgtggattg    960

tttctaattt cccagctgct tcctcttcca attgtggcga tgatgccatg atttctatgt   1020

taaaattttt ctaaccatga aatttttttt ttctagcgag aaaaaaaatc agaaaaatta   1080

ctattagtga gtattggaga cattgtcaat gggagatgtt ctctttataa tatcttcaac   1140

aggttctttc aactctggaa attcatccac aatcttgtca gcaagtgaat ctcttaattg   1200

cttcaatcca tgcatcttgc ctctttgata ttggttggat cttcttatgg cttccacgaa   1260

ctctcttgtg taaatatctg gatttctacc gtcctcaatg tattgaacaa cttccaaggg   1320

aatgtccacc ttagacaagc tggattgagg atcgttgctt ctcacgttca gcttgtacaa   1380

gcgatccaca tttctttgca agttggtgat cattcccttg gtggcttctg gagtaccagg   1440

aaaatcatat atcgagacac ctaattcaac gaaggactca ataatcgaag ccacttggtc   1500

ttgagtagtg gccagttctt gctgcaattg ttcattgtta gtgctgtttc cattcatctt   1560

atcggtttat ttttctatat atttgcctct ttctcaaaca ggagttagta gttaaaagta   1620

cgaagttctt gttctttaat gcgcgctgac aaaagaattg gataaaagag aatggtgggg   1680

ggacaagaag gaaatttgtc ctagtttaac atgaatggca tcttgttacc gggtggacat   1740

cacctattga ttctaaatat ctttacggtt tatcatactg ttctttattc cgtcgttatt   1800

ctttttattt ttatcatcat ttcacgtggc tagtaaaaga aaagccacaa catgactcag   1860

caaatctcga caaagtaaaa gctcatagag atagtattat attgatataa aaaaagtata   1920

ctgtactgtt tgtaaccttt tcaatgcttt aagatcaaaa ctaaggccag caaaggtatc   1980

aacccatagc aactcataaa                                                2000
```

<210> SEQ ID NO 10
<211> LENGTH: 2001
<212> TYPE: DNA

<213> ORGANISM: Saccharomyces cerevisiae

<400> SEQUENCE: 10

```
gaaaccatta aatcatattt aataaattgt tgcgacatgc aagaagttcg cggatggtca     60
tgcgtattta agaatagtca agtaacaatt tgcttattcg ttgatgatat gatattattc    120
agcaaagact taaatgcaaa taagaaaatc ataacaacac tcaagaaaca atacgataca    180
aagataataa atctgggtga aagtgataac gaaattcagt acgacatact tggattagag    240
atcaaatatc aaagaagcaa gtacatgaaa ttaggtatgg aaaaatcctt gacagaaaaa    300
ttacccaaac taaacgtacc tttgaaccca aaaggaaaga aacttagagc tccaggtcaa    360
ccaggtcatt atatagacca ggatgaacta gaaatagatg aagatgaata caaagagaaa    420
gtacatgaaa tgcaaaagtt gattggtcta gcttcatatg ttggatataa atttagattt    480
gacttactat actacatcaa cacattgctc aaccatatac tattcccctc taggcaagtt    540
ttagacatga catatgagtt aatacaattc atgtgggaca ctagagataa acaattaata    600
tggcacaaaa acaaacctac caagccagat aataaactag tcgcaataag cgatgcttca    660
tatggtaacc aaccatatta caagtcacaa attggtaaca ttttcctact caacggaaaa    720
gtgattggag gaaagtcgac aaaggcttcg ttaacatgca cttcaactac agaagcagaa    780
atacacgcgg tcagtgaagc tattccgcta ttgaataacc tcagtcacct tgtgcaagaa    840
cttaacaaga aaccaattat taaaggctta cttactgata gtagatcaac gatcagtata    900
attaagtcta caaatgaaga gaaatttaga aacagatttt ttggcacaaa ggcaatgaga    960
cttagagatg aagtatcagg taataattta tacgtatact acatcgagac caagaagaac   1020
attgctgatg tgatgacaaa acctcttccg ataaaaacat ttaaactatt aactaacaaa   1080
tggattcatt agatctatta cattatgggt ggtatgttgg aataaaaatc aactatcatc   1140
tactaactag tatttacgtt actagtatat tatcatatac ggtgttagaa gatgacgcaa   1200
atgatgagaa atagtcatct aaattagtgg aagctgaaac gcaaggattg ataatgtaat   1260
aggatcaatg aatattaaca tataaaatga tgataataat atttatagaa ttgtgtagaa   1320
ttgcagattc ccttttatgg attcctaaat cctcgaggag aacttctagt atatctacat   1380
acctaatatt attgccttat taaaaatgga atcccaacaa ttacatcaaa atccacattc   1440
tcttcaaaat caattgtcct gtacttcctt gttcatgtgt gttcaaaaac gttatattta   1500
taggataatt atactctatt tctcaacaag taattggttg tttggccgag cggtctaagg   1560
cgcctgattc aagaaatatc ttgaccgcag ttaactgtgg gaatactcag gtatcgtaag   1620
atgcaagagt tcgaatctct tagcaaccat tatttttttc ctcaacataa cgagaacaca   1680
caggggcgct atcgcacaga atcaaattcg atgactggaa atttttttgtt aatttcagag   1740
gtcgcctgac gcatatacct ttttcaactg aaaaattggg agaaaaagga aaggtgagag   1800
ccgcggaacc ggcttttcat atagaataga gaagcgttca tgactaaatg cttgcatcac   1860
aatacttgaa gttgacaata ttatttaagg acctattgtt ttttccaata ggtggttagc   1920
aatcgtctta ctttctaact tttcttacct tttacatttc agcaatatat atatatatat   1980
ttcaaggata taccattcta a                                             2001
```

<210> SEQ ID NO 11
<211> LENGTH: 2001
<212> TYPE: DNA
<213> ORGANISM: Saccharomyces cerevisiae

<400> SEQUENCE: 11

```
cactaccacc actacggttg tccatgacgt atcctgcgat tttttgaatt aatgattcaa      60
tagttgacat ttgctcgtca ttggggttcg actgagctgc ggatgtcaac ttcgcaacag     120
cttctgcatg gtttccttga gaaaaatgag actcagcctc tgagattaac ttatccgtat     180
ccatttcaga tctttgctat acgtttgtat cgctatatgt acgttctttt aatgaacttt     240
ctcctttctt tatcgtgtag cttgcttggg tatcttttaa tgagttgcgg acagtgagat     300
ttttcagaag ggcaattggc caagacacca aaaacgtttg gacgagacag gcatcaaagg     360
acaaggtaaa aggcgttgag ctgtggctgg ctgtgtatgc gtttgaaata ccatggatag     420
atatcaaaga aagataggat gtttcataca aatcccaaat ttggggcgcg gacaactgaa     480
atacgtgggt ccagtggaca cgaaagctgg aatgtttgct ggtgtagact tacttgccaa     540
cattggtaag aacgatggat cattcatggg gaagaagtat tttcaaacag agtatcctca     600
aagtggacta tttatccagt tgcaaaaagt cgcatcattg atcgagaagg catcgatatc     660
gcaaacctcg agaagaacga cgatggaacc gctatcaata cccaaaaaca gatctattgt     720
gaggctcact aaccagttct ctcccatgga tgatcctaaa tcccccacac ccatgagaag     780
tttccggatc accagtcggc acagcggtaa tcaacagtcg atggaccagg aggcatcgga     840
tcaccatcaa cagcaagaat ttggttacga taacagagaa gacagaatgg aggtcgactc     900
tatcctgtca tcagacagaa aggctaatca caacaccacc agcgattgga aaccggacaa     960
tggccacatg aatgacctca atagcagcga agttacaatt gaattacgag aagcccaatt    1020
gaccatcgaa aagctacaaa ggaaacaact acactacaaa aggctactcg atgaccaaag    1080
aatggtcctc gaagaagtgc aaccgacttt tgataggtat gaagccacaa tacaagaaag    1140
agagaaagag atagaccatc tcaagcaaca attggagctc gaacgcagac agcaagccaa    1200
acaaaagcag tttttttgacg ctgagaatga acagctactt gctgtcgtaa gccaactaca    1260
cgaagagatc aaagaaaacg aagagagaaa tctttctcat aatcaaccca ctggtgccaa    1320
cgaagatgtc gaactcctga aaaaacagct ggaacaatta cgcaacatag aagaccaatt    1380
tgagttacac aagacaaagt gggctaaaga acgcgaacaa ttgaaaatgc ataacgattc    1440
gctcagtaaa gaataccaaa atttgagcaa ggaactattt ttgacaaaac cacaagattc    1500
ctcatcggaa gaggtggcat ccttaacgaa aaaacttgaa gaggctaatg aaaaaatcaa    1560
acagttggaa caggctcaag cacaaacagc cgtggaatcg ttgccaattt tcgacccccc    1620
tgcaccagtc gataccacgg caggaagaca acagtggtgt gagcattgcg atacgatggg    1680
tcataataca gcagaatgcc cccatcacaa tcctgacaac cagcagttct tctaggcagt    1740
cgaactgact ctaatagtga ctccggtaaa ttagttaatt aattgctaaa cccatgcaca    1800
gtgactcacg tttttttatc agtcattcga tatagaaggt aagaaaagga tatgactatg    1860
aacagtagta tactgtgtat ataatagata tggaacgtta tattcacctc cgatgtgtgt    1920
tgtacataca taaaaatatc atagcacaac tgcgctgtgt aatagtaata caatagttta    1980
caaaattttt tttctgaata c                                              2001
```

<210> SEQ ID NO 12
<211> LENGTH: 2001
<212> TYPE: DNA
<213> ORGANISM: Saccharomyces cerevisiae

<400> SEQUENCE: 12

```
acaatgagga agaacatgcc gttttacaag aattaaatag tttaacccaa agaattaatg      60
```

```
aactaggcat ggaaagtata aattcaaact ccgattcgga cagaataaac gggtcatatt    120
cacaagtgga ttttggtaac aataacgacg aggacgatat gaacctgttc gacccagatt    180
ttatggcaca agaccaattg cgtgctgaag aaagagacta caacaaggat gatagaacac    240
ccttagctaa ggtccctgcg gcctttcaat caactggatt gggcataacc cccgatgacg    300
atatcgagag acaatacata acggaacaca gatcacgaca tgaagtgcca aagcggtctc    360
ccgagaaacc ctccaacccg ctggaaatag gtaacccata cgcgaaacct ggcacaaggt    420
tgaataccac tcacacccac agcaaaactg atcgtagcat tacccctcag aggggccagc    480
cagtcccatc aggccagcag atttcctcct acgtgcagcc agcaaacatt aatagtccta    540
acaaaatgta tggtgcaaac aactcggcaa tgggttcgcc caggaatcca aagacgagag    600
cgccaccagg tccatacaat cagggatgga ataaccgccc ctcgccttca aatatttacc    660
aacgtcctca tccctcagat acacaaccac aagcatatca tctccccgga aacccatact    720
caacggggaa caggccaaac atgcaagcgc aatatcaccc gcagcaggtg cccatgccta    780
tcctgcagca gcccaatcgc ccgtaccaac cttatgcgat gaatacgcac atgggctctc    840
ctggcggata tgctggggca gcaccaccat ttcagccagc taacgtcaac tacaatacta    900
ggcctcagca gccatggcct acacctaact caccatccgc acactaccgt ccgcccccta    960
acctgaacca gcctcaaaac ggtagtgctg gttactatcg tccgccggca ccacaattgc   1020
aaaactccca agcccgtcca caaaagaagg acggattctc acagttcatg ccatctgcaa   1080
ctacgaagaa cccatatgcc cagtaactcg accgactggt tgtaatttta caaaaagaga   1140
gacaattaag aaaagaaaca agcgccaggc ttccgtatcc cagtttttca tctcactttc   1200
tgggcacgat tgtaataata cttcatgata ataactaaac tatataagta gtgtctcatc   1260
cgtaaatata catttagaca gattcttgta ttttctccgg gcaattttta actttttttc   1320
tgttagggca catgacactt gcctattatg gacagccagt aaagatgtgc catatattgc   1380
cccctttacg ctctctgcca gtattagtgg gaaaaaaaaa actgaaaaaa aaaaaatcgc   1440
agactactaa taatcacgtg atatttcttt tcactctctt cataaagttg ctaaaaacac   1500
acaatcgaat gagcctctga gcagtataaa ttgtacttca aagcactagt catgaaaaac   1560
gcttacatta gttcagtttg tcaaggttat gctattactt gtacttattt cttgctattg   1620
ttagtggctc cccacattga cgtattttca cgtgatgcgc ctcactgcgg aaggcgccac   1680
acattgcctg caaaaaattg tggatgcact catttgatag taaactaagt catgttaatc   1740
gtttggattt ggcacacacc cacaaatata cacattacat atatatatat attcaaaata   1800
cagctgcgtc caatagatga gcttccgctt cgttgtacaa cctacctgct atcttgttca   1860
cggatatttc ttgcttttaa taaacaaaag taactctaga acagtcaagt cttcgataat   1920
ttttttagtc acagggtccg tctaaagttt ctctttattt ggaataatag aaaagaaaga   1980
aaaaaacgta gtataaaagg a                                             2001
```

<210> SEQ ID NO 13
<211> LENGTH: 2000
<212> TYPE: DNA
<213> ORGANISM: Saccharomyces cerevisiae

<400> SEQUENCE: 13

```
aaggatggca aatacccaat cggaggaact cgaacacttc agtatctgtg tcttctagtg     60
agtctttagc ggaagttatt cagccatctt ccttcaaaag tgggagtagt tcattgcatt    120
atctatcgtc ttctatctca agccaacctg gttcgtacgg ttcttggttc aacaaaaggc    180
```

```
caacaatttc tcagttcttt caaccaagcc cttctttaaa acacaacgag tcgtgggaga    240
ggctgcaaac aactgctgga aatatgcaaa ggacttcaag ttcgtcttct ttgcagcaag    300
caacctccag gttatcacta accactccgc aacaatcacc gtctatcagc gaatatgatg    360
agtatccttg gatgggcaca cctggctctc ctaatgttgg agatgtgtct cacgcacccc    420
cattggttaa gaatatatca tataaatttc cactaaagaa cgttgagttg aaaagagatt    480
gccaaaggat ctctcaggat gatcttttgg atgaggcttt tgaaagaata tgtcagccct    540
ctttggctga ccttaattcc acttacgaaa tttttccagg taactcttct tatgcggata    600
ttttgactac tgattctgat attgatgatg gcttgatgaa taaacctctg gaactattgc    660
cgaaatatac aatgtattta acccatttta acaatttttt ccagttgcaa gcatgtcctg    720
ctggtcaaga atcagagagc agaataacaa attctatgaa gattgacctg ttaaaggcgg    780
attacacaag aagtctatta gtatcgttac gttcaaggga cattagggat gtcgcattga    840
aaagagagtt tactggcaat aacaacaata acagcaacca gaatatctat gatgagaatt    900
ttgtcggaaa aaggaagtac gtgttgaaac agaagaccag aaaaatcttt tcctgtggca    960
agattggcaa gctaagtact agtttggaaa actgcgttaa ttttgttgaa aatagtataa   1020
agagtgcaat gatgttatat gatgataatg gaatagatag tgagcttcgc gattcagaag   1080
ctttacggat tttttcatct cttgttcatt attgtaatgc aggttaatgt tttctccttc   1140
tttacatgtt taatatattc caagttacct aagaggtgta cgatattttt ttcttttata   1200
tatatgattt tctctattca ttttttagtt ttttttgata cataagcgaa tcgcacattg   1260
cgcaacttca atttgttgat tcgccaaagt attcttacca taaaacaacc attcgttgct   1320
ttaccctttc gtaatcattt accgtgataa ccataatcag aaacttatta tttcagccta   1380
gtagaccggc caagcaggcc ttgtaatgtt tctcttgatt gcttgaatct tttaagcagc   1440
caaatctttc caaaaaaatg caattatcag aacaaaaacta tttaaggtga cttctccgta   1500
tttacaccac cagaagcgtt ctggctcccc ttttctctaa acgttaaaca ttttacaatt   1560
gaaatgttac caatcctata ttattgtacc acattgccag atttatgaac tctgggtatg   1620
ggtgctaatt ttcgttagaa gcgctggtac aattttctct gtcattgtga cactaattag   1680
gaaacttctc gactatcaat gtgtaaatga aggaataatg gcggaaactt tgaaactttg   1740
tcaataattg catcattgga tgcgtttcat ttggccgtta tcacggagag gcagagttct   1800
ctccacaatt tgggcagaag tcttttgaaa agacatatat atatatatat atgtatatga   1860
gtggatgctt aaggtaagaa taatttctga attcccaagt attcattttg tgcagtattc   1920
acatattcta ttttattgct ttttaacttt agaggcaatt aaatttgtgt aggaaaggca   1980
aaatactatc aaaattttcc                                               2000
```

```
<210> SEQ ID NO 14
<211> LENGTH: 2001
<212> TYPE: DNA
<213> ORGANISM: Saccharomyces cerevisiae

<400> SEQUENCE: 14

ttgccttcaa gatctacttt cctaagaaga tcattattac aaacacaact gcactcaaag     60
atgactgctc atactaatat caaacagcac aaacactgtc atgaggacca tcctatcaga    120
agatcggact ctgccgtgtc aattgtacat ttgaaacgtg cgcccttcaa ggttacagtg    180
attggttctg gtaactgggg gaccaccatc gccaaagtca ttgcggaaaa cacagaattg    240
```

```
cattcccata tcttcgagcc agaggtgaga atgtgggttt ttgatgaaaa gatcggcgac    300
gaaaatctga cggatatcat aaatacaaga caccagaacg ttaaatatct acccaatatt    360
gacctgcccc ataatctagt ggccgatcct gatcttttac actccatcaa gggtgctgac    420
atccttgttt tcaacatccc tcatcaattt ttaccaaaca tagtcaaaca attgcaaggc    480
cacgtggccc ctcatgtaag ggccatctcg tgtctaaaag ggttcgagtt gggctccaag    540
ggtgtgcaat tgctatcctc ctatgttact gatgagttag gaatccaatg tggcgcacta    600
tctggtgcaa acttggcacc ggaagtggcc aaggagcatt ggtccgaaac caccgtggct    660
taccaactac caaaggatta tcaaggtgat ggcaaggatg tagatcataa gattttgaaa    720
ttgctgttcc acagacctta cttccacgtc aatgtcatcg atgatgttgc tggtatatcc    780
attgccggtg ccttgaagaa cgtcgtggca cttgcatgtg gtttcgtaga aggtatggga    840
tggggtaaca atgcctccgc agccattcaa aggctgggtt taggtgaaat tatcaagttc    900
ggtagaatgt tttcccaga atccaaagtc gagacctact atcaagaatc cgctggtgtt    960
gcagatctga tcaccacctg ctcaggcggt agaaacgtca aggttgccac atacatggcc   1020
aagaccggta agtcagcctt ggaagcagaa aaggaattgc ttaacggtca atccgcccaa   1080
gggataatca catgcagaga agttcacgag tggctacaaa catgtgagtt gacccaagaa   1140
ttcccattat tcgaggcagt ctaccagata gtctacaaca acgtccgcat ggaagaccta   1200
ccggagatga ttgaagagct agacatcgat gacgaataga cactctcccc cccctcccc    1260
ctctgatctt tcctgttgcc tctttttccc ccaaccaatt tatcattata cacaagttct   1320
acaactacta ctagtaacat tactacagtt attataattt tctattctct tttctttaa    1380
gaatctatca ttaacgttaa tttctatata tacataacta ccattataca cgctattatc   1440
gtttacatat cacatcaccg ttaatgaaag atacgacacc ctgtacacta acacaattaa   1500
ataatcgcca taacctttc tgttatctat agcccttaaa gctgtttctt cgagcttttt    1560
cactgcagta attctccaca tgggcccagc cactgagata agagcgctat gttagtcact   1620
actgacggct ctccagtcat ttatgtgatt ttttagtgac tcatgtcgca tttggcccgt   1680
tttttccgc tgtcgcaacc tatttccatt aacggtgccg tatggaagag tcatttaaag    1740
gcaggagaga gagattactc atcttcattg gatcagattg atgactgcgt acggcagata   1800
gtgtaatctg agcagttgcg agacccagac tggcactgtc tcaatagtat attaatgggc   1860
atacattcgt actcccttgt tcttgcccac agttctctct ctctttactt cttgtatctt   1920
gtctccccat tgtgcagcga taaggaacat tgttctaata tacacggata caaaagaaat   1980
acacataatt gcataaaata c                                             2001
```

<210> SEQ ID NO 15
<211> LENGTH: 1999
<212> TYPE: DNA
<213> ORGANISM: Saccharomyces cerevisiae

<400> SEQUENCE: 15

```
ttttgtaaga aattattcac cgcatcttca tctggcaaac gaatgggaga ctttgaggaa     60
cccaatccat ttctgaataa cggagattta gaaatgtaaa aggtagcaaa tgtaaaaagt    120
gccaggacca tcacagcagt caatgccaac accaatttcc cttgccatga cactgttgga    180
tcttttgaag gagatttgta acctggaatc tcactataat gaacacattc accggattca    240
cacttcaaag taatataagg gtcaccaaac acggtcaata tcaaatcatt catagaaggc    300
tcactgaatt tacattgcct tgtttctaaa tcacagctga aatctcctgg cccttttatt    360
```

```
gtctctgtca ggaaatccga gatatctata gacccccttag caccacacaa cacagtgtcg    420

ggaacgcatt tgcattgaac gtcattacac ttataatggg aggtattctg ttccaagtcg    480

tattcaaagg cacaatcact taagccacaa tagaagcttt ctaactgatc tatccaaaac    540

tgaaaattac attcttgatt aggtttatca caggcaaatg taatttgtgg tattttgccg    600

ttcaaaatct gtagaatttt ctcattggtc acattacaac ctgaaaatac tttatctaca    660

atcataccat tcttataaca tgtcccctta atactaggat caggcatgaa cgcatcacag    720

acaaaatctt cttgacaaac gtcacaattg atccctcccc atccgttatc acaatgacag    780

gtgtcatttt gtgctcttat gggacgatcc ttattaccgc tttcatccgg tgatagaccg    840

ccacagaggg gcagagagca atcatcacct gcaaaccctt ctatacactc acatctacca    900

gtgtacgaat tgcattcaga aaactgtttg cattcaaaaa taggtagcat acaattaaaa    960

catggcgggc atgtatcatt gcccttatct tgtgcagtta gacgcgaatt tttcgaagaa   1020

gtaccttcaa agaatggggt cttatcttgt tttgcaagta ccactgagca ggataataat   1080

agaaatgata atatactata gtagagataa cgtcgatgac ttcccatact gtaattgctt   1140

ttagttgtgt atttttagtg tgcaagtttc tgtaaatcga ttaatttttt tttctttcct   1200

ctttttatta accttaattt ttattttaga ttcctgactt caactcaaga cgcacagata   1260

ttataacatc tgcataatag gcatttgcaa gaattactcg tgagtaagga aagagtgagg   1320

aactatcgca tacctgcatt taaagatgcc gatttgggcg cgaatccttt attttggctt   1380

caccctcata ctattatcag ggccagaaaa aggaagtgtt tccctccttc ttgaattgat   1440

gttaccctca taaagcacgt ggcctcttat cgagaaagaa attaccgtcg ctcgtgattt   1500

gtttgcaaaa agaacaaaac tgaaaaaacc cagacacgct cgacttcctg tcttcctatt   1560

gattgcagct tccaatttcg tcacacaaca aggtcctagc gacggctcac aggttttgta   1620

acaagcaatc gaaggttctg gaatggcggg aaagggttta gtaccacatg ctatgatgcc   1680

cactgtgatc tccagagcaa agttcgttcg atcgtactgt tactctctct ctttcaaaca   1740

gaattgtccg aatcgtgtga caacaacagc ctgttctcac acactctttt cttctaacca   1800

agggggtggt ttagtttagt agaacctcgt gaaacttaca tttacatata tataaacttg   1860

cataaattgg tcaatgcaag aaatacatat ttggtctttt ctaattcgta gtttttcaag   1920

ttcttagatg ctttcttttt ctcttttttta cagatcatca aggaagtaat tatctacttt   1980

ttacaacaaa tataaaaca                                                 1999
```

<210> SEQ ID NO 16
<211> LENGTH: 1999
<212> TYPE: DNA
<213> ORGANISM: Saccharomyces cerevisiae

<400> SEQUENCE: 16

```
aaacaaatgg caaaaataac gggcttcacc attgttcctg tatggtgtat tagaacatag     60

ctgaaaatac ttctgcctca aaaaagtgtt aaaaaaaaga ggcattatat agaggtaaag    120

cctacaggcg caagataaca catcaccgct ctcccccctc tcatgaaaag tcatcgctaa    180

agaggaacac tgaaggttcc cgtaggttgt ctttggcaca aggtagtaca tggtaaaaac    240

tcaggatgga ataattcaaa ttcaccaatt tcaacgtccc ttgtttaaaa agaaaagaat    300

ttttctcttt aaggtagcac taatgcatta tcgatgatgt aaccattcac acaggttatt    360

tagcttttga tccttgaacc attaattaac ccagaaatag aaattaccca agtggggctc    420
```

```
tccaacacaa tgagaggaaa ggtgactttt taagggggcc agaccctgtt aaaaaccttt    480

gatggctatg taataatagt aaattaagtg caaacatgta agaaagattc tcggtaacga    540

ccatacaaat attgggcgtg tggcgtagtc ggtagcgcgc tcccttagca tgggagaggt    600

ctccggttcg attccggact cgtccaaatt attttttact ttccgcggtg ccgagatgca    660

gacgtggcca actgtgtctg ccgtcgcaaa atgatttgaa ttttgcgtcg cgcacgtttc    720

tcacgtacat aataagtatt ttcatacagt tctagcaaga cgaggtggtc aaaatagaag    780

cgtcctatgt tttacagtac aagacagtcc atactgaaat gacaacgtac ttgacttttc    840

agtattttct ttttctcaca gtctggttat ttttgaaagc gcacgaaata tatgtaggca    900

agcattttct gagtctgctg acctctaaaa ttaatgctat tgtgcacctt agtaacccaa    960

ggcaggacag ttaccttgcg tggtgttact atggccggaa gcccgaaaga gttatcgtta   1020

ctccgattat tttgtacagc tgatgggacc ttgccgtctt catttttttt tttttcacc   1080

tatagagccg ggcagagctg cccggcttaa ctaagggccg gaaaaaaaac ggaaaaaaga   1140

aagccaagcg tgtagacgta gtataacagt atatctgaca cgcacgtgat gaccacgtaa   1200

tcgcatcgcc cctcacctct cacctctcac cgctgactca gcttcactaa aaaggaaaat   1260

atatactctt tcccaggcaa ggtgacagcg gtccccgtct cctccacaaa ggcctctcct   1320

ggggtttgag caagtctaag tttacgtagc ataaaaattc tcggattgcg tcaaataata   1380

aaaaaagtaa ccccacttct acttctacat cggaaaaaca ttccattcac atatcgtctt   1440

tggcctatct tgttttgtcc tcggtagatc aggtcagtac aaacgcaaca cgaaagaaca   1500

aaaaaagaag aaaacagaag gccaagacag ggtcaatgag actgttgtcc tcctactgtc   1560

cctatgtctc tggccgatca cgcgccattg tccctcagaa acaaatcaaa cacccacacc   1620

ccgggcaccc aaagtcccca cccacaccac caatacgtaa acggggcgcc ccctgcaggc   1680

cctcctgcgc gcggcctccc gccttgcttc tctccccttc cttttctttt tccagttttc   1740

cctattttgt cccttttttcc gcacaacaag tatcagaatg ggttcatcaa atctatccaa   1800

cctaattcgc acgtagactg gcttggtatt ggcagtttcg tagttatata tatactacca   1860

tgagtgaaac tgttacgtta ccttaaattc tttctccctt taattttctt ttatcttact   1920

ctcctacata agacatcaag aaacaattgt atattgtaca cccccccct ccacaaacac   1980

aaatattgat aatataaag                                                1999
```

```
<210> SEQ ID NO 17
<211> LENGTH: 2009
<212> TYPE: DNA
<213> ORGANISM: Saccharomyces cerevisiae

<400> SEQUENCE: 17

ggatgagaaa cgagtgcggt ttcgagagta gatattcaac ccacccgaag tagccttcag     60

gaactggttc cgttctctct tcctccggaa tagtctgaat gtccttaaga gaccgtggct    120

cgtatactct tctattcttg ggccgcaata gcaaaaagag ccagacaaac acgacggcgg    180

taagaccgta gataatcagg gttgaaatga acgccgaagt cgaagaactg tcagccatag    240

tacgtatgtg ctataaatat ctaacctttc gctgctttga atatgatgtg ctcaaatata    300

acttaatata atagtataac aaaaaggagt actatttgct aaatatcgta gacgtagtag    360

acatagtaaa tacaataaag gatagataac caagaaccca catcaagcga atacatacat    420

atatatatac tcgatgtata catgtttcta agcacttgcg cacatacgta tttaaagtat    480

ttcagggaga ttaacgtatt aaaacaagaa gagggttgac tacatcacga tgagggggat    540
```

```
cgaagaaatg atggtaaatg aaataggaaa tcaaggagca tgaaggcaaa agacaaatat    600
aagggtcgaa cgaaaaataa agtgaaaagt gttgatatga tgtatttggc tttgcggcgc    660
cgaaaaaacg agtttacgca attgcacaat catgctgact ctgtggcgga cccgcgctct    720
tgccggcccg gcgataacgc tgggcgtgag gctgtgcccg gcggagtttt ttgcgcctgc    780
attttccaag gtttaccctg cgctaagggg cgagattgga gaagcaataa gaatgccggt    840
tggggttgcg atgatgacga ccacgacaac tggtgtcatt atttaagttg ccgaaagaac    900
ctgagtgcat ttgcaacatg agtatactag aagaatgagc caagacttgc gagacgcgag    960
tttgccggtg gtgcgaacaa tagagcgacc atgaccttga aggtgagacg cgcataaccg   1020
ctagagtact ttgaagagga aacagcaata gggttgctac cagtataaat agacaggtac   1080
atacaacact ggaaatggtt gtctgtttga gtacgctttc aattcatttg ggtgtgcact   1140
ttattatgtt acaatatgga agggaacttt acacttctcc tatgcacata tattaattaa   1200
agtccaatgc tagtagagaa ggggggtaac acccctccgc gctctttcc gatttttttc    1260
taaaccgtgg aatatttcgg atatcctttt gttgtttccg ggtgtacaat atggacttcc   1320
tcttttctgg caaccaaacc catacatcgg gattcctata ataccttcgt tggtctccct   1380
aacatgtagg tggcggaggg gagatataca atagaacaga taccagacaa gacataatgg   1440
gctaaacaag actacaccaa ttacactgcc tcattgatgg tggtacataa cgaactaata   1500
ctgtagccct agacttgata gccatcatca tatcgaagtt tcactaccct ttttccattt   1560
gccatctatt gaagtaataa taggcgcatg caacttcttt tcttttttttt tcttttctct   1620
ctcccccgtt gttgtctcac catatccgca atgacaaaaa aatgatggaa gacactaaag   1680
gaaaaaatta acgacaaaga cagcaccaac agatgtcgtt gttccagagc tgatgagggg   1740
tatctcgaag cacacgaaac tttttccttc cttcattcac gcacactact ctctaatgag   1800
caacggtata cggccttcct tccagttact tgaatttgaa ataaaaaaaa gtttgctgtc   1860
ttgctatcaa gtataaatag acctgcaatt attaatcttt tgtttcctcg tcattgttct   1920
cgttcccttt cttccttgtt tctttttctg cacaatattt caagctatac caagcataca   1980
atcaactatc tcatatacaa tgtctatcc                                     2009
```

<210> SEQ ID NO 18
<211> LENGTH: 1943
<212> TYPE: DNA
<213> ORGANISM: Saccharomyces cerevisiae

<400> SEQUENCE: 18

```
ggcagtcatc aggatcgtag gagataagca ccctgacaag taacatgccg atgaagttgt     60
ttggttcatt gggcaaaaaa atcgggattc tagaaaaccc tgagttgaag atttttttcga   120
cagttttatc gtctaggatg gtatcggcac tcattgtgaa cacgttttca atcggagtca    180
tgatttcctc aaccctcttt gcctttagat ccaaaacagc agagatgatt gtaacttcgt    240
ctttagtcaa ccgttccacc cccatggtcc tatgcaaggt gaccaaagtc tttaagccgg    300
atttttgta catcgtacca tgatcttcac ccagcatata gtccaggaga gtcgcgatcg     360
gatatgcgac tgggtacatc agatacatca gtacaagaac aaaggggcag aagaatgccc    420
caacttgcag cccgtattta acacagacac tctgcggaat aatttcaccg aagatcacaa    480
ttagaatagt tgacgacact acagcctgcc aaccaccccc aagacacctg tccaaaacaa    540
taggcaatgt ttcgttggtt ataacattag aaagcagcag tgtgactaga acccaatgct    600
```

-continued

```
tccccctaga tattaggtca agcacccgct tggccagttt cttttcagaa ttcgagcctg    660

aagtgctgat taccttcagg tagacttcat cttgacccat caaccccagc gtcaatcctg    720

caaatacacc acccagcagc actaggatga tagagataat atagtacgtg gtaacgcttg    780

cctcatcacc tacgctatgg ccggaatcgg caacatccct agaattgagt acgtgtgatc    840

cggataacaa cggcagtgaa tatatcttcg gtatcgtaaa gatgtgatat aagatgatgt    900

atacccaatg aggagcgcct gatcgtgacc tagaccttag tggcaaaaac gacatatcta    960

ttatagtggg gagagtttcg tgcaaataac agacgcagca gcaagtaact gtgacgatat   1020

caactctttt tttattatgt aataagcaaa caagcacgaa tggggaaagc ctatgtgcaa   1080

tcaccaaggt cgtccctttt ttcccatttg ctaatttaga atttaaagaa accaaaagaa   1140

tgaagaaaga aaacaaatac tagccctaac cctgacttcg tttctatgat aataccctgc   1200

tttaatgaac ggtatgccct agggtatatc tcactctgta cgttacaaac tccggttatt   1260

ttatcggaac atccgagcac ccgcgccttc ctcaacccag gcaccgcccc caggtaaccg   1320

tgcgcgatga gctaatcctg agccatcacc caccccaccc gttgatgaca gcaattcggg   1380

agggcgaaaa ataaaaactg gagcaaggaa ttaccatcac cgtcaccatc accatcatat   1440

cgccttagcc tctagccata gccatcatgc aagcgtgtat cttctaagat tcagtcatca   1500

tcattaccga gtttgttttc cttcacatga tgaagaaggt ttgagtatgc tcgaaacaat   1560

aagacgacga tggctctgcc attgttatat tacgcttttg cggcgaggtg ccgatgggtt   1620

gctgagggga agagtgttta gcttacggac ctattgccat tgttattccg attaatctat   1680

tgttcagcag ctcttctcta ccctgtcatt ctagtatttt tttttttttt ttttggtttt   1740

actttttttt cttcttgcct ttttttcttg ttactttttt tctagttttt tttccttcca   1800

ctaagctttt tccttgattt atccttgggt tcttctttct actcctttag attttttttt   1860

tatatattaa tttttaagtt tatgtatttt ggtagattca attctctttc cctttccttt   1920

tccttcgctc cccttcctta tca                                           1943
```

<210> SEQ ID NO 19
<211> LENGTH: 2001
<212> TYPE: DNA
<213> ORGANISM: Saccharomyces cerevisiae

<400> SEQUENCE: 19

```
tgacaacgag taccaggaaa tcagtgcttc tgctttgaag aaggctcgta agggctgtga     60

tggtttgaag aaaaaggcag tcaagcaaaa ggaacaggag ttgaagaaac aacaaaaaga    120

ggcagaaaat gctgccaagc aattgtctgc tttgaatatc accattaagg aggacgaatc    180

gctaccagct gccattaaga ctagaattta tgactcttat tccaaggtcg gacaaagagt    240

taaggtttcc ggttggatcc atagattacg ttctaacaag aaggttattt tcgtcgtcct    300

cagagacgga tctggtttca ttcaatgtgt cttgtccggt gatttggcat tggctcaaca    360

aactttggac ctgactttgg aatccaccgt tactctgtac ggtaccatag tcaaattgcc    420

tgagggtaaa accgctccag gtggtgttga attgaatgtc gactattacg aagttgtagg    480

tttggccccc ggtggtgaag actcctttac aaacaaaatc gcagagggct cagacccttc    540

tttactgttg gaccaacgtc atttggcctt gagaggagat gccttgtctg cagtcatgaa    600

agtccgtgct gctctactga aaagcgttag acgtgtttat gatgaagaac atttgacaga    660

agttacccca ccatgtatgg tgcaaactca agtcgaaggt ggttccactt tgttcaagat    720

gaactattac ggcgaggaag cttacttgac ccaaagttcc caattatatt tagaaacctg    780
```

```
tttggcctcc ctaggtgatg tttataccat ccaagaatct ttcagagctg aaaagtccca     840
cacaagaaga catttgtccg aatataccca tatcgaagct gaattggcct tcttgacttt     900
cgacgatcta ttacaacata ttgaaacttt gatcgtcaaa tccgtgcaat acgttttgga     960
agacccaatt gctggcccac tcgtaaaaca attgaatcca aactttaagg ctccaaaggc    1020
tccattcatg agattacagt acaaggatgc cattacctgg ttgaacgaac acgacatcaa    1080
gaacgaagag ggcgaagact ttaaatttgg tgacgatatt gcagaagctg ctgaaagaaa    1140
gatgaccgat accatcggcg tcccaatctt tttgacgaga ttcccagtag aaatcaagtc    1200
tttctacatg aagcgttgtt ctgacgaccc ccgcgtcact gaatccgtcg acgttttgat    1260
gccaaacgtt ggtgaaatca ctggtggttc tatgagaatc gacgacatgg acgaactaat    1320
ggcagggttt aagcgtgagg gtattgatac cgacgcctac tactggttca ttgaccaaag    1380
aaaatacggt acttgcccac atggtggtta cggtatcggt accgaacgta ttttagcctg    1440
gttgtgtgac agattcactg tcagagactg ttccttgtat ccacgtttca gcggtagatg    1500
taagccatga tctttagtta ctgaagagta cgtgagcgct cacatatata caaatattta    1560
taccgattaa tatttacgtt cctccctctc tctaattatt cattgattta ttcaagaatt    1620
agcgttataa caataaatgg ttggcgcagg caattaattt ttctttactc ttccaaaccc    1680
tctgttaacg acaatcaaat aacctgatct gccaaggctc catcatatct ggcctagaac    1740
agttttttt tttcgattat ttgttcgttc ttgtggtggt tactcattgg cagaatcccg    1800
aaaatcatga ttagtagatg aatgactcac tttttggata agctggcgca aattgaaaca    1860
tgtgaaaaaa aaaaaaaagg attataaaag gtcagcgaag cacagaactc tgagataaga    1920
ctacctttct ttagctaggg gagaatattc gcaattgaag agctcaaaag caggtaacta    1980
tataacaaga ctaaggcaaa c                                              2001
```

<210> SEQ ID NO 20
<211> LENGTH: 1999
<212> TYPE: DNA
<213> ORGANISM: Saccharomyces cerevisiae

<400> SEQUENCE: 20

```
tcctaaggac atattccgtt cgtacttgag ttattggatc tatgaaatcg ctcgctatac      60
accagtcatg attttgtccc tggtaatagg ggttttggtt ttattaatta tattttttaa     120
tgacaacgaa gcttgtgttt tcaattctgc aatatttgct tttacttctc ttgtaggttt     180
gttaataata ttaagtgatg gtaatccaaa gctagtcagt cgtcgaaatt ttaggaccga     240
gcttttagtg gatgtcatca cacgtaaacc ggcggtagaa gggaaagaat ggaggatcat     300
cacatacaac atgaaccaat atttgtttaa tcatgggcaa tggcatactc cgtattactt     360
ttacagcgat gaggattgct accgttattt tctacgcctt gttgagggag taaccccaa     420
gaagcaaaca gccacgtcaa ttggcaattc tccggtcacc gctaagcctg aagatgccat     480
cgagtcagct tctcctagtt ccagactgaa ttatcaaaac tttttgctca aggcagcgga     540
gatcgaacga caagctcagg aaaattactg gcgaaggcgg catcccaata tcgatgcgct     600
tcttaaaaag acggaatagc ttagagacac taccatacgt aaagcgaaca taaactagag     660
tatgatatat aatcagcact aactggccgg aaaacggccg aaggaagcct cgaaaagtcg     720
attcgtgttg gacccatttg ctgaacaaag tggttcattg cctacctatt atggtagtag     780
tcgtgataat cgtgtggttg gttttgtcaa cggtgcattt gcattttcat gacaataaac     840
```

```
cttgcgtttt cgttctcggg atattacttt ccctccactt ctttcgcctc aatagctcct    900

ataagcattc tcagggcgta tgtcggtgat cgagatttcc aagcaagctt ttagtggaaa    960

tcatcgcgcg caagccagcg gtaaagggaa aagaacggag gacgattaca tacaagatga   1020

acgaataaat aaattaataa taaataataa taaaaagtac agtagcatta aatattatta   1080

agtttaatga ttaaaaattg gttaattgtc aagaaaatct aaggtattaa taaataaata   1140

atactatgac aacttgcagc gaaagcatca gccccaatga aaattaatca gaattgaatc   1200

tgagcgtatt tatttgataa cggtttacgt aactgttgga ataaaaatca actatcatct   1260

actaactagt gtttacgtta ctagtatatt atcatatacg gtgttagaag atgacgcaaa   1320

tgatgagaaa tagtcatcgt tttcaacgga agctgaaata caaggattga taatgtaata   1380

ggatcaatga atatcaacat ataaaacgat gataataata tttatagaat tgtgtagaat   1440

tgcagattcc cttttatgga ttcctaaatc ctcgagaaga acttctagta tatctacgta   1500

cctaatatta ttgccttatt aaaaatggaa tcccaacaat tatctcaaaa ttcccccaat   1560

tctcatcagt aacaccccac cccgtattac ttttaccgtg atgaagattg gcatcgttac   1620

tttctaaacg taggacgtgc ggaatgacaa aaccatcagc agtgtcacga tctctccagt   1680

cacaatggca atcatgagtg catagtccaa agtaaagggg caaggaaaag catgattgaa   1740

aggactcccc atctggactc tatatgtcat cagcggctaa aaaaaagcat atagcacaac   1800

atcagcatca gcatcagcac tagagtcatc ggcccggcgg tccgcggtca tccccgcgga   1860

ctttccgtcc gcccggcggg ctgtatcagc gtcaactgga acgcgcatat atatacaaga   1920

cacacataac atagaagcac acccacgaca ataaccacac gacaataacc acacccgccc   1980

acccctcctt tccgtatac                                                1999
```

```
<210> SEQ ID NO 21
<211> LENGTH: 6334
<212> TYPE: DNA
<213> ORGANISM: Sorghum bicolor

<400> SEQUENCE: 21

tggattcgga ctggaaaata actctaactt gtatggatca ccacgacgtc atatggactc     60

caactgggac gttcctatac ttgttggaaa gctcatgaag tctactttcc aatgggtcca    120

accacatatc tatgcggctt atgagtcggg cgcagtcctt gttttcgtgc cgacaccttt    180

ttctgttttg gtgctgcgtc actctatttt ggaccaatgg cccatgtatc aagttgagtc    240

cattagggac gcatcctagg gttggaggac gactctagca cccctttggt cgtcctcccc    300

tctatttatt tacatctaga gccgccatga acaactggat tttgtttaga tcaagtttag    360

ccttcgctac ttgcttgtag gcgcgcgtgc aggatcagcc gcccgcctcc ttgtcttcgg    420

aaccccattg ttgattaaga ttcagtttaa aaccttcaat tcatcttgca aattcagtgc    480

ttgtttcctc gttcttgcta gttcttcgat tgcttgcagg acgggagccc taggggctgg    540

ttgtcgcgct ccacaagatc gtgacggttg ttggacgtgg tgtatcggtt gctaaggcgc    600

ggtcttgagg gctgtagtcg ggccgtgaac gtcatctcca tccactaatc gagttatcca    660

gcgcctctca tcgaaagatc aggccaaaaa ccctagcggg ctcgcatcag ttggtaatca    720

gagcaaggtt cttcggtgag agacttctaa tcctttgctg tttttaatta atttcctata    780

gtccagaaaa gccaaaaaaa tatagtagat tagtttttcc ataatcctat taaacctttg    840

tgccttggct agtaccgttt tagttagggc ttgttgaatt tgcgttgctt cggtttgtgt    900

cgagttgctg gtcttagtgt ctagtccttt agagtttcga gttcttgtca ccatctatac    960
```

```
acagccgagt attaccatat cttctctctg tcgaatctgt tgcgaagtct gaattgaact   1020
gtggtcatgg tccggatcga gtagagttcc aatctgagtt caaaaagaaa gataactcta   1080
cttgttcggc cttactctag agagagagag agagtgtgga gcgaaaaaag tgtgtggagc   1140
gaattgctct tttgtattct tttgttcata taatcagttt tggaggttgc ccacaaaaaa   1200
agaaaaaaaa gaaaagagaa aagattcaaa aaaaagaggc tgtttttcat attgatttta   1260
ggtttgtccc accttgtttt cgggggtgtg ctgtggtttt cctttgtgtc caggctcgcg   1320
tctctagcac ggtctagcct aggaccagca cagtaccatc gtcgaacgct tattcagctc   1380
gcttttataa ctaacgtggt gctagttcgt tccttgtttc agcccaccta tagctccaca   1440
tactctacag cttgacaggt cttgtgctgc agcaccgata cacttcgtcc attgctatac   1500
acttgttggc agacgacccc tcctgtcaag caagataaga attggtaaga acttgtgtta   1560
caggttgagt gtgagcgact tgctatagct acatcctagt agttgtaggg attttatttc   1620
ttcacttgct ttttgttgtc tttgtctttg aaccatgcca ggggcagatg atggtaacga   1680
aacaccactt acacctcgca ctatgggcat catacaatat tttgaaagga aagtgaagct   1740
gcacacagag ggacttgata acgacttgca ggtgacgaat gaaaagctgg ggcagttgga   1800
ggctacgcag attgccacaa acaacaagct cacaagtttg gaggaatccg ttgctagtgt   1860
ggacaaaagc cttgctgctc tcctaaggcg atttgatgct ttccacaccg aagataaaga   1920
gaagcataaa gaagaaaagg agggagatcg agagcacggt agtcatgaag atgactacac   1980
tggtgatact gaacatgatg atcaagacac tcgtgatcga cgtcgccttc gtcacaaccg   2040
tagaggtatg ggtggcaacc gccgacgcga ggtacacaat aatgatgatg ctttcagtaa   2100
gattaaattt aagatacccc tttttgatgg taaatatgac cctgatgctt acatcacttg   2160
ggagattgct gttgatcaaa agtttgcatg tcatgaattt cctgagacta cacgtgttag   2220
ggctgctact agtgagttta cagattttgc ttctgtttgg tggatagaat atggaaagaa   2280
aaatcataat aacttaccta gaacttggga tgcgctgaaa agggccatga gagctagatt   2340
tgttccatct tactatgcgc gtgatatgat aaataagttg cagcagttaa gacaaggtgc   2400
taaaagtgta gaagaatatt atcaggaatt acaaacgggt atgttgcgtt gtaacctaga   2460
ggaggatgag gaaccggcta tggctagatt tttgggtggg ttaaatcggg aaattcagga   2520
catcctcgct tacaaagaat acaataatgt aacccgtttg tttcatcttg cttgtaaagc   2580
tgaaagggaa gtgcagagac gacgtgctag cacaaggagt aatatttctg cagggaaggc   2640
taattcatgg cagcaacgcg tggcttcaac tccatctaca cgtatttcta ctccatcatc   2700
tagtgacaag actcgagctg cccccaccaa ttcagttgcg aagacgatgc aaaagcctgc   2760
tgcgagtact tcatccgtgg catcgacggg tagaacaagc aacatacaat gtcaccggtg   2820
caagggatat gggcacatga tgcgtgactg tccaaacaag cgagttatga ttgtcaggga   2880
tgatggtgag tactcatctg ctagtgattt tgatgaggat acacttgcac tgcttgcgac   2940
tgaccatgca ggtaatgaag atcaaataga agaatatatt aatgcaggtg aagcggacca   3000
ctatgagagc ttgatcgtgc agcgagtgct tagtgcacaa atggagatgg cggaacaaaa   3060
tcagcgacac attttattcc aaacaaagtg tgtcatcaaa gagcgttctt gtcgcatgat   3120
cattgatgga ggtagctgca acaacttggc aagcagcgat atggtgcaga agcttgccct   3180
caacaccaaa ccacacccgc atccctacta catccaatgg ctgaacaaca gtggtaaggc   3240
aaaggtaact agacttgtga gaattaattt ttccatcgga tcctacaaag atattgttga   3300
```

```
atgtgatgtt gtgcctatgc aagcttgtaa cattctgcta ggtagacctt ggcaatttga   3360
tagagattct atgcatcatg gtagatcaaa tcagtattct tttctatacc atgatcgcaa   3420
aattgtgttg catcctatat cccctgaaac tattatgcaa actgatgttg ctagggctac   3480
taaagcaaag agcaagagca ataaaaatga taaatctgta attggtaaca aagatgagat   3540
aaaactgaaa ggacattgta tgatagctac caaatcagat attaatgagt tcaatgcatc   3600
cacttctgtt gcttatgctt tgatatgcaa ggatgctttg atttcagttg aggatatgca   3660
atgttctttg ccccctgctg ttgctaacgt tttgcaggag tattctgatg tgtttccaag   3720
tgatgtacca gcggggctgc ctccactacg cgggattgag caccaaattg atcttattcc   3780
tggatcagtt ttgccaaatc gtgcaccata caggacaaac ccggaggaaa caaaggaaat   3840
tcagcgacaa gtgcaagaac tactagacaa aggttatgtc cgagaatctc ttagtccttg   3900
tgctgttcca gtaattttag tgcctaagaa agatggaaca tggcgtatgt gtgttgattg   3960
tagagctatt aataatatca ccattcgata ttgacaccct attccacgat tagatgatat   4020
gctagatgaa ctgagtggtg ctgttgtgtt ttcaaaagtt gatttacgta gtgggtacca   4080
ccagattcgt atgaaattgg gagatgaatg gaaaactgct ttcaaaacta agttcggttt   4140
gtatgagtgg ttagtcatgc cttttgggtt aactaatgca cctagtactt tcatgagatt   4200
aatgaacgag gtcttgcgtg ctttcattgg gaaatttgtt gtcgtatatt ttgatgacat   4260
attgatttac agcaaatcat tggatgaaca tcttgatcat ttacgtgctg tttttaatgc   4320
actacgcgag gcacgtttat ttggtaacct tgagaagtgc accttttgca ccgatcgagt   4380
gtcttttctt ggttatgttg tgactccaca gggaattgag gttgatcaag ccaaggtgga   4440
agctatacag ggatggcctg tcccaaatac tatcacccag gtgcggagtt tcctaggact   4500
tgctagattc tatcgccgtt ttgtgaagga tttcagcacc attgctgcac cattgaatga   4560
gcttacaaag aagggggtgc cttttgattg gggcaaagca caagagaatt cattcaacat   4620
gttgaaagat aagttaactc atgcacctct cctacaactt cctgatttta ataagacttt   4680
tgagcttgaa tgtgatgcta gtggaattgg tttgggaggt gttttattac aagagggaaa   4740
acctattgca tattttagtg agaaattgag tgggcctgtt ctcaaattca acttatgata   4800
aagaactcta tgctcttgtt agaacattag agacatggca gcattatttg tggcccaaag   4860
agtttattat ccattttgat catgaatctt tgaaacatat tcgtagtcaa ggaaaactga   4920
atcgtaggca tgcaaagttg gttgaattta ttgaatcttt tccttatatt attaagcaca   4980
agaaaggaa ggaaaatatt attgctgatg ctttatcacg gagatatact ttgctgaatc   5040
aacttgatta caagatattt gggttagaaa caattaaaga ccaatatgtt catgatgctg   5100
attttagaga cgtgttgctg cattgtaaag atggaaaagg gtggaataaa ttcatcgtta   5160
gtgatgggtt tgtgtttaga gctaacaagc tatgcattcc agctagctct gttcgtttgt   5220
tgttgttgca ggaagcgcat ggaggtggct tgatgggaca ttttggagca aagaagaccg   5280
aggacatact tgctggtcat ttcttttggc ccaggatgaa gagagatgtg gagaggtttg   5340
ttgctcgttg cacaacatgt caaaaggcaa agtcacggtt aaatccccac ggtttgtatt   5400
tacctcttcc tgttcctaat gctccttggg aggatatatc tatggatttt gtgttgggac   5460
taccaaggac taggagggga cgtgatagtg tgtttgtggt tgttgataga ttttctaaga   5520
tggcacattt cataccatgt cataaaactg atgatgctac aaatattgct gatttgtttt   5580
ttcgagaaat tgttcgctta catggtgtgc ccaacacaat tgtttctgat cgtgatgcta   5640
aatttcttag tcatttttgg aagactttgt ggttcaaatt ggggactaag cttttatttt   5700
```

ccaccacctg tcatccccaa actgatggtc aaactgaagt tgttaataga actttatcca 5760
ctatgttaag ggctgtttta aagaagaata ttaagatgtg ggaagaatgt ttgcctcatg 5820
ttgagttcgc ctataatcgt tcattgcatt ctactacaaa aatgtgtcct tttgagattg 5880
tctatggctt cttgccacgt gctcctattg atttaatgcc tttgccaagt tctgaaaaaa 5940
taaattttga tgctaagcaa catgctgaat tgatgttaaa attgcatgaa gccactaaac 6000
aaaacataga gcgcatgaat gctaagtaca aatgcactgg agataaaggt agaaagcaat 6060
tgattctgga acctggggat ttggtttggt tgcatttgcg aaaagataga tttccagaac 6120
tgataaaatc caaattgatg cctagagctg atggtccttt taaagtgctg caacgaatta 6180
atgagaatgc atataagctt gatcttcctg cagattttgg ggttagtccc acatttaaca 6240
ttgcagattt gaagccttat ttgggtgagg aagatgagct tgagtcgagg acgactcaaa 6300
tgcaagaaag ggaggatgat gaggacatca acac 6334

<210> SEQ ID NO 22
<211> LENGTH: 132
<212> TYPE: DNA
<213> ORGANISM: Sorghum bicolor

<400> SEQUENCE: 22
aaactgagct tccacttgag cccctttacc aggagtatca tcgggtgcat ccaaaatggt 60
ttcttagcct atgatgcatt aggcgcaaac tgtgtaccta tcttgcacca aaactaactc 120
tgtctccaaa cc 132

<210> SEQ ID NO 23
<211> LENGTH: 133
<212> TYPE: DNA
<213> ORGANISM: Sorghum bicolor

<400> SEQUENCE: 23
aaactgagct tccacttgag cccctttacc caggagtatc atcgggtgca tccaaaatgg 60
tttcttagcc aatgatgcat taggcacaaa ttgtgtacct atcttgtacc aaaactaact 120
ctgtctccaa aca 133

<210> SEQ ID NO 24
<211> LENGTH: 133
<212> TYPE: DNA
<213> ORGANISM: Sorghum bicolor

<400> SEQUENCE: 24
aaactgagct tccacttgag cccctttaca caggagtatc atcgggtgca tccaaaatgg 60
tttcttagcc aatgatgcat taggcgcaaa ttgtgtacct atcttgtacc aaaactaact 120
ctgtctccaa aca 133

<210> SEQ ID NO 25
<211> LENGTH: 133
<212> TYPE: DNA
<213> ORGANISM: Sorghum bicolor

<400> SEQUENCE: 25
caaactgagc ttccacttga gcccctttac ctaggagtat gatcaggtgc atccaaaatg 60
gtttcttagc ctatgatgca ttaggcgcaa actgtgtacc tatcttgtac caaaactaac 120
tctgtctcca aac 133

<210> SEQ ID NO 26
<211> LENGTH: 133
<212> TYPE: DNA
<213> ORGANISM: Sorghum bicolor

<400> SEQUENCE: 26
caaactgagc ttccacttga gcccctttac ccaggagtat cttcaggtgc atccaaaatt 60
gtttcttagc ctatgatgca ttaggcgcaa actgtgtatc tatcttgcac caaaactaac 120
tctgtctcca aac 133

<210> SEQ ID NO 27
<211> LENGTH: 133
<212> TYPE: DNA
<213> ORGANISM: Sorghum bicolor

<400> SEQUENCE: 27
caaactgagc ttccacttga gcacctttac ccacgagtat catcgggctc atccaaaatg 60
gtttcttagc ccatgatgca ttaggcgcaa actgtgtacc tatcttgcac caaaactaac 120
tctgtctcca aac 133

<210> SEQ ID NO 28
<211> LENGTH: 133
<212> TYPE: DNA
<213> ORGANISM: Sorghum bicolor

<400> SEQUENCE: 28
caaactgagc ttccacttga gcccctgtac ccaggagtat catcgggtgc atccaaaatg 60
gtttcttagc ctatgatgca ttaggcgcaa actgtgtacc tatcttgcac taaaactacc 120
tttgtctcca aac 133

<210> SEQ ID NO 29
<211> LENGTH: 133
<212> TYPE: DNA
<213> ORGANISM: Sorghum bicolor

<400> SEQUENCE: 29
gaaccgacct tccacttgag cctctccacc taggattatc atcgggtgct tgcataatgg 60
tttctgagcc tatggtgcat tatgcgcaaa ccatgcacca atcctgcacc taaactaaca 120
ctgtctccaa aca 133

<210> SEQ ID NO 30
<211> LENGTH: 133
<212> TYPE: DNA
<213> ORGANISM: Sorghum bicolor

<400> SEQUENCE: 30
caaactgagc ttccacatga gcccctttac ccaggagtat attcgggtgc atccaaaatg 60
gtttcttagc ctatgatgca ttaggcgcaa agtatgtacc gatcttgcac caaaactaac 120
tctgtctcca aac 133

<210> SEQ ID NO 31
<211> LENGTH: 133
<212> TYPE: DNA
<213> ORGANISM: Sorghum bicolor

<400> SEQUENCE: 31
caaactgaga ttccacttga gcccctttac cggggagtat catcgtgtgc atccaaaatg 60
gtttcttagc ctatgatgca ttaggcgcaa actatgtacc tatcttacac caaaactaac 120
tctgtctcca aac 133

<210> SEQ ID NO 32
<211> LENGTH: 133
<212> TYPE: DNA
<213> ORGANISM: Sorghum bicolor

<400> SEQUENCE: 32
caaactgagc ttccacttga gcccctttac ctaggagtat catcgggtgc atccaaaatg 60
gtttcttagc ctgtgatgca ttaggagaaa actgtgtacc tatcttgcac caaaactaac 120
tctgtctcca aac 133

<210> SEQ ID NO 33
<211> LENGTH: 133
<212> TYPE: DNA
<213> ORGANISM: Sorghum bicolor

<400> SEQUENCE: 33
aaactgagct tccacttgag cccctttacc caggagtgtt atcgagtgca tccaaaatag 60
tttcttagcc tatgatgcat taggcgcaaa ctgtgtacct atcttgcacc aaaactatct 120
ctgtctccaa aca 133

<210> SEQ ID NO 34
<211> LENGTH: 133
<212> TYPE: DNA
<213> ORGANISM: Sorghum bicolor

<400> SEQUENCE: 34
aaactgagct tccacttgag ccccttact caggagtatc atcgggttca tccaaaatgg 60
tttcttagcc aatgatgcat ttggcgcaaa ctgtgtacct atctcgcacc aaaactaact 120
ttgtctccaa aca 133

<210> SEQ ID NO 35
<211> LENGTH: 133
<212> TYPE: DNA
<213> ORGANISM: Sorghum bicolor

<400> SEQUENCE: 35
caaactgagc ttccacttga gcccctttac ccaggagtat catcgagtgc atccaaaata 60
gtttcttagc ctatgatgca ttaggcgcaa actgtgtacc tatcttgcac caaaactgcc 120
tctgtctcca aac 133

<210> SEQ ID NO 36
<211> LENGTH: 133
<212> TYPE: DNA
<213> ORGANISM: Sorghum bicolor

<400> SEQUENCE: 36
caaactgagc ttccacttga gcccctttac ccaggagtat catcaggttc atccaaaatt 60
gtttcttagc ctatgatgca ttaggcgtaa actgtgtacc tatcttgcac caaaactaac 120
tctgtctcca aac 133

<210> SEQ ID NO 37
<211> LENGTH: 133
<212> TYPE: DNA

<213> ORGANISM: Sorghum bicolor

<400> SEQUENCE: 37
caaactgagc ttccacttga gcccctttgc ccaggagtat catcaggttc atccaaaatt 60
gtttcttagc ctttgatgca ttaggcgtaa actgtgtacc tatcttgcac caaaactaac 120
tctgtctcca aac 133

<210> SEQ ID NO 38
<211> LENGTH: 133
<212> TYPE: DNA
<213> ORGANISM: Sorghum bicolor

<400> SEQUENCE: 38
aaactgagct tccacttgag cccctttacc caggagtatc gtcgggtgca tccaaaatgg 60
tttcttaccc tatgatgcat taggcgcaaa atgtgtacct atcttgaacc aaaactaact 120
ctgtctccaa aca 133

<210> SEQ ID NO 39
<211> LENGTH: 133
<212> TYPE: DNA
<213> ORGANISM: Sorghum bicolor

<400> SEQUENCE: 39
caaactgagc ttccacttga gcccctttac ccaggagtat gatcgggtgc atctaaaatg 60
gtttcttagc ctatgatgca ttaggcgaaa actgtgtacc tattttgcac caaaactaac 120
tctgtctcca aac 133

<210> SEQ ID NO 40
<211> LENGTH: 133
<212> TYPE: DNA
<213> ORGANISM: Sorghum bicolor

<400> SEQUENCE: 40
caaactgagc ttccacttga gcccctttac ccaggagtat catcgggtgc atccaaaatg 60
gtttcttagg ctatgatgca ttaggcgcaa actgtgcacc tatcctgtac ctaaactaac 120
actgtctcca aac 133

<210> SEQ ID NO 41
<211> LENGTH: 133
<212> TYPE: DNA
<213> ORGANISM: Sorghum bicolor

<400> SEQUENCE: 41
caaactgagc ttccacttga gccccattac ctaggagtat gttcgggtgg attcaaaatg 60
gtttcttagc ctatgatgca ttatgcgcaa actgtgtacc tatcttgcac caaaactaac 120
tctgtctcca aac 133

<210> SEQ ID NO 42
<211> LENGTH: 133
<212> TYPE: DNA
<213> ORGANISM: Sorghum bicolor

<400> SEQUENCE: 42
aaactgagct tccacttgag cccctatacc tagtagtatc atcgggtgca tccaaaatga 60
tttcttatcc tatgatgcat taggcgcaaa ctgtgtacct atcttgcacc aaaactaact 120
ctgtctccaa aca 133

<210> SEQ ID NO 43
<211> LENGTH: 133
<212> TYPE: DNA
<213> ORGANISM: Sorghum bicolor

<400> SEQUENCE: 43
caaactgagc ttccacttga gccccttac ctaggagtat catcgggtgc atccaaaatg 60
gtttcttagc ctatgatgca ttaggcacag actatgtacc tatcttgcac caaaactaac 120
tccgtctcca aac 133

<210> SEQ ID NO 44
<211> LENGTH: 133
<212> TYPE: DNA
<213> ORGANISM: Sorghum bicolor

<400> SEQUENCE: 44
caaaccgacc ttccacttca gcctctttac ctaggattat catcgggtgc ttccataatg 60
gtttttgagc ctatggtgca tattgcgcaa accatgcacc aatcttgcat ctaaactaac 120
actgtctcca aac 133

<210> SEQ ID NO 45
<211> LENGTH: 133
<212> TYPE: DNA
<213> ORGANISM: Sorghum bicolor

<400> SEQUENCE: 45
aaactgagct tccaattgag cccctttacc caggagtatc atcgggtgca aacaaaatgg 60
tttcttagcc tatgatgcat taggcgcaaa ctgtgtacct atcttgcacc aaaaataact 120
ctgtctccaa aca 133

<210> SEQ ID NO 46
<211> LENGTH: 133
<212> TYPE: DNA
<213> ORGANISM: Sorghum bicolor

<400> SEQUENCE: 46
caaactgagc ttccacttga gcccctttac ctaggagtgt catcgggtgc attcaaaatg 60
gtttcttagc ctatgatgca ttaggcgcaa actgtgtacc tatcttgcac caaaactaac 120
tttgtctcta aac 133

<210> SEQ ID NO 47
<211> LENGTH: 133
<212> TYPE: DNA
<213> ORGANISM: Sorghum bicolor

<400> SEQUENCE: 47
caaactgagc ttccatttga gcccctttac ccacgagtat aattgggtgc atccaaaatg 60
gtttcttagc ctatgatgca ttaggcgcaa actgtatacc tatattgcac caaaactacc 120
tctgtctcca aac 133

<210> SEQ ID NO 48
<211> LENGTH: 133
<212> TYPE: DNA
<213> ORGANISM: Sorghum bicolor

<400> SEQUENCE: 48

```
caaactgagc ttccacttga gcccctatac cgaggagtat catcgggtgc attcaaaatg     60

gtttcttagc ctatgatgca ttaggcgcaa actgtgtacc tatcttgcac tgaaactaac    120

tctgtctcca aac                                                       133


<210> SEQ ID NO 49
<211> LENGTH: 133
<212> TYPE: DNA
<213> ORGANISM: Sorghum bicolor

<400> SEQUENCE: 49

caaactgagc tttcacttga gcccctttac ctaggagtat gaacgggtgc atccaaaatg     60

gtttcttagc ctatgatgca ttaggcgcaa actgtgtacc tatcttgcac caaaactaac    120

tctgtctcta aac                                                       133


<210> SEQ ID NO 50
<211> LENGTH: 133
<212> TYPE: DNA
<213> ORGANISM: Sorghum bicolor

<400> SEQUENCE: 50

aaactgagct tccacttgag cccctttaca caggagtatc atcgggtgca tccaaaatgg     60

tttcttagcc tatgatacat aaggcgcaaa ctgtgtatgt atcttgcacc aaatctaact    120

ctatctccaa aca                                                       133


<210> SEQ ID NO 51
<211> LENGTH: 133
<212> TYPE: DNA
<213> ORGANISM: Sorghum bicolor

<400> SEQUENCE: 51

caaactgagc ttccacttga gcccttttac ccaggagtat catcgagtgc atccaaaatg     60

gtttcttagc ctatgatgca ttaggcgcaa actgtgtacc tatcttgcac caaaactacc    120

tccgtctcca aac                                                       133


<210> SEQ ID NO 52
<211> LENGTH: 133
<212> TYPE: DNA
<213> ORGANISM: Sorghum bicolor

<400> SEQUENCE: 52

caaactgagc ttccacttga gcccctttac ctaggagtat catcgggtgc atccaaaatg     60

gtttcttcgc ctatgatgca ttaggcgcaa actatgtacc tatcttgcac caaaactaac    120

tttgtctcca aac                                                       133


<210> SEQ ID NO 53
<211> LENGTH: 133
<212> TYPE: DNA
<213> ORGANISM: Sorghum bicolor

<400> SEQUENCE: 53

aaactgagct tccacttgag cccctttacc caggtgtatc atcgggtgca tccaaactgg     60

tttcttagcc tatgacgcat taggcgcaaa ctgtgtacct atcttgcacc aaaactacct    120

ctgtctccaa aca                                                       133


<210> SEQ ID NO 54
<211> LENGTH: 133
```

<212> TYPE: DNA
<213> ORGANISM: Sorghum bicolor

<400> SEQUENCE: 54
caaactgagc ttccacttga gcccctttac ccaggagtat attcgggtgc atccaaaatg 60
gtttcttagc ctatgatgcc ttaggcgcaa agtgtgtacc tatcttgcac caaaactaac 120
tctgtctcca aac 133

<210> SEQ ID NO 55
<211> LENGTH: 133
<212> TYPE: DNA
<213> ORGANISM: Sorghum bicolor

<400> SEQUENCE: 55
caaactgagc ctccacttga gcccctttac ccaggagtat catcaggtgc atccaaaatg 60
gtttcttagc atatgatgca ttaggcgtaa actgtgtacc tatcttgcac caaaactaac 120
tctgtctcca aac 133

<210> SEQ ID NO 56
<211> LENGTH: 133
<212> TYPE: DNA
<213> ORGANISM: Sorghum bicolor

<400> SEQUENCE: 56
caaactgagc ttccacttga gcccctttac ccaggagaat caacagatgc atccaaaata 60
gtttcttagc ctttgatgca ttaggtgcaa actgtgtagc tatcttgcac caatactaac 120
tctgtctcca aac 133

<210> SEQ ID NO 57
<211> LENGTH: 133
<212> TYPE: DNA
<213> ORGANISM: Sorghum bicolor

<400> SEQUENCE: 57
gaactgacct tccacttgag cctctttacc taggattatc atcgggtgct tccataatgg 60
tttctgagcc tatggtgcat tatgcgcaaa ccatgcacca atcttgcacc taaactaaca 120
ctgtctccaa aca 133

<210> SEQ ID NO 58
<211> LENGTH: 133
<212> TYPE: DNA
<213> ORGANISM: Sorghum bicolor

<400> SEQUENCE: 58
aaactgagct tccacttgag ccctttttacc caggagtatc atcgagtgca tccaaaatga 60
tttcttaccc tatgatgcat taggcgcaaa ctgtgaacct atcttgcacc aaaactacct 120
ctgtctccaa aca 133

<210> SEQ ID NO 59
<211> LENGTH: 133
<212> TYPE: DNA
<213> ORGANISM: Sorghum bicolor

<400> SEQUENCE: 59
caaactgagt ttccacttga gcccctttac ccaggagtat catcgggtgc atccaaaatg 60
gtttcttagc ctatgatgca ttcggcgcaa attgtgtacc taacttgcac caaaactaac 120
tctgtctcca aac 133

<210> SEQ ID NO 60
<211> LENGTH: 132
<212> TYPE: DNA
<213> ORGANISM: Sorghum bicolor

<400> SEQUENCE: 60
aaactgagct tccacttgag ccccttttacc taggattatc atcgggtgca tccaaaatgg 60
tttcttagcc tattatgcat taggcgtaaa ctgtgtacca atcttgcacc aaaactaact 120
ctctctccaa ac 132

<210> SEQ ID NO 61
<211> LENGTH: 133
<212> TYPE: DNA
<213> ORGANISM: Sorghum bicolor

<400> SEQUENCE: 61
aaactgagct tccatttgag cccctttacc caggattatc atcgggtgcg tccaaaatgg 60
tttctgagcc tatgatgcat taggtggaaa ctgtgtacct attttgcacc aaaactaact 120
ctgtctccaa aca 133

<210> SEQ ID NO 62
<211> LENGTH: 133
<212> TYPE: DNA
<213> ORGANISM: Sorghum bicolor

<400> SEQUENCE: 62
accaaactgt gcttccactt aagcctcttc acctaggatt accatcaagt gcatccaaaa 60
tggtttctta gactatggtg aattaggcaa aaactgtgca cctatcttgc accaaaacta 120
acactatgtc caa 133

<210> SEQ ID NO 63
<211> LENGTH: 133
<212> TYPE: DNA
<213> ORGANISM: Sorghum bicolor

<400> SEQUENCE: 63
caaactgagc ttctgcttga gccccttttac ctaggagtat catcgggtgc atccaaaatg 60
gtttctcagc ctttgatgca ttaggcgtaa actgtgtacc tatgttgcac caaaactaac 120
tctatctcca aac 133

<210> SEQ ID NO 64
<211> LENGTH: 133
<212> TYPE: DNA
<213> ORGANISM: Sorghum bicolor

<400> SEQUENCE: 64
gatcaaacca agcttccact tgagcccctt ttcctaggag taccattagg tgtgtccaaa 60
aaggttctta gcctatggtg cattaggcgc aaaccattca cctatcttgc acagaaacta 120
atactgtctc aaa 133

<210> SEQ ID NO 65
<211> LENGTH: 133
<212> TYPE: DNA
<213> ORGANISM: Sorghum bicolor

<400> SEQUENCE: 65
cgaaccgacc ttccacatga gactcttcac ctaggattat catcgggtgc ttccataatg 60
gtttctgtgc ctatggtgca ttatgcgcaa accatgcacc aatcttgcac ctaaactaac 120
actctctcca aac 133

<210> SEQ ID NO 66
<211> LENGTH: 133
<212> TYPE: DNA
<213> ORGANISM: Sorghum bicolor

<400> SEQUENCE: 66
caaactgagc tttcccttga gccccttgag ccaggagtat catcgggtgc atccaaaatg 60
gtttcttagc tgtatgaagc attaggcgca aactgtgtac ttatcttgca ccaaaactaa 120
ctctgtctcc aaa 133

<210> SEQ ID NO 67
<211> LENGTH: 133
<212> TYPE: DNA
<213> ORGANISM: Sorghum bicolor

<400> SEQUENCE: 67
caaactgagc ttccacttga gcccctttac cttggagtat caacgggtgc atccaaaatg 60
ttttcttagc ctatgatgca ttaggcgcaa actgtgtacc tatcttgcac caaaactaac 120
tttgtctcca aac 133

<210> SEQ ID NO 68
<211> LENGTH: 133
<212> TYPE: DNA
<213> ORGANISM: Sorghum bicolor

<400> SEQUENCE: 68
aaactgagct tccacttgag ccccttacc caggagtatc atcgggtgca tccaaaatgg 60
attcttagcc tatgatgcat taggcgtaaa ctgtgtacct ttcttgtacc aaaactaact 120
ctgtctccaa aca 133

<210> SEQ ID NO 69
<211> LENGTH: 133
<212> TYPE: DNA
<213> ORGANISM: Sorghum bicolor

<400> SEQUENCE: 69
caaactgagc ttccacttga gcccctttac ctaggagtat catcggctcc atccaaaatg 60
gtttcttagc ctatgatgca ttaggcgcaa actgtgtacc tatcttgcac caaaactaac 120
tctgtctcct aac 133

<210> SEQ ID NO 70
<211> LENGTH: 133
<212> TYPE: DNA
<213> ORGANISM: Sorghum bicolor

<400> SEQUENCE: 70
caaactgagc ttccgcttga gcccctttac ctaggagtat catcgggtgc atccaaaatg 60
gtttctcagc ctatgatgcc ttaggagcaa actgtgtacc tatcttgcac caaaactaag 120
tctgtctcca aac 133

<210> SEQ ID NO 71

<211> LENGTH: 133
<212> TYPE: DNA
<213> ORGANISM: Sorghum bicolor

<400> SEQUENCE: 71
aaactgagct tccacttgag cccctttgcc caggagtatc atcaggttca tccaaaatgg 60
tttcttagcc tttgatgcat taggcgtagc ctgtgtacct atcttgcacc ataactaact 120
ctgtctccaa aca 133

<210> SEQ ID NO 72
<211> LENGTH: 133
<212> TYPE: DNA
<213> ORGANISM: Sorghum bicolor

<400> SEQUENCE: 72
accaaactgt gcttccactt gagcctcttc atctaggatt accatcaagt gcatccaaaa 60
tggtttctta gactacggtg aattaggcta aaattgtgca cctatcttgc accaaaacta 120
acactatgtc caa 133

<210> SEQ ID NO 73
<211> LENGTH: 133
<212> TYPE: DNA
<213> ORGANISM: Sorghum bicolor

<400> SEQUENCE: 73
caaactgagc ttccacttga gccccgttac ctaggagtat cttcgggtgc atccaaaatg 60
gtttcttagc ctatgatgca ttaggcacaa actatgtacc tatcttacac taaaactaac 120
tctgtctcca aac 133

<210> SEQ ID NO 74
<211> LENGTH: 133
<212> TYPE: DNA
<213> ORGANISM: Sorghum bicolor

<400> SEQUENCE: 74
aaactgagct tccacctgag cccctttacc caggagtatc atcgggtgca tccaaaatgg 60
tttcttagcc tatgatgctt taggcgcaaa ctgtgtacct atctagcacc aaaactagct 120
ctgtctccaa aca 133

<210> SEQ ID NO 75
<211> LENGTH: 133
<212> TYPE: DNA
<213> ORGANISM: Sorghum bicolor

<400> SEQUENCE: 75
cgaaccgacc tttcaattga gcctcttcac ctaggattat catcgggtgt ttccataatg 60
gtttctgagc ctatggtgca ttatgcgcaa accatgcacc aatcttgcac ctaaactaac 120
actgtctcca aac 133

<210> SEQ ID NO 76
<211> LENGTH: 133
<212> TYPE: DNA
<213> ORGANISM: Sorghum bicolor

<400> SEQUENCE: 76
caaactgagc ttccacttga gcccctttac ctaggagtat catcgggtgc atccaaaatg 60
gtttcttagc ctatgatgca ttaggagaaa actgtgtccc tatcttgcac caaaactaac 120
tctgtctcca aac 133

<210> SEQ ID NO 77
<211> LENGTH: 133
<212> TYPE: DNA
<213> ORGANISM: Sorghum bicolor

<400> SEQUENCE: 77
aaactgagct tccacttgag cccctttacc caggagtatc attgggtgca tccaaactgg 60
tttcttagcc tatgatgcat ttggcgcaaa ctgtgtacct atcttgcacc aaaactgact 120
ctgtctccaa aca 133

<210> SEQ ID NO 78
<211> LENGTH: 133
<212> TYPE: DNA
<213> ORGANISM: Sorghum bicolor

<400> SEQUENCE: 78
aaactgagat tccacttgag cccctttacc caacagtata atcgggtgca tccaaaatgg 60
tttcttagcc tatgatgcat taggcgcaaa ctgtgtaccg atcttgcacc aaaactaact 120
ctgtctccaa aca 133

<210> SEQ ID NO 79
<211> LENGTH: 133
<212> TYPE: DNA
<213> ORGANISM: Sorghum bicolor

<400> SEQUENCE: 79
caaactgagc ttccacttgg gcccctttac ccaggagtat caacagatgc atccaaaata 60
gtttcttagc ctttgatgca ttaggtgcaa actgtgtagc tatcttgcac caatactaac 120
tctgtctcca aac 133

<210> SEQ ID NO 80
<211> LENGTH: 133
<212> TYPE: DNA
<213> ORGANISM: Sorghum bicolor

<400> SEQUENCE: 80
caaactgagc ttccacttga gcccctttac ctaggagtat catcgggtgc atacaaaatg 60
gttccttagc ctatgatgca ttaggcgcaa actgtgtact tatcttgcac caaaactaac 120
tctgtctcca aac 133

<210> SEQ ID NO 81
<211> LENGTH: 133
<212> TYPE: DNA
<213> ORGANISM: Sorghum bicolor

<400> SEQUENCE: 81
aaactgagct tccacttgag cccctttacc taggagtatc atcgggtgca tccaaaatgg 60
tttcttagcc tatgatgcat ttggcacaaa ctgtgtacct atcctgcacc aaaactaact 120
ctgtctccaa aca 133

<210> SEQ ID NO 82
<211> LENGTH: 133
<212> TYPE: DNA
<213> ORGANISM: Sorghum bicolor

<400> SEQUENCE: 82
aaactgagct tccagttgag cccctttacc gaggagtatc atcaggtgca tccaaaatgg 60
tttcttagcc tatgatgcat taggcgcaac ctgtgtacct atcttgcacc aaaactacct 120
ctgtatccaa aca 133

<210> SEQ ID NO 83
<211> LENGTH: 133
<212> TYPE: DNA
<213> ORGANISM: Sorghum bicolor

<400> SEQUENCE: 83
caaactgagc ttccacttga gcccctttac ccaggagtat caacagattc atccaaaata 60
gtttcttagc ctttgatgca ttaggtgcaa actgtgtagc tatcttgcac caatactaac 120
tctgtctcca aac 133

<210> SEQ ID NO 84
<211> LENGTH: 133
<212> TYPE: DNA
<213> ORGANISM: Sorghum bicolor

<400> SEQUENCE: 84
aaacctacct tccacttgag cctctccacc taggagtatt atcgggtgct tccataatgg 60
tttccgagcc tatggtgcat tatgcgcaaa ccatgcacca atcttgcacc taaactaaca 120
ctgtctccaa aca 133

<210> SEQ ID NO 85
<211> LENGTH: 133
<212> TYPE: DNA
<213> ORGANISM: Sorghum bicolor

<400> SEQUENCE: 85
caaactgacc ttccacttga cactcttcac ctaggagtat tatccggtgc ttccataatg 60
gtttctgagc ctatggtgca ttatgcgcaa accatgcacc aatcttgcac ctaaactaac 120
actatctcca aac 133

<210> SEQ ID NO 86
<211> LENGTH: 133
<212> TYPE: DNA
<213> ORGANISM: Sorghum bicolor

<400> SEQUENCE: 86
caaactgagc ttccacttga gcccctttac cctggagtat cttcaggtgc atccaaaatt 60
gtttcttagc ctatgatgca ttaggcgcaa actgtgtacc tatcttgcac caaaactaac 120
tctgtctcca aac 133

<210> SEQ ID NO 87
<211> LENGTH: 133
<212> TYPE: DNA
<213> ORGANISM: Sorghum bicolor

<400> SEQUENCE: 87
caaactgagc ttccacttga gcccctttac ccaggagtat catcaggtgc atcagaaatg 60
gtttcttagc ctatgatgca ttaggtgcaa actgtgtacc tatcttgcac caaaactaac 120
tctgtctcca aac 133

<210> SEQ ID NO 88
<211> LENGTH: 133
<212> TYPE: DNA
<213> ORGANISM: Sorghum bicolor

<400> SEQUENCE: 88
caaactgagc ttccacttga gccccttac ccaagagtat catcgggtgc atccaaaatg 60
gtttcttagc ctatgacgca ttaggcacaa actgtgtacc tatgttgcac caaaactaac 120
tctgtctcca aac 133

<210> SEQ ID NO 89
<211> LENGTH: 133
<212> TYPE: DNA
<213> ORGANISM: Sorghum bicolor

<400> SEQUENCE: 89
caaactgagc ttcctcttga gccccttac ctaggagtat catcggttgc atccaaaatg 60
gtttcttagc ctatgatgca ttaggcgtaa actgtgtacc tatcttgcac caaaacttac 120
tctgtctcca aac 133

<210> SEQ ID NO 90
<211> LENGTH: 133
<212> TYPE: DNA
<213> ORGANISM: Sorghum bicolor

<400> SEQUENCE: 90
caaactgagc ttccacttga gccccttac ccaggagtat catcgggtgc atacaaaatg 60
gattcttagc ctatgacgca ttaggcgcaa actatgtacc tatcttgcac caaaactaac 120
tctgtctcca aac 133

<210> SEQ ID NO 91
<211> LENGTH: 133
<212> TYPE: DNA
<213> ORGANISM: Sorghum bicolor

<400> SEQUENCE: 91
aaactgagtt tccacatgag caccttacc ctggagtatc atcaggtgca tccaaaatgg 60
tttcttagcc tatgatgcat taggcgcaaa ctgtgtacct atattgcacc aaaactaact 120
ctttctccaa aca 133

<210> SEQ ID NO 92
<211> LENGTH: 133
<212> TYPE: DNA
<213> ORGANISM: Sorghum bicolor

<400> SEQUENCE: 92
caaactgagc ttccacttga gccccttac ctaggagtat catcgggcgc atccaaaatg 60
gtttcttagc ctatgatgca ttaggcacaa actatgtacc tatcttgcac caaaactaac 120
tctgtctcca aac 133

<210> SEQ ID NO 93
<211> LENGTH: 133
<212> TYPE: DNA
<213> ORGANISM: Sorghum bicolor

<400> SEQUENCE: 93
aaactgagct tccagttgag cccctttacc cagcagtatc atcgggtgga tccaaaatgg 60

```
tttcttcacc tatgatgcat taggcgcaaa ctgtgtacct atcttgcacc aaaactaact    120

ctatctcgaa aca                                                       133


<210> SEQ ID NO 94
<211> LENGTH: 133
<212> TYPE: DNA
<213> ORGANISM: Sorghum bicolor

<400> SEQUENCE: 94

aactgagctt ccacttgagc ccctttagcc aggagtatca tcgggtgcat ccaaaatggt     60

ttcttagcct atgaaatcat taggcgcaaa ctgtgtacct atcttgcacc aaaactaact    120

ctgtctctaa aca                                                       133


<210> SEQ ID NO 95
<211> LENGTH: 133
<212> TYPE: DNA
<213> ORGANISM: Sorghum bicolor

<400> SEQUENCE: 95

caaactgagc ttccacttga gcccctttac ctaggagtat catcgggagc atccaaaatg     60

gtttcttagc ctatgatgca taaggagcaa actgtgtacc tatcttgcac caaaactaac    120

tctgtctcca aac                                                       133


<210> SEQ ID NO 96
<211> LENGTH: 133
<212> TYPE: DNA
<213> ORGANISM: Sorghum bicolor

<400> SEQUENCE: 96

caaactgagc ttccacttaa gcccctttac ctaggagtat catcgggtgc atccaaaatg     60

gtttcttagc ctatgatgca ttacgcgcaa actgtgtacc tatcttgcac caaaactaac    120

tttgtctcca aac                                                       133


<210> SEQ ID NO 97
<211> LENGTH: 133
<212> TYPE: DNA
<213> ORGANISM: Sorghum bicolor

<400> SEQUENCE: 97

caaactgagc ttccacttga gcccctttac ctaggagtat aatcgggtgc atccaaaatg     60

gtttcttagc ctatgatgca ttagacgtaa actatgtacc tatcttgcac caaaactaac    120

tctgtctccg aac                                                       133


<210> SEQ ID NO 98
<211> LENGTH: 133
<212> TYPE: DNA
<213> ORGANISM: Sorghum bicolor

<400> SEQUENCE: 98

aaactgagct tccacttgag cccctttacc taggagtatc atcgggtgta tccaaaattg     60

tttcttagcc tacgatgcat taggcgcaaa ctgtgtacct atcttgcacc aaaactaact    120

ctgtctccaa aca                                                       133


<210> SEQ ID NO 99
<211> LENGTH: 133
<212> TYPE: DNA
<213> ORGANISM: Sorghum bicolor
```

<400> SEQUENCE: 99
caaactgagc ttccacttga gcccctttac ctaggagtat cattgggtgc atccaaaatg 60
ctttcttagc ctatgatgca ttaggtgcaa actgtgtagc tatcttgcac caaaactatc 120
tctatctcca aac 133

<210> SEQ ID NO 100
<211> LENGTH: 133
<212> TYPE: DNA
<213> ORGANISM: Sorghum bicolor

<400> SEQUENCE: 100
aaactgagct tccacttgag cccgtttacc gaggagtatc atcgagtgca tctaaaatga 60
tttcttagcc tatgatgcat taggcacaaa ctgtgtacct atctagcacc aaaactaact 120
ttctctccaa aca 133

<210> SEQ ID NO 101
<211> LENGTH: 131
<212> TYPE: DNA
<213> ORGANISM: Sorghum bicolor

<400> SEQUENCE: 101
accgaccttc cacttgagac tcttcaccta ggattatcat cgggtgcttc cataatggtt 60
tctgagccta tggtgcatta tgcacaaacc atgcaccaat attgcaccga aactaacact 120
gtctccaaac a 131

<210> SEQ ID NO 102
<211> LENGTH: 133
<212> TYPE: DNA
<213> ORGANISM: Sorghum bicolor

<400> SEQUENCE: 102
caaactgagc ttccacttga gcccctttac ctaggagtat catcgggtgc atccaaaatg 60
gtttcttagc caatgatgca ttaggagaaa actgtgtacc aatcttgcac caaaactaac 120
tctgtctcca aac 133

<210> SEQ ID NO 103
<211> LENGTH: 133
<212> TYPE: DNA
<213> ORGANISM: Sorghum bicolor

<400> SEQUENCE: 103
caaactgagc ttccacttga gcccctttac ctaggagtat catcgggtgc atccaaaaag 60
gtctcttagc ctatgatgcc ttaggagaaa actatgtacc tgtcttgcac cataactaac 120
tctgtctcca aac 133

<210> SEQ ID NO 104
<211> LENGTH: 133
<212> TYPE: DNA
<213> ORGANISM: Sorghum bicolor

<400> SEQUENCE: 104
aaactgtgct tgcacttgag cccctttacc caggagtatc atcgggtgca tccaaaatgg 60
tttcttagcc tatgatgcat taggcgcata ctgtgtacct atcttgcagt aaaactaact 120
ctgtctccaa aca 133

<210> SEQ ID NO 105
<211> LENGTH: 133
<212> TYPE: DNA
<213> ORGANISM: Sorghum bicolor

<400> SEQUENCE: 105
aaactgagct tccacttgag gccctttatc taggagtatc atcgggtgca tccaaaatgg 60
tttcttagcc tatgatgcgt taggcgcaaa ctatgtacct atcttgcacc aaaactaact 120
ctgtctccaa aca 133

<210> SEQ ID NO 106
<211> LENGTH: 133
<212> TYPE: DNA
<213> ORGANISM: Sorghum bicolor

<400> SEQUENCE: 106
aaactgagct tccacttgag cccctttacc taggagtatc ttcgggtgca tcagaaatgg 60
tttcttagcc tatcatgcat taggcacaaa ctgtgcacct atcttacatc aaaattaact 120
ctgtctccaa aca 133

<210> SEQ ID NO 107
<211> LENGTH: 133
<212> TYPE: DNA
<213> ORGANISM: Sorghum bicolor

<400> SEQUENCE: 107
caaactgagc ttccacttga gcccctttac ccaggagtat attcgggtgc atccaaaatg 60
gtttcttagc ctatgatgcg ttaggcgcaa actgtgtacc tatcttgcac cacaactaaa 120
tctgtctcca aac 133

<210> SEQ ID NO 108
<211> LENGTH: 133
<212> TYPE: DNA
<213> ORGANISM: Sorghum bicolor

<400> SEQUENCE: 108
caaactgagc ttccacttga gcccctttac ccaggagtat caacagatgc atccaaaata 60
gtttcttagc ctttgatgca ttaggtgcaa actgtgtagc tatcttgcac caatactaac 120
tctgtctgca aac 133

<210> SEQ ID NO 109
<211> LENGTH: 133
<212> TYPE: DNA
<213> ORGANISM: Sorghum bicolor

<400> SEQUENCE: 109
caaactgagg ttccgcttga gcccctttac ctaggagtat catcgggttc atccaaaatg 60
gtttctcagc ctatgatgcc ttaggcgcaa actgtgtacc tatcttgcac caaaactaac 120
tctgtctcca aac 133

<210> SEQ ID NO 110
<211> LENGTH: 133
<212> TYPE: DNA
<213> ORGANISM: Sorghum bicolor

<400> SEQUENCE: 110
aaactgagct tccacttgag cccctttacc caggagtatc atcgggtgca tccaaaatgg 60
attcttcgcc tatgatgcat taggcgcaaa ctgtgtacct atcttgcacg aaaactaact 120
ctatctccaa aca 133

<210> SEQ ID NO 111
<211> LENGTH: 133
<212> TYPE: DNA
<213> ORGANISM: Sorghum bicolor

<400> SEQUENCE: 111
cgaaccgacc ttccacttga gccccttcac ctaggattat catcgggtgc ttccataatg 60
gtttttgagc ctatggtgca ttatgcacaa accatgcacc aatcttgcac ctaaactaac 120
actgtctcca aac 133

<210> SEQ ID NO 112
<211> LENGTH: 133
<212> TYPE: DNA
<213> ORGANISM: Sorghum bicolor

<400> SEQUENCE: 112
caaactgagc ttccacttga gcccctttac ctaggagtat catcgggtgc atccaaaatg 60
gttaattagc ctatgatgca ttaggcgcta actgtgtacc tatcttgcac caaaactaac 120
tctgtctcca aac 133

<210> SEQ ID NO 113
<211> LENGTH: 133
<212> TYPE: DNA
<213> ORGANISM: Sorghum bicolor

<400> SEQUENCE: 113
caaactgagc ttccacttaa gcccctttac ccaggagtat cttcaggtgc atccaaaatg 60
gtttcttagc ctatgatgca ttaggcacaa actatgtacc tatcttacac caaaactaac 120
tctgtctcca aac 133

<210> SEQ ID NO 114
<211> LENGTH: 133
<212> TYPE: DNA
<213> ORGANISM: Sorghum bicolor

<400> SEQUENCE: 114
aaccgagacc tccacttgag gcctcttcac ctaggagata ccatcggatg cgtctaagat 60
ggtttcttat cctatggtgc attatgcgta acccgtgcac atatcttgct ccaaaactaa 120
tgctgtctct aaa 133

<210> SEQ ID NO 115
<211> LENGTH: 133
<212> TYPE: DNA
<213> ORGANISM: Sorghum bicolor

<400> SEQUENCE: 115
caaactgagc ttccacttga gcccctttac ccagtagtat catcgggtgc atccaaaatg 60
gtttcttagc ctatgatgca ttatgcgaaa attgtgtacc tatattgcac caaaactaac 120
tctgtctcca aac 133

<210> SEQ ID NO 116
<211> LENGTH: 133
<212> TYPE: DNA

<213> ORGANISM: Sorghum bicolor

<400> SEQUENCE: 116
caaactgagc atccacttga gcccctttac ctaggagtat catcgggtgc atacaaaatg 60
gtttcttaac ctatgatgca ttagacgcaa actgtgtacc tatattgcac caaaactaac 120
tctgtctcca aac 133

<210> SEQ ID NO 117
<211> LENGTH: 133
<212> TYPE: DNA
<213> ORGANISM: Sorghum bicolor

<400> SEQUENCE: 117
caaactgagc ttccacttga gcccctttac cttggagtat catcgggtgc atccaaaatg 60
gtttcttagc ctatgatgca ttaggcacaa actgtgtacc tatcttgaac caaaactaac 120
tctgtctcca aac 133

<210> SEQ ID NO 118
<211> LENGTH: 133
<212> TYPE: DNA
<213> ORGANISM: Sorghum bicolor

<400> SEQUENCE: 118
aaactgagct tccacttgag cccctttacc caggagtatc ttcaggtgca tccaaaattg 60
tttcttagcc tatgatgcat taggcgcaaa ctgtgtacct atctttcacc aaaactaaca 120
ctgtctccaa aca 133

<210> SEQ ID NO 119
<211> LENGTH: 133
<212> TYPE: DNA
<213> ORGANISM: Sorghum bicolor

<400> SEQUENCE: 119
caaactgagc ttccacttga gcccctttac ctagaagtat catcgggtgc atccaaaagg 60
gtttcttagc ctatgatgta ctaggcgtaa actgtgtacc tatcttgcac caaaactaac 120
tctgtctcca aac 133

<210> SEQ ID NO 120
<211> LENGTH: 133
<212> TYPE: DNA
<213> ORGANISM: Sorghum bicolor

<400> SEQUENCE: 120
caaactgagc taccacttga gcccctttac ctaggagtat catcaggttc atccaaaatt 60
gtttcttagc ctatgatgcg ttaggcgtaa actgtttacc tatcttgcac caaaactaac 120
tctgtctcca aac 133

<210> SEQ ID NO 121
<211> LENGTH: 133
<212> TYPE: DNA
<213> ORGANISM: Sorghum bicolor

<400> SEQUENCE: 121
caaactgagc ttccatttga gcccctttgc ctaggagtat catcgggtgc atccaaaatg 60
gttccttagc ctatgatgca ttaggtgcaa actgtgtacc tatcttgcac caaaactaac 120
tttgtctcca aac 133

<210> SEQ ID NO 122
<211> LENGTH: 133
<212> TYPE: DNA
<213> ORGANISM: Sorghum bicolor

<400> SEQUENCE: 122
caaactgagc ttccacctga gccactttaa ccaggagtat catcgggtgc atccaaaatg 60
ttttcttagc ctatgatgct ttaggcgcaa attgtgtacc tatcttgcac caaaactaac 120
tctgcctcca aac 133

<210> SEQ ID NO 123
<211> LENGTH: 133
<212> TYPE: DNA
<213> ORGANISM: Sorghum bicolor

<400> SEQUENCE: 123
caaactgagc ttccacttga gcatctttac ccaggagtat catcaggtgc atccaaaata 60
gtttcttagc ctatgatgca ttaggcacaa actgtgtacc tatcttgcaa caaaactaac 120
tctgtctcca tac 133

<210> SEQ ID NO 124
<211> LENGTH: 133
<212> TYPE: DNA
<213> ORGANISM: Sorghum bicolor

<400> SEQUENCE: 124
caaactgagc ttccacttga gcccctttac ctaggggtaa catcgggtgc atccaaaatg 60
gtttcttagc ctatgatgca ttaggcacaa actgtgtacc tatcttgcac caaaactaac 120
tctgtctcca aac 133

<210> SEQ ID NO 125
<211> LENGTH: 133
<212> TYPE: DNA
<213> ORGANISM: Sorghum bicolor

<400> SEQUENCE: 125
caaactgagc ttccacctga gcccctttac ctaggagtat catcgtgtgc atctaaaatg 60
gtttcttagc ctatgatgca ttaggcgcaa actgtgtacc tatcttgcac caaaactaac 120
tctgtctcca aac 133

<210> SEQ ID NO 126
<211> LENGTH: 133
<212> TYPE: DNA
<213> ORGANISM: Sorghum bicolor

<400> SEQUENCE: 126
caaactgagc ttccacttga gcccctttac ctaggagtat catcgtgtgc atcaaaaatg 60
gtttcttagc ctatgaagca ttaggcgcaa actgtgtacc tatcttgcac caaaactaac 120
tctgtctcca aac 133

<210> SEQ ID NO 127
<211> LENGTH: 133
<212> TYPE: DNA
<213> ORGANISM: Sorghum bicolor

<400> SEQUENCE: 127

```
caaactgagc ttccacatga gcccctttac ctaggagtat catcgggtgc atccaaaatg     60

gtttcttagc ctatgatgca ttaggcacaa actgtgtacc tatcttgcac caaaactaac    120

tctgtatcca aac                                                       133
```

<210> SEQ ID NO 128
<211> LENGTH: 133
<212> TYPE: DNA
<213> ORGANISM: Sorghum bicolor

<400> SEQUENCE: 128

```
caaactgagc ttccacttga gcccctttac ccaggagtat catcgagtgc atctaaaaag     60

gtttcttagc ctatgatgca ttaggcgcaa actgtgtacc tatcttgcac caaagctacc    120

tctgtctcca aac                                                       133
```

<210> SEQ ID NO 129
<211> LENGTH: 133
<212> TYPE: DNA
<213> ORGANISM: Sorghum bicolor

<400> SEQUENCE: 129

```
caaactgagc ttccacttga gcccctttac ccaggagtat caacagatgc atccaaaata     60

gtttcttagc ctttcatgca ttaggtgcaa actgtgtagc tatcttgcac caatactaac    120

tctgtctcca aac                                                       133
```

<210> SEQ ID NO 130
<211> LENGTH: 133
<212> TYPE: DNA
<213> ORGANISM: Sorghum bicolor

<400> SEQUENCE: 130

```
aaactgagct tccacttgag cccctttacc ctggaatatc atcgggtgca tcccaaatgg     60

tttcttagcc tatgatgcat taggcgcaaa gtgtgtacct atcttgcacc aaaactaact    120

ttgtctccaa aca                                                       133
```

<210> SEQ ID NO 131
<211> LENGTH: 133
<212> TYPE: DNA
<213> ORGANISM: Sorghum bicolor

<400> SEQUENCE: 131

```
aaactgagct tcaacttgag cccctttacc taggagtatc atcgggtgca tccaaaatgg     60

tttcttagcc tatgatgcat taggcgcaaa ctgtgtacct gtcttgcacc aaaactaacc    120

ctgtctccaa aca                                                       133
```

<210> SEQ ID NO 132
<211> LENGTH: 133
<212> TYPE: DNA
<213> ORGANISM: Sorghum bicolor

<400> SEQUENCE: 132

```
caaactgagc ttccacttga gcccctttac ccaggagtat caacagatgc ttccaaaata     60

gtttcttagc ctttgatgca ttaggtgcaa actgtgtagc tatcttgcac caatactaac    120

tctgtctcca aac                                                       133
```

<210> SEQ ID NO 133
<211> LENGTH: 133

<212> TYPE: DNA
<213> ORGANISM: Sorghum bicolor

<400> SEQUENCE: 133
caaactgagc ttccacttga gcccctttac ccaggagtat caacagatgc atccaaaata 60
gtttcttagt ctttgatgca ttaggtgcaa actgtgtagc tatcttgccc caatactaac 120
tctgtctcca aac 133

<210> SEQ ID NO 134
<211> LENGTH: 133
<212> TYPE: DNA
<213> ORGANISM: Sorghum bicolor

<400> SEQUENCE: 134
aaactgagct tccacgtgag ccccttttacc caggagtata atcgggtgca tccaaaatgg 60
tttcttagcc tatgatgcat taggcgcaaa ctgtgtacct atcttgcacc aaagctatct 120
ctgtctccaa aca 133

<210> SEQ ID NO 135
<211> LENGTH: 133
<212> TYPE: DNA
<213> ORGANISM: Sorghum bicolor

<400> SEQUENCE: 135
caaactgagc ttccacttga gcccctttac ctaggagtat catcgggtgc attcaaaatg 60
gtttcatagc ctatgatgca ttaggcgcaa actatgtacc tatcttgcac caaaactacc 120
tccgtctcca aac 133

<210> SEQ ID NO 136
<211> LENGTH: 133
<212> TYPE: DNA
<213> ORGANISM: Sorghum bicolor

<400> SEQUENCE: 136
caaactgagc ttccacttga gcccctttac ctaggagtat catcgggtgt atccaaaatg 60
gtttcttagc ctatgatgca ttaggcatag actgtgtacc tatattgcac caaaactaac 120
tccgtctcca aac 133

<210> SEQ ID NO 137
<211> LENGTH: 133
<212> TYPE: DNA
<213> ORGANISM: Sorghum bicolor

<400> SEQUENCE: 137
caaactgagc ttccacttga gcccctttac ccaggagtat catcgggtgc atccaaaatt 60
gtttcttagc ttatgatgca ttaggtgtaa actgtgtacc tatcttgcat caaaactcac 120
tctgtctcca aac 133

<210> SEQ ID NO 138
<211> LENGTH: 133
<212> TYPE: DNA
<213> ORGANISM: Sorghum bicolor

<400> SEQUENCE: 138
caaactgagc ttccacttga gcccctttac ccaggagtat cttcaggtgc atccaaaatt 60
gtttcttagc ctatgatgca ttaggcgcaa actgtgtacc tttcttgcac caaaactaac 120
tctgtctcca aac 133

<210> SEQ ID NO 139
<211> LENGTH: 133
<212> TYPE: DNA
<213> ORGANISM: Sorghum bicolor

<400> SEQUENCE: 139
aaactgagct tccacttgag cccctttacc caagagtacc atcgggtgca tccaaaatgg 60
tttcttagcc aatgatgcat taggcgcaaa ttgtgtacct atcttgtacc aaaactaact 120
ttgtctccaa aca 133

<210> SEQ ID NO 140
<211> LENGTH: 133
<212> TYPE: DNA
<213> ORGANISM: Sorghum bicolor

<400> SEQUENCE: 140
caaactgagc ttccacttga gcccctttac ctagcagtat aatcgggtgc atccaaaatg 60
gtttcttagc ctatgatgca ttaggcacaa actatgtact tatcttgcac caaaactaac 120
tctgtctcca aac 133

<210> SEQ ID NO 141
<211> LENGTH: 133
<212> TYPE: DNA
<213> ORGANISM: Sorghum bicolor

<400> SEQUENCE: 141
aaactgagct tccacttgag cccctttacc gaggagtatc atcgggtgca ttcaaaatgg 60
tttcttagcc tatgatgcat taggcgcaaa ctgtgtacct atcttgcaca aaaactagct 120
ctgtctccaa aca 133

<210> SEQ ID NO 142
<211> LENGTH: 133
<212> TYPE: DNA
<213> ORGANISM: Sorghum bicolor

<400> SEQUENCE: 142
caaactgagc ttccacttga gcccctttac ccaggagtat catcaggttc atccaaaatt 60
gtttcttagc ctttgatgca ttaggcgtaa actgtgtacc tatcttgcac caaaactaac 120
tctgtctcca aac 133

<210> SEQ ID NO 143
<211> LENGTH: 133
<212> TYPE: DNA
<213> ORGANISM: Sorghum bicolor

<400> SEQUENCE: 143
aaactgagtt tccacatgag cacctttacc caggagtatc atcaggtgca tccaaaatgg 60
tttcttagcc tatgatgcat taggcgcaaa ctgtgtacct atcttgcacc aaaactaact 120
ctgtctccaa aca 133

<210> SEQ ID NO 144
<211> LENGTH: 133
<212> TYPE: DNA
<213> ORGANISM: Sorghum bicolor

<400> SEQUENCE: 144

```
aaactgagct tccacttgag cccctttct caggagtatc attgggttca tccaaaatgg     60

tttcttagcc tatgatgcat taggcgcaaa ctgtgtacct atcttgtacc aaaactaact    120

ctgtctccaa aca                                                       133


<210> SEQ ID NO 145
<211> LENGTH: 133
<212> TYPE: DNA
<213> ORGANISM: Sorghum bicolor

<400> SEQUENCE: 145

caaactgagc ttccacttga gcccctttac ccaggagtat catcgggtgc atccaaaatg     60

gtttctttgc ctatgatgca ttaggcggaa actgtgtacc tgttttgcac caaaactaac    120

tctatctcca aac                                                       133


<210> SEQ ID NO 146
<211> LENGTH: 133
<212> TYPE: DNA
<213> ORGANISM: Sorghum bicolor

<400> SEQUENCE: 146

aaactgtgct tccacttgag cccctttacc taggagtatc atcagggtgc atccacaatg     60

gtttcttagc ctatgatgca ttaggcgcaa actgtgtacc tatcttgcac caaaactaac    120

tctgtctcca aac                                                       133


<210> SEQ ID NO 147
<211> LENGTH: 133
<212> TYPE: DNA
<213> ORGANISM: Sorghum bicolor

<400> SEQUENCE: 147

caaactgagc ttccacttgg gcccctttac ccaggagtat cttcaggtgc atccaaaatt     60

gtttcttagc ctatgatgca ttaggcgcaa actgtgtacc tatcttgcac caaaactaac    120

tctgtctcca aac                                                       133


<210> SEQ ID NO 148
<211> LENGTH: 133
<212> TYPE: DNA
<213> ORGANISM: Sorghum bicolor

<400> SEQUENCE: 148

aaactgagct tccgcttgtg cccctttacc caagagtatc gacgggtgca tccaaaatgg     60

tttcttagcc tacgatgcat taggcgcaaa cagtgtagct atcttgcacc aaaactaact    120

ttgtctccaa aca                                                       133


<210> SEQ ID NO 149
<211> LENGTH: 133
<212> TYPE: DNA
<213> ORGANISM: Sorghum bicolor

<400> SEQUENCE: 149

caaactgagc ttccacttga gcccctttac ctaggagtat catcaggtgc atccaaaatg     60

gtttcttagc ctatgatgca ttaggagaaa actgtgtacc tatcttgcac caaaactaac    120

tctgtctcca aac                                                       133


<210> SEQ ID NO 150
```

<211> LENGTH: 133
<212> TYPE: DNA
<213> ORGANISM: Sorghum bicolor

<400> SEQUENCE: 150
caaactgagc ttccacttga gccccttttac ctaggagtat catcgtgtgc atccaaaatg 60
gtttcttagc ctatgatgca ttaggcacaa actgtgtacc tatcttgcac caaaagtaac 120
tctgtctcca aac 133

<210> SEQ ID NO 151
<211> LENGTH: 133
<212> TYPE: DNA
<213> ORGANISM: Sorghum bicolor

<400> SEQUENCE: 151
caaactgagc ttccacttga gccccttttac caaggagtat catcgggtgc atccaaaatg 60
gtttcttagc ctctggtgca ttaggcacaa gctaggtacc tatcttgcac caaaactaac 120
tctgtctcca aac 133

<210> SEQ ID NO 152
<211> LENGTH: 133
<212> TYPE: DNA
<213> ORGANISM: Sorghum bicolor

<400> SEQUENCE: 152
aaactgagct tccacttgag cccctttact caggagtatc atcgtgtgcc tccaaaatgg 60
tttcttagcc tatgatgcat taggcgcata ctgtgtacct atcttgcacc aaaactacct 120
ctatctccaa aca 133

<210> SEQ ID NO 153
<211> LENGTH: 133
<212> TYPE: DNA
<213> ORGANISM: Sorghum bicolor

<400> SEQUENCE: 153
aaactgagct tccacttgag cccctttaca cacgagtatc atcgggtgca tccaaaatgg 60
tttcttagcc tatgatgcat taggcgcaaa ctgtgtacct atcttgtacc aaaactaact 120
ctggctctaa aca 133

<210> SEQ ID NO 154
<211> LENGTH: 133
<212> TYPE: DNA
<213> ORGANISM: Sorghum bicolor

<400> SEQUENCE: 154
caaactgagc ttccacttga gtccctttac ccaggagtat catagggtgc atccaaaatg 60
ttttcttagc ctatgatgca ttaggcgtaa actgtgtacc tatcttgcac caaaactaac 120
tctgtctcca aac 133

<210> SEQ ID NO 155
<211> LENGTH: 133
<212> TYPE: DNA
<213> ORGANISM: Sorghum bicolor

<400> SEQUENCE: 155
caaactgagc ttccacttga gccccttttac ctaggagtat catcgggtgc atccaagatg 60
gtttcttagc ctatgatgca ttagacgcaa actgtgtacc tatcttgcac caaaactaac 120
tttgtctcca aac 133

<210> SEQ ID NO 156
<211> LENGTH: 133
<212> TYPE: DNA
<213> ORGANISM: Sorghum bicolor

<400> SEQUENCE: 156
aaactgagct tccacttgag ccccttaca caggagtatc atcgggtgca tccaaaatgg 60
tttcttagca tatgatgcat tagtcgcaaa ctgtgtacct atcttgtacc aaaactaact 120
ctgtctccaa aca 133

<210> SEQ ID NO 157
<211> LENGTH: 133
<212> TYPE: DNA
<213> ORGANISM: Sorghum bicolor

<400> SEQUENCE: 157
caaacggagc ttccgcttga gcccctttac ctaagagtat catcgggtgc atccaaaatg 60
gtttgtcagc ctatgatgca ttaggtgcaa actgtgtacc tatcttgccc caaaactaac 120
tctgtctcca aac 133

<210> SEQ ID NO 158
<211> LENGTH: 133
<212> TYPE: DNA
<213> ORGANISM: Sorghum bicolor

<400> SEQUENCE: 158
caaactgagc ttccacttga gcccctttac ctaggagtat catcgggtgc atccaaaaag 60
gtttcttagc ctatgatgct ctaggagaaa actgtgtacc tatcttgcac caaaactaac 120
tctgtctcta aac 133

<210> SEQ ID NO 159
<211> LENGTH: 133
<212> TYPE: DNA
<213> ORGANISM: Sorghum bicolor

<400> SEQUENCE: 159
caaactgagc ttccacttga gcccctttac ccaggagtat catcgggtgc atctaaagtg 60
gtttcttagc ctacgatgca gtaggcgcaa actgtgtaca tatcttgcac caaaactaac 120
tctgtctcca aac 133

<210> SEQ ID NO 160
<211> LENGTH: 133
<212> TYPE: DNA
<213> ORGANISM: Sorghum bicolor

<400> SEQUENCE: 160
tgaaacggag ctttcacttg agccccttga cctaggagta ccatcgggtg catccaaaat 60
ggtttcttat cctatggtgc attaggtgta aaccgtgcac ctatcttgca ccgaaactaa 120
cgttgtctct aaa 133

<210> SEQ ID NO 161
<211> LENGTH: 133
<212> TYPE: DNA
<213> ORGANISM: Sorghum bicolor

<400> SEQUENCE: 161
caaactgagc ttccacttga gccccttac ccgggagtat catcgggtgc atccaaaatg 60
gtttcttatc caatgatgcg ttaggcgcaa actatgtacc tatcttgcac caaaactaac 120
tctgtctcca aac 133

<210> SEQ ID NO 162
<211> LENGTH: 133
<212> TYPE: DNA
<213> ORGANISM: Sorghum bicolor

<400> SEQUENCE: 162
caaactgagc ttccagttga gcctctttac ccaggagtat catcgggtgg atccaaaatg 60
gtttgttagc ctatgatgca ttaggagcaa actatgtacc tatcttgcac caaaactaat 120
tctgtctcca aac 133

<210> SEQ ID NO 163
<211> LENGTH: 133
<212> TYPE: DNA
<213> ORGANISM: Sorghum bicolor

<400> SEQUENCE: 163
caaactgagc ttccacttga gccccttac ccaggaggat cttcgggtgc atccaaaatg 60
gtttcttagc ctatgatgca ttaggcgcaa actgtgtacc tttcatgcac caaaactaac 120
tctgtctcca aac 133

<210> SEQ ID NO 164
<211> LENGTH: 133
<212> TYPE: DNA
<213> ORGANISM: Sorghum bicolor

<400> SEQUENCE: 164
caaaccgagc tttcacttta gccccttgac ctaggagtac catcgggtgc gttcaaaacg 60
gtttcttatc ctatggtgca ttaggtgcaa accgtgcacc tatcttgcac tgaaactaac 120
actgtctcta aac 133

<210> SEQ ID NO 165
<211> LENGTH: 133
<212> TYPE: DNA
<213> ORGANISM: Sorghum bicolor

<400> SEQUENCE: 165
aaactgagct tcgacttgag cccctttacc caggagtatc atcgggtgca tccaaaaggg 60
tttcttagcc tatgatgcat taggcgcaaa ctgtgtacgt atcttgcacc aaaactacct 120
ctgtctctaa aca 133

<210> SEQ ID NO 166
<211> LENGTH: 133
<212> TYPE: DNA
<213> ORGANISM: Sorghum bicolor

<400> SEQUENCE: 166
aaactgagct tccacttgag cccctttacc caggagtatc atcgggtgca tccaaaagag 60
tttcttagcc tatgatgcat taggcgcaaa ctgtgtacgt atcttgcacc aaaactacct 120
ctgtctccaa aca 133

<210> SEQ ID NO 167
<211> LENGTH: 133
<212> TYPE: DNA
<213> ORGANISM: Sorghum bicolor

<400> SEQUENCE: 167
caaactgagc ttccacttca gcccctttaa tcaggaatat catcgggtgc atccaaagta 60
gtttcttagc ctatgatgca ttaggcgcaa actgtgtacc tatcttgcac caaaactaac 120
tctgtctcca aac 133

<210> SEQ ID NO 168
<211> LENGTH: 133
<212> TYPE: DNA
<213> ORGANISM: Sorghum bicolor

<400> SEQUENCE: 168
caaactgagc ttccacttga gcccctttac ccaggagtat catcgggtgc atccaaaata 60
gtttcttagc ctacgatgca gtaagcgcaa actgtgtacc tatcttgcac caaaactaac 120
tcggtctcca aac 133

<210> SEQ ID NO 169
<211> LENGTH: 133
<212> TYPE: DNA
<213> ORGANISM: Sorghum bicolor

<400> SEQUENCE: 169
caaactgagc ttccacttga gcccctttac ctaggagtat gatcaggtgc atccaaaatg 60
gtttcttagc ctatgatgca ttaggcacaa actgtgtacc tatcttgcac caaaactaac 120
tctgtctcca aac 133

<210> SEQ ID NO 170
<211> LENGTH: 133
<212> TYPE: DNA
<213> ORGANISM: Sorghum bicolor

<400> SEQUENCE: 170
aaactgagct tccacttgag cacctttacc caggagtatc atcaggtgca tccaaaatgg 60
gttcttagcc tatgatgcat taggcgcaaa ctgtgtacct atcttgaacc aaaactaact 120
ctatctccaa aca 133

<210> SEQ ID NO 171
<211> LENGTH: 133
<212> TYPE: DNA
<213> ORGANISM: Sorghum bicolor

<400> SEQUENCE: 171
caaactgagc ttccacttga gcccctttac ccaggagtat cttcaggtgc atccaaaatt 60
gtttcttagc ctatgatgca ttaggcgcaa actgtgtacc tatcttgcac caaaactaac 120
tttgtctcca aac 133

<210> SEQ ID NO 172
<211> LENGTH: 133
<212> TYPE: DNA
<213> ORGANISM: Sorghum bicolor

<400> SEQUENCE: 172
caaactgagc ttccacttga gcccctttac ctaggagtat aatcgggtgc atccaaaatg 60

```
gtttcttagc ctatgatgca ttaggtgcaa actatgtacc tatcttgcac caaaactaac    120

tttgtctccg aac                                                       133


<210> SEQ ID NO 173
<211> LENGTH: 133
<212> TYPE: DNA
<213> ORGANISM: Sorghum bicolor

<400> SEQUENCE: 173

caaacagagc ttccaattga gaccctttac tcaggagtat catcgggttc atccaaaatg     60

gtttcttagc ctatgatgca ttaggcgcaa actgtgtacc tattttgcac caaaactaac    120

tctgtctcca aac                                                       133


<210> SEQ ID NO 174
<211> LENGTH: 133
<212> TYPE: DNA
<213> ORGANISM: Sorghum bicolor

<400> SEQUENCE: 174

caaactgagc ttccacttga gcccctttac ccacgagtat catcgggctc atccaaaatg     60

atttcttagc ctatgatgca ttaggcgcaa actgtgtacc tatcttgcac caaaactaac    120

tctgtctcca aac                                                       133


<210> SEQ ID NO 175
<211> LENGTH: 131
<212> TYPE: DNA
<213> ORGANISM: Sorghum bicolor

<400> SEQUENCE: 175

actgcgcttc cacttgagcc ccattaccca ggagtatcat cgggtgcatc caaaatagtt     60

tcatagccga tgatgcatta ggtgtaaact gtgtacctat cttgcaccaa aactaactct    120

gtctccaaac a                                                         131


<210> SEQ ID NO 176
<211> LENGTH: 131
<212> TYPE: DNA
<213> ORGANISM: Sorghum bicolor

<400> SEQUENCE: 176

aactgagctt gcacttgagc ccctttaccc aggagtatca tcgagtgcat ccaaaattgt     60

ttcttagcct gtgatgcatt aggcgcaaac tgtgtacctg tcttgcacca aaactaactc    120

tgtctccaaa c                                                         131


<210> SEQ ID NO 177
<211> LENGTH: 7572
<212> TYPE: DNA
<213> ORGANISM: Sorghum bicolor

<400> SEQUENCE: 177

tgatgaagac atccacacta ctgatgcatc tataccaata caagtaccaa tttctggtcc     60

cattactcgc gctcgtgctc gtcaactcaa ccatcaggtg attacactct tgagttcatg    120

tccatcatat ttagaccatg gagacccgtg cactcttgtt ttgcttagga atcagggaga    180

agaccgaaag ggaaaaggat ttgaacatgc tggattcgga ctgcagaaga acaccaactt    240

gtgacggtca ccacggtcag atgcgggctc ggattggaat gttcaagcac aacatggaaa    300

gcttatcaag tctactttca tatggatccg gaattatagt catatctgtt ctgaggccgc    360
```

```
cgtaatcatt gttttcttac cgagacattt cctgcctttt ctgcccatgg tgctgcgtca    420
ccctattttg gcccaatggg tcgtgtatca agttaggtcc attagggacg catcctaggg    480
ttgcagcacg accccaatac ccttgtggtc gtcctcccat gtttataaac cccctagccg    540
ccaccaagaa cagcgggttt tgtttagatc aagtttagct ctcgctactt gcttgcaagc    600
gcgcgtgcta gttcagccgc ccgtcttctt gtcttcggaa ccccaccata ttggagtttg    660
atctttaaac ctacatttag atctggtaat tcagtacttg ttctacttgt tcttgctagt    720
tcttcgattg cttgcaggac gagtgcccta gtggccaggg tgtcacgctc cacaagatcg    780
tgacagccat aggaggtggt gtatcggttg ctaaggcgca gcgtctttgg aaggctgtag    840
tcgggccgtg aacgtcgtct cctcccccaa tcgagttatt ccacaccctc tcatcgaaag    900
atcgggcaat cacccaacgg gtgcacatca gttggtaatc agagcaaggt ttatcggtga    960
gagatttact tttcttcgct gttttcttat ctcctatagt ccagaaaaag ccaaaaaaat   1020
agtagattag ttttaccgca atcctataaa ccattgagca tttactagta ctacttagtt   1080
agggcttgtt gagtttttgg ttgcatcggt tgtgtcgagt tgctggtctt agtttattcc   1140
tttagagttt tgagttctac cacgttttgg tcaccacgag atccaccatc accaaaaaca   1200
tctctggttc gtttttgcca ccacggatac atatcatatc cgatttggaa gtttaaatac   1260
aatctggaaa gcttatctta tcttctttcc aacggatctg accttatctc aaaattcgtt   1320
ctgagcgctc cgcaatcatc gtagagattt ctggactttc tatattaaca agatttgtta   1380
aatctgattt aaaggggttg ttagcaatat ctttattgtt tgggttgtca tagtgaaaaa   1440
aagggtttag gcccctgcaa aaaaaaacag aagaagaaga aaaaaaaaga atagaaaaga   1500
aaaaaaagga aaagaagaag aagggggctg aatctctaaa tctgttgttt ctctttgtgc   1560
tgtgctagtt gttctttttc agtgactacc tttgtgccta ggctcacgtc tctagcctgg   1620
tttagcctag gaccagcaca gtaccaccgt tgaacgatta ttcagcttgc ttttgtaact   1680
aacgtggtac tagtgtattc cttgcttcag cccacctaca actctacata tttcgactac   1740
agtttgacag gtcgtgttgc tgcggcaccg atacacttat tccacggttg cagacttgtt   1800
ggttgctgac ccctcctgtt gtgcaaggta agaattggta agagcttgtg tggcaggttg   1860
agagtgagcg ccttgcagta gctacatcct aatagttgta gagtttttat tccttcacat   1920
tttttttct tgttgcctct gttcgtctaa ccatggcagg attggaggtt gatgatgctt   1980
ctcgtaatat gccacactct cctcgcacca agggtatcat acaacacttt gtaaggctgg   2040
tgaaaacgca cacggaaggt cttgataatg acatgcaggt gacgaatgaa aagatggggc   2100
aattggaggc cacacagatc gacacaaaca ccaaacttgc aaatgtggaa atgacagttg   2160
ctcatattga caagagcctt gtcgcactct tgaggcgatt tgatgagatg catgctaata   2220
ccaatggtgg gcgtgatgag ggcgccgaag gtaactggga tgactatgtt gctgatactg   2280
aacaagatga ccaagaagca cctaatcgcc ggcgactacg tactaaccgt agaggtatgg   2340
gtggttttca ccgacgtgag gtacatggta atgatgatgc ttttagtaag gttaaattta   2400
aaatacctcc ttttgatggt aaatatgacc ctgatgctta cattacttgg gagattgcgg   2460
ttgatcaaaa gtttgcatgc catgaatttc ctgagaatgc gcgggttaga gctgctacta   2520
gtgagtttac tgaatttgct tctgtttggt ggatagaaca tggtaagaag aatcctaata   2580
acatgccaca aacttgggat gcgttgaaac gggtcatgcg ggctagattt gttccttctt   2640
attatgcacg tgatatgtta aacaagttgc aacaattgag acagggtact aaaagtgtag   2700
```

```
aagaatatta tcaggaatta caaatgggta tgctgcgttg taacatagag gagggtgagg   2760
aatctgctat ggctagattt ttgggcgggt taaataggga aattcaggac atccttgctt   2820
ataaagatta tgctaatgta acccgattgt ttcatcttgc ttgcaaagct gaaagggaag   2880
tgcagggacg acgtgctagt gcaaggtcta atgtttctgc aggaaaatct acaccatggc   2940
aacagcgcac gactacgtcc atgaccggcc gtacactagc accaactccc tcgccaagtc   3000
gaccagcacc cccgccttcc tccagcgaca aaccacgtgc atcttccaca aattcagcaa   3060
ccaaatctgc ccagaaacca gcaggtagtg cctcttcagt agcctccacg ggtagaacaa   3120
gagatgttct gtgttatcga tgcaagggct atggacacgt gcagcgtgat tgtcctaatc   3180
agcgtgtttt ggtggtaaaa gacgatggtg ggtattcctc tgctagtgat ttggatgaag   3240
ctacacttgc tttgcttgcg gctgatgatg caggcactaa ggaaccaccc gaagaacaga   3300
ttggtgcaga tgatgcagag cattatgaga gcctcattgt acagcgtgtg cttagtgcac   3360
aaatggagaa ggcagagcag aatcagcgac atacgttgtt tcaaacaaag tgtgtcatta   3420
aggagcgttc atgtcgtttg atcattgatg gaggtagctg caacaacttg gctagcagcg   3480
acatggtgga gaagcttgca cttacgacca aaccgcaccc gcatccatat cacattcaat   3540
ggctcaacaa tagtggtaag gtcaaggtaa ccaagctggt acgaattaat tttgctattg   3600
gttcatatcg tgatgttgtt gactgtgatg ttgtgcctat ggatgcttgt aatattctgc   3660
taggtagacc atggcaattt gattcagatt gtatgcatca tggtagatca aatcaatatt   3720
ctctcataca ccatgataag aaaattattt tgcttcccat gtcccctgag gctattgtgc   3780
gtgatgatgt tgctaaagct accaaagcta aaactgagaa caacaagaat attaaagttg   3840
ttggtaataa caaagatggg ataaaattga aaggacattg cttgcttgca acaaaaactg   3900
atgttaatga attatttgct tccactactg ttgcctacgc cttggtatgc aaggatgctt   3960
tgatttcaat tcaagatatg cagcattctt tgcctcctgt tattactaac attttgcagg   4020
agtattctga tgtatttcca agtgagatac cagaggggct gccacctata cgagggattg   4080
agcaccaaat tgatcttatt cctggtgcat ctttgccgaa tcgtgcgcca tataggacaa   4140
atccagagga aacaaaagaa attcagcgac aagtgcaaga actactcgac aaaggttacg   4200
tgcgtgagtc tcttagtccg tgtgctgttc cggttatttt agtgcctaaa aaagatggaa   4260
catggcgtat gtgtgttgat tgtagggcta ttaataatat cacgatacgt tatcgacacc   4320
ctattccacg tttagatgat atgcttgatg aattgagtgg tgccattgtc ttttctaaag   4380
ttgatttgcg tagtgggtac caccagattc gtatgaaatt gggagatgaa tggaaaactg   4440
ctttcaaaac taagttcgga ttgtatgagt ggttagtcat gccttttggg ttaactaatg   4500
cacctagcac tttcatgaga ttaatgaacg aggttttgcg tgccttcatt ggaaaatttg   4560
tggtagtata ctttgatgac atattaatct acagcaaatc tatggatgaa catgttgatc   4620
acatgcgtgc tgtttttaat gctttacgag atgcacgttt atttggtaac cttgagaagt   4680
gcacattttg caccgatcga gtttcgtttc ttggttatgt tgtgactcca cagggaattg   4740
aggttgatca agccaaggta gaagcgatac atggatggcc tatgccaaag actatcacac   4800
aggtgcggag tttcctagga cttgctggct tctatcgccg ttttgtgaag gactttagca   4860
ccattgctgc acctttgaat gagcttacga agaagggagt gcattttagt tggggcaaag   4920
tacaagagca cgctttcaac gtgctgaaag ataagttgac acatgcacct ctcctccaac   4980
ttcctgattt taataagact tttgagcttg aatgtgatgc tagtggaatt ggattgggtg   5040
gtgttttgtt acaagaaggc aaacctgttg catattttag tgaaaaattg agtgggtctg   5100
```

```
ttctaaatta ttctacttat gataaggaat tatatgctct tgtgcgaaca ttagaaacat   5160
ggcagcatta tttgtggccc aaagagtttg ttattcattc tgatcatgaa tctttgaaac   5220
atattcgtag tcaaggaaaa ctgaaccgta gacatgctaa gtgggttgaa tttatcgaat   5280
cgtttcctta tgttattaag cacaagaaag gaaaagagaa tatcattgct gacgctttgt   5340
ctaggagata tactttgctg aatcaacttg actacaaaat ctttggatta gagacgatta   5400
aagaccaata tgttcatgat gctgatttta aagatgtgtt gctgcattgt aaagatggga   5460
aaggatggaa caaatatatc gttagtgatg ggtttgtgtt tagagctaac aagctatgca   5520
ttccagctag ctccgttcgt ttgttgttgt tacaggaagc acatggaggt ggcttaatgg   5580
gacattttgg agcaaagaaa acggaggaca tacttgctgg tcatttcttt tggcccaaga   5640
tgagaagaga tgtggtgaga ttggttgctc gttgcacgac atgccaaaag gcgaagtcac   5700
ggttaaatcc acacggtttg tatttgcctc tacccgttcc tagtgctcct tgggaagata   5760
tttctatgga ttttgtgctg ggattgccta ggactaggaa gggacgtgat agtgtgtttg   5820
tggttgttga tagattttct aagatggcac atttcatacc atgtcataaa actgacgatg   5880
ctactcatat tgctgatttg ttctttcgtg aaattgttcg cttgcatggt gtgcccaaca   5940
caatcgtttc tgatcgtgat gctaaatttc ttagtcattt ttggaggact ttgtgggcaa   6000
aattggggac taagctttta ttttctacta catgtcatcc tcaaactgat ggtcaaactg   6060
aagttgtgaa tagaactttg tctactatgt taagggcagt tctaaagaag aatattaaga   6120
tgtgggagga ctgtttgcct catattgaat ttgcttataa tcgatcattg cattctacta   6180
caaagatgtg cccatttcag attgtatatg gtttgttacc tcgtgctcct attgatttaa   6240
tgcctttgcc atcttctgaa aaactaaatt ttgatgctac taggcgtgct gaattgatgt   6300
taaaactgca cgaaactact aaagaaaaca tagagcgtat gaatgctaga tataagtttg   6360
ctagtgataa aggtagaaag gaaataaatt ttgaacctgg agatttagtt tggttgcatt   6420
tgagaaagga aaggtttcct gaattacgaa aatctaaatt gttgcctcga gccgatggac   6480
cgtttaaagt gctagagaaa attaacgaca atgcatatag gctagatctg cctgcagact   6540
ttggggttag ccccacattt aacattgcag atttaaagcc ctacttggga gaggaagttg   6600
agcttgagtc gaggacgact caaatgcaag aaggggagaa tgatgaagac atccacacta   6660
ctgatgcatc tataccaata caagtaccaa tttctggtcc cattactcgc gctcgtgctc   6720
gtcaactcaa ccatcaggtg attacactct tgagttcatg tccatcatat ttagagccat   6780
ggagacccgt gcactcttgt tttgcttagg aatcagggag aagaccgaaa gggaaaagga   6840
tttgaacatg ctggattcgg actgcagaag aacaccaact tgtgacggtc accacggtca   6900
gatgcgggct cggattggaa tgttcaagca caacatggaa agcttatcaa gtctactttc   6960
atatggatcc ggaattatag tcatatctgt tctgaggccg ccgtaatcat tgttttctta   7020
ccgagacatt tcctgccttt tctgcccatg gtgctgcgtc accctatttt ggcccaatgg   7080
gtcgtgtatc aagttaggtc cattagggac gcatcctagg gttgcagcac gaccccaata   7140
cccttgtggt cgtcctccca tgtttataaa ccccctagcc gccaccaaga acagcgggtt   7200
ttgtttagat caagtttagc tctcgctact tgcttgtaag cgcgcgtgct agttcagccg   7260
cccgtcttct tgtcttcgga accccaccat attggagttt gattttgaaa cctacattta   7320
gatctggtaa ttcagtactt gttctacttg ttcttgctag ttcttcgatt gcttgcagga   7380
cgagtgccct agtggccagg gtgtcacgct ccacaagatc gtgacagcca taggaggtgg   7440
```

tgtatcggtt gctaaggcgc agcgtctttg gaaggctgta gtcgggccgt gaacgtcgtc 7500
tcctccccca atcgagttat tccacaccct ctcatcgaaa gatcgggcaa tcacccaacg 7560
ggtgcacatc ag 7572

<210> SEQ ID NO 178
<211> LENGTH: 1004
<212> TYPE: DNA
<213> ORGANISM: Sorghum bicolor

<400> SEQUENCE: 178
tacgtaagct tcgtttcgtc tgtttggaca tagtgctaat ctttatgcaa gatagatgca 60
cggtttacgt ggaacatatg atatgctcag aagcaattta ggacgcacct aatataactc 120
cttgatgatg tgtgtcacat ggaatcttgc ttcggtttct ttagagacag tgttagtttt 180
ggtagaagat atgtgcacag tgtacgccta atgcaccata ggctaaagaa accattttag 240
acgcacccga tggtactcgt agttgaagag gctcaactgg aggctcgatt tggtctgttc 300
ggatatagtg ctaatcttga tgcaagatag ttgcacaatt tgcaggcaac gtaccatatg 360
ttaagaaatc aatttggacg cacccaatgg aactcctaga tgacgtgtgt catatggaac 420
tcgcttcggt ctgtttggtg accatattag tttcactgca ggaaaggtgc atagtttgtg 480
cctaatgcac catagtctaa gaaaaccatt tttgatgcac ctgtttgtac ttctatgaag 540
aggctcaagt ggaagctcgg ttcggtctgt ttggagatag tgctaatctt gatgcaagat 600
aggtgtacgg tttgtatgga acataccata tgcttggaaa tcaatttgga tgcacccgtt 660
ggaactcctt gagaagtgtg tcttatgtac cctcgctttg gtctgtttag aaatagtgtt 720
agtttcagtg caagatatga gcatggtttg cgcctaacgc accatagtct aagaaaccat 780
tttggaagca cctgttggta cttcggtgaa gaagctcaag tggaagctcg gtttgacctg 840
tttggagata gtgctaatct tgatgcaaga tagtgcatga tttgcaagga acataccata 900
tgcttagaaa tcaacttgga cgcacgcccc gcaactccta catcacgtgt gtcatatgga 960
atcttacttc ggtccatttg taacattgta agttttagtg caag 1004

<210> SEQ ID NO 179
<211> LENGTH: 22
<212> TYPE: DNA
<213> ORGANISM: Artificial sequence
<220> FEATURE:
<223> OTHER INFORMATION: synthesized oligonucleotide

<400> SEQUENCE: 179
gggaagtaca gggacgaaga gc 22

<210> SEQ ID NO 180
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 180
tgcaaccaaa ccaaatcacc ag 22

<210> SEQ ID NO 181
<211> LENGTH: 25
<212> TYPE: DNA
<213> ORGANISM: Artificial sequence
<220> FEATURE:
<223> OTHER INFORMATION: synthetic oligonucleotdie

<400> SEQUENCE: 181
gtcacccagc agttccatcg ggtgc 25

<210> SEQ ID NO 182
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 182
actgctgggt gacgtggctc aagt 24

<210> SEQ ID NO 183
<211> LENGTH: 2408
<212> TYPE: DNA
<213> ORGANISM: Sorghum bicolor

<400> SEQUENCE: 183
cggcactcag ttcacgggca aaagttcttg gacttctgcg atcagcatca catccgtgtg 60
aactggtctg cagtggccca ccctcgaact aacggccagg tcgagcgtgc caatggcatg 120
attttgcaag ggctcaaacc aaggatttac aatcgcttga agaaatttgg caagaaatgg 180
gtcgaggaac tttcctcggt cctatggagc ctaaggacga cgccaagcag ggccacattc 240
atggtctacg gctctgaggc tgttctccca acagacctcg agtatgggtc ccctcgactc 300
aaagcataca acgaacaatc aaataaagag tctcaagaaa acgtggttga ccaactcgaa 360
gaagctcgag acatggccct catcaactct gctagatacc agcagaaact tcgacgctac 420
cacgacaagc acgtgcgcaa gagggacttg aacgtaggtg acctcgtcct acgacgacgg 480
caaaataatc aaggacgcca caagttgact ccaccttggg agggcccgta cgtggtagcc 540
gaggtcttga agccagggac atacaagctc acggacgaaa agtgggcgat cttcaccaac 600
gcgtggaaca ttgaacagct acgttgattc taccccaaga atttcaaagc tttatgttcc 660
tgcgtacatt ctgtaaatga ataaatgaat aaataaagtc tttttctcga gcgacttacc 720
ttttcacagg tctcaacgtt agaagggagt atcgactatg acccatcata gtcgacaccc 780
cctcgggggc tagcaaggga ggtgaccccc ccaagtgtcg aaaaaaacca agtaatcctt 840
tcgttcctat cggcaatctc atgcagtcga gtagtaaagg tacctcgagc cccttaagga 900
ccgagaaacg acgagcctga gaactcctac gcccccgggc tatggaaact ctactcgtct 960
cctcaccctt gaggtaatcg agaccgcctc gaacaaaaga ccaagtgaga aaaacaaaca 1020
taggcgcaaa aaggaataaa ggagcttcga gaggaaagac agacaaacat ttaacaaacc 1080
acttaaagac attgtattac ttaaagacaa gttaacagag tactatacaa ggggccccag 1140
gcacccagag caggctcgca ggccttagtc cacagcatgg tcctcaccac cctcgcctgc 1200
gcctgagcta gtctcagggg gaagcacctc gggctcaaat agcttggcca gcctctctcc 1260
aggaacctcc gtgtcgtcga tcaaagcgtg aagcctctcc tcgttctccg tgtcagtctt 1320
ggagatatcg gtaacaaagc catgagatac cacctccata tcgtaggaaa agcccgagca 1380
cacaaccgcc attgcccgct ttaccccgat atggagagcg tcacgcaccc gatccctcag 1440
cgtcgcgcct aagtagcaca actgatcgac cagcgcgtcg cctcgagctt cctccttcga 1500
ctcgtccata ggctcgactt cccaagaggt cgagagatcg cttatcaccg tccgcagtca 1560
acggttcaaa gcaacctccc gctcgagctg ggcctgggcg ttgcgagcct cgacttgggc 1620

```
ggccaagagc tcgtctttaa gccctgtgaa tgccaacaaa aataaaagct ttagataaaa   1680

ccaagcacat ctcgaaaaga aaacccgaca atagaaacgt actgcggaca ctctcctcca   1740

gagctgtgtt ctcgccaact aatttagtgt tggccctctc gatctccctg ttagagcgtg   1800

ccagctcagt gttggcaaca cgcagatctt cgattgcctt gccagcctga gcaatggctc   1860

cactcttctc cagcagctct cccttcagac gatcgatgtc gtcggagagg ctgcgggatc   1920

gagtccgctc cgcctcgagg tcctcgaggg ccttcttctt ggcttcctcc gtggcgcccc   1980

tagcgatctc gccatacaca tgctccacct tcatcctctg aaaggattct cgaagggagt   2040

ccaagtcagt cttgaggagg cccttctcct tgtccagatc agcaacgacg ttcatgtagg   2100

acaggacctc ctcccgggca ttggacgcag cctcctcaac cgtcagagcc cgctccctca   2160

gcagcacggc ctcttccata gccttcttcg aggcctctcg agcctcggcc agggcagcct   2220

ccctctcctt cttctcctcc tcgagcgcta agagatcttt ataggcttgg aggagtttct   2280

cctgcgactc caggagttgg tctttgacga ggggaagcta ctcccagcca cccctcgtgg   2340

cgtgaatgaa gcttgactta atgcgggagg tctctttcaa gtcctgtgaa ccgatgatcg   2400

agcagtta                                                            2408
```

<210> SEQ ID NO 184
<211> LENGTH: 2013
<212> TYPE: DNA
<213> ORGANISM: Sorghum bicolor

<400> SEQUENCE: 184

```
gaggagccat cttgagggtt cgatgtgcat gtacatctca tgagcattga tcttccccaa     60

tatggtggtt ggtgtagcgg tggaaagatc gccttgatgg agcacggtta ctatgtgccc    120

atatttctca atgggaagca cacatagtat cttccttgct acatccgccg tactcatttg    180

tgtaagccca agtccattta gctcctctac aatgacattg aagcgagaat acatttcatt    240

agcattttct ttaggaagca tttcaaatgt attaagcttg ttcatcacta ggtgatagcg    300

ttcctcgcgt tcactcttag ttccctcatg gagcgcacaa agttccttcc aaagttcatt    360

ggcggttttg tggctccgaa cacggttgaa cacctctttg caaagacctc taaagatgtg    420

gtttttggcc tttgcattcc acttctcgtt ttcttgctct tgtggagtaa gagcggtggc    480

tcttttcgga gggacaaacc cttcggtcgt ggcttttagg cactttacat cgcatgcctc    540

aaggtatgac tccatccgta ttttccaata cgggaagtca ttcccatcga acatgggtgg    600

cggtccatcc ccgttagaca tctttctcta ggcggtgaag cctaaataat gagcactagg    660

ctctgatacc aattgaaagg atcaagatgc ccaagagggg gggtgaattg ggcttctcta    720

aaaatttaag caacctataa gctccaattc aaccccttgt gcctagtgtg acttagagag    780

ctaccggata aaagttttgc aacctagttc caatcctatt ctagcatggc aaatctaaga    840

atgtaaaagc acaaagtaaa tgctagaaag taaaggagta gtggaagaaa gtgctcggcg    900

atgttttgcc gaggtatcgg agagtcgcca ctctccacta gtcctcgttg gagcacccgc    960

acaagggtct tgctccccct tggtccgcgc aaggaccaag tgctctctac gggctgattc   1020

ttcgacactc cgtcgcggtg aatcgcccaa aaccgctcac aagcttgaca cgtgccaccc   1080

acaagaactc cgggtgatct tcgtgcctcc aatcaccacc gaaccgtcta ggtgatggcg   1140

atcaccaaga gtaacaagca aagaactctc acttgaccca aacaaggcac tagaaagtgg   1200

tggatgcaca cttgactctt ggaactcact agaggaggat tctctcaaga attcactcaa   1260

aaactcaatc ctctctaggc ttttgcaact ctcttgctcc acaacaagtt tctctgaagt   1320
```

```
tcaaatgggc aagagaggtc tcatggacga ggtggaggag tataaatact atccacgaag   1380

tccaaaggtc ggccaaccgt tttccactga aaacggggtc accggacgca cattatgttg   1440

caccggacgc tctgcaccga gcgtccggtg tgacataacg gctacctgcg tttttctctg   1500

acaggtcacc ggacgctaac tcccagcgtc cggtgcaccg tccggtgctt ggggaaactt   1560

tacatgctcc ctgcgcatgg gaccggacgc tacccggtgc gtccggtgct taggggaact   1620

ttgcaagctc cctgggtaag ggaccggacg ctaccaggtg cgtccggtgc ccctttgggc   1680

acccaaactt cgtcgaaacg cgatcgctcc aaaacgaagt ttgatcctct cgatctaagg   1740

actatctcta agctgcctag agctaggttt accaagtgtg caccacacct aaacctaaag   1800

ccttgcctaa gtcaagctac tagatcaaag cccctcttaa tagtacggtc aaaggaaaaa   1860

aaagtcctac caagtgccct tcttcaccat atggcactta gacctagtct agccttgacg   1920

atgtccatcc atcctttgaa aaccgaaacg atttctacca ttaagtaggc atgtacgtcc   1980

ctgtccatcg agaacctatt taccatgacc tta                                2013
```

<210> SEQ ID NO 185
<211> LENGTH: 1546
<212> TYPE: DNA
<213> ORGANISM: Sorghum bicolor

<400> SEQUENCE: 185

```
catcctctga cgcctcgtta ccaccagacg tgtcgctgat ggtgattggg tccgcctcga     60

cccccggttg aggaggctcg ggagctcctt cttgcccctg agtctggggt gcctcgtcac    120

gcgtctacgg catcagggta ggctcgggac gaggctgagc actctcgtcg tctaccggag    180

gtcgagagtc ggaggaagct gcaaaacaaa gaatagaggc cggtcactat aatgcccaac    240

ataagaacgt cacaagtccc aaaagtaagc cacaaaccta gctccttgga ggctgccccc    300

gctttgagcc tcttcgccat tgaaggctga gcttgttcaa gcgtccgctt taatctgaaa    360

caaaaagaac cagcgtaaaa agactggtaa acaaggaggc gcaggacaaa agccacaaca    420

tcgaagagct tacccgacgg ggaggacagc tcgcctgcca gtgccccgac cggcgggtct    480

cgacccaccc cgtgtcaaga tcctgggctc ctcgagggca ggcactggcc ttggctcggc    540

accttccgcc aggcgggccc cgggactgat gcttctgcga ccagtctcgc ccttctcgga    600

ggccgcggtg cgaccgcggg tcagcggccc cgtcgcctgg ggcttagcat ggctatccgc    660

ctacggcacc aggggagggc gcggggcggt ctggcctatc gcgggcacgg gaggagtatc    720

ggcacggggg cggtgagatc cgcttggacc ttccctcggc gttcccgtct gtggggcgtc    780

gacgtcacct cgaggcggac cctcgaggat ccggtcgagg cgagaggcca tcccctcaga    840

gtcatcgctg tcttcatccc caccatcatc gtcgctgggg gactcttcct caggctcccc    900

cctctgcctg gatttagccc gacgcgcctc caacgcttgg cggtcgaggt tcttcttttt    960

ctcccctttc ttcgcagagt ccttggcgga cttctgcttc tcggcggacc ggcgtcgcgc   1020

gtcgcgatca acctcgtcct cctttgctgg aggcctcgag gatcggacgt cgatccgtcc   1080

ctgccagaac aaaggtggac ttagaaaaaa gaaaagaaac cctgaatcaa agctgcgcac   1140

gaacagaaag cataccagat cgatcgagcc cgcatccggc ctcatgggga aaccgttaac   1200

gtgctccggc ttgaagtcgc cagcaatggc agccctgacc cgggccgcta cttcgtcgtt   1260

caccggagcc tcgctcgaca tccggcatgc ctcgaggtcc cgggacgaga cacctgggcc   1320

catctcgtcc atcctcagcg ggcgagacat caaggggaga acccttcgat gatggacggc   1380
```

```
tgagagaacg agagcggcgg tcaaaccctc cgagcgtagc ttcttcatga cgtcgaggag   1440

ggggtcgagc cgagatggtg agcaacgacg acgccgtacg tccaattttc cggacgctcc   1500

gtgatcagac gtccggtgta ggcgggcagg aggtcgtcgt cgtttc                   1546
```

<210> SEQ ID NO 186
<211> LENGTH: 1161
<212> TYPE: DNA
<213> ORGANISM: Sorghum bicolor

<400> SEQUENCE: 186

```
ctcactaaag gaagacgatc agatcaaaac atcttttatc actcctttcg gcgcgtattg     60

ctacacgacc atgtccttcg gactcaaaat gctggagcta cttatcaacg ggctattcat    120

taatgcctcc acgacgagat tcgtgacgac ctcgtcgagg cttatgtaga cgacgttgtt    180

gtcaaaacaa gggacgcgag caccctaatc gacaacctag accgaacctt taaggcgcta    240

aataaataca agtggaaact aaaccccaaa aaatgtatct ttggggtccc ctctggacta    300

ctactcgaca acgttgtcag ccgcgatggc atacgaccga atccttcaaa agtaaaggta    360

gtgctcgacg tgcgaccacc caagaatgtc aaggatattc aaaagctcac cggttgtatg    420

gctgctctca gccgttttat ctctagactg ggagaaaaag gcctcccctt cttcaaactt    480

ataaaggcat cggaaaaatt ctcctggaca gaggaagctg acgttgcgtt tacccagctc    540

aaaactttcc tcacctcacc acccgtcctc acggcgcctc aacctaacga gaacctgctc    600

ctttacataa cagcaaccga tcgggtcgtc tccacggcaa tggtggtcga gcgggacgag    660

ccaggtcatg tctacaaagt ctagaggcct gtttatttca taagtgaagt cttaaacgaa    720

tctaagacca ggtacaaaag ttaatctacg ctatcctgat aacctcaaga aagctgaagc    780

attacttcga cggtcattgg gtcttggtaa ccaccagttt ccctctaggg gacattttgc    840

gcaacaagga cgctaatggc agaattgtaa aatgggcaat ggaattgtgc ccattctccc    900

tagatttcca gagccgcact accatcaagt cccaggccct ggtcgatttc atcgtagaat    960

ggacggacct caacgagccc ccccccctcc ggacacttcc gaccactggt caatgttctt   1020

cgacgggtcc ctaaacatca atggcgccgg tgctagaata ctcttcgtat cgcctaacaa   1080

ggacaaactt cgctatgtcc ttagaatcct cttttcggca tctaacaacg tcgccgagta   1140

cgaagcatgc ctacatggta t                                              1161
```

<210> SEQ ID NO 187
<211> LENGTH: 474
<212> TYPE: DNA
<213> ORGANISM: Sorghum bicolor

<400> SEQUENCE: 187

```
ttgagcctct tcaccaagga gtaccatcgt gtgcgtccaa aatagtttat tagcctatag     60

tgcattaggc acaaaccgtg tacctatctt gcatcgaaac taacactatc tccaaagaga    120

tcgaagtgag attctatatg acacacgtca tctaggagtt ctattgggtg catccaaata    180

tatttcgaag catatggtat gttccatgaa attcatgcac ctatctttgt gggggtataa    240

acccctatac cctttcggct agacttgggc taggagactt ggcccatcac gaagacagtt    300

cgaggcttga tccaacagtt cggagtttca tgcaaggaaa cgagacgcag aggtcaagca    360

ggattctagt cggttagaat aggaattgat atcgcactat ctatggcaat tgtaaccgac    420

taggattagt ttccagattt ataaccctac cctctggact atataaggag aggt           474
```

<210> SEQ ID NO 188
<211> LENGTH: 110
<212> TYPE: DNA
<213> ORGANISM: Sorghum bicolor

<400> SEQUENCE: 188
tctagtcggt tagaatagga attggtatcg cactatctat ggcaattgta accgactagg 60
aatagtttct agatttgtaa ccctgccctc tagactatat aaggagaggc 110

<210> SEQ ID NO 189
<211> LENGTH: 211
<212> TYPE: DNA
<213> ORGANISM: Sorghum bicolor

<400> SEQUENCE: 189
aagggacccc cctaggcaat tcatctcaac tcaatccaat acaatcagac gcaggacgta 60
ggtattacgc ccacgcggcg gccgaacctg gataaaaacc ttgtctgtgt cttgcgtcac 120
catcgagttc gtagcttgcg caccgtctac cgataaacta ctaccgtggg tataccccaa 180
ggtagactgc cgactagctt tcatcgacaa t 211

<210> SEQ ID NO 190
<211> LENGTH: 4946
<212> TYPE: DNA
<213> ORGANISM: Sorghum bicolor

<400> SEQUENCE: 190
tatttgtctt tccgctcgag gttcttttat ttctcttttg tcgtcctacg tatgtgttcc 60
ttgttcgatt ttcgtaaaga cagcttcgat cacctcgagg gtgagggagc gagtagagtt 120
tccatagccc gggggcgtag gtgttctcag gctcgttatc cctcggccct taaggtgctc 180
gaggcgcctc aactactcga ccatgcaagg tttactaagt aagaaagaga gaaatttttg 240 gctttttcg acacttgggg gggggtcgcc cccctggtag cccccgaggg ggtgttgact 300
atgatgggtc atagtcggcg ccccccttcta acgtcgagat tataacttgt aaagccttgg 360
tacaaaaaga agttgctcga gggaaggact tcatctattc atacattcac ttacaaagtc 420
tcggtacaaa atatacgtag gaacataaag ttttgaactt ctaggggtag aacaacgtag 480
ctgttcgatg ttccacgcgt tggtgaagac tgcccccttc tcgtccgcta acttgtacgt 540
tcctggcttc aaaacctcgg ccaccacgta cgggccttcc caaggcggag tcagcttgtg 600
gcgtccttga ttgctttgcc gtcgtcgcag gacaaggtcg cccacgttta agtccctctt 660
tcgtacgtgt ttgtcgtggt agcgtcgaag cttctgctgg tatctggcag aattgaggag 720
ggccatgtct cgagcctcct cgagctgatc gatcacgttc tcttgagtct ccttattcga 780
ttgctcgttg tacgctttga gtcgagggga cccgtattcg aggtctgtgg ggaggacagc 840
ctcacagccg tagactatga agaaaggggt aaattttgtg gccctgctcg gtgttgtcct 900
taggctccat aggaccgagg aaagttcctc gacccacttc ttgccgaatt tcttcaagcg 960
attgtagatc cttggtttga gtccttgcaa aatcatgccg ttggcatgct caacctggcc 1020
gttagtttga gggtgggcca ctgccgacca gttcacacgg atgtgatgct gatcgcagaa 1080
gttcaagaac tttttgccgg tgaactgagt gccgttgtcg gtgatgatga cgttgggaat 1140
cccaaaccga tggatgatgt cggtgaagaa aaggacggct tgctcggagc ggatgttggt 1200
gatgggtcga gcctcgatcc acttggagaa tttgtcgatg gccactagca agtgggtgta 1260
tcctcctttc gcctttttgt aggggcccta ctaagtcgag cccccacacc acaaatggcc 1320

-continued

```
atgtaatggg gatcatctga agagcgtggg cgggcaggtg cgtctgtttg gcgtagaact   1380
ggcacccacg acatgagcgt acgagctcga tggcatctgc tacggctgtt ggccagtaga   1440
agccttgtcg aaaggcgttc cctacgagag tccgtggagc agcgtggtgg ctgcaagccc   1500
ccgagtgtag gtcctcgagt agtttccggc cttcttccac ggtgatgcaa cgctgcaaga   1560
cacccgtcgg gcttcgttgg tacagctcat tgccttcgcc atatatcaca tatgacttgg   1620
cccgtcgagc gattcggcgg gcttcagatc gatcttctgg cagctcgcag cggattaggc   1680
agtcaaggaa cggtgtgcgc cagtcgaacg gtcgaccggg ccgccgttct acctccatca   1740
cctcagctgc catcaatagt gcgttgacgg tgtcggttgg ctgggcggga gcggcatcga   1800
cgtcagcccc cgagcctaag tcgacggatg gctcatgaag atctctcgag aacgcgtcag   1860
gcggtaccgt gcctcgggtc gacgcgattt tggcgagttc gtcggctgct tcgttgtagc   1920
gtcgggcgac atggacgagc tcgaggccat ggaacttgtc ctcgagtcga cggacttctt   1980
tgcagtacgc ctccattttc gggtcgtggc agcttgaggt ctttattact tgatcgatga   2040
cgagttggga gtcgcctcgg acgtcaaggc gtcggactcc tagctcgatg gcgatcttga   2100
gaccgttgac gagggcctcg tattctgcga cattgttgga tgcggcaaag tgaatcctga   2160
tgacgtacct catatggacg cccaagggtg agatgaacag caggccggcc ccggcccacg   2220
ttttcatgag tgacccgtcg aaatacatcg tccacagctc cacctggacc tgagtcgggg   2280
ggagctagga gtctgtccat tccgcgacga aatccaccag ggcttgcgat ttgatggcct   2340
ttcgaggcgc ataagtgaga gtctcactca taagctcgac cgaccattta gctattcttc   2400
ccgtggcctc cttactctgg attatctcgc ccagggggaa agacgagacc accgtgatgg   2460
ggtgaccgag gaagtagtgc tgcagcttac ggcgtgcgag gattacggcg tagatcagct   2520
tctgaatttg gggtaacgt gccttggtct ccgagagcac ctcgctgacg aaataaactg   2580
gcctctggac tggcagcgca tgcccctcct cctgcctctc gaccacgacc gccgcactga   2640
tgacctgggt cgtcgacgcg acgtaaagga gcagtggttc tgcaggttga ggtgggacta   2700
ggactggtgc tgaggtcaat gttttcttca gcttttcgag agcttcctcg gcctcggggg   2760
tccaagaaaa acgctcgacc ttctttagaa gtcgatacaa tggtaacgcc ttttctccta   2820
gtctcgagat gaaacggctc agagccgcca ggcatcccgt gactctttga acacccttga   2880
tgtctcggat cggccccatt cttgtgatgg tcgagacttt ctcggggttg gcctcgatgc   2940
cgcgctggga aacaatgtaa cccaagagca tgcctcgagg cacgccgaag acgcatttct   3000
cgggattgag cttgatctgg ttggtgcgta agcagctaaa agcgatttcg aggtcttgga   3060
tcaggtctcc tcgccgcttt gatttgacga caatgtcgtc gacataagcc tcgaccgccg   3120
accctatgtg tttgccaaat acgtggagca tgccacgctt tttgcttctt cttgttcttc   3180
ttgagccctc gactgggggt tccatcttca tcgacgggcc gcttgccttt ccctccttca   3240
ccactgaaga aggcgccgac tgcctcctcc cctgctgcat agtttgccac tacatccatc   3300
agctcatcga cggtctgagg gcgatttcgg cccaactccc gcactaagtc tcgactggtg   3360
gtaccagaga caaaagccag gatgacgtca tggtcaggga tgtgtggcag ctcagtgcgc   3420
tgcttcgaga agcgtcgagc atactctcga agagtttgtc ctgacttctc cttgcatttg   3480
ctgaggtccc acgagttccc gggccgtatg taggtccctt tgaaatttcc ctcgaagact   3540
ttaaccaaat cgacccagtc gtggatctga tttgctggaa gttcctcgag ccatcgacgg   3600
gcggtgtcgg agaggaagag gggtagctgt ctgatgatgg ctcgatcatc ccctcgagcg   3660
ccacctagct gacaggccag cctaaaatcg gccagccaca attctggttt ggtctcacca   3720
```

```
ttgtatttcg cgatgctggt cgggggtcgg aatggactgg gtagaggcgt gctgcggatt   3780
gccctgctga acacctgtgg gcttggtggc tcgggggcca cccgatcctc gtcgctgtcg   3840
tacctcccac cacgatgtgc gttgtaaccg cgctcttccg cgtctctgtg ccggcggcgt   3900
cgattctctt cgatgtcatg ccgcgcgtcg tgtcgacgct gattgtcgac ggggaggacg   3960
agagtggtct ttcttcctcg agggggcggc tgttgatgga ctgacacttc ctttttattt   4020
tgaggcggct cgtcgcgctt ttcagtggca gctcctcgcc gtcgagaagc tgagctttcg   4080
acttgttgaa ctgccgccac ttggagcaga gtttgtacct cgtctcgaat gcgccgagcc   4140
tgagagttcg atggtttcgg catgttgcgc agtagcatcg tcgccgccac tacattctgg   4200
cccgctcgag ggaaatggct gacaggctgc tctggctctg cgtctccgat gatttgtcga   4260
tgtacctctc gagcgcgtct gcagacactt ccgcccggcg ggtagggtag gtcttgctca   4320
aggatttgct cgagcaggac gaggcgctca cggtcttcgt cgagcttcat cttgagctcc   4380
tgtagctgtg caagctgcgc agccctgtct tcttgtggag gggggtcgac ttgtccgtca   4440
ttcccaggcg tcctggggtc ttcccgtgat acaggggctc gaccgcccgc agcagcaacc   4500
tgcgtctcgt cggtagtctc taccgccccg tcgacgtgat agcattccct tgtagggtcg   4560
tagctatcag tctcggagtc ggagtccggc ttggcggcat agaaacatcc acgtccctcc   4620
tccagcagcc gttgcctgac tgaggtgatc gtgtatcgcc cagggcctag gcggcggagg   4680
cctcgcacct gggagaaatc cggcagttca gacgtcggct gtagtgtttc agagtcacgt   4740
gggaggacca ttggtctctc cacgtacgtc tgggcgtttg ggcatattgc cctggcaagc   4800
gacgctgcgg cgttgtctaa tccgaatggc agtgcccttc ttggagtgaa caacccgtgt   4860
ggaagtacct tagcagcggt gggggagggc gcgcgagaca cgtccccccc ccgtcgtcgt   4920
gcggtgttga gccgtcgtgc ccgtgg                                        4946
```

<210> SEQ ID NO 191
<211> LENGTH: 1281
<212> TYPE: DNA
<213> ORGANISM: Sorghum bicolor

<400> SEQUENCE: 191

```
cgctcgctct atcgagagta cgtcgaaacc ttcgcacaaa acgagccaat cagaaccctc     60
caccacaggt gtcgacggcg tttctgtgaa ttaggcaata taaccctcga aggagtcaaa    120
aactcctcca agggctcgag ggctaccccc acggggtcgc tcgcgtgccc ccacgaaaac    180
tcaacccaag aatacagcct ccactcgagc gccagcgctc gaatggagac tcgggggcta    240
ctgtcgaggg tatcaataag gggtaccctc accgatgcac ataacaagat tatccgtacg    300
caggtcgagg ccctcaactc ggcgctctga tcatacatac gcacagccat caacaaccgc    360
agcctcgaag acagaaatga tgtcgagcga atcgatcaag ggtcgagcgc cagctatcgt    420
cgaatacgga gacaggcccg agcgaattga gaagcgtcga gcgcaaggac actgtccgcc    480
gcctgacgcg cgcacgagag ccaggacatt taatgcgccc gccgcattcc cacctaacac    540
actggtcacg ggaggcgtga taggaaatag gcacccgtcc catcgttctt tttgcagcct    600
tccccaccaa acgacccagg ggtgtcagga cgcgggaaac gaggatggaa cgtctaatcg    660
gaaccccctc gagacaacca aggtcagcgc tctggacatc agggcattac acggcgtccg    720
accctcgacc tgacgtaact ccttcctggg gacgagctgg gcgtcgaccg acaacaccgc    780
aaccactctg ccggatttgt cgccatgtcg tacaggcgtg cgactggtga accagcccaa    840
```

```
gacggcgcgc aggagcggga tacaggggca cgcgtaatca tcaccaggct actaagtcgg    900

gacggctcga ggtcacgccg gtatggaggc ctcgaatagg tcagcgcgcc atgctcctat    960

cgacccctac tctgacacct atacatgtac cctgggtctc tccttgatgc tataaaagga   1020

agggctcggg aatagataga catcaggcga taccacgtcc atacgcagta gaactctcac   1080

actccatacc acgcttgtgt tcacccctgt acaagcactt cggtgcaaga taatacagac   1140

tcccctcccc cgctggacgt agggccttct cttgcccgaa ccaggataaa tttctgtttc   1200

ttcttgcatc accatctggg aaagggagca cgcatacaaa tttactcgtt agtgtgaccc   1260

cccaggggga aacaccgaca g                                              1281
```

<210> SEQ ID NO 192
<211> LENGTH: 582
<212> TYPE: DNA
<213> ORGANISM: Sorghum bicolor

<400> SEQUENCE: 192

```
gcttattttg taagtatctt tcggtcctta attctcatag atcctttggt tttgtgttct     60

aaccgttcaa ccccggctcg caggacatga aagagacctc ccgcattaag tcgagcttca    120

ttcacgccac aagaggcggt tgggagcagc tccccgtcct caaggatcaa ctcctcgagt    180

cgcaagagaa gctccttaag gcctataaag accttatagc gctcgaggag gagaagaagg    240

cgagggaggc tgccttggtc aaggctcgag aggccttaag gaaggcagag gaggagacga    300

cgttgctgcg ggagcgcgct ctgacggtcg aggaggccgc gtccaaagcc cgggaggagg    360

ccctgtccta taagagtgtc attgcagact tagataagga gaagggtctt ctcaagatcg    420

acttggactc ccttcgagag tccttccaaa agatgaaggt ggagcacgtg aatggcgaga    480

tcaccaggag cgccgcggtg gaaaccaaga agaaggccct cgaagatctc gaggcggagc    540

gggctcaatc ccacaggctc tctgacgacg tcgaacgtct ga                       582
```

<210> SEQ ID NO 193
<211> LENGTH: 1194
<212> TYPE: DNA
<213> ORGANISM: Sorghum bicolor

<400> SEQUENCE: 193

```
caaaaggaat ttgtatgtat gtatggtacc actattgttt ctatgatgga ttgatctagt     60

ggtagcatat gacatgtttg tgagcttgta agcctagtgt tgaatctaga atatgagctt    120

atgatgtgta attcaacatg gtcaagataa cccttatact tcatgaggtg tgaaaaagct    180

tgtccttgga tcaaaccgaa ttacatgttc taggcaagtg atctagattg gaccataatt    240

tgaccctcac attgattgac ttaattctca ttaaaaattg aacctttgtg gtcattgatg    300

acaaagtggg agagaaacaa agataagtcg taaaggggga gaaaagtgct taagggggag    360

agaaaacttt tgaaaataga aaggggtaaa ttaaacttga gcacacaaat agggggagca    420

agctcatgaa ccatttgttg catttgtatg tgcactaaca taatgaagtg ttgcattaca    480

agtttaaatt cactactctt gtttgattga tgattgctag aaataaaact tgaatgatgc    540

tttgaattct agcatagagt ttttattttc atgtggtatc tagacatata atgtgatctc    600

acgaggtatc ttgagttttt gatgtatgtc tagctacatt ggtgctaagg atggtatatt    660

ggcaactccg attggtatca cgcttcaaag gtccattcta tataccttag catcattttg    720

gtagtaataa atctcccaaa attccaattc atgcatatgt gcaaacttga accaaactca    780

tggaagcaca tatgtagggg gagctagtac taccaaacgt gaaattaaag tgtttgtcca    840
```

```
atattggttt catgattaaa attctctgga caaacaattc aagttcatta tgatttcatt    900
tcatatcttt gtgatggttg tcatcaatta ccaaaaaggg ggagattgaa agcccaagtt    960
tggttttggt aattaatgac accaagttgc taatgctttg tgttcaagtg atttgagtta   1020
ggcatagcaa cacattttaa gaaggagcaa tgtgacatga gtggtggaca catggtcata   1080
aagagagaag gcatgaagtg gagatcatgg tgatggacaa ggagtaaagt gatcaaggca   1140
aaggtataaa cataggattt tgcttttgcc ggtctaagat gagtagagaa gtga         1194
```

<210> SEQ ID NO 194
<211> LENGTH: 607
<212> TYPE: DNA
<213> ORGANISM: Sorghum bicolor

<400> SEQUENCE: 194

```
aagaacggga agcaggacag gcgtgctcac gaagacgaag acgatgacca ggatagggac     60
ccacgacacc agtatgtcag tcccatcgac gtggtccact ccatcttcgg aggcaaagtt    120
tctatcgagt ctaaacgaga gagaaagctc ctgaagagag cctgcctcaa tgtggacagc    180
gcagatggtc tggtcgccga tccgaaattt cctccctggt cacacaggga gatctccttc    240
aacaggaagg accaatgggc cgccatcccg gagccaggat gtttccctct gatcctggac    300
ccttgcatca acaacgtcag attcgagcgc gtgctcgttg atgggggcag ctccattgac    360
atccttttcc gcaacagtct gcctgctctg aagataaccc cggcgcaact aaagtcgtat    420
gacgctcaat tttggggagt cctgccaggt caaagttcag taccccctcgg acagataacg   480
ctgcctgtcc aatttggaac acctgaccac tttcgaatag agtttgtcaa ctttgtggtc    540
gccgacttcg acggcactta ccacgcaatt ctgggccgac catcgctgac aaagttcatg    600
gcagttc                                                              607
```

<210> SEQ ID NO 195
<211> LENGTH: 1373
<212> TYPE: DNA
<213> ORGANISM: Sorghum bicolor

<400> SEQUENCE: 195

```
ctatctccaa acagaccaaa ctgagctttc acttgagcat cttcacctag tgaaagccct     60
agtttggttt tgtataattg atgaaaccct agtactaacc tctatactaa gtgtgtgtag    120
acttaatgag gttggtacat gccaagtgat ggagcaagtg atgatcatat tgatgatggt    180
gatgactaca agatgatcaa gtgctcaact tggaaaagaa gaaagagaaa aacaaaaccc    240
tatggagatc aaggcaaagg tattgcttag ggttttggtt ttggtgatca agacaccata    300
gagggtgtga tcacatttag gatagagagc cgtactataa agaggggaat tctttggcta    360
aagcggttat caagtgccac taggtgtctt tgttcatgtg catgcattta gaacctagtg    420
agctaactta actccttcaa agaaaatgat tgtgaaaatg ctaacacacg tgcacttgtt    480
ggtttacaca tcgtggtgtt ggcacacttt gagaaggagg tggagtttga agagtagaga    540
gaggatgggt tcctctctcc ctcccaccga gcttgcgact agggattcgg cgcttttcga    600
gaaaatgaag tgcatatttt ctattgcgcc ggtgggaaat ttggagaagt cgcgggagtg    660
ttcctcgcag agaaacactc accggacgct ggcctatgag gcaccggacg ctgaggctga    720
gcgtccggtg tgctgtggtg ctagggttaa gcaccggacg gtgaacaccg gatgctgggg    780
agctcttgtt catgcgtccg gtgctatctg acttcggtca gagtgtttga ctggaagcac    840
```

```
cggacgatca gggaccgtcc ggtggttagc gtccggtgtg cgggcgtttt gcaaccctct    900

ctacgcatgg gtccggtgag caccggacgc taccggtgct tagcgtccgg tgacccacag    960

gtttgcggaa ctctgtgcgc ctgagtccgg tgtgcactgg acgtgtccgg tgctaacttg   1020

ctcagcgtcc ggtgcactac aggtgaccgt tagactctga cacgggaagt tcaaaaggtg   1080

acacgtggct gacgttggag caccggacgc aagggctgag cgtccggtgc ccctttaaga   1140

gcgtccggtg accccgagtt tttgcccagt gaaagagcca acggctctat ttgtttgagg   1200

ggctataaat acgtgtttgg ctggcttggg gctcactctc ttagcattct agcatacttg   1260

acattcttgt gagcctaagc aaacacctcc cactcatctc cttcatagat taaacatctt   1320

tgtgagattg ggagtgattt caagtgcatt tgcttgagtg attgcatcta gtg          1373
```

<210> SEQ ID NO 196
<211> LENGTH: 1100
<212> TYPE: DNA
<213> ORGANISM: Sorghum bicolor

<400> SEQUENCE: 196

```
ccctttggca tcaagcgcca aaaacctaag aagacggcgg aggaggcgga gcagaagagt     60

ccctcggcgc ggccacgaaa cgagctgcat catctgaagt atcggtcgtc gaggcggagg    120

aggtggagtg accctctgaa gctgcaggtg ctggtgaagc ggtccgggtc tgctctggag    180

ctgtcacagg ctgtgctggc tgctcgagtc cggctgacga agctggcacg gactcggtcg    240

ctgtagcagt cgtctctggt acggtagtag acggtgcaag ctgctcggac gacgctactg    300

acgacgacag aagctctgta gtggtaactg gcaccgtaaa gactgcagga gcctgcagag    360

gaggaggcgt agggtcacca gtcagagcac tgtaggtgaa gctgaggtgc ggatctgtct    420

gcgagtccca cacaagctgt gacgctgaag ctgactgagg ggtgaaacct gagcagagag    480

gggtaaactg cggtacctgc tcaaagcctg aagagatggc accctgagag acctggtgct    540

gtggcgtcga gaacggctga ctctgagctg gtagctggag cggctgctgt gacgggctct    600

gagtctgggg cgcaggagta gggggcctga cggacgacgt gcctgggagc tgtatctgcg    660

gtagctgaat cccggaggca gccatgagag cggccatcat cgctgtctgc tgggcctgga    720

aagcaagctg ctgctcctga aaggtgagaa gctgacgctg gagctcatcc tgcctagcct    780

gcatggctgc attgatggca gctgatccct gtctcgcctc acctgctcct cagctgcgcg    840

gtgctggtct gccctcatac cctctagtat agcaagcagg gcggggtctg acgcactcga    900

agaaccgctt gcctcgtggt cgtgtgctct gggagggaga tctgtcactg gcggctgata    960

gtcgtcatct gagctgtctg aggcgaagtc aaactctccc tcagcctctg catcggcgaa   1020

agccccaatg gctatgtcct actgctcctc tgtctctgca acagctgctg tactgcgggt   1080

gcccctagga gaaggcgggg                                               1100
```

<210> SEQ ID NO 197
<211> LENGTH: 519
<212> TYPE: DNA
<213> ORGANISM: Sorghum bicolor

<400> SEQUENCE: 197

```
tcattctcgc cttagccctt tcgctgcctt agttcccttg ccatcccacg cgtgtgtgcc     60

ccctcgagta gtagcggatc cgccattctt ttggcaagga tgcctgtgag gcttgtcgcc    120

gctgacgact ggcgcccgtc gtcgatgacg gagcgccggc tgcaagagct tgagagggag    180

ggactcctgc gccaccgcac ctcgctgtcg tcgccggagt ggatcgcgcc ggcggcggac    240
```

caaagggagc ccaggccgcc taaaggctat gtggttttgt tcgccaagtt ccaccgccac 300
gggctgggcg ctcccccgag ccgcttcatg cgggcgctct gccaccacta cggggtggag 360
cttcagcact tctccccaaa cgccatcacc gtcgcggcgg tcttcgccgc ggtgtgtgag 420
ggctatttgg ggatgatgcc gcactgggag ctgtggctcc acctctacag ggcgagctc 480 ttcaacgccc ctacgggtac caccggcgtg aggaagccg 519

<210> SEQ ID NO 198
<211> LENGTH: 661
<212> TYPE: DNA
<213> ORGANISM: Sorghum bicolor

<400> SEQUENCE: 198
aatactatct ccaactcgac tgaagcaaga ttccatatga tacacttcat ctagtaattt 60
catcgggtgc atctacagtt ccatcgggtg tggccaaatt gctttctgag catgtggtat 120
gtaccatgca aaccgtgcag ctatcttgca tcaagattag aactatctcc aaacagacaa 180
ccatgattcc acatgagccc cttcaccaag gagtaccatc gcgtgcgtcc aaaatagttt 240
cttagcctat ggtgcattag gaacaaaccg tgtaccgatc ttgcaccgaa actaacacta 300
tctccaaaga gaccaaagtg agattctatg tgacacacgt catctaggag ttttattagg 360
tgcttccaaa tatatttcta agcatatgtt acgttcgatg taattcgtgc acctaccttg 420
catcaagatt ggcactatct ccaaacaaag caaactgagc ttccagttga gccccttttac 480 ctaggagtat gatcgggttg tcacgcccgg ttttaaagaa caaaaccagg ctagccatat 540
gtgtgcccag gaagtccaca catacaacaa caaaaccaat agtatcaaaa caatgttata 600
tagcgaaaac atacttataa ttaacactta cattagagaa atcgcggact caggctcaat 660
c 661

<210> SEQ ID NO 199
<211> LENGTH: 2166
<212> TYPE: DNA
<213> ORGANISM: Sorghum bicolor
<220> FEATURE:
<221> NAME/KEY: misc_feature
<222> LOCATION: (2149)..(2149)
<223> OTHER INFORMATION: n is a, c, g, or t

<400> SEQUENCE: 199
cggaccactg acgttcttgg tacgagccat tgcgaaacaa gtgtccgact aacaaccgac 60
taacaatgga gattaacgcg ctgcagggaa atgacaagat aggatatata taagaaaaca 120
tatcgactag agatgagaca atcctataga tcgtaagaag tgataacgaa tggacgcgaa 180
cggcttacga tccacggacg agacgcgttc cggaagaaag ctatcgatcg acaaccaccg 240
gagaacgcaa atctgctcct caagatgctg cagcgagatg acaatcgaga tcggaatcaa 300
aacctaaatc aaatgccttt tactcatagg aacaaacatc ttgagggcaa agtccaagga 360
tcttacccaa acccttgaat ctcttcgtga tttggagaac cacgcgaaga gaagagagag 420
gagaagatca ggggcagatc tggcgcggag agagcttcaa agggcgccgg gaatcgacgc 480
acgcacgacg gcggcggcgc tagggcacgg gcgcggctcg ggcgatgttg gcggaagaga 540
aagaaaacgc ccgctcaaag cccctcggtg cgggctttat gcgcccgccg cggggtcacc 600
ggacactctt aaagttgcac cggacacgtc cggtgaccac cggactcatg cgcagagagg 660
attgcaaatc ggcattgcac cggacgatgg gcaccggacg ctggctttag cgtccggtgc 720
ttcaggtcac accaggtgag caccggacgc accgcaccgg acgctacagg gatactgttc 780
ctgcgtccgg tgcgtgcagc ctggcacact caccacaccg gacgctcaga ggcagcgtcc 840
ggtgcatcgt ccggtgctcc tctgagcact ttttggacta agcaccacgt ctgactttga 900
cccaaccaag ttccatcttc aaaagcacac aaataaacac caaatggaac tggtatgagt 960
gacttctctc aaaccctcaa attttcacaa atatttagcc ataggcttag tagtttttat 1020
gaaaatagtt cgagaaaatc accaaggagc atcgtatggc cataaagcta ggggtttgaa 1080
tcataatgag ctttgaatgc tccccctatc tatggacgaa cacagcggat gctcaacgaa 1140
taaccgaaaa gaaacgatca actaacaagc atgcacatga catgagttgt aatgcaatac 1200
ttgaaagaaa actaatgctt gtcaagtttg atccaaggtt aagctttttc acacacaaaa 1260
gggggttatc ttaaccatgt tagacaagcc ctacatgcaa gttatatttt tagttttagt 1320
atgcatgata tgcaaagcaa aagttattta caagattcaa cacacaactt ttatctttta 1380
gtgaagttgg ataggtcaag cacattaagt tcatttctca acatacaaaa ttagcttcat 1440
ctaggggttt tgtgaagata tccgccaatt gattttccgt tcccacattc tctaaggata 1500
tgtcactttt agcaacgtga tccctaagga aatggtggcg gatgtcaata tgttttgtgc 1560
gggtgtgttg aaccgggttg tttgcaagtt ttacggcact ttcgttgtca cacaacaaag 1620
gtactttgtc tagtactact ccatagtcta gaaaagtttg tttcatgtag agtatttgtg 1680
cacaacaagc accggcggct atgtattccg cctcggccgt tgacaaggca acactatttt 1740
gtttctttga catccaagag acaagagatc gacctaggaa gtggcaccct ccggatgtgc 1800
tttttctatc aatccgacac ccggcataat ccgaatcgga atagcctaca agttggaatc 1860
ttgcaccttt gggataccac aagcctaggc aaggtgtgta ttttagatac ctaagaattc 1920
tcttgaccgc aatcaagtga gattccatag gcattgcttg atatcttgca cacatacaca 1980
cactaaacat tatatcgggc ctagatgcgg tgaggtagac ttcctatcat ggagcgatag 2040
agagtcttgt caatagggtt acctccctca tccaagtcga gatgcccatt tgatgccatg 2100
ggagtcttga ttggcttgca gtccatcatc ttgaacctct tgagaagtnt cttgtgtgta 2160
cttctc 2166

<210> SEQ ID NO 200
<211> LENGTH: 1072
<212> TYPE: DNA
<213> ORGANISM: Sorghum bicolor

<400> SEQUENCE: 200
gttctctata tgcaagcttc ttgtcttgat caagtgactc aatcacattg gtcttgtgct 60
tggcttgttc ttgcaactct ttcttgagca tgacattttc atccttgagc ttgatagtgt 120
cctcataatt ctcggccact accactttct tgcccttgca atcaacacat ttgcttgtgc 180
tctccacaag taagtcatca caagatgtgg ctacatcaag cttagcaaca ttgttagtag 240
caacatgtgt ttcatcaatt gcaagttcat aagcaatctc aaggttgtca tagtttgctt 300
ttagagttgt tagttcttct ttcattgctc tatatctagt gataagctca tcatgaacac 360
tctcaagttt atcatgtttt tctttgagct cttttagaga gagtttgagc tccttgagct 420
tagtggtcat gatctcattt tggtctctaa gctcatcact agacttaagc tttgctagaa 480
gtgtgtcatt ttcaagttca agcttttcat tttcacttct agtctttctt atgacttttg 540
tgtatttgtt tagcaatttt acaagttcat cataagaggg tgattcatat tcactatcac 600
tttcactact ctcatcctca ctttgtacct tccggtcacc tttggccaca aggcataggt 660
gtgtagagga tgtagatggt ggtgaagatg atggtgatgg agcatcgatg gcgatagcgg 720
caaccttctc atcatcactt tcattgccgg aggagtcacc acttgagctt tcaatgtcgg 780
tgagccaatc accaacaata taagccttgc cattcttctt cttgtagtgc tccttcttct 840
tgccaccttt cttcttgtat tgcttcttgt catttttctc atcatcgctt gagtcatctt 900
gctctttgtt cttcttcttg tacttgtcct tcttgggctt tggacattga tgagcaagac 960
gaccaagctc accacaattg tagcaatcca tctcggagat gggattcctc ttgctacttg 1020
tgaagaactt cttcttcttg gagtcaaatt tgactccatt cttgttgagc tt 1072

<210> SEQ ID NO 201
<211> LENGTH: 1003
<212> TYPE: DNA
<213> ORGANISM: Sorghum bicolor

<400> SEQUENCE: 201
ccccggccaa cttcaagttc atcctcgtac taatttacaa attctcgaag tggatcgagt 60
acatgccact ggtgaaagca acctccgaga aggctgtgga gttcctcaat caaatcatac 120
acaaattcgg gatccccaat agcataatca ctgaccaggg cactcagttc actggcacta 180
cattttggga cttctgcgtt gacaggggca tagtcataaa gtacgtgtcg gtagctcacc 240
cacggggcaa cggtcaagta gagcaagcga atggaatgat tatcgatgct ctaaagaaaa 300
ggctgtacac cgagaacgac agagcaccac gacgatggat gaaaaagtta ccggctgtgg 360
tctggggtct ccgaacacag gctagtcgca acacgagtgt atcaccctat tcatggttta 420
cggcaccgaa gcagtgcttc cgtccgacgt gacctttgga tctccaagag tcgaaaattt 480
tgaccagtct tcggccgacc tcgccagaga gctcgaaatc aactacacag aagaaaaggg 540
cctaatctca tgccttcgaa cagcaaaata tcttgaagcc attaggcggt accacaacag 600
gaacgtcaaa gactgttcgt tcgtgttcgg tgatctggta ctcaagtgga aaacaagcca 660
agaaggaacg cacaagttat ccacaccttg ggaaggaccc tttgtggtcg ccgaagtcac 720
acgacctaca tcgtacaaac tggcgtaccc agacggaaca cgcctgccta actcatggca 780
catagacaaa ctgcgccgtt tctatccata agttccagta catttagttt gtaaatctct 840
tatgatcagt agtaataaaa ttttttcttt cttgctatat acttctttta tatgcagaac 900
ttccgacaag tgccacaatc ttgttttagg acgaaggtcc ttaagtgtta ttaacccgat 960
tcagtgatac atcactcaga caacattgca gcgctacaaa acc 1003

<210> SEQ ID NO 202
<211> LENGTH: 689
<212> TYPE: DNA
<213> ORGANISM: Sorghum bicolor

<400> SEQUENCE: 202
gatatcttga gtaagcctat tgttattgct tctactaacc cttcatgtag cacatctaca 60
tcatcctcat ctagtagtga tggtttcact tgtgacacca cactaaaagt tgagaatgaa 120
attctcaaga aggaggtgaa agagctcaat cacactttag ctaaggctta tggtggtgag 180
gaccgcttgc ttatgtgctt gggtagccaa agagcttctc tctataaaga gggattgggc 240
tataacccca agaaaggcaa ggccgccttt gctcctcaca agacacgttt tgtgaagaac 300
aatggccggt attgcaaagc ttgcaagcaa gttggtcact tagagcaaca ttacatgaac 360
aagaaatcca aagcaaatgt atcctcaatt aagcttaatt ctttctatgt gcttactaag 420

```
gatacaaaag gtgttcatgc taagttcatc ggtgcaccat ggatgggctc aaacaagaaa    480

gccatttggg taccaaagag cttagttgct aaccttggag gacccaatca agtttgggca    540

cctaaaagga attgatcttg tcttgtaggt caattacaaa gccggaggaa ggcattgggt    600

gcttgatagt gggtgcactc aacatatgat cggagagtct tgtatgttca aatcaattga    660

tactagtcaa aatggtggct ttgattctt                                      689
```

<210> SEQ ID NO 203
<211> LENGTH: 959
<212> TYPE: DNA
<213> ORGANISM: Sorghum bicolor

<400> SEQUENCE: 203

```
ttcttcgacc agcaaggctt gacatcttca atcagcatga aagtcgccca aacagttgca     60

acggtatttt aaccaactca aaagatagtt gatcaacatt gacatcgaag aagcaggctg    120

ttcgaaaaat gcatggtgct cttaatcaaa aaagattttc ttcctagtga agtgtgccca    180

ctttttcttt ttctgaaaag gacagacttt caaaaagcaa gcattttcac cgcaaggtga    240

agtgtgccca cttaatcccc gagcctggta gtaggtgtcg tatgcacgtg gtgccaggat    300

caaaaaggtc ttcatagaaa ttccaaaact gagatgcatc gctagatgca tcgtaccgat    360

gtagtcctcg agcttgctgg aaagcgaatt atgagccttg tagcaaagtc taaaaattga    420

atttaccagt ccccgagcat atcatgctcg tctgcaactg aatagactaa tcgaccagtc    480

cccgagcata tcatgctcgt ctgtaatgga acagactggt cgaccagtcc ccgagctctc    540

aaattggtgg gctggtcgac cagcctccga gcgtatagtg ttcggtggtc ggtacagtcc    600

ccaaactctc aaattggtgg gctagtcgac cagtccccga gcgtatagtg ctcggtggtc    660

gggacagtcc ccaaactctc aaattggtgg gctggtcgtc cagtccccga gcgtatagtg    720

ctcggtggtc ggtacagtcc ccaggtatgt catacacagt cctctaccag gcccacttgt    780

cctttggaaa aagcatcttg ccacattaac gcatgatgcg acaaggcatc ctagcgtatt    840

gttagacggt tgcgtaaaaa ggtgcgcctg ataactgtgt agccgctctt tgtgtggttc    900

aagaaaagga aaccaccaat tatataaaaa agccaccata ttaactgccg gtaattatt     959
```

<210> SEQ ID NO 204
<211> LENGTH: 449
<212> TYPE: DNA
<213> ORGANISM: Sorghum bicolor

<400> SEQUENCE: 204

```
gaagccagag cagacaaccg ccatcgcccg cttcaccccg atgtggaggg catcccgcac     60

ccgatctctc agcgtcgcgc ctaagtagca cagctggtcg accagtgcgt caccttgagc    120

gtcctccttc gactcgtcca taggctcgac ctcccaggag gtcgagaggt cgtttatcgc    180

cgtccgcacg cgacggttca aagcaacctc cgcctcaagc tgggccttag cattacgggc    240

ctcgacttgg gcggctagga gctcgtcctt aagccctgta aatgccaata caagaaacct    300

taggaaaaac caagcacacc tcgaaaaaag aaatccgaca gaggaaacgt accgcggacg    360

gtctcctcca gggccgtgtt cttgccgacc agcctggtgt tggccctctc gatctctctg    420

ttggagcgtg ccagctcggt gttggcaac                                      449
```

<210> SEQ ID NO 205
<211> LENGTH: 418
<212> TYPE: DNA
<213> ORGANISM: Sorghum bicolor

<400> SEQUENCE: 205

```
ctcctatgcg gacttccatt catggacccg aacttccggt tatggaccgg aacttctggt     60
catggactgg aagttcggtc agacaccgga aatgttttct caaacgcgag cgcatctctc    120
acagcccaac cggaacttcc tgtccggcta atcgaaactt ccggtcaggc actggaagta    180
ccacccgtcc tgcattttca gcaccaagtc aaaccttgtt aggatgctaa cttttagctc    240
cgaactccga attcgatgat cttggacatt ttggaaagct tactcagagg gctatacaat    300
ccatatggat actcaatcca agtcataatg tatcaaagca gtatttcaat ctaaaagcca    360
tcctaatgtc cggagaacac cgaaaagcct actttctctt ctccaagttg atcaaaat      418
```

<210> SEQ ID NO 206
<211> LENGTH: 590
<212> TYPE: DNA
<213> ORGANISM: Sorghum bicolor

<400> SEQUENCE: 206

```
atcgcccagg gcctaggcgt cggaggcctc gtacctggga gaaatctggc agctcggacg     60
tcggctgctg tgcttccgag tcacgtggga ggaccattgg tctctctacg tacgtctggg    120
cgtttgggca tatcgccctg gcgagcgacg ctgcggcatt gtccaggccg aacggtaagg    180
ctcctcttga ggcgaactgc ccatgtggaa gtagcctagc ggtgggggag agtgcgcggg    240
gcgcgtcacc taccgtcatc gtgtgatcat cacggcactg agccgtcgcg cccgtggtgc    300
gaggggctat cggctctcgt cccgcctcct gcctggcacg gactgccggt cgcggcgagg    360
cagatgggcg acggtggtgc tgtccacgcc tcttcttggg cggggaggcg tggtggtggg    420
gacgtcttgg ggccctcatc cgggttggcg caacgcgggc tcctcccggc cctttgatcg    480
agagcaagat catgtcatag ccggaaccag tggacatgaa ctcgagactt ccaaaccaaa    540
tcaccgtgga gtgcggaatc ggtgaagaag agtggccatc tggaaagagt               590
```

<210> SEQ ID NO 207
<211> LENGTH: 470
<212> TYPE: DNA
<213> ORGANISM: Sorghum bicolor

<400> SEQUENCE: 207

```
ttttagtttg tctcattttc acatttgtta actagagagg aatgagcttc ttcaagctta     60
gtgtgagcct tttgaagctt cttatgatct tcctttagac tctcataaga tgctctaagc    120
gcatcaagtt cttgctcaag ggttttctta tccttaagca aggccttgca ctcctttcta    180
gtttctttat agtgatgagt gcaatcttct agcatagtga ttagttcatc tttagttggt    240
tcatcatcat cactatcact atcactagca tggtcactct catcattgga tgataccttta   300
gtggccttag ccatggagca tgatggagtg tcgaagatgg agctctttcc ttgaattgca    360
atgctagcgt gccccttctt cttggtgctc tcatcatcac ttgaggagtc atcactatcc    420
caagttgcaa catgggcatc acccttcttc ttgtttgagc cttccttctt               470
```

<210> SEQ ID NO 208
<211> LENGTH: 476
<212> TYPE: DNA
<213> ORGANISM: Sorghum bicolor

<400> SEQUENCE: 208

```
atcatgaact tcttctaatg tgccacttgc caaagttcca aaactactat aatgccttgc     60
```

```
ttgtggtgga ataaccaagt aagaaccctt catcacattt cttttcaaac ttgctcaatc    120

tagtgccttt cttgagaata tagcatttgt aaccaaacac tctaaagtat gcaatgttgg    180

gctttcttcc attcaatagc tcatatggtg tcttcccaag cttcccatgg caatagagac    240

ggttgctaca atagcaagcc gtgttgatag cttcactcca aaatgaatgg ctaacattgt    300

attcactaag cattgatcta gccatgtcaa tcaaggttct attattcctt tcaactacac    360

cattggattg aggagtgtat gttggagaga attgatgtcc aatgccaaga tcatcacaca    420

attcctcaat tcttgtgttc ttgaattcac taccattgtc acttctaatc ttcttg       476


<210> SEQ ID NO 209
<211> LENGTH: 2823
<212> TYPE: DNA
<213> ORGANISM: Sorghum bicolor

<400> SEQUENCE: 209

gctcaaggaa gaaaatcaat atctcaagct tggtttgatg tatgacaagc aagaagaaga     60

tgagacattc atcttggatg agttagctag caacaatgac ccaatcatca agaagctaac    120

tcaagagaac aacaagctca agaaagagaa ggaacaccta accatggggt tagcaaagtt    180

cacaaagggg aaggaccttc aaagtgagct ttttatgaac accgtcatga agatggacaa    240

gagtgggatt ggctacaagg ctcatcaaac aaagctcatc aagtcactag ccactcatga    300

tcaaccaagc aagccaaagc ccaagagatg ctttgagtgt ggtcaagaag gacactttgc    360

tcatgagtgt aaggcaccac taccaccacc cttgcccaag catgcaagac catttgcctt    420

caatgctcac tacattgtaa ggaaagacaa gagtggcaag gtcaaggtta gcttcatggg    480

gccgcccaac aagcaaaggc caaagaagat ttgggtgcca aagcaactag tagagaagct    540

caagggccct aagcaaatgt gggtccctaa atctcaagct tgatctcttg tgtgtaggtg    600

aactacaaga ccggtggatc acattgggta attgatagtg gttgcactca acatatgacc    660

ggagatcccc agatgttcac ctctcttgat gaagatgttg acaaccaaga gaagatcaca    720

tttggtgata attcaaaagg caaggtcaaa ggattaggaa aggttgctat atcaaatgac    780

aactccatca ccaatgtgct ctatgtgcaa tctttgagtt tcaacttgct ctcggttgga    840

caactttgtg atcttggatt tgaatgccta ttcaagaaga aggaagtaat tgtgaccaag    900

gaagatgaca atgaagtgat attcaaaggc ttccttcaca acaacttata tgtggttgac    960

ttctcatcca atgaagttga tgtcaagact tgcttattca ccaagacttc acttgggtgg   1020

ttgtggcata gaaggttagc acatgttgga atgggcacac tcaagaagtt gataagaaga   1080

aagaattgat tagaggcttg aaaaggatgc gacatttgaa aaggacaaac tttgtagtgc   1140

atgtcaagcg ggcaaacaag ttgcaacact catccaacca aagcctatct ctctacttca   1200

agagtgcttg agctacttca catggatttg tttggaccaa ccacatatgc tagtcttgga   1260

ggcaataaat attgcttggt catagttgat gatttctccc ggtacacttg gacattcttc   1320

ttgcaagaca aggccgaagt tgcatcaata ttcaagaagt ttgcaaagaa tgcccaaaat   1380

caatttgatg tgaagatcaa gaaaattaga agtgacaatg gaaaagaatt tgacaacacc   1440

aacattgaag agtattgtga tgaagtggga atcaagcatg agttctcctc aacatacaca   1500

ccacaacaaa atggggttgt agaaagaaag aaccggacat tgatcacctt ggcaagaaca   1560

atgctagatg agtataacac ttcggagaag atgtgggccg aggcaatcaa cacggcatgc   1620

tatgcttcaa accggctctt tcctcacaag ttcctagaga agacaccata tgagttgctc   1680

aatgggaaga agcccgatgt ctcattcttt agagtgtttg gatgcaagtg ctacatccac   1740
```

```
aagaagcgcc aacacttggg aaagttccaa agaagatgtg acattggtta cttggttggc   1800

tattcatcaa agtccaaagc atatagggtc tttaaccatg ccacaaacat ggttgaagaa   1860

acatttgatg ttgaatttga tgaaactaat ggctcccaag gagcaagtga taatcttgat   1920

gatgtaggtg gtgaaccatt gagggatgcc atgaagaaca tgccggtggg agacatcaag   1980

cctaaagaag atgatgatga tgtgcaagtc attgagccac catccacctc acatgtatca   2040

caagatgaag acaaggatgt gagagatgct catgaagaca cccaagtcac tcatgagcaa   2100

gcggtggcac aagcacaaga tgttgatgct ccccaaccaa cccctcaagt ggcaccaaga   2160

agaacatcac atctcctcca agatcactct caagatctca tcatcgggag tccgtcacgt   2220

ggtgtaacta ctcgttctag acatgcttta tttattaaac atcaagcttt tgtgtctctt   2280

gaagatgaac caaagactat agaggaagct cttcgtgatg cggattggat catggccatg   2340

caagaggagt tgaacaactt cactcgcaac caagtatgga cacttgaaga gcgaccccaa   2400

gatgcaagag tgattggaac aaagtgggtc tttcagaaca agaaggatga tcaaggcaaa   2460

gtggtgcgca acaaggcaag acttgtggca aaaggctttt cacaagtgga aggtcttgac   2520

ttcggtgaaa cctttgcacc ggtggcaaga cttgaagcaa tccgtatcct acttgcatat   2580

gcatctagtc atgatatcaa gttatttcaa atggatgtga aaagtgcctt tttaaatggt   2640

tatattaatg agcttgtcta tgttgagcaa ccccccggtt ttgaagaccc taggtacccc   2700

aagcatgtgt accggttgtc caaggcactc tacggtctca agcaagctcc tagagcttgg   2760

tatgagaggc ttagggactt cctcattgag aagggcttca agattgggaa agttgacaca   2820

aca                                                                 2823
```

<210> SEQ ID NO 210
<211> LENGTH: 554
<212> TYPE: DNA
<213> ORGANISM: Sorghum bicolor

<400> SEQUENCE: 210

```
atttggacaa acccgatgga actgtagatg cacccgatgg aactactaga tgaagtgtat     60

catatggaat ctcgcttcag tccagttgga catagtgatg tgaacccact agggttttcg    120

cctgatcttt cgatgagagg cgctggataa ctcgattagt gaatggagat gacgttcacg    180

gcccgactac agccctcaag actgcgcctt agcaaccgat acaccacctc caatggctgt    240

cacgatcttg tggagcgcaa cacccggcca ctagggcact cgtcctgcaa gcaatcgaag    300

aaccagcaag aacaagtaga acaagtacta aattaccaga tgtaaatgaa ggtttcaaac    360

tcaatctcta atgaagtggg gtttcgaaaa caagaagacg ggcggctgga tcagcacgcg    420

cgcttacaag caagtagcga aggctaaact ttatctaatc aaaacccagt tgttcatggc    480

ggctctagat gtaaataaat agaggggagg atgaccaaag gggtgctaga gtcgtcctcc    540

aaccctagga tgcg                                                      554
```

<210> SEQ ID NO 211
<211> LENGTH: 3139
<212> TYPE: DNA
<213> ORGANISM: Sorghum bicolor

<400> SEQUENCE: 211

```
gacagatcga gcagaccaac acgaaggtcg tctgcctcct gcggaccaac ctccttggga     60

tacccccgct ccagtcggga caagtcaacc agggggtagt gggcgcgcac catgctgagg    120
```

```
acgtgcgcac cggcaaattc cctggcgtcc ttgacaaact gctgaagcca gtcccacgct    180
cattgcgcct tctcgaccgg ggtcagcctc ggtgcgtagg gctggtcttc tgggagttca    240
gggctgatca agtcgagaac cggggccact cctttccaga tcttgatgca gttggccttc    300
taggagtccc ggtccttgat cagctcgtcg aggtgcttct tagtattgac tttgagcact    360
atgaaccaag caggaagtca gtgcacacac aagaaaagga acgttgagta atcaaaaaac    420
agggtaacac ggttctcacc agacaactcc cgactcttgt tccttagctc ctcgttagcc    480
cggcgcccgg cctccagcgc gccggcacgc tcctggtcga gcttctcctt ttcttgtcgg    540
aggcgtgcaa cctcctcctc caagtctgca ggagcaattt ctggtcaaca aaaatgacta    600
cgtggtaata tagaactgct cggaatgcat gactgacctt tcctttcccg atctctgtcg    660
gctagtcgcg gattgagatc gagcaggcgc tcttcctgag cacccatctc ggccgccttc    720
tcctcggcct ctgaccgaag acggtctact tccgcggaca gggccttatt ctcggccatg    780
atcccttcaa tctggtcgaa gcaccttttc cggtacttcg ctgttttcat tgtgccctat    840
aggaatcaca catattgacg taagcgacaa cgcgtataca tttcaagcag aatggaagac    900
cacttacctt aacctcatca acgagccgct tagctgcgcg ctccaccctc acggcctcat    960
ccgtctccac gagctcctca tgaccaatga aatggtcccc acgttagcgc cacacgtaaa   1020
cgtgctggcg accgtcatgg agcgaccttg gatttcttca acttcgtcgt cggaggccgc   1080
ttagtctcct cgccctctac gcttccctca gctgtggtca taggtatcac tagaccttta   1140
tcctggccag gggagccctt tggcgaagag gtttccgctc ggggttgagt tgcagccctc   1200
ctttcttcag cgggcggggg agtcggggct ctatctccct cctccgcgac actgctcggg   1260
ggaggcgtcc tcatagcctc atcatccctt gtaggggtgc tcattccggt cctcgcctga   1320
gctgggacct cctcgacagt ctctgccatg ctcactaccg agggctgctc ctcggtctgc   1380
tcctgggtgg tctgctgagc ggcatcttcg acgacaacag tcggctcggc cgtcttcagg   1440
ctagcgacgt tgtctggatc aacgtcagac gccgtactaa caaaaataca acattttacc   1500
aatgtcaaaa gtagcagcaa caaaacaaaa aacaaatatg aggaagtgca aaagtgagat   1560
tgaaaaactt acagatcgga gcgcctgtgt gtcgctgtga agaacctcct cctggtccta   1620
ccagtcgccg ccgccacccc tgtctctcca agacgcgtcg gctcggcgtg tggagcagga   1680
ggatcactgg tcacctgacc agtagtggtc ggcacgacgt ctggacgact gcgcggtctt   1740
cggactaaag agggtgcagc ctcctcctcg tcctcgtcgt cgtcagtgat cctaacgagc   1800
tgatgatgtt tcggagcttg gctggtcttc gccggcagcg cctccgtagg agatgggtcc   1860
accgccattg gccttttccc cgccacccta tcctcggtgg tcggggcggg gcggttctat   1920
tcctcttcac tgctggtgta ttgaggacac cgagcagcat cgtcctccgg cgggtccatc   1980
ccagcaggat tttccatacc aggtgccagt gacacgtaca ctgcgcaccg gttaatgtcc   2040
ccaatctgca atagaacgaa cgacaagtca tcaactagga ggcaacagta ttcatatagc   2100
aatactagtc aataacaata tttatttacc ttaggagctg gtcgtcccaa cttgaaggcc   2160
tgcatcggat cactgcttcg aacgatgttg tcatctgata agttgaacag ctcgttcatc   2220
agctgctgga cctccgcctt ctccaaacca tcagggctca ttctggtcgg gttctggctc   2280
cccgcgtact catacgccga gtgtaccctc ctctagcagg gcatcaccca acgcacaatg   2340
tagttcccga ccactcctgg cccatccaag cgggaccagt cgatcaggct catcaggtct   2400
gcaacctgcc cagcgaattc cgggcggtcc gtccagctga ccctcttctc ggggatgtaa   2460
cccacgtcgc agaacgtggc gctgcccggc tcttccctga tgtagaacca cttcttgtac   2520
```

```
cattcggtga gagaagtgtt ccatgggcag ctgaggtacc ggttcttcat cccatcgcgc   2580
agattaaggt atactccacc tgcaatattg gagcctccaa ctgccccttt cttcctcaaa   2640
tagaaaagat aacgaaagag gtcgaagtgc ggctctattc aaacataggc ctcgcacaag   2700
tgaataaagg tggagatgag aagaatagag ttcgggtgca ggttgcagat cccgatctca   2760
tagtaaagaa gaaggccctg gaggaaagga tggataggaa tcccaaagcc cctcttgaag   2820
aaatcttaca aaaacgacaa tctcaccggc gcgggggtcg aggtagcttt ccccttccgg   2880
tgccctccaa ccgccgagct cttggttatg aagcagaccc attccgacga ggtcgttgag   2940
ggacctcgtg ctgctccggg acttcttcca ctccttcgcc ctcagctcgg cccttttctt   3000
cgagtcactc ttcgccattg acgccgaaga aaagactttg agctggaagt taaagatgga   3060
agttgcagga ggcaggaatg gcaagagcag aaggtttgta agcaaaggca gggtaaagaa   3120
tatgggcgct gcattgagc                                                3139
```

<210> SEQ ID NO 212
<211> LENGTH: 309
<212> TYPE: DNA
<213> ORGANISM: Sorghum bicolor

<400> SEQUENCE: 212

```
gatggtagtt cttggtgaag agactcaagt ggaatcttgg ttctgtctgt ttggagatag     60
ttctaatcct gacgcaagat aggtggacag tttgcatgga acataccata tgctcagaaa    120
tcaatttgga caaacccgat ggaactgtag atgcacccaa tggaactact agatgaagtg    180
tatcatatgg aatctcactt cggtccagtt agagatagta ttagtttcgg tacaagatag    240
ttgcatggtt tgtgcccagt gcaccatagg ctcagaaatt gttgtggatg ttcccgatgg    300
tactcctac                                                            309
```

<210> SEQ ID NO 213
<211> LENGTH: 1222
<212> TYPE: DNA
<213> ORGANISM: Sorghum bicolor

<400> SEQUENCE: 213

```
aaaaaatgtt ttcatacacg acttttaata attctaaaga taatccgtct taaccctaaa     60
cctcctatgg ccaaaatttt tttttgctct ttacactaat ataatggatg gatcaagacc    120
tgtgcaactc tttttctcgt tgaatccggt gcatctgttt tttttgtttt gttcgttggg    180
cctgcttgac gagagaatga cataatccat gtaagaagct aataaacaag ctaatactac    240
tagaacctag caaaccagta ttgtatgcgt acacgataag gaaagctagt cctgcacact    300
gtatgtgtcc atctataaat agcgagctcc cctgctgccc tagctagacg catcctatgt    360
gccgccgcta atctcgccgt ccgctgctcg gaatctcatc gagctcgcaa acccactgcc    420
ggtgctgtag atgccttcca caactgccag ggtgagcaag cgccttcatg tcatcgcctt    480
ggatcacacc atcgagaagg agttctctcg tcattcgtca agtgtagcaa attccactgc    540
tgaaactatg gcacctcatc tctacagcat gtggcattgt gcagcaaatt cctcaagtgt    600
atatgcctct gtacgcccct acaggttctg atcatgaccc cttgcagatt gatcatcaaa    660
taaactgact attatcttcc ggcccaataa attcctaaag ctttaatcca ttagctctgc    720
ttatctgttc aggttacatt agttttaagt cttggactat gtgataacat tgtcgttcac    780
aatatcgtat gtttatgtgt ttattacaat taaattttaa tttgattaat atactaatat    840
```

```
tagctttcta attaaaagcc aagccacata ggatattttt aatattggtg tacttctgaa    900

ttataatttt gtttagtatt aacacatact gtgacatatt agttgctatc accatgtttt    960

tgaattatta attgtttagt ttaaaacgac atcataagca gatcgtttag gtgtttcacc   1020

tatcctttta tttggcaaag ttagtgtata atttgtttaa atatacaata atatttataa   1080

gtaaaatata actagatttt acttggcttt caaactaaat taagatttat ctaatttaaa   1140

ttaaacctct ttatgatttt gtttaactaa aaataaaatc aagtttgtag ttgctccttt   1200

tataaaataa actcacgata tt                                            1222
```

<210> SEQ ID NO 214
<211> LENGTH: 1091
<212> TYPE: DNA
<213> ORGANISM: Sorghum bicolor

<400> SEQUENCE: 214

```
tataatgacc gacgtaagga cgacacagat cccatgaata agctgctaac ctgagtcctt     60

gaggccgctc ccactttgag ccgttttgcc atcgaaggct gggcctgctc gagcgtccgc    120

ttcaatctga ggaaagaggg acggacataa agaaaaccgt tatatgagaa aacgcgaaga    180

atcaggagaa taaaaatcgc aacgtcgaag aacttacccc acaggaagaa cggctcgcct    240

gccggtacct cgaccggtgg gcctcgaacc accccgcgtc aaggccccgg gctcctcgag    300

agcaggcgca ggcctgggcc cagtgactcc cgcctggcgg gcgccaggac tggcgcttcg    360

gcggccggtc tctcccttct cggaggccgc agcgcgaccg cgggtcaacg gcctcgtcgc    420

ctggggctta gcttggccac ccgcctttgg cgcaggggga tgttgggggc gcggggcggc    480

ctgactggtc gtgggcgcag gaggggtgtc agtacggggg cggtgagatc cgcctggtcc    540

ctcctttggc gctcccatcc gcggggcgtc gatgtcgcct cgaggcggac cctcgaggat    600

ccggtcgagg cgagacgcca tcccctcgga gtcgtcgcta tcgtcgtcgc cattcccacc    660

atcatcctca ctaggggatt cttcttcagg ctcacccctc tgcctagatt tagctcgacg    720

cgcctctagc acttggcggt cgaggttctt cttccttttc cctttcttct cagagtcctt    780

ggtggacttc agtttctcga cggactggcg ccgtttgtca cggtcgacct cgtcctcctt    840

tacagggggc ctcaaggatc ggacatcaat gcgtccctgc cagaataagg taggcttaaa    900

aaggatcgaa agaaatccag aattgaagct gtgtacgagg gaagagcatg ccaggtcgat    960

cgaaccctcg tcgggcctca tagggaagcc attgacgtgc tccgacttaa agtcgccggc   1020

aatggccgcc ctaacccggg cagcggtctc gttgtccgcc agggcctcgt tagacatccg   1080

gcatgcctcg a                                                        1091
```

<210> SEQ ID NO 215
<211> LENGTH: 841
<212> TYPE: DNA
<213> ORGANISM: Sorghum bicolor

<400> SEQUENCE: 215

```
cccactgtcc tgctagagcc ctccccaaaa ggtgcacgga agcatggagc cacgaagtca     60

accggtggta tctcaccacc atgaggacga cgaaggggat ccacgttccc gtagcacagc    120

tggtgaatcc tggtgggaga ggctcgcagt ccaagcacct ctctggccct ctgagctgtc    180

actctgtagt ctgtccccgc cagtgcgtag tggatatagc tgtgatctgg agaaacccac    240

actgacgcgt agaactctct gacccactgc tcacagtaag tgccggggag tgctagtaac    300

tctggaagtc tgtggaggta ggtgaaatac tgacgaatgt ctgctcctac cacgttcccc    360
```

```
agtatctcta ggtcgatcac tctgtgctcc ctgaactggg cctgagagcg aaccagtgcc    420

tcgtagatgt cctcctggac gactgtgtag aacctggcac cggctctagg atccctggca    480

gctggaaacc aggtgggaaa cggaacgaac ctcagctgct ggatctctct ggctgacaca    540

agagagagat ccctgtggat cctgactggc ctcgggcgtg aagctggtgt gcctctcgct    600

ggtgtggcac gagctgtgga agtgtactga cccggcgtgc cggtccgagg aacggcctgg    660

gtacgagcac gagtcgacct cctgagtggc tgctcctgct cctgctcctg tgctggaccc    720

tctgcctggg tctctgtctc agtgtctgga tcctcctgag ctggatccct gaccacaagc    780

ttaacctctg tcctccaatc gtcacggtgc ctggagggga tccgtggaat gcctctgcct    840

c                                                                     841
```

<210> SEQ ID NO 216
<211> LENGTH: 638
<212> TYPE: DNA
<213> ORGANISM: Sorghum bicolor

<400> SEQUENCE: 216

```
acaaatcagc aatattgtag catcatcagt tttatgacat ggtataaaat gtgccatctt     60

agaaaatcta tcaacaacca caaacacact atcacgtccc ctcctagtcc tcggtagtcc    120

caacacaaaa tccatagata tatcctccca aggagcatta ggaacagaag aggtaaatac    180

aaaccatggg gatttaaccg tgactttgcc ttttgacatg ttgtgcaacg agcaacaaac    240

ctctccacat ctctcttcat ccttggccaa aagaaatgac cagcaagtat gtcctcggtc    300

ttctttgctc caaaatgtcc catcaagcca cctccatgcg cttcctgcaa caacaacaaa    360

cgaacagagc tagctggaat gcatagcttg ttagctctaa acacaaaccc atcactaacg    420

atgaatttat tccacccttt tccatcttta caatgcagca acacgtctct aaaatcagca    480

tcatgaacat attggtcttt aattgtttct aacccaaata tcttgtaatc aagttgattc    540

agcaaagtat atctccgtga taaagcatca gcaataatat tttccttccc tttcttgtgc    600

ttaataatat aaggaaaaga ttcaataaat tcaaccca                            638
```

<210> SEQ ID NO 217
<211> LENGTH: 996
<212> TYPE: DNA
<213> ORGANISM: Sorghum bicolor

<400> SEQUENCE: 217

```
cggaatcgtc ttgagcggcc cgctgttgtt gttagtattg tcttttgagg acacgacatt     60

cttccaccgt gtgattggac ttgggatgga gttggcacgg tcccttcaac gtcttgttgt    120

agtcctcctg gtagtctcgt cgcccattgg ggcgcttgac cgtattcacc tcgtggtcat    180

ggtcacgagg gcgcttgccc cggaagtcat cacgattgtc acgccgcctg tcccaacctt    240

ctctatggtc gcggttgtca gtgcgacgat ggttcctgtt gtcaaaacgt ccacgactgt    300

tgtctcgtcg acgaggctgg tcgggacctc tcgcatcttc ttggatgagc ttttctgcgt    360

catcagcgtc agcgtagttt tgtcgtggcg aggagctcgg ccatcgtggt cggccttttg    420

cacagtagct tattccttag tgctttgtgg aagcatagcc ctttgatgaa ggctgatatg    480

gcctcatcct gagaaatttt tggaacctta aggcgcatat ccgagtaccg tcggatgtaa    540

tcacgcaaag gctcgttttc ctgtccctta ttctctcggg atcgtacttg ttcctaggct    600

gctcgcaggt agcgatgaaa ttgtcaataa acgcctggca cagttcttcc caagagtcaa    660
```

aagagtcctt gggcaggccg aggagccact gatgggcatc ctggtcgagg acaactgaga 720
agtaatttgc catgacgtgc tcgtctcctg ctgctgaccg aactgcaatc tcgtagagag 780
tgatccagtt ttcagggttt tccttgccgt catatttttt aagcttctcg agtttaaagt 840
tgtggggcca tacggacttg gcgaaggtgt gaagaaaatt gtcttagtcc gtggcacgcc 900
ggttgatacg gtcgcgggcg tccttgggag ggatgttgta tcgtagatcc ctgtcctggt 960
ttacttcctg accacaccca cacttctgct cgcggt 996

<210> SEQ ID NO 218
<211> LENGTH: 379
<212> TYPE: DNA
<213> ORGANISM: Sorghum bicolor

<400> SEQUENCE: 218
ttggcgcgcc aggtaggggt cctgcgtgtt tttcatcgat ttcccactcc tttccagatg 60
gcagctcacg cctcgccgat tccgtgctcc acgatgattt ggtttgggag tctcgagttc 120
atgtctacgg gctccggcta cgacatgatc ttgctctcag tcaaaggacc aggaggagcc 180
cgcgttgcac cagcacggtt gagggccccg agacgccctc gccaccacgc ctccccgccc 240
aaaaagaggc gcggacagca ccaccccgc ccctatgcct catcacgacc ggcaactcgt 300
gcgaggcagg aggcgggcca cgagccggca gcaccatgtg ccggaaccac gggcacgacg 360
gctcaacacc gcacgacgg 379

<210> SEQ ID NO 219
<211> LENGTH: 1139
<212> TYPE: DNA
<213> ORGANISM: Sorghum bicolor

<400> SEQUENCE: 219
acaagatggt catcattcca gctccgcgac cgtggctgaa ggcctcacgt tcaccgtcgg 60
ccagattacg tggacgactc atggcagcgg cctcacgacc atgacctcgg aaggaactca 120
gatccgatct gggacagcag gggcgtcaat tccgatcacg ccggcaccga gcacccgacc 180
tccgctccct cgttacaggg gaaaaaaggt caacgacttg gatcttttct gagcgcttga 240
tcgtgtcgat cttaggctcc ttgaagcttc caaactggta gattggatct cgtgcctgtc 300
agatcaagcg gcgttgacaa actctttcga ctcctgccgg ccaacttgtg tcatcacaca 360
cgaacagctg gggacgtctc tgacaataac gtccaccccc acgggtcggt tcgtcaagct 420
gaagacagct caagactaga gtcctcctta tggactaaac aactcggccg atcactactc 480
acggcacacc caatcccttt tcaacagggc gagctagtcg ccgagacaga gcagccgagc 540
agctcgccat tacgtcaaca tggtatcaat ccaagtagta ccgaacgatg aggctgccag 600
tacgaactcc agcacagggt ctgtccctac cgaggttcta aacttcgagg acgaagatta 660
cgacctagat ttaacaccgt atcctccggg cttttctcgc ttcccagtct ttccacctcg 720
gcggggagat cttattttca atgtcagcaa tgatgccagt tgtcgacgga gaaacagacg 780
agcagaagca gctccgtgaa cagcgcaata ccgatcgcgc tcggcggcgc gcggatgagg 840
aacgacagct tgcgccgcac aacctcaatg acggtttcga catggtcgga gatcagccag 900
tctacaagac gccgagtgct aacgtgggca ttgctatggc aaacctggac cgactccctg 960
atactcctga gtgccagggc gtccgatcca gtatacgtgc acacctgatc gccgcgatgg 1020
gacagacagc caccttgctc aaaaggatcc aagccatctc ctacacagag gtctcttccg 1080
accagactca tcgcatccgg acttcaccac aacccagcga gcgccaccgt agccgctct 1139

<210> SEQ ID NO 220
<211> LENGTH: 181
<212> TYPE: DNA
<213> ORGANISM: Sorghum bicolor

<400> SEQUENCE: 220
ctaatattga tgtaagatag gtgcacgaat tgcatcgaac gtaccatatg cttagaaata 60
tatttggacg cacccaatag aactcctaga tgacgtgtgt catatagaat ctcacttcga 120
tctctttgga gataatgtta gtttcggtgc aagataggtg cacggtttgt gcctaatgca 180
c 181

<210> SEQ ID NO 221
<211> LENGTH: 392
<212> TYPE: DNA
<213> ORGANISM: Sorghum bicolor

<400> SEQUENCE: 221
ctatcatagg gacacttggc gatgagatga tccttgctat ggcatctaaa gcacctcatg 60
gaatggtcat tcttcttgga ggagttcttc ttccttcttg cctgatagcc cttcttcttc 120
ataaacttgc caaatctctt gacaagaaga gccatctcct catcttcatt actatcacaa 180
gagcttgctt cttcttcact tgatgactct atcttggctt tgcccttgga tgaggaggcc 240
ttgaatgcca cacttttctt cttctcatca tccttcttct caccatcctt cttcttcttc 300
ttgatcaact catcgttctc atcatcttct ctataagcat catcggtcat cacttcttga 360
aacacttgtt ggggagttga ttcactaagt gt 392

<210> SEQ ID NO 222
<211> LENGTH: 706
<212> TYPE: DNA
<213> ORGANISM: Sorghum bicolor

<400> SEQUENCE: 222
tttctcaatg gatatataaa tgagttggtt tatgttgatc aacctccctg tcacacccat 60
attttaagaa caaaatagga tgcataaaag actcatatgt gccccaggaa tagtcacaca 120
cataagtaga caaatctcaa atgtaccatt gcagtgttta ttacatagtg gaacataata 180
aataacatag tctcatacaa atatgatagc ataaaacaaa caacgctctc gacggaagct 240
ccacataggg acactgttga ctggttgact ccaaacctag tactcataac gatagtcctc 300
attccagtca ccttcattat catatcctga ggtgttggga aattgcaaga gtgagcacat 360
atcgtactca acaagtataa tcaagggttc atgaggctca aatagctgac actggtttga 420
ctgcatttag cttttaatag tggataacat gtttaatcat tggatagcaa atatcaaggt 480
agcataatta atcccataac cacatgatca atgtatacaa gaattaagaa taacacatat 540
aaacaacata ataaaccatc atttaatatc attattcacg ttcatcagtg tccatctatt 600
ccgtcagttt tctgggccac ccgtatccgt gggcacggct agtataccag ttttacactc 660
tgcagaggtt gtacatcttt acccatgagt cgtgatttac cctttc 706

<210> SEQ ID NO 223
<211> LENGTH: 457
<212> TYPE: DNA
<213> ORGANISM: Sorghum bicolor

<400> SEQUENCE: 223

```
gaggccgaat acattagtgc cgatagttgt tgtgcacaat tgctttggat gaaagctacc     60

ttgaatgact ttggaatcaa atttaagaat gtgcctttgc tatgtgacaa tgagagtgca    120

atcaagatga cacaaaatcc ggttcaacat tcaagaacca agcacattga cataaggcac    180

catttcataa gagatcatca acaaaagggt gatataagca ttgaaagcat tggcaccgaa    240

gatcaactag ccgacacctt cacaaagcca cttgatgaga agagattttg caagttgaga    300

aatgaattga acatacttga cttctccaac ttgagatgag tgcaccccta tatttatata    360

tgacatgcct ctcctccaac aaagcaaggt aaagatggtt gacatagcat tcatactttg    420

ctaaggacat gtttagaaca tatagacatg cttgcat                             457


<210> SEQ ID NO 224
<211> LENGTH: 506
<212> TYPE: DNA
<213> ORGANISM: Sorghum bicolor

<400> SEQUENCE: 224

agccaatcgg gatgatacac ttctttaatg aatccggctg ctagaagccg cgttatttct     60

atcctaatag cctccttttt gtcacgagcg aaccgtcgta gcttctgctt gataggtctt    120

gcggtcttcg agacgtttaa ggagtgctcg atcaggtttc atgggacgcc gggcatgtct    180

gcgggtttcc atgcaaaaac gctcatgttg tcccttagaa acctgacgag cgtgtcttcc    240

tatttagggt ccagattggc cccgatgaga gccgtcttct cggggctgcc gtcgaccagc    300

tgcacctcct tgtgctcttt ggactttgaa tttttcctcg ggtctcccta ctcgggtagt    360

ggaagctggt tgggtggaaa ctgcgtagct tgggctacgg tttttgccat gcgaatcgag    420

agatcgattg cctcagtgat cttgaagctt tcctcctcgc aagtgtatgc gatatagaca    480

ttgtctctga cagttaggac gccctt                                         506


<210> SEQ ID NO 225
<211> LENGTH: 344
<212> TYPE: DNA
<213> ORGANISM: Sorghum bicolor

<400> SEQUENCE: 225

cgaaacctcc gcacaaaacg agctaatcag aaccttccac cactggtgtc gacagcgttt     60

ctgcgaatta ggcaatataa cctttgaagg agtcaacaac tcctccaagg gttcgggggc    120

taccccgtgg ggtcgctcgc acgcccccac ggaaacccga ccaaggaata cagcctccat    180

tcgagtgcca gcgctcaaat ggagactcgg gggctactgt cgagggtatc agtaaggggt    240

atcctaactg atgcacataa cgagattacc tatacacaga ttgaagtcct caactcggcg    300

ttctaatcag ccatacggtc atcgacggcc gcagcctcga agtc                     344


<210> SEQ ID NO 226
<211> LENGTH: 127
<212> TYPE: DNA
<213> ORGANISM: Sorghum bicolor

<400> SEQUENCE: 226

gtctttgagg ctgcggccgt cgatgaccgt atggctgatt agaacgtcga gttgaggact     60

tcgatctgtg tataggtaat ctcgttatgt gcatcagtta ggatacccct tgctgatacc    120

ctcgaca                                                              127


<210> SEQ ID NO 227
<211> LENGTH: 596
```

<212> TYPE: DNA
<213> ORGANISM: Sorghum bicolor

<400> SEQUENCE: 227

```
cctctccgac acaacctata gctggtcctc ttactcgtgc tcgtgcccgt caactcaacc     60
ttcaagtaag ttcatcttta aactcttgtc aatcatatta ggcaatggag acacgtgcac    120
tttcgtgttg ctcaggaata atggacaaga tcagcaaggg aaggttcaac tgcattcaga    180
atttgaggca acaccaactt caagggctga ttgcatatgg gaagagtgat aacttaacaa    240
aggtgattgg agatcaggtc caagcctcca caacatcctc tatcaagtta ccacgtcgct    300
tctaaagcaa ggaaacaaag agtccaaacc caacacgttt tgggagttgg attcggactg    360
gaaaataact ctaacttgta tggatcacca cggcgtcata tggactccaa ctgggacgtt    420
cctatacttg ttggaaagct catgaagtct actttccaat gggtccaacc acatatctat    480
gcagcttatg agtcgggcgc agtccttgtt ttcgtgccga caccttttc tgttttggtg     540
ctgcgtcacc ctattttgga ccaatggccc atgtatcaag ttgagtccat taggga        596
```

<210> SEQ ID NO 228
<211> LENGTH: 493
<212> TYPE: DNA
<213> ORGANISM: Sorghum bicolor

<400> SEQUENCE: 228

```
aagtagatgg attgacgacc aaagaggtgt tggggttgtc ctccaaccct aggacgcgtc     60
cctaatggac ccaacttgat acatgggcca tcagcccaaa atgaggtgac gcagcaccct    120
ggacagcaag acctatcgac ggtaattgga tcattgtcgc tgctgccgaa caggtattga    180
cgtgggactt gattcataag aaagtagact tgataagctt tccaacaagt cctgaagcgc    240
ctgaatctga atccgtatgc aaccgtggta acggtcacaa gttggcgctt tgctgctgtc    300
cgaatccagc gagcgtgagt ccttctccct ttcggtcttc tccttggttc ctaatcaaaa    360
cagagtgcac gcatttccat tgtctaaaca agatggacac gagcttatca aggaactcac    420
ttgattatta agttgacgaa cacgagcacg agtaagagga ccagctattg gttgtgtcgg    480
agaggatgta tcg                                                       493
```

<210> SEQ ID NO 229
<211> LENGTH: 913
<212> TYPE: DNA
<213> ORGANISM: Sorghum bicolor

<400> SEQUENCE: 229

```
ctggtgttga tgtcctcatc atcctccctt tcttgcattt gagtcatcct cgactcaagc     60
tcatcttcct cacccaaata aggcttcaaa tctgcaatgt taaatgtggg actaacccca    120
aaatctgcag aagatcaagc ttatatgcat tctcattaat tcgttgcagc actttaaaag    180
gaccatcagc tctaggcatc aatttggatt ttctcagttc tggaaatcta tcttttcgca    240
aatgcaacca aaccaaatcc ccaggttcca gaatcaattg ctttctacct ttatctccag    300
cgcatttgta cttagcattc atgcgctcta tgttttgttt agtggcttca tgcaatttta    360
acatcaattc agcacgttgc ttagcatcaa aatttatttt ttcagaactt ggcaaaggca    420
ttaaatcaat aggagcacgt ggcaagaagc catagacaat ctcaaaagga cacatttttg    480
tagtagaatg caatgaacga ttataggcga actcaatatg aggcaaacat tcttcccaca    540
tcttaatatt cttctttaaa acagccctta acatagtgga taaagttcta ttaacaactt    600
```

```
cagtttgacc atcagttttg gatgacaagt ggtggaaaat aaaagcttag tccccaattt    660

gaaccacaaa gtcttccaaa aatgactaag aaatttagca tcacgatcag aaacaattgt    720

gttgggcaca ccatgtaagc gaacaatttc tcgaaagaac aaatcagcaa tatttgtagc    780

atcatcagtt ttatgacatg gtatgaaatg tgtcatctta gaaaatctat caacaaccac    840

aaacacacta tcacgtcccc tcctagtcct tggtagtccc aatagaaaat ccatagatat    900

atcctcccaa gga                                                       913
```

<210> SEQ ID NO 230
<211> LENGTH: 943
<212> TYPE: DNA
<213> ORGANISM: Sorghum bicolor

<400> SEQUENCE: 230

```
ggacgggttg gactggaggt aatatatgcc tagcacttct tgtatcctga gaacgtcctt     60

cgtaactcct tcgctcctct gataactctt actagtaaac tggagtggtg ggaaatagca    120

agagtgagca catgtcgtat tcaacaagta taaccagggg ttcatgaggc tcaattagct    180

gacactggtt tgactgcatt tagcatttat ttgtatgtag catatttatc attttgtagc    240

atcaacaaca aggtcgctta taatctcata accacatgat caatgtatac aagaattaag    300

aataacacat ataaccaaca taataaacca tcatttatca ttattaatca tgttcatcag    360

agtctatcta ttccgtcagt tttccgggcc gcccgtatcc gtgggcacgg ctagtatacc    420

agatttaaca ctctgcagag gttgtacatc tttacccacg agtcatgatt tacctttttcg    480

cccgaggccc gtagacctct tagctcactt ccaaggaaag ccggcagggt tcactatgaa    540

gcctttcaaa gtttcgtcta acaagttagg gccgcttggt ttcattagtc agtccatgtg    600

attcacctgc gggaatccac ggtctgctat tccccaattg cgccacatgg gtaaccgcta    660

acgagctaga aagttactca tacttgacta aagccagagc catatagccc tcaaggttgt    720

acgagttgtc ccagcttttg ccaagggata agtccttatg gagggtcaag atcattccag    780

caaaagctag agttctttcc accctttata ttcaagttgc tagaaagctt attttattgt    840

ttattgtata tccaaacatt catgttacaa gatcatggat tataatcaag cactagcaag    900

aactacccaa atgcatatcc aaataggtaa caaggaattc agg                      943
```

<210> SEQ ID NO 231
<211> LENGTH: 1130
<212> TYPE: DNA
<213> ORGANISM: Sorghum bicolor

<400> SEQUENCE: 231

```
ttcactttcc gatctctgac cggaagttcc gatggaactt ccggtgggtc tgagtctctc     60

acaatggtca gatctgcttg gccacaacgg tcagatctgc ttggatcgag gctccaacgg    120

tcagatctgg tcagaccgga agttccggtc ccaggcaccg gaacttccgg taccacacta    180

taaatactcg tttcccttgt ttccaactgg ggactttgca tagaacacat tttctgactt    240

ccggtggctc ttccaaagag tagagaaagc tctcccctcc tcctctctca ctccctaagc    300

tttgtgctcc attcaagtga gagattgagc tctagtgata gatctgagag cttcaagagc    360

atctcttccc tctcctctcc atccccatag cttggtgctc tttggtgaga ggatttggga    420

aaccctagtg ttgtgcattt gtgatttcat tcttgtggca ctaggtggtg attgcaagtg    480

tggatttctt gttactcttg ggtgtttccc gacgccctag acggcttggt gcaagggagg    540

tgttgagctc gtgattggag attgtttcga gcctcaccaa gtgatttgtg aggggttctt    600
```

```
gagccttccc cgcaggagat cgcaattggg tactctagtg gattgctcgt ggcttggagg    660

atccccatct tatgagtgga tgtgcggcac ccgctgaggg tttggctttg gattgccaat    720

tagctcgtga tccatcaagt gggtgtatcg ccataacaag gactagcttg ccgggaagca    780

agtgaacctc ggtaataatc ttgtgtcatc tcttgccgag gactctcttg tgattgtgag    840

tgattggttg gatatatctc tactctacaa cgttggtata acaatcacta tccactcctt    900

tacttacttg tttatcttgc tagttgttta gcttgtttag tttagtcttc tttgtttagg    960

agtgtagcaa gtttgtagtt gtgctttctt gttgtaactt gtgtttagct ttcttgctag   1020

acttgtgtag gtggcttgca tagcttagtt gtgctagtgc tagaatagct tcaccttttg   1080

ttttactaac caacttgtct agttgaagtt tgtagaaatt ttaaataggc              1130
```

<210> SEQ ID NO 232
<211> LENGTH: 788
<212> TYPE: DNA
<213> ORGANISM: Sorghum bicolor

<400> SEQUENCE: 232

```
ctcttgagga gcagaaaaag aaagaagagg aggaggaaga gcgggagcgc gaggcaacgg     60

ggcagccgta ggatcagcag cagcaacagc agcagcaaga gcagcaatag cagcagcaag    120

atcggggggg ccaagaggta ggaccgctcg agcccccgcc tcaaggtctg gcccaaccag    180

tactaccggc gccgcaagag cccggcgagc aggaggaaga tttgccagta tacggccctc    240

cgactccagc gtggctcctt ccgggggcgc ctgccgcgat ccgggcagag tcgggacgag    300

cggacggagt ggtggcactt gcgtgcatga tgcacacccc cgccgacccc gagtccgaga    360

tcaggagggc gatctacggc ttggacggga tcgccccagg gttcctccgg gagcgccggg    420

catgggagga ccactttccc tctgaggaag acgagatcgg gtcgtcgggg agtaaggacg    480

gtacctggaa gacggtggac gacgacgggc ggttcccgtg cctcgtcgac ctgttcttgc    540

gccacggggg ttccctcgag accgtcgaga acctcatccg cggcatcaag gcgcgggctg    600

atcgagagat ggagaactgg tgccccgatc ggattcgtat ccgggcttcc accgatccgt    660

ccgagcccaa catcttcctc gacgacaaga aggaggccga gaagtgggaa catgtcgagg    720

agctccgcct ttggatgaag cacgtggtgg ggctcgttat cggacatcat caacacgcgc    780

tcgggccg                                                             788
```

<210> SEQ ID NO 233
<211> LENGTH: 1304
<212> TYPE: DNA
<213> ORGANISM: Sorghum bicolor

<400> SEQUENCE: 233

```
ctttgcatgc ctacgattca gttttccttg actacgaata tgtttcaaag attcatgatc     60

agaatggata ataaactctt tggccacaa ataatgctgc catgtctcta atgttctaac    120

aagagcatcg agttctttat cataagttga ataattgaga acaggcccac tcaatttctc    180

actaaaatat gcaataggtt ttccctcttg taataaaaca cctcccaaac caattccact    240

agcatcacat tcaagctcaa aagtcttatt aaaatcagga agttgtagga gaggtgcatg    300

agttaactta tctttcaaca tattgaatga attctcttgt gctttgcccc aatcaaaagg    360

cacccccttc tttgtaagct cattcaatgg tgcagcaatg gtgctgaaat ccttcacaaa    420

acggcgatag aatccagcaa gtcctaggaa actccgcacc tgggtgatag tatttgggac    480
```

```
aggccatccc tgtatagctt ccaccttggc ttgatcaacc tcaattccct gtggagtcac    540

aacataacca agaaaagaca ctcgatcggt gcaaaaggtg cacttctcaa ggttaccaaa    600

taaacgtgcc tcgcgtagtg cattaaaaac agcacgtaaa tgatcaagat gttcatccaa    660

tgatttgctg taaatcaata tgtcatcaaa atatacgaca acaaatttcc caatgaaagc    720

acgcaaaacc tcgttcatta atctcatgaa agtactaggt gcattagtta acccaaaagg    780

catgactaac cactcataca aaccgaactt agttttgaaa gcagttttcc attcatctcc    840

caatttcata cgaatctggt ggtacccact acgtaaatca acttttgaaa acacaacagc    900

accactcagt tcatctagca tatcatctaa tcgtggaata gggtgtcgat atcgaatggt    960

gatattatta atagctctac aatcaacaca catacgccat gttccatctt tcttaggcac   1020

taaaattact ggaacagcac aaggactaag agattctcag acataacctt tgtctagtag   1080

ttcttgcact tgtcgctgaa tttcctttgt ttcctccggg tttgtcctgt atggtgcacg   1140

atttggcaaa actgctccag gaataagatc aatttggtgc tcaatcccac gtagtggagg   1200

cagccccgct ggtacctcac ttggaaacac atcagaatac tcctgcaaaa cgttagcaac   1260

agcagggggc aaagaacatt gcatatcctc aattgaaatc aaag                    1304
```

<210> SEQ ID NO 234
<211> LENGTH: 151
<212> TYPE: DNA
<213> ORGANISM: Sorghum bicolor

<400> SEQUENCE: 234

```
cgtacttcct aggacggtcc gagtttgggc ctctcttaag gtagcagata acttcgtata     60

atgtatgcta tacgaactta tgcggccgct ggatcatgaa tctttgaaac atattcgtag    120

tcaaggaaaa ctgaatcgta ggcatccaaa a                                   151
```

<210> SEQ ID NO 235
<211> LENGTH: 408
<212> TYPE: DNA
<213> ORGANISM: Sorghum bicolor

<400> SEQUENCE: 235

```
gcaactccaa cccacctcct aaacaagtcc ttattctaaa tctagggact tgattcaaaa     60

aaatcaactc caacccacct actttgatga ggacatcaac accatcaata tatccacacc    120

tacaccagtt ttaattgatg cgaacccgct agggtttttg gcctgatctt tcgatgagag    180

gcgctggata actcgattag tggaaggaga tgacgttcac ggctcgacta cagccctcaa    240

gaccgcgcct tagcaaccga tacaccacgt ccaacagccg tcacgatctt gtggagcgcg    300

acaaccagcc cctagggccc ccgtcctcca agcaatcgaa gaactagcaa gaacgaggaa    360

acaagcactg aatttgcaag atgaattgac ggttttaaac tgaatctt                 408
```

<210> SEQ ID NO 236
<211> LENGTH: 111
<212> TYPE: DNA
<213> ORGANISM: Sorghum bicolor

<400> SEQUENCE: 236

```
caatatctcc aaacagatcg aaccgacctt ccacttgagc ctcttcacct aggattatca     60

tcgggagctt cgataatggt ttctgagcca tggtgcaata tgcgcaaacc a             111
```

<210> SEQ ID NO 237
<211> LENGTH: 107

<212> TYPE: DNA
<213> ORGANISM: Sorghum bicolor

<400> SEQUENCE: 237
aactatgtcc aaacacacag aaccaagatt ccacaaaata gtttcttagc ctatggtgca 60
ttaggcacaa accgtgtaca tatcttgcac cgaaactaac actatct 107

<210> SEQ ID NO 238
<211> LENGTH: 182
<212> TYPE: DNA
<213> ORGANISM: Sorghum bicolor

<400> SEQUENCE: 238
cgatggtact cctaggtgca cggtttgcat ggaacatatc atatgctcag aaatcaattt 60
ggacacaccc gatggaaatg tagatgcacc cgatggaact actagatgaa gtgtatcata 120
tggaatctcg cttcggtcca gttggatata gtattagttt tggtgcaaga tagttgcatg 180
gt 182

<210> SEQ ID NO 239
<211> LENGTH: 245
<212> TYPE: DNA
<213> ORGANISM: Sorghum bicolor

<400> SEQUENCE: 239
acttcgatct gtttggagat agtgctaatc ttgatgcaag ataggtgcgg gatttgcatg 60
gaacatacca tattctcaga aatcaatttg gacgcacctg atacaactcc tagatcatgt 120
gtttcatatg gaatcccgct tcaatctgtt tggagatagt gttagtttag ttgcaagatt 180
ggtgcatggt ttgcgcataa tgcaccatag gatcagaaac cattatgcaa gcacccgatg 240
ataat 245

<210> SEQ ID NO 240
<211> LENGTH: 483
<212> TYPE: DNA
<213> ORGANISM: Sorghum bicolor

<400> SEQUENCE: 240
tggagtcttg cttcagtcga gttggagata gtattagttt cagtgcaaga taggtgcata 60
gtttgtgccc agtgcaccat atggtcagaa accattgtgg aagttcacga tggtactcct 120
aggtgaaatg tcctaatatg gctagagggg gggtgaatag cctattcaaa attctacaaa 180
ttcactagag cgagaggtta gtaagtaaca aagcaaagct ttttgctcta gctctaaaag 240
gggtgtttgc aagccaccta accaacaatt ctagttgata taatcactag gcacacaata 300
gctatgtcac tacttacaca agagagctaa ctaaaatttt tatactagta agtaagctac 360
tctaacttgc gggaatgtaa gagagatggt ttgatcttta taccgccgcg tagaggggat 420
aaaccaatca ataaaatgaa gtccaatctc cgggagaaat ccaatcaaca aacacaatgg 480
aga 483

<210> SEQ ID NO 241
<211> LENGTH: 470
<212> TYPE: DNA
<213> ORGANISM: Sorghum bicolor

<400> SEQUENCE: 241
gagaagttat tcttgtgaga tactttctat gtgtgctact tcatcatgca tcatgtttac 60

```
ttttatgcat tgcacttatg tgagatacct tggttgtgag acatgacttg tggttattat    120

gatatcttag tgtcatgtgt tttggctcac attacctttg cttccgcgtt tctactccgt    180

tgtaactatg agccttttg tttataccct gttgtatatc actcacatat ttggatgcag    240

gatattggtt ttggttgata taagcatgac taatcccttt gttcttattg taaaatgctt    300

attgaaacca attctattta aaaacctcaa ctctttttat acacgaggtt gtcatcaatc    360

accaaaaagg gggagattga aagagcatct aggcccctag tgatttcggt gattaatgac    420

attattgatt actatgacta acgtgtgttt tgcagagaca aagtcatacg              470
```

<210> SEQ ID NO 242
<211> LENGTH: 748
<212> TYPE: DNA
<213> ORGANISM: Sorghum bicolor

<400> SEQUENCE: 242

```
acgacggaat agtttgaatc tcgtgagcag gcacatgggt cctcttggca aagaacaggc     60

atcattcgca gtgtcggacc agtttctcgg cgtcggcaac cgcggttggc caggaaaagc    120

ctgctcggaa ggccttcccg actagtgttc tggaggcagc gtggttgccg caggacccga    180

cgtgtatgtc atctaagagc ttgacgccat catcttggga tatgcatttc agcaacactt    240

ctgagcttgc attctttcgc ataagtttac catcaaccag tatgtaattc ttagaccgcc    300

ggaggaccgc tcgttctccg ttttatcttg aaaacccgat ccatccgata tatacttgat    360

gaagggagca cgccaatcat ggctgctggt tgtcggattg gtatcgtcta tgagcattgc    420

ctcattggat tgcttttcga ccaggtctgt accaacactt ggcgcgtgta tgtcttgaac    480

aaaaacgcct tgcggaatct gggcccgaga tgaccctatc tttgacaaca catctgctgc    540

ctggttccta tcccgaacca cgtggatgta ttctatgccg tagaaattgg attcccattt    600

ccgaatttct ttgcaataga ggtccatctt ttcgtgggtt atgtcccatt ccttgtgaaa    660

gagcatctag gcccctagtg atttcggtga ttaatgacat tattgattac tatgactaac    720

gtgtgttttg cagaggcaaa gtcatagg                                        748
```

<210> SEQ ID NO 243
<211> LENGTH: 364
<212> TYPE: DNA
<213> ORGANISM: Sorghum bicolor

<400> SEQUENCE: 243

```
ctcggttcgg tcgtgtttgg agatagtgct aaccttgatg aaatataggt gtacggtttg     60

catggaacat accatattct tggaaatcaa tttggacgca cccgatagaa ctccaagatc    120

atgtgtgtca catggaatct tgcttcaatc tgtttagaga cagtgttagt ttaggtgcaa    180

gattggtcca tggtttgcgc ataatgcacc ataggctcgg aaaccgttat ggaagcaccc    240

gataatactc ctaggtgaag aggctcaagt ggaaggtcag tttgatctat ttggagatag    300

tgttaatctt gaagcaagat aggtgcacgg tttgcatgga acataccata tgctaagaaa    360

tcca                                                                  364
```

<210> SEQ ID NO 244
<211> LENGTH: 1493
<212> TYPE: DNA
<213> ORGANISM: Sorghum bicolor

<400> SEQUENCE: 244

```
aaataaaatt catcatcagt ttagaaactt gaattttgca tctcatgctg gagcatattt     60
```

```
aattctgtgt tgttgtcctt tttgtttgaa tttatttgat tcaaatttct tttggaaaat    120

gctttagaaa gaggaattaa aaaagaaaaa ggggaaggac cccagccgaa ccccactttc    180

ccccccccct cgtgcgcgtg gcccagaccc ctcggcccag cgagcggccc cgctcgcccc    240

cgcgcgtgcc tccccctcct ctcccccacc gaagactggg ccccactgcg cagcgcctcc    300

ttctccccct tcctttcttc tccaccggtc ggggacgagc cggactcggt ccgagcggta    360

acaaactccg gattctcagg gattcgatct ccctgagtct gttttaagca tcctggagcc    420

acccgtcacc tcctcttgcc atcctttgca ccccgggaac cctagccgcc acttttcgtc    480

gagtttcgaa tctcgcagag cttcaaacta aaccgccgcc gtcgcgggtc acctctgtgc    540

cgtctcagct cgagcaaacc atcctagcga gttcggggta agctcctcca cgcgttggta    600

tttttatttc ggagtttggt gttgggaaac gagaaacccg cgaacgccgg cgagcttcgc    660

ggcggtggcc atggcgccac cgaaccggtg ccgagctccg gccggacgat ggctctgcgt    720

gaccaggaag ccgcccagga agcctgccaa ccgttcaacc gaagatcaac ggccacgatt    780

caaacatacc ctttcactgc ggtttttgat aaagattccc taggtagttt tgtatttcgc    840

ccgcggtcct tggcgccctg caccagatta cgttttccta ttgcgaaagc gtactcctgt    900

ccggttgagt tcaaaggcgt tttcacctat ttacatcttt gccactagat ttgttttgct    960

tataaaatgc tcattttaat tccgtttttg tccattcaaa ttgcgttagg ttcgtaatta   1020

tatgctctac atgttagaaa cattagttta ctgttttgaa actttttatt tctgcagtac   1080

tatttaatta attatttctc tataggaaat cttagaaaat tcatatcttt ctcgttttaa   1140

ttctgatttt cgtgaacttt acgttcgtgt gatcgtagcg ctgcgtagaa tattttcata   1200

aacttttatc tttgatttct cactgttggt gtaatgttct aattatagct tgtttgcttt   1260

gtgtatgatt gtctacattg gattgcgtgt tgttgattga tgattgggat tagacggtga   1320

gccgtacgtt ggtgctcaag atcaagcatt tgaagaccag caggctcagg agagctttga   1380

tcaaggcaag tataacttgg gatcatcctt gttacctata cacaattaat ataacattta   1440

tcatatgcat gctatcacct tgaagacctt agtaaaatca tagatgatta tta           1493
```

<210> SEQ ID NO 245
<211> LENGTH: 127
<212> TYPE: DNA
<213> ORGANISM: Sorghum bicolor

<400> SEQUENCE: 245

```
ataatagtct atgattttgc taaggtcatc aaggtggaca catgcatatg atatatgtat     60

taaaattggg taggtaacaa ggataatccc aagttatact tgccttaaac ttgctttaca    120

cccaaag                                                              127
```

<210> SEQ ID NO 246
<211> LENGTH: 467
<212> TYPE: DNA
<213> ORGANISM: Sorghum bicolor

<400> SEQUENCE: 246

```
ctcaaaacta gattatatga acagaagaat acaaaagaag caattcgcta cacacacaca     60

cactctctct ctagagtaag gccgaacaag tatggagtta tctttctttt tggatcacag    120

aaggactcac atagacggag ttcaggctat attaacaagc ggactccaag ttctattcgg    180

tttccactca gaaccaacca caaaacggat tccacctatt gccgagttct actcggtttc    240
```

cttctttttt tatcacgttg gtggaactca gattggaact ctactcgata cggaccaaga 300
ccacagttca attcggactt cgcaacagat tcgatagaga gaagatatgg taatacttgg 360
ctgtgtatag atggtgacaa gaactcgaaa ctctaaagga ctagacacta agactagcaa 420
ctcgacacaa accgaagcaa cgcaaattca acaagcccta actaaaa 467

<210> SEQ ID NO 247
<211> LENGTH: 411
<212> TYPE: DNA
<213> ORGANISM: Sorghum bicolor

<400> SEQUENCE: 247
tatctccaac tggactaaag caagattcaa tatgatacac ttcatctagt aattccatcg 60
ggtgcatcta cagttccatc gggtgtggct aaattgattt gtgagcatat ggtatgtaca 120
atgcaaaccg tgcacctatc ttgcatcaag attagaacta tctccaaaca gacaaccaag 180
attccacatg agcctcttca ccaaggagta ccatcgcgtg cgtccaaaat agtttcttag 240
cctatggtgt tttaggaaca aaccgtgtac ctatcttgca tcgaaactaa cactatctcc 300
aaagagacca aagtgagatt ctatgtgata cacgtcatct aggagttcta ttgggtgctt 360
ccaaatatat ttctaagcat atggtacgtt cgatgcaatt catgcaccta t 411

<210> SEQ ID NO 248
<211> LENGTH: 176
<212> TYPE: DNA
<213> ORGANISM: Sorghum bicolor

<400> SEQUENCE: 248
ttgatttccg agaatatggt atgttccatt caaaccgtac acctatcttg catcaagatt 60
agcactatct cgaaatagac cgaaccaagc tttcacttga gcctcttcac ctaggagtac 120
catcgggaac ttccacaacg tttctgagcc tatggtgcac tgggcacaaa ccatgc 176

<210> SEQ ID NO 249
<211> LENGTH: 557
<212> TYPE: DNA
<213> ORGANISM: Sorghum bicolor

<400> SEQUENCE: 249
gattggtgca tggtttgcgc ataatgcacc ataggctcag aaaccattat ggaagcaccc 60
gataatactc ctaggtgaag aggctcaagt gaaaggtcgg ttcgatctat ttggagatag 120
agataatctt gatgcaagat aggtgcatgg tttgcatgga acaaaccata tgctaagaaa 180
tccatttgga tgcatcccaa tagaactcct agatgacatg tgtcatatag aatctcgctt 240
tggtctattt ggagacagag ttagttttag tgcaagaaag gtacacagtt tgcgcctaat 300
gcatcatagg ctaagaaacc atttaggatg cacttgatga tactcctggg taaaggggct 360
caagtggaag ctcagtttgc tttgtctgga gatagtgcta atcttgacgc aagataggcg 420
cacgaattgc atcgaacgta ccatatcctt agaaatatat ttggaagcac caaatagaac 480
tcctagatga tgtgtgtcat atagaatctc acatcggtct ctttggagat agtgtttgtt 540
tcggtgcaag ataggta 557

<210> SEQ ID NO 250
<211> LENGTH: 243
<212> TYPE: DNA
<213> ORGANISM: Sorghum bicolor

<400> SEQUENCE: 250

```
ggtttgtttg gagatagtgc taattgatgc gaacccgcta gggtttttgg cctgatcttt     60

cgatgagagg cgctggataa ctcgattagt ggatggagat gacgatcacg gcccgactac    120

agccctcaag accgcgcctt agcaaccgat acaccacgtc caacagccgt cacgatcttg    180

tggagcgcga caaccagccc ctagggctcc cgtcctgcaa gcaatcgaag aattagcaag    240

aac                                                                  243
```

<210> SEQ ID NO 251
<211> LENGTH: 265
<212> TYPE: DNA
<213> ORGANISM: Sorghum bicolor

<400> SEQUENCE: 251

```
cctaggtaaa ggggctcaag tggaagcaca gtttgcttct tttggagata gtgccaatct     60

tgatgcaaga taggtgcacg aatcgcatcg aacgtaccat atgcttagaa atatatttgg    120

aagcacccaa tagaactcct agatgacgtg tgtcacatag aatctcactt cgatctcttt    180

ggagatagtg ttagttttgg tacaagatag gtacacgatt tgtgcctaat gcaccatagg    240

ctaagaaact attttggacg cacat                                          265
```

<210> SEQ ID NO 252
<211> LENGTH: 2236
<212> TYPE: DNA
<213> ORGANISM: Sorghum bicolor

<400> SEQUENCE: 252

```
aagaaaagag aaaagattca aaaaaggggc tgtttttcat attgatttta ggtttgttcc     60

accttgtttt tgggggtgtg ctgtggtttt cctttgtgtc caggctcgcg tctctagcac    120

ggtctagcct aggaccagca cagtaccatc atcgaacgct tattcagctc gcttttataa    180

ctaacatggt gctagttcgt tccttgtttc agcccaccta tagctccaca tactctacag    240

cttgacaggt cttgtgctgc agcaccgata cacttcgtcc attgctgtac acttgttggc    300

agacgacccc tcctgtcaag caaggtaaga attggtaaga acttgtgtta caggttgagt    360

gtgagcgact tgctgtagct acatcctagt agttgtaggg cttttatttc ttcacttgcc    420

tttttgttgt ctttgtcttt gaaccatgct aggggcagat gatggtaacg aaacaccaca    480

tacacctcgc actaagggca tcatacaaca ttttgaaagg aaagtgaggc tgcacacaga    540

gggacttgat aacgacttgc aggtgacaaa tgaaaagctg gggcagttag aggctacgca    600

gattgccaca aaaaacaagc tcacacgttt ggaggaatct gttgctagtg tggacaaaag    660

ccttgctgct ctcctaaggc gatttgatga ttatcaagac actcgtgatc gacgtcgcct    720

tcgtcacaac cgtagaggta tgggtggcaa ccgccgacgc gaggtacaca ataatgatga    780

tgctttcagt aagattaaat ttaagatacc tccttttgat ggtaaatatg accctgatgc    840

ttacatcact tgggagattg ctgttgatca aaagtttgca tgtcatgaat ttcctgagac    900

tacacgtgtt agggctgcta ctagtgagtt tacagatttt gcttctattt ggtggataga    960

atatggaaag aaaaatccta ataacttacc tagaacttgg gatgcgctga aaagggccat   1020

gagagctaga tttgttccat cttactatgc gcgtgatatg ataaataagt tgcagcaatt   1080

aagacaaggt gctaaaagtg tagaagaata ttatcaggaa ttacaaacgg gtatgttgcg   1140

ttgtaaccta gaggaggatg aggaaccggc tatggctaga tttttgggtg ggttaaatca   1200

ggaaattcag gacatcctcg cttacaaaga atacaataat gtaacccgtt tgtttcatct   1260
```

```
tgcttgtaaa gctgaaaggg aagtgcaggg acgacgtgct agcacaagga gaaatatttc   1320

tgcagggaag gctaattcat ggcagcaaca cgtggcttca actccatcta cacgtatttc   1380

tactccatca tctagtgaca agactcgaac tgcccccacc aattcagttg cgaagacgat   1440

gcaaaagcct gctgcgagta cttcatccgt ggcatcgaca ggtagaacaa gcaacataca   1500

atgtcaccgg tgcaagggat atgggcacat gatgcgtgac tgtccaaaca agcgagttat   1560

gattgtcaga gatgatggtg agtactcatc tgctagtgat tttgatgagg atacgcttgc   1620

actgcttgca ggaccatgca ggtaatgaag atcaaataga agaacatatt aatgcaggtg   1680

aagcggacca ctatgagagc ttgatcgtgc agcgagtgct tagtgcacaa atggagatgg   1740

cggagcaaaa tcagcgacac attttattcc aaacaaagtg tgtcatcaaa gagcgttctt   1800

gtcgcatgat cattgatgga ggtagctgca acaacttggc aagcagcgat atggtgcaga   1860

agcttgccct caacaccaaa ccacacccgc atccctacta catccaatgg ctgaacaaca   1920

gtggtaaggc aaaggtaact agacttgtga gaattaattt ttccatcgga tcctacaaag   1980

atattgtcga atgtgatgtt gtgcctatgc aagcttgtaa cattctgcta ggtagacctt   2040

ggcaatttga tagagattct atgcatcatg gtagatcaaa tcagtattct tttctatacc   2100

atgatctcaa aattgtgttg catcctatgt cccctgaaac tattatgcaa actaatgttg   2160

ctagagctac taaagcaaag agtgagagca ataaaaatga taaatctgta attggtaaca   2220

aagatgagat aaaact                                                   2236
```

<210> SEQ ID NO 253
<211> LENGTH: 1013
<212> TYPE: DNA
<213> ORGANISM: Sorghum bicolor

<400> SEQUENCE: 253

```
aaaaggacgt tgtatgatag ctaccaaatc agatattaat gagttcaatg catccacttc     60

tgttgcttat gctttgatat gcaaggatgc tttgtgtcgg tgttttcccc acggggggtc    120

acaccaacga gtgaatttgt atgcgtgctt ccctttccca gatggtgatg caagaagaca    180

ccaagattta tcctggttcg ggcaagagaa ggccctacgt ccagcgaggg aggggagttt    240

gtattatctt gcacctaagt gcttgtacag gggcgaatac aagtgtgtat gaactgggat    300

ggagtatgga gactcctcta tgtgtgggtg tgctgttttc gtgatgtgtg ttcattcccg    360

ggtctcccct tttatagctc caaggagaga cctagggtac atgtataggt gacagagtag    420

gggtcgatag aggcatggtg cgctgaccta ctcgaggcct ccgtaccggc gtggtctcga    480

gccgtcccgt cctggtagct tgacgatgat tacgcgtgcc ctcatatccc gctctgtacg    540

ccgtcttggg ccggtttgtc cgttgcacgc ttgtacgtca tggcggcaga tacgtcagag    600

tggtggcagt gccgtcagtc gacgcccaac ccttcccaag aaggaaacac gtccggtcga    660

gggtcggacg ccatgtagcg ccttgctatc tagaccattg acttttggcg tctcgagggg    720

gtcctgacta gacgttccat cccggctccc cgcgtcctga cacgctcagc gtcatttggt    780

ggggaaggct gcaaaaagaa tgacgggacg ggtgcctgtt ccccatcatg cttcccgtga    840

ctagcgtgtt aggtgggaaa gcgacaggcg cattaaatgc ccgggttctc gtgcgcgcgt    900

caggcggcgg gcggtgtcct tgcgctcgac gcctcctggt tcgctcgagc ccatttccgt    960

attcgacggt agttaatgct cgacccctga gcggttcgct cgacgccttt tcc          1013
```

<210> SEQ ID NO 254
<211> LENGTH: 121

<212> TYPE: DNA
<213> ORGANISM: Sorghum bicolor

<400> SEQUENCE: 254
gtgtgtccaa aatagtttct taccctatgg tgcattaggc acaaatcatg tacctatctt 60
acaccgaaac taacactatc tccaaaaaga ccgaagtgag attctatatg acacacgtca 120
t 121

<210> SEQ ID NO 255
<211> LENGTH: 181
<212> TYPE: DNA
<213> ORGANISM: Sorghum bicolor

<400> SEQUENCE: 255
tgcatggaac gtaccatatg cttagaaata tatttgcaag cacccaatag aactcctaga 60
tgatgtgtgt catatagaat ctcacttcgg tctctttgga gataatgtta gttttggtgc 120
aagataggta cacggtttgt gcctaatgca ccatggggta agaaactatt ttggacacac 180
g 181

<210> SEQ ID NO 256
<211> LENGTH: 125
<212> TYPE: DNA
<213> ORGANISM: Sorghum bicolor

<400> SEQUENCE: 256
accgaaacta acactgtctc caaatagatt gaatcgagat tccatatgac acacatgatc 60
taggagttct atcgggtgtg tccaaattga tttatgagaa tatggtacgt tctgcaaacc 120
ataca 125

<210> SEQ ID NO 257
<211> LENGTH: 332
<212> TYPE: DNA
<213> ORGANISM: Sorghum bicolor

<400> SEQUENCE: 257
aatcttttct cttttctttt ttttttcttt tttgtttctt tttttttggg caacctcaaa 60
aactgattat atgaacaaag gaatacaaaa gagcaattcg ctacacacac tctctctctc 120
tctagagtaa ggccgaacaa gtatggagtt atcttttctt ttggatcaca gttcaattcg 180
gacttcacaa cagattcgac agagagaaga tatggtaata ctcggctgtg tatagatggt 240
gacaagaact cgaaactcta aaggactaga cactaagacc agcaactcga cacaaaccga 300
agcaacgcaa attctacaag ccctaactaa at 332

<210> SEQ ID NO 258
<211> LENGTH: 221
<212> TYPE: DNA
<213> ORGANISM: Sorghum bicolor

<400> SEQUENCE: 258
caaatcttgt acaaatatta aattcatttt attttgttta gtgtttttct aatgcacaac 60
ccaaaattag aaattttggg gtgtgacagg gtgcatccaa aatggtttct taacccatga 120
tgcattaggc gcaaactgtg tacctatctt gcaccaaaac taactcggtc tccaaacaga 180
ccgaagcgag attccatatg acacatgtca tctaggagtt a 221

<210> SEQ ID NO 259

```
<211> LENGTH: 170
<212> TYPE: DNA
<213> ORGANISM: Sorghum bicolor

<400> SEQUENCE: 259

aatggtactc cttggtgaag aggctcaagt ggaatcttga ttctgtctat ttggagatag     60

ttctaatctt gatgcaagat agttgcacga tttgcatgga acatacccta tgctcagaaa    120

tcaatttgga caaacccgat ggaactgtag atgagatgtg tcatatggaa               170


<210> SEQ ID NO 260
<211> LENGTH: 133
<212> TYPE: DNA
<213> ORGANISM: Sorghum bicolor

<400> SEQUENCE: 260

tactcgtttt gtgcctaatg caccataggc taagaaacta ttttagacgc acgcgatgat     60

actccttggt gaagaggctc atatggaatc ttggttctat ctgtttggag atagttccaa    120

tcttgatgca aga                                                       133


<210> SEQ ID NO 261
<211> LENGTH: 191
<212> TYPE: DNA
<213> ORGANISM: Sorghum bicolor

<400> SEQUENCE: 261

aggagtatca tcgagtgcat ccaaaatggt ttcttagcct atgatgcatt aggcgtaaac     60

tgtgtaccta tcttgcacca aaactaactc tgtctctaaa tagaccaaag cgagattcca    120

tatgacacat gtcatctagg agttctattg ggatgcatcc aaatggattt cttagcatat    180

ggtttgttcc a                                                         191


<210> SEQ ID NO 262
<211> LENGTH: 187
<212> TYPE: DNA
<213> ORGANISM: Sorghum bicolor

<400> SEQUENCE: 262

aatcaacaat ggggttccga agacaaggag acgggcggct gatcctgcac gcgcgcctac     60

aagcaagtag cgaaggctaa acttgatcta aacaaaaccc agttgttcat ggcggctcta    120

gatgtaaata aatagagggg aggacgacca aaggggtgct agagtcgtcc tccaacccta    180

ggacgca                                                              187


<210> SEQ ID NO 263
<211> LENGTH: 121
<212> TYPE: DNA
<213> ORGANISM: Sorghum bicolor

<400> SEQUENCE: 263

taggtgcacg gtttgcatgg aacataccat atgctcagaa atcaatttgg acacaccgat     60

ggaactgtag atgcacccga tggaactact agatgaagtg tatcatatgg aatctcgctt    120

c                                                                    121


<210> SEQ ID NO 264
<211> LENGTH: 286
<212> TYPE: DNA
<213> ORGANISM: Sorghum bicolor

<400> SEQUENCE: 264
```

```
gtgcattagg cacaaatcgt gtaccaatct tgcaccgaaa cgaacactat ctccaaagag     60

accgaagtga gattctatat gacacacgtc atctaggagt tctattgggt tgcttccaaa    120

tatgtttcga agcaaatggt atgttccatg caattcatgc acctatcttg catcaagatt    180

agcactatct ccaaacaaaa gcaaacggag cttccactgg agccccttta cccaggagta    240

tcatcaggtg catccaaaat ggtttcttag cctacgatgc attagg                   286
```

<210> SEQ ID NO 265
<211> LENGTH: 119
<212> TYPE: DNA
<213> ORGANISM: Sorghum bicolor

<400> SEQUENCE: 265

```
gcaaaccgtg cacctatctt gcatcaagat tagctctatc tccaaataga tcgaaccgac     60

cttccacttg agcctcttca cctaggagta ttatcagggt gcttccataa tggtttctg     119
```

<210> SEQ ID NO 266
<211> LENGTH: 331
<212> TYPE: DNA
<213> ORGANISM: Sorghum bicolor

<400> SEQUENCE: 266

```
tggaatctcg cttcggtcca gttggagata gtattagttt cagtgcaaaa tatgttttgt     60

gcctagtgca ccataggctc agaaatcgtt gtggaagttc ctgatggtac tccttgatgc    120

gaacccgcta ggggttttgc ccgatctttt gatgagagac ggggataact cgattggtgg    180

atggagatga cgttcacggc ccgactacag ccctcaagac cgcgccttag aaaccgatac    240

accacgtcca atagccgtca cgatctagtg gagcgcgaca accagcccct agggctccca    300

tcctgcaagc aatcgaagaa ctagcaaaaa c                                   331
```

<210> SEQ ID NO 267
<211> LENGTH: 152
<212> TYPE: DNA
<213> ORGANISM: Sorghum bicolor

<400> SEQUENCE: 267

```
tttggagata gttctaatct tgatgcaaga taggtgcaca gtttgcatgg aacataccat     60

atgctcagaa atcaatttgg acaaacccga tggaactgta gatgcacccg atggaactac    120

tagatgaagt gtatcatatg gaatctcgct tt                                  152
```

<210> SEQ ID NO 268
<211> LENGTH: 138
<212> TYPE: DNA
<213> ORGANISM: Sorghum bicolor

<400> SEQUENCE: 268

```
ttgatttctt agaatatggt acgttccatg caaaccgtac acctatcttt catcaagatt     60

agcactatct ctaaacagac caaaccaagc tttcagttga gcctcttcac ctaggagtga    120

tgaggacatc aacaccag                                                  138
```

<210> SEQ ID NO 269
<211> LENGTH: 139
<212> TYPE: DNA
<213> ORGANISM: Sorghum bicolor

<400> SEQUENCE: 269
acacacccga tgtaactgta gatgcaccca atggaactac tagatgaagt atatcatatg 60
gaatctcgct tcagtccagt tggagatagt attagtttcg gtgcaagata gttgcatggt 120
ttgtgcccag tgcaccata 139

<210> SEQ ID NO 270
<211> LENGTH: 169
<212> TYPE: DNA
<213> ORGANISM: Sorghum bicolor

<400> SEQUENCE: 270
agattagaac tatcaccaaa cagatcgaac cgaccttgca cttgagcctt ttaacctagg 60
attatcattg ggtgcttcca taatggtttc tgagcctgtg gtgcattatg cgcaaaccat 120
gcaccaatct tgcacctaaa ctaacactat ctctaaacag attgaagcg 169

<210> SEQ ID NO 271
<211> LENGTH: 465
<212> TYPE: DNA
<213> ORGANISM: Sorghum bicolor

<400> SEQUENCE: 271
ctaggagtat tatcggatgc ttccataatg gtttccgagc ctatggtaca ttatgcgcaa 60
accatgcacc aatcttgcac ctaaactaac actgtctcca aacagattga agaaagattc 120
catttgacac acataatcta ggagttctat cgggtgcatc caaatttatt actgagaata 180
tggtatgttt catgcaaatc atacacctat cttgcatcaa gattagcact gtctccaaat 240
agaccgaacc gagctttcgc ttaagcctct tcacctagga gtaccatcgt ggacttccac 300
aacggtttct gagcctatgg tgcagtgggc acaaaccatg cacctatctt gcaccgaaac 360
taatactatg tgatgaggac atcaacacca gcgatacata tcctacatcc accagcgata 420
catatcctac atcctctccg gcacaaccta tagctggtcc tacat 465

<210> SEQ ID NO 272
<211> LENGTH: 205
<212> TYPE: DNA
<213> ORGANISM: Sorghum bicolor

<400> SEQUENCE: 272
actgagcttc cacttgagcc cctttaccca tgagtatcat cgggtgcatc caaaatggtt 60
tcttagccta tgatgtatta ggcgcaaatt gtgtacctat ctcgcaccaa tactaacttt 120
gtctccaaac agaccaaagc gaaattccat atgacacatg tcatctaggg gttctattgg 180
ggtgtgtcca aatagatttc ttagc 205

<210> SEQ ID NO 273
<211> LENGTH: 100
<212> TYPE: DNA
<213> ORGANISM: Sorghum bicolor

<400> SEQUENCE: 273
tgcaaactgt gcacctatct tgcatcaaga ttagctctat ctccaaatag atcgaatcga 60
ccttccactt gagcctcttc acctaggagt attatcgggt 100

<210> SEQ ID NO 274
<211> LENGTH: 166
<212> TYPE: DNA
<213> ORGANISM: Sorghum bicolor

<400> SEQUENCE: 274

```
atagaactcc aagatcatgt gtgttatatg gaatctcgct tcaatctgtt tggagaaagt     60

gttagtatag gtgcaagatt agtgcatggt ttgcgcataa tgcaccatac gctcagaaaa    120

cattatggaa gcacccgatg ataatcctag gtgaagaggc tcaagt                   166
```

<210> SEQ ID NO 275
<211> LENGTH: 107
<212> TYPE: DNA
<213> ORGANISM: Sorghum bicolor

<400> SEQUENCE: 275

```
cacccaatag aactcctaga tgacgtgtgt cacatagaat ctcacttcga tctctttgga     60

gatagtgtta gtttcggtgc aagataggta cgcgatttgt gcctaat                  107
```

<210> SEQ ID NO 276
<211> LENGTH: 159
<212> TYPE: DNA
<213> ORGANISM: Sorghum bicolor

<400> SEQUENCE: 276

```
aagattccat atgacacaca tcatcaagga gttatatcag gtgcgtccta attgatttct     60

aagccaagtg gaggcttggt tcggtctgtt tagagatagt gctaatcttg atgcaagatt    120

ggtgcaccat atgctcagaa atcaaattgg acgcaccag                           159
```

<210> SEQ ID NO 277
<211> LENGTH: 730
<212> TYPE: DNA
<213> ORGANISM: Sorghum bicolor

<400> SEQUENCE: 277

```
tagaatttgg catgagattg gattgctttt agtcagcctc ttatagccta aagtctttga     60

gtgactagat gacatatcat gtaagttgct gataggtttc cagttttccg ctcctaggtc    120

tgcatattgt acttttcctc ttactcgact taaccagtac caacccagct tctcaacgga    180

tttataccat ggcactttaa agccagcatc actgacaatg agcggtgtgg tgttactcgg    240

tagaatgctc gcaaggtcgg ctagaaattg gtcatgagct ttctttgaac attgctctga    300

aagcgggaac gctttctcat aaagagtaac agaacgaccg tgtagtgcga ctgaagctcg    360

caataccata agccgttttt gctcacggat atcagaccag tcaacaagta caatgggcat    420

cgtattgccc gaacagataa agctagcatg ccaacggtat acagcgagtc gctctttgtg    480

gaggtgacga ttacctaaca atcggtcgat tcgtttgatg ttatgttttg ttctcgcttt    540

ggttggcagg ttacggccaa gttcggtaag agtgagagtt ttacagtcaa gtaaggcgtg    600

gcaagccaac gttaagctgt tgagtcgttt taagtgtaat tcggggcaga attggtaaag    660

agagtcgtgt aaaatatcga gttcgcacat tttgttgtct gattattgat ttttcgcgaa    720

accatttgat                                                           730
```

<210> SEQ ID NO 278
<211> LENGTH: 408
<212> TYPE: DNA
<213> ORGANISM: Sorghum bicolor

<400> SEQUENCE: 278

```
gaaactaaca ctatctccaa acggaccaaa gcaaggttac atatgacata caacatctag     60

tagttccatc gggcgtgtcc aaattgattt cgggcatata gcacgttaca tgcaaaccgt    120
```

```
gcacctatct tgcatcaaga ttagcagtat ctccaaacag accaaaccaa gcttccactt    180

gagtctcttc acctaggagt agcaacaggt gcatccataa tggtttctta tgctattgtg    240

cgttaggcgc aaactgtgca catatcttcc accaaaatta acactacctc caaacagacc    300

aaagtgagat ttcatatgac acacatcatc taggagttcc atcgggtgtg tccaaattga    360

tttccgagca tatagtacgt tcatgcaaac cgtgcaccta tcttgcat                408


<210> SEQ ID NO 279
<211> LENGTH: 113
<212> TYPE: DNA
<213> ORGANISM: Sorghum bicolor

<400> SEQUENCE: 279

ggtttgcatg ggacatacca tattcttgac aatcaatttg gatgcacctg atggaactcc     60

tagtgacttg tgtcatatgg aatctcgctt cgcccgtttg gagacagtgt tag          113


<210> SEQ ID NO 280
<211> LENGTH: 243
<212> TYPE: DNA
<213> ORGANISM: Sorghum bicolor

<400> SEQUENCE: 280

agatagtgct aatcttgatg ctagataggt gcacaatttg catggaacat accatatgct     60

cggataaatt tggacgcacc caatggaact cctagatgat gtgtgtcata tggaatcttg    120

cttcggtttg tttagagata gtgttagttt tggtgcaaga taggtgcacg gtttgcacct    180

aatgcaccat actctaagaa aacattttgg atgcacctga tggtactcct agctaaagag    240

gct                                                                 243


<210> SEQ ID NO 281
<211> LENGTH: 516
<212> TYPE: DNA
<213> ORGANISM: Sorghum bicolor

<400> SEQUENCE: 281

aaaccatttt ggatgcactt gttggtactc ctaggtgaag gggctctagt ggatgctcgg     60

ttcggtctgt ttggagatag tgctaatctt gatacaagat agatgcacag tttgcatgga    120

acataccaaa tgcttggaaa tcaatctaga cgcacttgct ggaactccta gatgacatgt    180

gtcatacaaa atcttgcttt ggtctattta gagatagtgt tagttccggt gcaagatagg    240

tgcaaggttt gcacataatg cagcataggc aaagaaacca ttttagacgc acccaatggt    300

actcctaggt aaaaggctca agtgaaagct cgatttggtc tatttggaga tagtgctaat    360

ctggatgcaa gatagatgca cggtctgcat gaaacgtacc atgtgcttag aaattaattt    420

ggacacaccc gatacaactc cttgatgatg tgtgtcgtat ggaatcttgc tttggtgtgt    480

ttagagatag tattagtttc ggtgcaagat atgtgc                             516


<210> SEQ ID NO 282
<211> LENGTH: 314
<212> TYPE: DNA
<213> ORGANISM: Sorghum bicolor

<400> SEQUENCE: 282

ttgggttcag tctgtttgga ggtattgcta atcttgatgc aagataggtg catggtttgc     60

atggaaggta ctatatgttt ggaaatcaat ttggacgcat ccgatgaaac tcctagatgt    120

catgtgtcat atgtaacctc gtcttggtct gtttggagat agtgttggtt tcggtgcaag    180
```

ataggtgcac ggtttgtgcc taatgcacca tactctaaca aaccattttg gacacacctg 240
attatactcc tagcagaaga ggcacaagtg gaagctcggt ttggtctgtt tggagatagt 300
gctaatcttg acgc 314

<210> SEQ ID NO 283
<211> LENGTH: 776
<212> TYPE: DNA
<213> ORGANISM: Sorghum bicolor

<400> SEQUENCE: 283
gatcgaacca agcttccact tgagcctctt catctaggag tacaaacagg tgcgtccaaa 60
atggtttctt agactatggt gcattaggca caaactatgc acgtatcttg caccagaact 120
aacattgtct ccaaacagac cgaagcgaga ttccatatga cacacgtcat ctaggagttc 180
cattgggtgg gtccaaattg atttcttaac atatggtacg ttgcatgcaa actgtgtaac 240
tatcttgcat caagattagc actatatccg aacagaccaa atcgagcctc cacttgagcc 300
tcttcaacta tgagtatcat cgggtgcgtc taaaatggtt tcttacccta tggtgcatga 360
ggcgtatacc gtgcacatat catctataaa aactaacact gtctctaaac gtatcgaagc 420
aagattcaat atgacacaca tcatcaagga gttatatcag gtgcgtccta gttaattttt 480
gagcatatcg tatgttccat gcaaaccgtg catctatctc gcatcaagat tagcactacc 540
tccaaacata ccaaactgag ctttctcttg agtcccttga cctaggagta ccatcgggtg 600
cgtccaaaac tgtttcttat cctatggtgc attatctgca aactgtgcac ctatcttgca 660
ccgaaactaa cattgtctct aaacaaaccg aagtgagatt ccatatgaca tgtgtcatct 720
aggagtttca tctggtgcgt caaaattgat ttctgagtat atggtatgtt ccatgc 776

<210> SEQ ID NO 284
<211> LENGTH: 311
<212> TYPE: DNA
<213> ORGANISM: Sorghum bicolor

<400> SEQUENCE: 284
tagaccaaac tgagctttca cttgagcccc ttgacctagg agtaccatcg ggtgtgtcca 60
aaatggtttc ttatcctatg gtgcatttgc tgcaaatcat gcacctatct tgcaccgaaa 120
ctaacactgt ctctaaacgg accgaagtga gattccatat gacacatgtc atctaggagt 180
tccatctggt gcatctaaat tgatttctga gcatatggta tccatgcaaa tcgtgcacct 240
atcttgcatc aagattagca ctatctctaa acagaccgaa ccggggcctc cacttaagcc 300
tcttcaccta c 311

<210> SEQ ID NO 285
<211> LENGTH: 433
<212> TYPE: DNA
<213> ORGANISM: Sorghum bicolor

<400> SEQUENCE: 285
gtaatatagg tgcacggttt gcatggaaca taccatatgc attaaaatca ttttggacgc 60
acccgataga actcctagat gatgtgtgtc atctgatatc tcgctttggt ctgtttgaat 120
atagttttag tttcggtgca agatggtgaa tggtttgtgc ctaatgcacc atactctaaa 180
aagatattgc acggtttatg cctaatgcac catactctaa gaaacggttt tggacgcacc 240
cgatggtact cctaggtgaa gggtctcaag tgaaagctca gtttggtcta tttggagata 300
ctgctaatct tgatgcaaga tatttgcatg gtttgcgtag aatgtcccat atgctcagaa 360
atcaatttgg atgcacctga tggaactcct agatgacgtg tgtcatatgg aatctcggtt 420
tggtccgttt gta 433

<210> SEQ ID NO 286
<211> LENGTH: 767
<212> TYPE: DNA
<213> ORGANISM: Sorghum bicolor

<400> SEQUENCE: 286
cttcctcttg agcctcttca gctaggagta ccatcgggtg cgtccaaaat ggtttcttag 60
tattatggtg catttggcac aaaccgtgca cctatcttgc accaaaatta acactatctc 120
caaacagacc aaagtgagat attagatgtc ttacacaatc taggagttct atcgggtgcg 180
tccaaattga ttttcaacca tatggtatgt tccatacaaa ccgtgcacct atcttatatg 240
aagattagca ctatctccaa acagatcgta ccgagctttc actttagcct cttcacctag 300
gagtaccatc gggtgcttcc acaactgttt ctaagcctat ggtgcattag gcgcacatca 360
tgcacctatc ttacaccgaa actaacacta tctccaaacg gatcaaagtg agattccata 420
tgagacacgt catctaggag ttctatcaag tgcgtcgaaa ttgatttccg agcatatggt 480
acgttccatg cataccgtgc acctatcttg cgtcaagatt tgtagtatct ccaaacagac 540
cgaaccaagc ttccacttga gcctcttcac ctaggagtac caacaggtgc atctaaaatg 600
gtttcttggg ctatggtgca ttaggcataa actgtgcacc tatcttgcac tgaaactaac 660
actgtctcca aatagatgaa gcgagattcc atatgacaca cgtcatctag gagttccatc 720
acgtgcatcc aaatcgattt tcaagcatat ggtatttccc atgctaa 767

<210> SEQ ID NO 287
<211> LENGTH: 415
<212> TYPE: DNA
<213> ORGANISM: Sorghum bicolor

<400> SEQUENCE: 287
ttgtatgcaa gataggtgca cagtttgcat ggaatatcgt agatgcttgg aaatcaaatt 60
ggatgcaccc gatggagctc ctagatgaag tgtgccatat ggaatctcgc ttcggtccgt 120
ttggagacaa tattagtttc agtgcaagat aggtgcacag tttgcgccta atacaccata 180
gtctaagaaa ccattttta cacacctgtt ggcactcctg ggtgaagagg ctcaagtgga 240
atctcggttt ggtctatttg tagatagtgc tagtctggat gcaagatagg tgcatgcttt 300
gcatggaaca taccatatgc ttagaaatca atatggacgc acctcatgaa actcctagat 360
gacgtgtgtc atatgaaatc tcgctttggt ctatttggag atagtgttag tttcg 415

<210> SEQ ID NO 288
<211> LENGTH: 749
<212> TYPE: DNA
<213> ORGANISM: Sorghum bicolor

<400> SEQUENCE: 288
caccatagcc taagaaacca atttggacgc acccgattgt actcctagct gaagaggctc 60
aagtggaagc tcggtttggt ctgtttggaa attgtgctaa tcttgacgca agacaggtgc 120
acggtttgca tggatgtacc atatactcag aaataaattt ggacgcaccc gatagaactc 180
ctagatgacg tgtgtcatat ggaatctcac tttgatccgt ttggagatag tgttagtttc 240
ggtgtaagat aggtgcacag tgtgcgccta atgcaccata ggcttagaaa cagttgtgga 300

```
agcacccgat ggtactccta ggtgaagagg ctcaagtgaa agcttggtaa gatttgtttg    360

gagatagtgc taatcttcat gtaagatagg tgcaaggttt gtatggaaca taccatatgc    420

ttgaaaatca atttgcacgc acccgataga actcctagat ggtgtgtgtc atctaatatc    480

gctttggtct atttggagat agtgttagtt tcggtgcaag ataggtgcac ggtttgtgcc    540

taatgtacca tactctaaga aaccattttg gatgcagcca atggtactcc tagccgaaga    600

ggctcaagtg gaaggttggt tcggtctgtt tggagatagt gctaatcttg atgcaagatt    660

gcacagtttg catggaatgt atcatatgct cagaattcaa tttggatgca cctgatagaa    720

ctcctagctg aagaggctca agtggaagc                                      749
```

<210> SEQ ID NO 289
<211> LENGTH: 185
<212> TYPE: DNA
<213> ORGANISM: Sorghum bicolor

<400> SEQUENCE: 289

```
atggaactcc tagatgacat gtgtcatatg gaatctcact tcggtctgtt tagaggcagt     60

gttagtttcg gtgcaagata ggtgcactgt ttgcacctaa tgcaccatag gataagaaac    120

cattttggac gcacccgatg gtactcctag gtcaaggggc tcaagtgaaa gatcggtttg    180

gtctg                                                                185
```

<210> SEQ ID NO 290
<211> LENGTH: 149
<212> TYPE: DNA
<213> ORGANISM: Sorghum bicolor

<400> SEQUENCE: 290

```
aatggaaaac ctagatgacg tctgtcatat ggaatctcgc ttcgatttgt ttggagacaa     60

tgttagtttt ggtgcaagat aggtgtatag tttgtgccta atgcaccata gtctaagaaa    120

ccatttttga gcacctgttt gtactccta                                      149
```

<210> SEQ ID NO 291
<211> LENGTH: 180
<212> TYPE: DNA
<213> ORGANISM: Sorghum bicolor

<400> SEQUENCE: 291

```
aatggaactc ctagatgacg tgtgttgtat ggaatctcac ttcggtctgt ttggagacaa     60

tgttagtttc ggtgcaagat cggtgcatag tttgtgccta atgcaccata gtctaagaaa    120

ccatttttga cgcacctatt tgtactccta gatgaagaag ctcaagtgga agcttagttc    180
```

<210> SEQ ID NO 292
<211> LENGTH: 167
<212> TYPE: DNA
<213> ORGANISM: Sorghum bicolor

<400> SEQUENCE: 292

```
ggtctattca gagatattgc ctaatcttga tgcaagatag gtgcactatt agtgtggaac     60

atatcatatg ctcggaaatc aatttcgaca cacccaatga aactcctaga tgacgtgtgt    120

catatggaat cttgcttcgg tctttttaga gactgttagt ttcactg                  167
```

<210> SEQ ID NO 293
<211> LENGTH: 301
<212> TYPE: DNA

<213> ORGANISM: Sorghum bicolor

<400> SEQUENCE: 293

```
acctaggagt accaataggt gcttccaaaa tggtttctta gactttggtg cattaggcgc     60
aaatcgtgta catatcttgc accgaaacta atactctcta tggacaccaa agcgagattc    120
catatgacac acgtgatgaa ggagttctat cgggtgtgtc caaattaatt tctaagcata    180
tggaacgttc catgcagacc gtgcatctat cttgcatcaa gattaacact atctccaaac    240
agatcaaacc gagcttccac ttgagcctct tcaccgaagt accaacaggt gcattcaaaa    300
t                                                                    301
```

<210> SEQ ID NO 294
<211> LENGTH: 591
<212> TYPE: DNA
<213> ORGANISM: Sorghum bicolor

<400> SEQUENCE: 294

```
ctatgagtac catcgggtgc gtctaaaatg gtttcttagc ctattgtgca ttaggcgtaa     60
accatgcaca tatcttctac caaaactaac actgtctcta aatcaaacga agcaagattc    120
catatgacac acatcatcaa ggagttatat catgtccgtc ctaattgatt tctgagcata    180
tcatatgttc catgcaaacc gtgcatctat cttgcatcaa gattagcact atctccaaac    240
agaccaaagc aagctttcac ttgagcacgt tgacctggga gtaccatcgg gtgcgtccaa    300
aaaggtttat tatcctatgg tgcatttggt gcaaaccgtg cacctatctt gcaccgaaac    360
taacaatatg tctaaatgga tcgaagtgag attccatatg acacatgtca tctaggagtt    420
ccatctggtg cgtccaaatt gatttccgag catatggtat attccatgca aatcgtgcac    480
ctaccttgca tcaagattaa cactatctct aaacagaatg aaccaagcct ccacttgagc    540
ctcttcacct aggagtacca acaggtgctt caaaaatggt ttcttagact a             591
```

<210> SEQ ID NO 295
<211> LENGTH: 104
<212> TYPE: DNA
<213> ORGANISM: Sorghum bicolor

<400> SEQUENCE: 295

```
gatagtgtta gtttcggtgc aagataggtg gacagtttgc gtctaatgca ccatagtcta     60
ggaaaccatt ttggacgcac ctattggtcc gaggtgaaga ggct                     104
```

<210> SEQ ID NO 296
<211> LENGTH: 1077
<212> TYPE: DNA
<213> ORGANISM: Sorghum bicolor

<400> SEQUENCE: 296

```
gatctatttg gagatagtgc taatcttgat gcaagatagg tgcatgattt gcagggaaca     60
taccatatgc ttagaaatca atttggacgc acctaatgga agtcctagat gacgtgtgtc    120
atatggaatc ttgcttcagt ccgtttgtag acattgtaag ttttagtgca agataggtgc    180
atagtttgcg cctaatgcac catagtctaa gaaactattt tggacgcaat atttggtact    240
cctaagtgaa gaggctcaag tggaagcttg gttcggtcag tttggagata gtgctaatcc    300
atatgcaagg aaggtgcatg gtttgcatgg aacataccat atgcttggaa atcaatttgg    360
atgcacccga tggaactcct tgatgacgtg tgtcatatgg aatctcgctt cggtcaattt    420
ggagagattg ttagtttcgg tgcaagatag gtgcacggtt tgcacctaat gcaccatagg    480
```

```
ataagaaacc attttggacg cacccgatgg ttctcctaga tcaaggggct caagtgaaag    540

cttggtttgg tctgtttgga gatagtgcta atcttgatgc aagatagatg cacggtttgc    600

atggaacata cgatatgctt agaaatcaat taggacgcac ctgatataac tccttgatga    660

tttgtgtcgt atggaatgtt gctttggttc gtttagagac agtgttagtt ttggtagaag    720

atatgtgcac ggtttacgcc taatgcacca taggctaaga aaccatttta acgcacccga    780

tggtactcgt agttgaagag gctcaagtgg aggctcgatt tggtctgttc ggatatagta    840

ctaatcttga tgcaagatag ttgcacagtt tgcatgcaac gtaccatatc ttaagaaatc    900

aaattggacg cacccaatgg aactcctaga tgacgtctgt catatggaat ctcgcttcgg    960

tctgtttgga gacaatgtta gttttggtgc aagataggtg catagtttgt tcataatgca   1020

ccatagtcta agaaaccatt tttgacacac ttgtttgtac tcctagatga agaggct      1077
```

<210> SEQ ID NO 297
<211> LENGTH: 4657
<212> TYPE: DNA
<213> ORGANISM: Sorghum bicolor

<400> SEQUENCE: 297

```
aggcatatcg tatattccat gcaaaccgtg catcgatctt gcatcaagat tagcactatc     60

tacaaataga ccgaaccgag agcatccact tgagcccctt caccttggag taccaacagg    120

tgcgtccaaa atggtttctt acactatggt gcattaggtg caaactgtgc acctatcttg    180

caccaaaact aacaatgtca tgtgttgtgt gcacccacga tcaagtaccc aatgccttcc    240

tccggcttta taatttatct acaaaacaaa tcaatgtttc ttaggtaccc atacttgttt    300

gggtctttgg aggttagtga ctaagctttt tggtacccaa atggccttct tctttggacc    360

cacaattggt gtaccaacaa acttagcatg cacacccttc tcacccttgg taagcacata    420

acaagaatca aatagaatgt aagatacatt agcatgtttc ttgttcttgt tcactttatt    480

gcaattaagc tctaggtgcc caacttgctt gcatttgttg caataccaac tattgctctt    540

cacaaagcta ggcttgtgag ttgcaaaggc cgccttgcct ttcttggggg tatagcctaa    600

tccctctttg ttgagagaaa acctttgact acccaagcac tttagcaagc gggcctcacc    660

accataggcc ttgcctaggg tgtgagtgag ctcatccacc tctctcttga gagtctcatt    720

ctcaaccttt agtgaggtat cacaagtgac actaacacta gaagtagagg tagagttggt    780

ggtggatgaa gacctacaag aagagttagt ggcaacaaca ataggtgggt tgggtgattc    840

tttaattaag tcacaagttg tgcccacatc acatgataca acaacctttt ccctgttctc    900

ttctaacaac aaggagtgag ctttctcaag cttggtgtga gccttgccaa gcttctcatg    960

ggcttccact agcctctcat gattagcatt gagctcatca aaggattgct caagagcttt   1020

taacttcttg gccaattctt tgcacttctt gtttttagat tgaatgagag attcggcttg   1080

ttctaacatg tccatgagtt gttcattagt gaatttattt tcatcatcac tatcatgttc   1140

atgttcactt tcactttcat catattgtac cttgtggcac ttggccatga agcaagaagg   1200

agtgttgaag agtgatggct tgttgatagc aatgcttgca agtgccttct ttttggatga   1260

tttgtcatca tcgcttgagt tatcatccga agaggcatca ctatcccatg tcacaacata   1320

ggatccaccc ttcttcttct tcttgaagac catcttcttc tctttctttt ctttcttctc   1380

cttcttgttc ttcttgttat gctcatcatt gtcactattg taaggacaat ccgccacaat   1440

atgatcgggg ctcttgcact tgtagcatag cctcacatat tccttgttct tggagttgtc   1500
```

```
ccttctcttc cttatatggt agccettttt cttcatcatc ttgccaaact tgcggacaaa   1560
gagtgctagt gcttcatcat cactatcatc attggaacac tcctcatcac ttgattcttc   1620
cttgttcttg ctcttagatg aagagctagc tttgaatgct ccactcttct tcttcttatc   1680
atcatcatcc ttcttcatga cctcatcatc atcattgtca ttatattgat cttcggtcat   1740
gacatctcca agtacctcat taggagatac acctgtcaat ccacctctaa agatgattgt   1800
tctcaatgtc ttgaacctct tgggcaagca catcaagaac ttgtgaatga agtcctcatc   1860
cttcactttc tcaccaaggc ccttgaggtc attgatgatg acttggagcc tatagaacat   1920
ttctggaatt gactcatcat ccttcatatt gaagtttgat agcttgtcct tgagcatgta   1980
caacttggca ccctttaccg ttgtagtgcc ctcatatgtt tcttctagcc ttgtccacac   2040
ttcttgcctt ctcaagatct ttgacttgtt caaatacctt tgaatcaatg ccattatagt   2100
tgtgttgaga gccattgtat tgcattgctt gtttgctctc tcattgtcgg tggggttagc   2160
ggggtcaagg atcacaaaat cattcttcgt gacttctcac actctatcat tgattgatcc   2220
aagatacatt ttcatttttc tcttccaata gtcaaaagaa cttgctccat caaagaacgg   2280
tggtttgccc ccaacatggt tgaacactat ttgagccata atttgagcat cgaggttgtt   2340
aagccttcac aaaactgtga ccacggctcc aataccactt gaaaggtcct aatatggcta   2400
gaggggaggt gaatagccta tttaaaaatc tacaaactca tagagcaaga ggttagtaga   2460
taacaagcat agctttttga tctagctcta aaggggtgtt tgccagccac ctatccaaca   2520
attctagttg ctatgatcac tatgcacaca agagctatgt cactacttac actagagagc   2580
tatctaaagt ttctatacaa gtaagtaagc tactctagtt tgcgggaatg taagagagag   2640
atggtttgat ctttataccg ccgcatagag ggatgaaccc aatcaataat atgaagtcca   2700
atcaccagga gaaatccact gaacaatcac aatggagaca cacaattttc tcccgaggtt   2760
cacgtgcttg ctggcatgct acgtccctat tgtgtcgacc aacacttggt ggttcggcgg   2820
ctaagaggtg tagcatgaac cttgtcctca ctaggacacc gtaagaactg acccacaagt   2880
gaggtaactc aatgacacga gcaatccact aaagttacct ttcggctctc cgcagggaag   2940
gtacaagacc cctcacaatc actaggagat agcgacgaac aatcactaac tcgtgccaat   3000
gctcctccac tgctccaagt cgtctaggtg gcgcaaccac caagagtaac aagaaaaccg   3060
cagccaaatc gatccccaag tgccactaga tgcaatcact caagcaaatg cacttggaat   3120
cactcccaat ctcacaaaga tgaataatct atgaaggaga tgagagggag gtgtttgctt   3180
aggctcacaa ggattcaagt atgctagaat gccaagagag tgagccctaa gtcggccaat   3240
aactatttat aagctcctca aaacaaacag agccattggc tctttcactg ggctaaaaac   3300
ggggtcactt gatgaaccac agggggcatc ggacgctcaa cccctgtgtc tggtgctcta   3360
gaaacagcca cgtgttgccc tatccacttt cgcatgttga tatctaacgg tcacctgcag   3420
agcaccggac gcgctcaagt tggcaccgga cgcgtctcgt actcaccgga cttaaactca   3480
gggaggtctg caaactcgcg gggtcactgg acgctgagca cggactgtcc ggtgctcact   3540
ggtctcatac ctagagagca ttgcaaaaga gtagaacact ggactcaaaa caccggacgc   3600
tcaaatagga tctaacctgc gtccggtgtt gggcgtccgg tgcctaaccc tagctgagct   3660
agacactgcc tacacaccgg atgcacagac acagcgtctg gtgcctctga gccagcgtcc   3720
ggtgagtgtt tctcagcgag aaacacaccc gcaacttctc caattttccc acctgtgcta   3780
ttgaaaaatt gcacatcatt ttctctctac ccttcaaact tcacctcctt ttcaaagtgt   3840
gccaacacca caatgtgtaa accaatatgt gcacgtgtgt tagcattttc acaaacattt   3900
```

```
tcttcaaagg agttaagtta gctcactagg ttctaaatgc atgcacatga ataatgacac   3960

ctagtggcac ttgataaccg cttagccaaa gaattcccct ctttatagta tggctatcta   4020

tcctaaatgt gatcacaccc tctatggtgt cttgatcacc aaaaccaaaa ccctaagcaa   4080

tacctttgcc ttgatctcca tagggttttg tttttctctt tcttcttttc taagttgagc   4140

acttgatcat cttgtggtca tcaccatcat aatcatgatc atctcttgct ccatcaattg   4200

gcatgtacca acctcattaa gtctgcacac acttagtata gaggttagta caagggtttc   4260

atcaattatc caaaaccaaa ctagggattt cgacagtttg cgcctaatgc accatagtct   4320

aagagaccat tttggacgca cctgttggta ctcctaggtg aagaggctca agtggaagct   4380

cagttcggtc tttttggaga tagtgctaat cttgatgcaa gataggtgca cagtttgcat   4440

ggaacgtacc atatgctcaa aaatcaattt ggacgcacta gatggaagac ctagatgatg   4500

tgtgtcatat ggaatctcgc tttggtctgt ttggagacag tgttggtttt ggtgcaagat   4560

atgtgcacaa tttgcaccta atgcaccata ggctgagaaa ccattttaga tgcacctgat   4620

cgtactcctt ggtgaagagg ctcaagtgga agctcgg                            4657
```

<210> SEQ ID NO 298
<211> LENGTH: 547
<212> TYPE: DNA
<213> ORGANISM: Sorghum bicolor

<400> SEQUENCE: 298

```
tttggagata gtgctaatct tgatgcaaga tagatgcacg gtttgcatgg aacatacgat     60

atggtcagaa atcaattagg acgcacttga tataactcct tgatgatgtg tgtcatatag    120

aatcttgctt cggttcgttt agagactgtg ttagttttgg tagaagatat gtgcacggtt    180

tacgcctaat gcaccatagg caaagaaacc attttagacg catcagatgg tactcgtagt    240

tgaagagcct caagtggagg cttgatttgg tctgttcaga tatagtgcta tcttgatgca    300

agatagttgc acagtttgca tggaacgtgg catatgttat gaaatcaatt tggatgcacc    360

taatggaact cctagatgac gtgtgtcata tggaatcttg ctttggtctg tttggagata    420

atgttagttt cggtgcaaga taggtgcatg gtttgtgcct aatgcactat agtctaagaa    480

accatttttg acgcacctgt ttgtactcct agatgaagag gctcaagtgg aagctcggtt    540

tggtctg                                                              547
```

<210> SEQ ID NO 299
<211> LENGTH: 535
<212> TYPE: DNA
<213> ORGANISM: Sorghum bicolor

<400> SEQUENCE: 299

```
ctatctccaa acaaaccgaa gtgagattcc atatgacaca tgtcgtctag gagttccatc     60

tagtgcatcc aaattgattt ttgagcatat ggtatgttcc ttgcaaatcg tgcacctatc    120

ttccgtcaag attagcacta tctctaaaca gaccgaaccg agtctccact tgagcctctt    180

cacctaggag taccaacagt tgcttccaaa atggtttctt agactttggt gcattacgcg    240

caaaccgtgc acatttcttg caccgaaact aatactgtcc ctaagcacac caaagtgaga    300

ttccatatga cacacgtcat caaggagatc tatcgggtgt gtccaaatta atttctaatc    360

atatggtacg ttccatgtag accgtgcatc tatcttgcat caagattagc actatctcca    420

aaaagaacaa accgagcttt cacttgagcc ttttacctag gagtaccatc gggtgcgtcc    480
```

aaaatggttt cttagcctat gctgcattat gtgcaaacct tgcacgtatc tgagc 535

<210> SEQ ID NO 300
<211> LENGTH: 232
<212> TYPE: DNA
<213> ORGANISM: Sorghum bicolor

<400> SEQUENCE: 300
agatagtgct aatcttgacg caagataggt gcccggtttg catggacata ccatatgctc 60
aaaaatcaat ttggacgcac ccgatagaac ttctagatga cgtgtgtcat atggaatctc 120
acttcggtcc atttagagat agtgttagtt ttggtgcaag ataagtgtac ggtttgcgcc 180
taatgtacca taggctcaaa aaccattgtg gaagcacccg atggtactcc ga 232

<210> SEQ ID NO 301
<211> LENGTH: 1187
<212> TYPE: DNA
<213> ORGANISM: Sorghum bicolor

<400> SEQUENCE: 301
tgccagatag atgcacggtc tgcattgaac gtaccatatg cttagaaatt aatttagaca 60
cacccaatag aactccttga tgacatgtgt catttggaat ctcgctttag tgtgcttaga 120
gacagtatta gcttcggtgc aagatatgtg cacggtttac gcctaatgca ccaaagtcta 180
agaaaccatt ttggaagcac ctgttggtac tcctaggtga agaggctcaa gtggaggctc 240
ggtttggtct gtttagagat tgtgctaatc ttgatgcaag ataggtgcac gatttgcatg 300
gaacgtacca tatgctcata aatcaatttg gacgcaccag atggaactac tagatgacat 360
gtgtcgtatg gtatctcact tcggtccatt taatgacagt gttagtttcg gtgcaagata 420
ggtaaccggt ttgcacctaa tgcaccatag gataagaaac cattttggac acacccgatg 480
gtactaatag gtcaaggggc tcaagtgaaa gcttggtttg gtctatttgt agattagtgc 540
taatcttgat gcaagataga tgcacggttt gcatggaaca tacgatatgc ttagaaatca 600
attaggacgc accggatata attccttgat gatgtgtgtc atatggaatc ttgcttcgga 660
tcgtttagag acagtgttag ttttggtaga agatatgtgc acggtttacg cctaatgcac 720
cataggctaa gaaaccattt tagacgcacc tgatggtact cgtagttgaa gaggctcaag 780
tggaggctcg atttggtctg ttcggatata gttccaatct tgatgcaaca tagttgcaca 840
gtttgcatgc aatgtaccat atgttaagaa atcaatttgg acgcacccaa tggaactcct 900
agatgacatg tgtcatatcg aatctcgctt cagtcttatt ggtgacatgt tagtttcggt 960
gcaagatagg tgcatatttt gtgcctaatg caccatagtc taagaaacca tttttgatgc 1020
gcctgtttgt actcctagat gaagaggcac aagtggaagc tcggttcggt ctatttggag 1080
atagtgctaa tcttgatgca agataggtgc acggtttgca tggaacatac catatgcttg 1140
gaaatcaatt tggatgcacc cgatggaact ccttgatgac gtgtgtc 1187

<210> SEQ ID NO 302
<211> LENGTH: 402
<212> TYPE: DNA
<213> ORGANISM: Sorghum bicolor

<400> SEQUENCE: 302
aagtcatatg gtatgttcca tgcaaaccct acacctacct tgcataagga ttagcactgt 60
ctccaaactg accaaaccaa gcttccactt gagcctcttc acccaggagt actaaatagt 120
gcgtccaaaa tggtttctta gactatggtg cattaagagc aacctgtgca cctatcttgc 180

```
actaaaactt acaatgtcta caaatgaacc gaagcaagat tcaatatgac acacgtcatc    240

taggggttcc attgggtgcg tccaaattga tttctaagca tatgttatgt tccttgcaaa    300

ccatgcacct atcttgcatc aagatttgca ctatctccaa acaaatcaaa ccgagcttcc    360

actgagcctc ttcaccgaag taccaacagg tgctaccaaa at                       402
```

```
<210> SEQ ID NO 303
<211> LENGTH: 999
<212> TYPE: DNA
<213> ORGANISM: Sorghum bicolor

<400> SEQUENCE: 303

agaaatacaa gttttggtac gcacccgata gaactcctag gtgatgtgtg tcatatggaa     60

tctcacttca gtccatttgt agatagtgtt agtttcggta caagataggt gcacggtgtg    120

cgcgtaatgc accataggct tagaaacagt tgtggaagca cctaatggta cttctaggtg    180

aagagactag agtgaaagct cggtacgata tgtttggaga tagtgctaat cttcatgtaa    240

gataggtgca cagtttgcat ggaacatacc atatgcttaa aagtcaatat agacgcaccc    300

aatagaactc ctagatgatg tgtgtcatct gatatcttgc tttggtctgt ttggagatag    360

tgttagtttt ggtgcaagat aggtgcgcgg tttgtgccta atacaccata tctctaaaca    420

gaccgaacct cttcacctag gagtaccaac aggtgcttcc aaaatggttt cttagacttt    480

ggtgcattag gtgcaaaccg tgcacatatc ttgcaccata actaatactg tctctaagca    540

caccaaagca agattccata tgacacacat catcaaggag ttatatgggg tgtgtccaaa    600

ttaatttcta agcatatggt acgttccaag cagaccgtgc atctttcagt tgagcctttt    660

accaaggacg ggtgcgtcca aatagaccaa actgagcttt cacttgagcc ttttaccaag    720

gacgggtgcg tccaaaatgg tttcttagca tatgttgcat tatatgcaaa ccttgcacct    780

atcttgcacc gaaactaaca ctgtctccaa acagaccgaa gcaagatttc gtttgacaca    840

cgtcatctag gagttccatc atgtgcgtcc agattgattt ccaagcattt ggtatgttcc    900

atgcaaactg tgcacctatc ttgcattaag attagcacaa tctccaaaca gactgaaccg    960

agcatccact tgagccccct cacctaggag taccaacaa                           999
```

```
<210> SEQ ID NO 304
<211> LENGTH: 141
<212> TYPE: DNA
<213> ORGANISM: Sorghum bicolor

<400> SEQUENCE: 304

gatctatttg tagatattgc taatcttgtt gcaaccatat gcttagaaat taatttggat     60

gcacccaatg gaactcctag atgacgtgtg tcatatggaa tcttgcttcg gtccgtttgt    120

agacattgta agtttaagtg t                                              141
```

```
<210> SEQ ID NO 305
<211> LENGTH: 282
<212> TYPE: DNA
<213> ORGANISM: Sorghum bicolor

<400> SEQUENCE: 305

gaccgaagca agattccata tgacacaagt catctaggag ttccatccga aaagaccaaa     60

ttgatttcct aacatatggt acgttccgtg caatatatgc aactatcttg tatcaagctt    120

agcactatat ctgaaaagac caaatcaaga ctccacttga gcctcttcaa caacgagtac    180
```

```
catcggatgc gtctaaaatg gtttcttagc ctatgacgca tttggcgtaa accgtgcaca    240

tatcttctgc aaaaataaca ctgtctctaa acgaaccgaa gc                       282


<210> SEQ ID NO 306
<211> LENGTH: 118
<212> TYPE: DNA
<213> ORGANISM: Sorghum bicolor

<400> SEQUENCE: 306

agatagtgct aatcttgatg caagaaaggt gcatggtttg catggaacat accaaatgct     60

tggaaaacaa tctagacgca cataatggaa ctcctacatg acgtgtgtca taggaaat      118


<210> SEQ ID NO 307
<211> LENGTH: 9853
<212> TYPE: DNA
<213> ORGANISM: Sorghum bicolor

<400> SEQUENCE: 307

atatggaatc tcgcttcggc ccatttggag acattgttag tttcggtgaa agataggtgc     60

acagtttgca cctaatgaac catagtctaa gaaaccattt tggacgcact tgtttgtact    120

cctaggtgaa ggggctcaag tggttgctcg gttcggtctg tttggagata gtgctaatct    180

tgatgcaaga taggtgcacg atttgcatgg aatataccaa atgcttggaa aacaatctgg    240

aagcacatga tggaactcct agatgatgtg tgtcatacga aatcttgctt cggtctgttt    300

ggagacagtg tgtcgagggt atcagtaagg ggtatcctaa ctgatacaca taatgagatc    360

ccccatacgc aggtcgaggc cctcaactcg acgctctagt ctgtcatacg aacagtcatc    420

gacaaccgca gcctcgaaga cagaaaaggc gacgagcgaa tcgatcaggg ctcgagcgcc    480

gctaccgtcg aatacggaag taggctcgag cgaaccagga ggcgtcgagc gcaaggactc    540

cgcccgcctt gacgcgcgca tgggaagcag ggcatttaat gcgcctgtcg cattctcacc    600

taacacgcca gtcacgggaa gcgtgatagg gaacaggcat ccgtcccgtc attctttttg    660

cagccttccc cgccaaacaa cccagagcgt gtcaggacac gggaagtagg gatggaacgt    720

ctagtcagga ccccctcgag acatccaggg tcaacgctct agacagcgga gcgttacaca    780

gcggccaacc ctcgaccaga cccgtttcct tccaggggaa gggttggacg tcgaatggca    840

acaaggcaac cactccgacg gatccgctgt tatatcgtac aggcgtgccg ccaatgaacc    900

agtccaagac ggcatgcaga gcaggattcc agggcacgcg taatcatcat caagctacga    960

ggacgggatg gctcgaaacc acgccggtac ggaggcctcg agtaggtccg cgcgccatgc   1020

ctctatcgac ccctactctc acacctatat ttgtaccctg ggcttctcct tggaactata   1080

aaaggggaag cccgggagcg gactcaggag gagatcaacc agacaacacc acactcatac   1140

gcagtagaac ttccatactc cataccacgc ttgtattcac ccctgtacaa gcacttaggt   1200

gcaaaataat acaaactctc tccccccagc tggacgtagg gccttctctt gcccgatcca   1260

ggataaatcc ttgtgtcttt ttgcatcacc atcagggaaa gggaagcacg catacaaatt   1320

cactcgttgg tgtgaccccc cgtggagaaa acaccgacag ttggcgcgcc aggtaggggt   1380

cctgcgtgtt ttttcatcga tttcccattc tttcccagat ggccactctt tcttcgccaa   1440

ttctgcgctc ctcggtgatt tggttctgga gtctcgagtt tatgtccact ggctccggct   1500

atgacatgat cttgctctcg atcaaaggac cgggaggagc ccgcgtcgcg ccaacccgga   1560

tgagggcccc gagacgtcct cgccaccacg cctccccgcc caagaagagg cgtggacagc   1620

accatcatcg cccttctgcc tcgccacgac cggcagtccg tgccaggtag gaggcggcac   1680
```

```
gagagccgat agccttgtgc accacgggca cgacggctca gcgccgagag gatcacacga   1740

tgacgggagg tgacgcgccc cgcgcactct cccccaccgc taggctactt ccacatgggt   1800

tgttcgcctc aagaggagcc ttgccgatcg gcatggacaa tgccgcagcg tcactcgcta   1860

gggcgatatg cccaaacgcc cagacgtacg tggagagacc aatggtcctc ccacgcaacc   1920

ctgaagcaca gcaaccgacg tccgagctac cggatttctc ccaggtacga ggcctccgcc   1980

gcctgggccc tggacgctac acgattacct cccttagaca gcggctgctg gaggaaggac   2040

gcggatgttt ctacgccacc gagccggact ccggctcgga atccgacagc cacgacccta   2100

ctagggagtg cttccatatc gacggtgcgg tggaaaccac cgacgagaca caagacgccg   2160

ttgtaggtgg gtgggcccct gcagcgaggg aagaccccgg acgcctggga atgacggtca   2220

agtcgatccc cctctgcaag aagacagagc cgtgcaaatt gcgcagctac gagaactcaa   2280

ggcaaagctt gacgacgacc gcgagcgcct tgtcctgctt gagcagatcc tcgagcagga   2340

cctgccttac ccgcctggtg ggagtgtccg cagacgagct cgagaggtat accgacagat   2400

cgttggagac acagagccag aacagcccgt cagccatttc cctcgagcag gccagaacgt   2460

cgtggcagca acaatgctac tgcgaaacat gccggagccg tcgaactccc aagctcgacg   2520

cattcgagac gaggtgcaga cactactcca ggtggcggca gttcaacagg ccgaaagctc   2580

ggcttctcga cgtcgaggag ctgccactaa aaagcgcgat gagccagccc aaaacgaaaa   2640

ggaggtgtcg gtccatcagc agccgcctcc tcgaggaaaa aagaccatgc tcattctccc   2700

cgtcgacaat cagcgtcgac acgacgcgcg atgtgacatt gaagagaatc gacgccgtcg   2760

gtacggggac gcggaagagc gcggttacag tgcccatcgc ggtgggaggt acgacagtga   2820

tgaagatcgg atggctctag agccaccagg cccacgggta ttcagcaggg caatccgcag   2880

cacaccgctg cccagcccgt tccgaccccc gaccagcctc gcgaagtaca acggagagac   2940

caacccggag ctgtggctgg cagacttcag gctggcctgt cagctgggag gtgctcgagg   3000

agacgatcga gccatcatca gacagctgcc actcttcctt tccgacaccg ctcgcaggtg   3060

gcttgaagag ctcccggccg atcagatcca tgactaggtc gatctggtta gagttttcga   3120

aggtaacttc aaagggacct acatacggcc tgggaactcg tgggacctca gcaagtacaa   3180

gcagaagtca ggagaaactc ttcgagagta tgctcgatgc ttctcaaagc aacacaccga   3240

gctaccgcac atccccaatc acgaccgcac atcaccgagg taccaccagt cgagacttgg   3300

tacgggaatt aggccgaaat caccctcagt tcgtcgacga gctgatggat atggtggcca   3360

actacgcggc aggagaagaa gcggtcggcg ccttcttcag ctgtgaagaa aggaaaggca   3420

agcagcccgc cgacgatggt gaaggcccca gtcgagggcc caagaagagc aagaagaaga   3480

agaagacccg gccgttccaa cgggaagacc tcgacgacga tctcgtcgct gccatggaat   3540

gctaaaagcc tcgaggcccc ccagatgggg gcatctttga taaaatgcta gaagagtcgt   3600

gccctttcca taagggagga gccaaccaca agctcaagga ctgtcgtatg ctgagaaagc   3660

atttcgacgg tctggggttc aagaaggacg cgcgcgatga cccaaagaaa gagaagggcg   3720

gcgaaaagga ggacgacaaa gacgacggtg gtttccctgc cgtccatgac tgctacatga   3780

tctacggcgg gccctcgacg cagctgaccg caaggcagtg caagagggaa cgccgtgagg   3840

tcttcgcggc gaggatggcg gtgccccagt acctcagctg gtcgagcacc cctatctcct   3900

ttgatcgaga ggaccacccc gacaaagtag ctgcccctgg cgtctacccg ctcgtcgtcg   3960

accctatcat catcaacacc cggctctcaa aggtaccgat ggacggtggc agcagcctta   4020
```

```
acatcatcta cctcgagacc ctcgacctcc tcggcatcag cagggcacag ctccaaccaa   4080
gcgccggcgg cttccacggc gtcgtactag gaaagaaggc gctgccggtt ggtcgaatcg   4140
atctaccggt ctgttttggc acggcggcca acttcagaaa ggagaccctc acctttgagg   4200
tggtggggtt ccggggcatg taccacgcca tcatcggatg accgggttac gccaaattca   4260
tggctatccc caactacacc tacctaaagc tgaagatgcc cggccccaag ggtgtcatca   4320
tagtcagctc ctccttcgag cacgcatatg agtgcgacgt cgagtgcgtc gagtatgggg   4380
aggcagtcga gagttccacc gagctcgcct caaaactcga ggccctggcc gctgaggctc   4440
cagagcccaa gcgccacgca ggcagcttcg agccggcgga aggaaccaag aagatcccac   4500
tcgaccccaa caactccgat ggcaagatgc tgacgatcag cgctgacctt aatcccaaat   4560
aggaagccgt gctcgtcgac tttctccgtg caaacgccga catatttgca tggagtcctt   4620
tggacatgcc tggcataccg agggaagtcg ccgagcactc cttggaaatt cgagccggtt   4680
ccaagccagt gaagcagcgg ttgcgccgat tcaacgagga gaagcgcaag atcattggtg   4740
aggagatcca aaagcttttg acggccggat tcatcaagga ggttcaccat cccgactggt   4800
tagcaaatcc tgtactagtt aagaaaaaga atgggaaaat gaggatgtgt gtcgattata   4860
caagtttaaa taaagcatgt ccgaaagttc cttttccatt acctcgtatc gatcaaattg   4920
ttgactcaac tgcgggatgt gaaacccttt ctttccttga tgcatattct ggttaccatc   4980
aaataaaaat gaaagagtcc gaaattcatt acaccttttg ggatgtattg ttatgtgacc   5040
atgccgttcg ggctttgaaa cgcgggggcc acatatcagc gctgcatgct ccacatgttt   5100
ggcaagcaca tagggtcgac agtcgaggcc tatgtcgacg acatcgttgt caagtcgaag   5160
cggcagggag acctgatcca ggacctcaaa atcgctttca gctgtttacg cgcaaaccag   5220
atcaagctca accctgagaa gtgtgttttt ggcgtacctc ggggcatgct cctgggttac   5280
atcgtttccc agcgtggcat cgaggccaac cccaagaaag tctcggccat cacaagaatg   5340
gggccgatcc gagacatcaa gggcgtacaa agggtaacgg gatgcctagc ggcgctgagt   5400
cgttttatct caaggttggg agaaaaggcg ttgcccctat accgacttct gaagagagag   5460
agcgcttctc ttggacccct gaggccgagg aagccctcga aaacctgaag aaaacgttga   5520
cctcagcacc agttctggtc ccacctcaac ctagagaacc gctactcttt tatgttgcct   5580
cgacgaccca ggtcgtcagc gtagctgtgg tggtcgagag gcaggaggag gggtgtgcat   5640
tgcctgtcta gaggccggtc tatttcgtca gcgaggtact ctcggagacc aaagcgcgtt   5700
acccacagat ccagaagctg atctacgccg taatcctcgc ccgacgcaag ctgcagcact   5760
acttcctcgg ccatcctatc acagtggtct catccttccc cttaggagag atcatccaaa   5820
gttgagaagc cacgggaaga atcgccaaat ggtcggtcga gctcatgagt gagactctca   5880
cttatgcgcc ccgtaaggct atcaagtcgc aagcccttgt ggattgcgtc gcggaatgga   5940
cagactccca gctcccccg gcctaggttc aggcggagct gtggacgatg tacttcgacg   6000
ggtctctcat gaagacagga gctggggcgg gcctgctatt catttcgccg ctgggcatcc   6060
atatgaggta cgtcgtcagg atacactttg ccgcatccaa caatgttgca gagtacgagg   6120
cccttgtcaa tggtctgaag atcgccatcg agctgggagt ccgacgcctc gatgttcgag   6180
gcgactccca gctcgtcatc gaccaagtaa tgaaagcctc gaactgtcac gacccaaaaa   6240
tggaagcata ctgcaaggag gtccgtcgac tcgaggacaa gttccacggc ctcgatctcg   6300
tccacgtcgc ccgatgctaa aacgaggcag ccgacgaact cgccaggatt gcgttgaccc   6360
gaggcacggt ccctcctgac gcgttttcaa gagatctaca cgagccatcc atcgacctgg   6420
```

```
gctcgggggc tgacatcgag accgctcctg cccagcaaac caacgccgtc gaggcactac   6480
taatggcggc tgaggtaatg gaagtgcggc ccggtcgacc gttcgattgg cgcacgccgt   6540
tcctcgactg cctgatccgc tgcgagctgc tataagatcg atctgaggcc cgccgtattg   6600
ctcggcgggc caagtcatat gtaatctatg gcgatgacaa ggagctatat cgacgaagcc   6660
cgataggggt cttgcagcgt tgcgtcacca tagaggaagc cggaaactcc tcgaggatct   6720
acactcgggg gcttgtgggc accatgctgc tccacggacc cttgtaggga acgccttccg   6780
acaaggcttc tactggccaa cggtcgtagc tgacgccatc gagctcgtac gctcatgcca   6840
cggatgccaa ttctacgcca agcagacgca cctgcctgcc cacgctctcc agatgttccc   6900
gatcacatgg ccgttcgcgg tatgggggct cgacttagta gggcctctac aaaaggcaaa   6960
agggggggtac actcacttgc tggtggctat cgacaagttc tccaaatgga ttgaggctcg   7020
acccatcacc aacatccgtt ccgagcaagc cgtccttttc ttcaccgaca tcatccaccg   7080
gtttgggatt cccaacgtca tcatcaccga caacggcact cagttcaccg gcaaaaagtt   7140
cctggccttc tgcgatcagc atcacatcca tgtgaactgg tctgtagttg cccaccctcg   7200
aactaacgac caggttgagc atgccaacgg catgattttg caggggctca aaccgagaat   7260
ctataatcgc ttgaagaaat tcggcaagaa atgggttgag gagctttcct cagtcctatg   7320
gagcttaagg actacgccaa gcagggccac aaaatacacc ccatttttca tggtctatgc   7380
tctgaggccg tgctcccgat ggatctcgag tatgggtccc ctcgactcaa agcatacaac   7440
gagcaatcaa ataaggagac tcaagagaat gcggtcgacc agctcgagga agctcgagac   7500
atggccctcc tcaactctgc caggtaccag cagaagcttc gacgctacca cgacaagcac   7560
gtgcgcaaga gggacctgaa cgtggccgac ctcgtcctac gacggcggca aagcaatcaa   7620
ggacgccaca agctgactcc accttgggaa ggcccatacg tggtggccga ggtcttgaaa   7680
ccgggaacat acaagctcgc agacgaaaag ggagcgatct tcaccaacgc gtggaacatc   7740
aaacagctac gtcgattcta cccctagaat ttcaaagctt tatgttccca cgtacattct   7800
gtaccgaggt tttgtaaatg aatgcatgaa taaataaagt ctttccctcg agcaatttgc   7860
tttttcacga gtcaaaatct tgacgattag aagggggtac cgactatgac ctatcatagt   7920
cgatacctcc tcgggggcta gcaggagggc gaccccccca ggtgtcgaaa aaaccaagta   7980
accctttcgt tcccatcagt aatctcgtgt ggttgagtag taaaggtacc tcgagcccct   8040
tacgggccga gaaacgacga gcctgagatc tcctacgccc ccgggctacg gaaactctac   8100
tcgcctcctc acccttaagg caatcgagac cgccttaaac aaaagaccga gcgggaaaaa   8160
acaaacatag gcgcaagaag aagtaaagga gcctcgagcg gaaagacaga taaacatttg   8220
acaaccattt aaaagacgtc atactactta aagatagagt agcaaagtac tgtacaaagg   8280
ggcctaggca cccagagcag gctcgcaggc ctcagtccgc atcatggtcc tcaccgccct   8340
cgcctgcgcc cgagctagtc tcaggaggca gtacctctgg ctcgaacagc ctagccaacc   8400
tctctccagg aacctctgcg tcgtcgatca aggcgtggag cctctcttcg ttctccacgt   8460
cggtcttgga tatgtcggtg acgaagccgt gggacaccac ctccatgtca taggagaagc   8520
ctggacagac aacggccatt gcccgcatca ccccgatgtg gagagcgtcc cgcacccgat   8580
ccatcagcat cgcgcctaag tagcacagct gatcgaccag cgcgtcgcct cgagcttcct   8640
ccatcgactc gtccatgggc tcgacctccc aagaggtcga gagatcgctt atcgccgtcc   8700
gaagtcgacg gttcaaaaca acctccccct cgagctgggc tttggcattg cgagcctcga   8760
```

```
cttgggcggc caagagcttg tctttaaggc ctgtgaatgc aaaaagcttt agataaaacc   8820

aagcacatct cgaaaagaaa atctgacaaa agaaacacac cgcggacact ctcctccaga   8880

gttgtgttct cgctaactaa tttggtgttg gccctctcga tctctttgtt ggagcgtgcc   8940

agctcagtat tggcaacacg aagatcctcg atcgccttgc cagcctgagc aatagctcca   9000

ttcttctcca acagctctcc cttcaaacga tcgacgtcgt cagagaggct gtgggatcga   9060

gcccgcttcg cctcgaggtc ttcaatggcc tttttctttg cctcctccgc ggcacccctg   9120

gcgacctcac tgtccacata ctccaccttt atcctccgga aggattctcg gatggagtcc   9180

aggtcggtct tgaggaggcc cttctccttg tccaggtcag caacagtgct cttataggac   9240

agagcctcct ctcgggcttt ggacccggcc tcctcgaccg tcagaacccg ctccctcagt   9300

agcacggcct cttccacagc cttctttgag aactctcaag cctcggctag ggcagcctcc   9360

ctctccttct tctcctcctc gagcgccaag agctctttat aagctttgag gagtttatcc   9420

tgcgactcca ggggttggtc tttgaggagg gggagctgct cctagtcgcc tctcgtggca   9480

tgaatgaagc ctgacttaat acgggaggtc tctttcaggt cctgcgagcc ggtgatcgag   9540

cagttagaac ccaaaaccaa cgagttccct aaaggttaaa agactaggag acttacaaag   9600

taggccggcc cgagcccgtt gtttacaacg tccgacaaga gccccaccgt gtgcttcatc   9660

caaaggcgga gctcctcgac gtgctcccac ttctcggctt ccttccgatc atccagaaaa   9720

atgttgggct tggacggatc cgtggaagca cggatgcgga tccagcggcc gcataagttc   9780

gtatagcata cattatacga agttatctgc taccttaaga gaggcccaaa ctcggaccgt   9840

cctaggaagt acg                                                      9853
```

```
<210> SEQ ID NO 308
<211> LENGTH: 1397
<212> TYPE: DNA
<213> ORGANISM: Sorghum bicolor

<400> SEQUENCE: 308

aggtgaaggg gctcaagtgg atgctcggtt cggtctcttt ggagatagtg ctaatcttga     60

tgcaagatag gtgcacggtt ttcatggaac ataccaaatg cttggaaatc aatctggacg    120

cacatgatgg aactcctaga tgacgtgtgt catatgaaat cttgcttcgg tctgtttgga    180

gatagtgtta gattcggtgc tcagatacgt gcaaggtttg cacataatgc agcataggct    240

aagaaaccat tttggacgca cccgatggta ctcctaggta aaaggcttaa gtgaaagctt    300

ggttaggtct atttggagac agtgctaatc ttcatgcaag atagatgcac ggtgtgcatg    360

gaacgtacca tatgcttaga aattaatttg gacacacccg atataactcc ttgatgacgt    420

gtgtcatatg gaatcttgct tttgtgtgct tagagagagt tttagttccg gtgcaagata    480

tgtgcacggt ttgcgcataa tgcaccaaag tctaaaaaac cattttggaa gcacctgttg    540

gtactcctag gtgaagaggc tcaagtggtg gctcggttcg gtctatttag agatagtgct    600

aatcttgatg caagataggt gcacgatttg catggaacat accatatgct cagaaatcca    660

ttttgacaca ccagatgaaa ctcctagatg acatatgtca tatggaatct cacttcggtc    720

tgtttagaga cagtgttagt ttcggtgcaa gataggtgca tagtttgcac ttaatgcacc    780

ataggataag aaactgtttt ggacgcaccc gatggtactc ctaggtcaag ggactcaagt    840

gaaagctcgg tttggtatgt ttggaggtag tgctaatctt gatgcgagat agatgcacag    900

tttgcatgga acatatgata tgctcaaaaa ttaactagga cgcacctgat ataactcctt    960

gatgatgtgt gtcatattga atcttgcttc ggtacgttta gagacagtgt tagttttgat   1020
```

```
agatgatatg tgcacggtat acgcctaatg caccataggg taagaaacca ttttagacgc   1080

acccgatgat actcatagtt gaagaggctc aagtggaggc tcgatttggt ctgttcggat   1140

atagtgctaa tcttgatgta agatagttgc acaatttgaa tggaacgttc cacttgttaa   1200

gaaatcaatt tggacacacc caatggaact cctagatgat gtgtgtcata tggaatctca   1260

ctttggtctg tttggagaca atgttagttt cggtgcaaga taggtgcata gcttgtgcct   1320

aatgcaccat agtctaagaa accattttta acgcacctgt ttgtactcct agatgaagag   1380

gcaagctcgg ttcagtc                                                  1397
```

```
<210> SEQ ID NO 309
<211> LENGTH: 262
<212> TYPE: DNA
<213> ORGANISM: Sorghum bicolor

<400> SEQUENCE: 309

aagctcggtt cggtctattt ggagatagtg ctaatcttga tgcaagatag ttgcacggtt     60

tgcatggagc gtaccatatg ctcgaaaatc gatatggacg caactgatgg aactcctaga    120

tgacatgtgt catatagaat ctcgttttgg tctatttgga gactgttagt tttggtgcaa    180

gatattgcac ggtttgtgcc taatgcacca taggctaaga aaccattttg gagcacctgt    240

tggtactcta ggtgaagagg ct                                             262
```

```
<210> SEQ ID NO 310
<211> LENGTH: 671
<212> TYPE: DNA
<213> ORGANISM: Sorghum bicolor

<400> SEQUENCE: 310

ctaggtgaag aggctcaagt ggaggcttgg ttcggtctgt ttagagatag tgctagtatt     60

gatgcaagat aggtgcacga tttgcatgga aactattttg gatgcactat ttggtactcc    120

tgggtgaaga ggctcaagtg gaagcttggt tcggtcattt tggagatagt gctaatcctt    180

atgcactgta ggtgcatggt ttgcatggaa cctaccatat gcttggaaat caatttggat    240

gcacccgatg gaactccttg ttgacctgtg tcatttggaa tctcgcttca gtccatttgg    300

agacattgtt agtttcggtg aaagataggt gcatagtttg cacctaatgc accttagtct    360

aagaaaccat tttggacaca cttgtgggta ctcctaggtg aaggggctca agtggatgct    420

cggttcgatc tgtttggaga tagtgctaat cttgatgcaa gatagatgca cagtttgcat    480

ggaacatacg atatgcttag aaatcaatta ggacgcacct gatataactc cttgatgatt    540

tgtgtcatat ggaatcttgc ttcagttcgt ttagagaaag tgttagtttt ggtagaagat    600

atgtgcacgg tttacgcctg atgcaccata ggctaagaaa ccattttaga cgcacccgat    660

ggtactcgta g                                                         671
```

```
<210> SEQ ID NO 311
<211> LENGTH: 338
<212> TYPE: DNA
<213> ORGANISM: Sorghum bicolor

<400> SEQUENCE: 311

agaaatcaat taggacgcac ctgatataac tccttgatga tttgtgtcat atggaatctt     60

gctacggttc gtttagagac agtgttagtt ttggtagaag atatgtgcac ggtttatgcc    120

taatgcacca taggctaaga aacaatttta gacgcacccg atggtactcg tagttgaaga    180
```

```
ggctcaagtg gaggctcgat ttggtctgtt cggatatagt gctaatcttg atgcaagata    240

gttgcacagt ttgcatgcaa cgtaccatat gttaagaaat caatttggac gcacccaatg    300

gaactcctag atgatgtgtg tcatatggaa tctcgctt                            338


<210> SEQ ID NO 312
<211> LENGTH: 169
<212> TYPE: DNA
<213> ORGANISM: Sorghum bicolor

<400> SEQUENCE: 312

agtgttagtt tcggtgcaag aaaggtgcac ggtttgcgcc taatgcacga taggctaaga     60

aacaattttg gtcgcaccca atggtattcc taggtaaagg ggcacaagtg aaagcttggt    120

atggtttctt tggagatagt gctaatcttg atgcaaaata ggtgcacgg                169


<210> SEQ ID NO 313
<211> LENGTH: 102
<212> TYPE: DNA
<213> ORGANISM: Sorghum bicolor

<400> SEQUENCE: 313

tttgcatgga acgtaccata tgctcagaaa tcaatttgga cgcacctgat ggaactcgta     60

gatgacgtgt gtcatatgga atcttgcttt ggtccgtttg ga                       102


<210> SEQ ID NO 314
<211> LENGTH: 123
<212> TYPE: DNA
<213> ORGANISM: Sorghum bicolor

<400> SEQUENCE: 314

ttgaagaggc tcaagtggag gctcgatttg gtctgttcgg atatagtgct aatcttgatg     60

caagatagtt gcacagtttg catggaacgt accatatgtt aagaaatcaa tttggacgca    120

ccc                                                                  123


<210> SEQ ID NO 315
<211> LENGTH: 397
<212> TYPE: DNA
<213> ORGANISM: Sorghum bicolor

<400> SEQUENCE: 315

caagataggt gcacggtttg cgcctaacgt gatgtctgtc acatgcaatc tagctttggt     60

ctgtttggag atagtgttag attcagtgca agataggtgc acggtttgcg cctaatgcac    120

cataggctaa gaaatgattt tgacccaccc gatggtactc ctaggtaaag gggctcaagt    180

gaaagctcgg tttggtctgt ttggagatag tgctaatctt gatgcaagat aggtgcacag    240

ttagcatgga atgtaccata tgctcagaaa tcaattagga tgcacccgat agaactccta    300

gatgacgtgt gtcgtacgga atctcacttt agtccatttg gagatagtgt tagttttggt    360

gaaagattgg tgcacggttt ccgcctaatg caccata                             397


<210> SEQ ID NO 316
<211> LENGTH: 288
<212> TYPE: DNA
<213> ORGANISM: Sorghum bicolor

<400> SEQUENCE: 316

gtgcacctat cttgcatcaa gattagcact atctccaaac aaactgaacc gagcatccac     60

ttgagactct ttagctagga gcacaatcgg gtgcatccaa aatggtttgt tagagtatgg    120
```

```
tgcattaggc acaaaccatg cacctatctt gcactgaaac taacactatc tccaaacaaa    180

aaaagtgaga tatcagatga cacacatcac ctaggagttc tatagggtgt gtccaaattt    240

attttcaagc atatggtatg ttccatgcaa accgtgcacc tatcttac                 288


<210> SEQ ID NO 317
<211> LENGTH: 13826
<212> TYPE: DNA
<213> ORGANISM: Sorghum bicolor

<400> SEQUENCE: 317

cctatcttgc accgaaacta acaatgtctc caaatggacc gaagcgagat tccatatgac     60

acacgtcgtc aaggagttcc atcgggtgca tccaaattga tttccaagca gcaagacaag    120

gtgaaaacct ttgtcagacg agcacaatag gaatttggtc ttcctatcaa gaaagtaaga    180

agtgacaatg ggaccgaatt caaaaacact cactcaagtt gaagagtttc ttgatgatga    240

aggcatcaag catgaatttt caaccgcgta caccccacaa caaaatggtg tggtagagag    300

aaagaataga acacttatcg acatggcaag aactatgctt gatgaataca agacgtcgga    360

tatattttgg tgtgaggcca tcaacaccgc ttgccatgcc atcaatcgcc tctatctaca    420

caagaaactc aagaagactt catatgagct tctcaccggt aacaaaccca aggtgtccta    480

ctttagagtg tttgggtgta aatgcttcat actaaacaaa agacccaaaa cctctaagtt    540

tgcacctaaa gtagatgaag gatttcttct tggctatgga tcaaatgagc acgcctatcg    600

agtcttcaac aaaactctag gtagagttga agtgtcgata gatgtgacat ttgatgaatc    660

taatggctct caagtggagc aagttgatct aagtgttgta ggaaaggaag atccaccttg    720

taaggcaatc aagcaaatgt ccatcggtga cattaggcca ctggaaggat aagtctcaga    780

aaaggaggat ccaccagctg ttgctgcaca aatttccact gacgtactcg acaaggatgc    840

acaacacaca cctactagaa atcagcaggg cggcagtgcc gccccctcca cctcagcagc    900

agaccctcct gcttctatat cacaagttga aggaatcaac ctagagccca tttttgaaca    960

agaagaagct gaaggttcag aggagtagaa aaagcttgat gagtatccaa gacttccaca   1020

aactatacaa caagatcatc ccatcgacaa cattcttgga agcattcgaa aaggggtaac   1080

aactagatct catttggtta acttttgtca attttactcg ttttgtctcc tctttggaac   1140

cactcaaggt cgaacaggca cttggagatc cggattgggt catggcaatg caagaggagc   1200

ttaacaactt tgagagaaat caagtatgga ccttggttga aaggtcaaat accaatgtta   1260

ttggaacaaa atgggtcttt cgcaacaagc aagatgaaca tggtgtggtg acaagaaaca   1320

aggcaagatt ggtagctcaa ggatttactc aagtagagag attggatttt gaagaaacat   1380

atgcaccggt agcaaggctt gaggcaattc gaatgctctt agcttttgct gcccatcatg   1440

acttcaagtt atatcaaatg gatgtcaaga gtgcattcct caatggtcca atacaagaat   1500

tggtctacgt tgagcaacca ccgggatttg aagaccccaa gtttccaaac catgtgttca   1560

aactccgaaa ggcactctat gggctgaaac aagcaccaag agcatggtat gaatgcctta   1620

aggaattctt ggttaaacaa ggctttcaca tagggaaagc cgatcctaca ctcttcactc   1680

ataaagttcg tgatgaggac atcaacacca gcgatacata tcctacatcc tctccggtac   1740

aacctatagc tggtcctaca tcctctccga cacaacctat agctggtcct cttactcgtg   1800

ctcgtgcccg tcaactcaac cttcaagtaa gttcagtttt aaactcttgt caatcatatt   1860

tagacaatgg agacacgtgc actttcgtgt tgctcaggaa taatggacaa gatcagcaag   1920
```

```
ggaaggttca actgcattca gaatttgagg caacaccaac ttcaagggct gattgcatat   1980
gggaagagtg ataacttaac aaaggtgatt ggagatcagg tccaagcctc cacaacatcc   2040
tctatcaagt taccacgtcg cttctaaagc aaggaaacaa agagtccaaa cccaacacgt   2100
tttgggagtt ggattcggac tggaaaataa ctctaacttg tatggatcac cacagcgtca   2160
tatggactcc aactgggacg ttcctatact tgttggaaag cacataaagt ctactttcca   2220
atgggtccaa ccaaatatct atgcggctta tgagtcgggc gcagtccttg ttttcgtgcc   2280
gacacctttt tctgttttgg tgctgcgtca ccctattttg gaccaatggc ccatgtatca   2340
agttgagtcc attagggatg cgtcctaagg ttggaggatg actctagcac ccctttggtc   2400
gtcctcccct ctatttattt acatctagag ccgccatgaa caactgggtt ttgattagat   2460
aaagtttagc cttcgctact tgcttgtaaa cgcgcgtgct gatccagccg cccgtcttct   2520
tgttttcgaa accccacttc attagagatt gagtttgaaa ccttcattta catctggtaa   2580
tttagtactt gttctacttg ttcttgttgg ttcttcgatt gcttgcagga cgagtgccct   2640
agtggccggg tgttgcgctc cacaagatcg tgacagccat tggaggcggt gtatcggttg   2700
ctaaggcgca gtcttgaggg ctgtagtcgg gccgtgaacg tcatctccat tcactaatcg   2760
agttatccag cgcctctcat cgaaagatca ggcgaaaacc ctagtgggtt cacatcagtt   2820
ggtaatcaga gcaaggttta tcggtgagag atttccaatt cttcgtgttt gtttttccta   2880
tagtccaaaa aaaaagacaa aaaatatagc agatttgttt tccataatcc tataaatcct   2940
ttgtgccgtg gctagtacta cttagttagg gctggttgaa tgagtgtttg cttcggtcgt   3000
gtccagtgct ggttttagtt tagtccttta gagttttgag ttcttgtcac catctagtca   3060
caactgcgtc caatctattg tgggttggaa tttgagtaga tcttgataat aggtgcagcc   3120
acttgttggt ctattctgcg tttccatcaa cgtgatccaa aaggaaagat agcacttcat   3180
acttgtgcta gatatattga attttgaggt tcaaccttac tctagtgaga gggtgagagt   3240
ggtgaagtga tattttgtac tattttgttt atataatcag gttttgaggt tccccaaaaa   3300
aaagaaaaga gaaagaaaaa aataaagaaa aaaaaagaaa gaaagaaaga aaaaagaaaa   3360
aaaatcaaaa aaagggattg ttgttccttt tgtttccagt agggctgctc attttgtttc   3420
tagtggtgtg atgtgttttc cctttgtgtc caggctcgcg tctctagcac ggtctaggct   3480
aggaccagca cagtaccacc gttgagcgtt tattcagctc gcttttataa ctaacgtggt   3540
gctagttcgt tccttgtttc agcccaccta tagctccaca tactctacag cttgacaggt   3600
cttgtgctgc agcaccgata cacttcgtcc attgctgtac acttgttggc agacgacccc   3660
tcctgtcaag caaggtatga attggtaaga acttgtgtta caggttgagt gtgagcgact   3720
tgctgtagct acatcctagt agttgtaggg cttttatttc ttcacttgcc tttttgttgt   3780
ctttgtcttt gaaccatgcc aggggcagat gatggtaacg aaacaccact tacacctcgc   3840
actaagggca tcatacaaca ttttgaaaag aaagtgaagc tgcacacaga gggacttgat   3900
aacgacttgc aggtgacaaa tgaaaagctg ggacagttgg aggctacgca gattgccaca   3960
aacaacaagc tcacaagttt ggaggaatcc attgctagtg tggacaaaag ccttgctgct   4020
ctcctaaggc gatttgatgc tttccacaca atggacaaag agaagcataa ggaagaaaac   4080
aaggaggaag accgagtgga tggcaattat gatgatgatt acactgctga tacgaaacga   4140
gatgatcaag acactcatca tcgacgtcac ctacgtcaca cccgtagagg tatgggtggc   4200
caccaccgac gcgaggtaca caataataat gatgctttca gtaagattaa atttaaaata   4260
cctccttttg atggtaaata tgaccctgat gcatacatta cttgggagat tgctgttgac   4320
```

```
caaaagttta catgtcatga attccctgag gatacacgtg ttagggctgc tactagtgag   4380
ttcactgatt ttgcttccgt ttggtggata gaacatggca agaaaaatcc taataacata   4440
cctagaactt ggaatgcgtt gaaacaagtc atgagggcta gatttgttcc ttcttactat   4500
gcacgtgaca tgattaataa gttgcagcaa ttgagacaag gtgctaaaag tgtagaagaa   4560
tattatcagg aattacaaat gggtatgctg cgatgtaatt tagaggagga agaagaacct   4620
gctatggcta gatttttggg cgggttaaat cgtgaaatcc aggacattct tgcttataaa   4680
gattatacta acgtaacccg tttgtttcat cttgcttgta aagctgaaag ggaagtgcag   4740
ggacaacgtt ctagtgccaa atctaacaat tctgcaggga aatcctggca acaacgcaca   4800
tctgctacat tgtcgggtgg tgtacctctt ccatcaagcc gatcaatagc tccaccacct   4860
tcctacagcg acaaaccaca tgattcttcc acaaatacag caactaaatc agtccagaga   4920
ccaatcgcta gtgccacctc ggttaattcc acgggaagaa caagagatgt tcagtgccat   4980
cgatgcaagg gatatgggca catgatgcgt gactgcccaa acaagcgagt tatgattgtc   5040
agggatgatg gtgagtactc atctgctagt gattttgatg aggatacact tgcactgctt   5100
gcgactgacc atgcaggtaa tgaagatcaa atagaagaac atattaatgc aggtgaagcg   5160
gaccactatg agagcttaat cgtgcagcga gtgcttagtg cacaaatgga gatggcggag   5220
caaaatcagc gacacatttt attccaaaca aagtgtgtca tcaaagagcg ttcttgtcgc   5280
atgatcattg atagaggtag ctgcaacaac ttggcaagca gcgatatggt gcagaagctt   5340
gccctcaaca ccaagccaca cccgcatccc tactacatcc aatggctaaa caacagtggt   5400
aaggcaaagg taactagact tgtgagaatt aatttttcca tcggatccta caaagatatt   5460
gttgaatgtg atgttgtgcc tatgcaagct tgtaacattc tgctaggtag accttggcaa   5520
tttgatagag attctatgca tcatggtaga tcaaatcagt attcttttct ataccatgat   5580
cgcaaaattg tgttgcatcc tatgtcccct gaaactatta tgcaaactga tgttgctagg   5640
gctactaaag caaagagcaa gagcaataaa aatgataaat ctgtaattgg taacaaagat   5700
gagataaaac tgaaaggacg ttgtatgatc aaatcagata ttaatgagtt caatgcatcc   5760
acttctgttg cttatgcttt gatatgcaag ggtgctttga tttcaattga ggatatgcaa   5820
tgttctttgc cccctgctgt tgctaacgtt ttgcaggagt attctgatgt gtttccaagt   5880
gaggtaccag cggggctgcc tccactacgc gggattgagc accaaattga tcttattcct   5940
agagcagttt tgccaaatcg tgcaccatac aggacgaacc cggaggaaac aaaggaaatt   6000
cagcgacaag tgcaagaact actagacaaa ggttatgtcc gagaatctct tagtccttgt   6060
gctgttccag taattttagt gcctaagaaa gatggaacat ggcgtatgtg tgttgattgt   6120
agagctatta ataatatcac cattcgatat cgacacccta ttccacgatt agatgatatg   6180
ctagatgaac tgagtggtgc tgttgtgttt tcaaaagttg atttacgtag tgggtaccac   6240
cagattcgta tgaaattagg agataaaggt agaaagcaat tgattctgga acctggggat   6300
ttggtttggt tgcatttgcg aaaagataga tttccagaac tgagaaaatc caaattgatg   6360
cctagagctg atggtccttt taaagtgcag caacgaatta atgagaatgc atataagctt   6420
gatcttcctg cagattttgg ggttagtccc acatttaaca ttgcagattt gaagccttat   6480
ttgggtgagg aagatgagct tgagtcgagg acgactcaaa tgcaagaaag ggaggatgat   6540
gaggacatca acaccagcga tacatatcct acatccacca gcgatacata tcctacatcc   6600
tctccggtac aacctatagc tggtcctaca tcctctccga cacaacctat agctggtcct   6660
```

```
cttactcgtg ctcgtgcccg tcaactcaac cttcaagtaa attcagtttt aaactcttgt   6720
caatcatatt tagacaatgg agacacgtgc actttcgtgt tgctcaggaa taatggacaa   6780
gattagcaag ggaaagttca actgcattca gaatttgagg caacaccaac ttcaagggtt   6840
gattgcatat gggaagagtg ataacttaac aaaggtgatt ggagatcagg tccaagcctc   6900
cacaacatcc tctatcaagt taccacgtcg cttctaaagc aaggaaacaa agagtccaaa   6960
cccaacacgt tttgggagtt ggatccggac tggaaaataa ctctaacttg tatggatcac   7020
cacggcatca tatggacacc aactgggacg ttcctatact tgttggaaag ctcatgaagt   7080
ctactttcca atgggtccaa ccacatatct atgcggctta tgagtcgggc gcagtccttg   7140
ttttcgtgcc gacacctttt tctattttgg tgctgcgtca ccctattttg gaccaatggc   7200
ccatgtatca agttgagtcc attaggaacg cgtcctaggg ttggaggacg actctagcac   7260
acctttggtc atcctcccct ctttttattt acatctagag ccgccatgaa caactgggtt   7320
ttcattagat aaagtttagc cttggctact tgcttgtaaa cgcgcgtgct gatccagccg   7380
cccgtcttct tgttttcgaa accccacttc attagagatt gagtttgaaa ccttcattta   7440
catctggtaa tttagtactt gttctacttg ttcttgctgg ttcttcgatt gcttgcagga   7500
cgagtgccct agtggtcggg tgttgcgctc cacaagatcg tgacagccat tgcaggcggt   7560
gtatcggttg ctaaggcgca gtcttgaggg ctgtagtcga gccgtgaacg tcatctccat   7620
tcactaatcg agttatccag cgcctctcat cgaaagatca ggcgaaaacc ctagtgggtt   7680
cacatcagtt cgtaatgata tatttgtgtg ccaaatatat gtcaatgaca taatatttgg   7740
cagtactaat catttgtatg ttgaagaatt tagtaggacc atgacgaaga gatttgagat   7800
gtccatgatg ggtgaattga agttcttcct tggatttcaa atcaaacaag tgaaggaagg   7860
aactttcata agtcaaacca actacactca tgatatgctt aagaagtttc acatggtgaa   7920
tgccaagcct atcaaaactc ccattccaac taatggacat cttgatctaa atgaagaagg   7980
gacagccgtg gatatcaagg tatatcgttc catgattggc tctcttcttt acttatgtgc   8040
atctaggccg gacataatgc ttagtgtgtg catgtgtgct agatttcaag ccaacccaaa   8100
agagtgtcac ttagtggctg ttaagagaat cttacgatat ctagttcaca cactgaacct   8160
tggcttgtgg tatcctaagg gttccaagtt caatctactt ggctattcgg actccgatta   8220
cgccggttgc aaagtagata gaaaaagcac ttcggggaca tgtcaattgc ttggacggtc   8280
cttattgtct tggagctcta agaagcaaaa ttgtgtagcc ctttccactg cggaggccga   8340
gtatgttgta gccggcgcat gctgtgctca actactttgg atgaagcaaa cccttcaaga   8400
tttcggatgt cacctcacca aaatcccaat attatgtgac tatgaaagcg ccataaagct   8460
tgcaaacaac cccgtaagtc actcaagaac taaacacata gacatccgac atcatttctt   8520
gagagaccac gaagctaaag gagatattga aattcgtcat gtgagcaccg aaaagcaact   8580
agccgatatt ttcactaaac ccctcgatga gtcaaggttt tgtgagctgc gtagtgaact   8640
aaatatcctt gattctcgta acgtgacttg aaatcctgca catatatgtt tgtcaaccta   8700
gcgacatagg caaaatcttg aaaagctgat ttacaagtct ttcaaaacat ttacaaaatg   8760
tctcttagta ttatgatcat agtatgtatt gttgtttgtt tgctgatcat aatacttagg   8820
gattaacctg tccttatcta aagtaaagaa taggaaaagg atttagctgt acccctgcaa   8880
gttggacagg gcgacagtgc cgccctttga atccacaatg gattcgggcc caatttggct   8940
gaggcgcggg gcccatctcc ctctacctct tttctctctg gctccgcccc tcctctttcc   9000
tttctctccc agacgtgcac agcacctccc ttctccttct tctctcctct agggttaggg   9060
```

```
caaggtgcaa gtgctcatag ccatgttctc cacggccctt ggcgagttcc cagcctctcc   9120
tctcgttgct ggtgactgcc cccctgctca agccttgggc attgctcttc tttcctcttc   9180
attcaacacg taagatggat cgagaaggat atgatgctag ggaaaagagg aaagtgttgg   9240
cgaagcaatt ggctcgcaga ggcaggggga ggacagcggg aggtagtggt gcagcacctc   9300
gagccactga tagagcagca catgatcaat atgtgtctga ggaggaaatg aatcaaagga   9360
ttggatacac catccccatt atgcatggca caccaaatca cctcacaggg tttgatgaca   9420
actatatgag ggacaatgag gatgagtttg ttctcacaga gcctcacaac aatgtgagac   9480
atacagtggt tgactatggg aggagttgga aggctactgg tgatgccaaa gagattgatc   9540
cctatgctgc agataagctg ttggggttga ttatagattt tcgaatgtgt tccactccaa   9600
cttctatgcc acagccatca tgacaaagcc taggggcaaa atctgcaaga tgcaatatgt   9660
tgatttcaat gagctgcaag atagaaatga gtttgctgct gccataaaga catgtgacag   9720
attccagttg actgatatca tgagtttcag gtatgattgg aatagagaaa tacttgcaca   9780
gtttcatgcc acatattttt ggaacaggga tgaggatgag atccactgga tgacagatga   9840
taggcattat cgcattgatt ttgtcagctt ctgtcatatt cttggttttg gacagattca   9900
tagatctttc agtaggatcc atgatgtgcg tcgccttgag ccacatgagg tgagttttat   9960
gtgggaagat cctagcaagg ctgatgggag aaggacaggg ttcaaggcaa tttattacac  10020
catgaacaac ctgtttagaa tcactctcaa tcccaaggac aatgcaactg atctaaatgg  10080
atatatcact aatgtgttat ctagattccc agagtggtga gagattcaat gtaggaagat  10140
ttatttgggt tgagttagct tatgccatgg atgatggaag aaggtcgctg ccatatgcac  10200
cttatctgat gttcatgatt aagagggttt taggtcagag attccccaat gactgcattc  10260
atggtgttta caacataaag aagacacatg ggggtaaggg gagcagcggg gcagcagccg  10320
gttcacccac tagagagaca tcctttgctc acagagatgt ttctgagtcc tctaggagtg  10380
gcaggaaaaa gaagagcaag aagctgggga agatgagtga atggatcaag gcctacctgt  10440
acctatgctg caaacactgc ttatgaggat cgtttggaga acagagaggc agttagggta  10500
gctagggagt tggctggtct tccacctctt gccccagtta ggcctcctcc tcaattccct  10560
aacctaccta gtctgtcaga cacctcttct gaggatgagc agccccatgg agatgcatag  10620
gagcagcact ttgagcagcc tgatggtgat gatagtgatg atgaggggat ctgggcagga  10680
gaggaagatc cacaggttca ggagaccttg ctacgtgtct actctcgacg tcctcgtgac  10740
cctttagagg cagctgggcc ttcttcttta gctccacctc gacgttcgct tcacctcgac  10800
cactcatgtt cagggacgtg ctagagttga ctccgacagc gacgacgagt gatttctctt  10860
cttttctctt ctctttttgg tgtttgatgc caaaggggga gaaaattaga ggggtcaaat  10920
tagttttgag atctagctgc gcttcatgtc ctatcttttg agagtagtct ttaggttgtg  10980
agagaaaacc gttgaaaaac tctattttat gtattatggc tacctcatct cactatttgc  11040
tttggatatg gacttgtttt aagaacaacg gttttattat ttagttcagt tcactgtgtt  11100
gtctctcctc tctagtttct gctgtgtttt tctggttgtt gtctgactgt tgggtattag  11160
gccggcagtg ccgcccttct aggccggcag tgccgcccta tgcctcagca gccaagcagc  11220
tctgttgttt aactatctgt ttgcatcacg tcttgtcttg tgacactttg cacaacaccc  11280
catagcaggc atggatgtag ggggaggtcc tcctacttga agatgtaaga ccttgcatca  11340
taaagcaagc ttttaggatt caatcctcat ttacatcttc agggggaggc ccctataatc  11400
```

```
ctggctcgaa aatcttaatt cttgtttata ttgttgaaag ctctaattag gttgtcatca  11460
atcaccaaaa agggggagat tgtaagtgga atcaagccct attgtgggtt ttggtgttaa  11520
tgacaacaaa attagaagac taacaagttt tatcgagtta atgagcaggg gatcaattta  11580
tggaaatgat gtacaggttg ctgatattct aaaaatatgt ttgagctgat ccaaactcaa  11640
ggatgtgtta cttcatttta ttttctttat ttgagtttag gaaaagccgt actataaagg  11700
ggaattctag aattgttggt caactgtgca accagatgct cgtcttcaca aaacaacatc  11760
ctctttctca gccaaagcag cacgcaaaac agtttctttc ttaacctgct ctggccaggg  11820
tggcagtgcc gccctctcct gaccgttggg acctagggga tatctttacc tctggacgct  11880
cctcacaacg gtcatcacag acctcagatg acttatctct tgctcagaca gaccagagct  11940
ctctctctct ctcctccatt gttgccctcc atccctcaag catcaatctt ttaagaaaaa  12000
aggtagcaaa actcgattgg agagtagatc cactgattcc caaggtctaa gagcattttg  12060
ttcacgtttg gtcggaggtt ctagggtttg ttactcttgg agcttgctcc tagccggcta  12120
ggcgtcgccc atgagcttgc cctcttgtgt ggcagccttg ggaggtttgt aaacttgttt  12180
tgcagctaag aaattacccc tcacttcaag agttcactct cttgacttga gaacgagggt  12240
agggcaagcc tttgtggcaa gcctaagcct agtgtggctt cctcaacaac gtggacctag  12300
gcaagccttt gtggtgagct gaaccacggg ataaatcact gagtcttgtg tgcttcttgc  12360
agattatttc tcaagttata ctcttctagg gtttggtggc cctatctagt cttgagagac  12420
ttttctttga catccagtct tcgtactgga tcttatcttt gttttgcagg attgtgttct  12480
tcaccaccta agtttacttc ctccaaagtt gtaccacctt tggtatttta tttgaaggct  12540
agcagtaccg ccctctgttc taacagagtt ttgagttgaa tttttgcagg cctattcacc  12600
ccccctctag gcctctttag cttccaggag atcctacagt atgttccttg caaatgatgc  12660
acctatcttg catcaagatt ggcactatct ccaaatagat caaaccgagc tttcacttga  12720
gcctcttcac cgaagtgatg aggacatcaa caccatcgat atatccgcac ctacaccagt  12780
tggaataatg gacaagatca gcaagggaag gttcaactgc attcggaatt tgaggcaaca  12840
ccaacttcaa gggctgattg catatgggaa gagtgataac ttaacaaagg tgattggaga  12900
tcaggtccaa gcctccacaa catcctctat caagttacca cgtcgcttct aaagcaagga  12960
aacaaagagt ccaaacccaa cacgttttgg gagttggatt cggactggaa aataactcta  13020
acttgtatgg atcaccacgg cgtcatatgg actccaactg ggacgttcct atacttgttg  13080
gaaagttcat gaagtctact ttccaatggg tccaaccaca tatctatgca gcttatgagt  13140
cgggcgcagt ccttgttttc gtgccgatac ctttttctgt tctggtgctg cgtcacccta  13200
ttttggacca atggcccatg tatcaagttg agtctattag ggacgcgtcc tcgggttgga  13260
ggatgactct agcacccctt tggtcgtcct cccctctatt tatttacatc tagagccgcc  13320
atgaacaact gggttttgat tagataaagt ttagccttcg ctacttgctt gtaaacgcgc  13380
gtgctgatcc agccgcccgt cttcttgttt tcgaaacccc acttcattag agattgagtt  13440
tgaaaccttc atttacatct ggtaatttag tacttgttct acttgttctt gctggttctt  13500
cgattgcttg caggacgagt gccctagtgg tcgggtgttg cgctccacaa gatcgtgaca  13560
gccattggag gcggtgtatc ggttgctagg gcgcggcctt agaaggctgt agtcgggccg  13620
tgaacgtcat ctccattcac taatcgagtt atccagcgcc tctcatcgaa agatcaggca  13680
aaaaccctag tgggttcaca tcacgaagta ccaacacgtg cttccaaaat ggtttctgag  13740
actatggtgc attaggcgca aaccatgcac atatcttgca ccgaaacgaa cactatttct  13800
```

aaacagacca aagcgagatt ccatac 13826

<210> SEQ ID NO 318
<211> LENGTH: 682
<212> TYPE: DNA
<213> ORGANISM: Sorghum bicolor

<400> SEQUENCE: 318
cggtctgttt ggagacaatg ttagtttcgg tgcaagatag gtgcagggtt tgtgcctaat 60
gcaccatagt ctaagaaacc attttggatg cacttgttag tactcctagg tgaaggggct 120
caagtggatg ctcggttcgg tctgtttgga gatagtgtta atcttgatgc aagaaggtgc 180
acggtttgca tggaacatac caaattcttg gaaatcaatc tagacgcaca tgacggaacc 240
ctagatggcg tgtgtcatac aaaatcttgc tttggtctgt ttggagacag tgttagtttt 300
ggtgcaacat aggtgcaagg tttgcacata atgcagcata ggctaagaaa ccattttgga 360
tgcaccggtg gtactcctag gtaaaaggct caagtgaaag cttggtttgg tctatttgaa 420
gacagtgcta atcttgatgc aagatagatg cacggtcagc atggaacgta ccatatgctt 480
agaaattaat ttggacacac ccaatagaac tccttgatgg cgtgtgtcat atggaatctc 540
gcttttgtgt gcttagagac agtattagtt tcggtgcaag atgtgtgcac ggtttgcgcc 600
taatgcacca aagtctaaga aaccattttg gaagcacgtg ttggtactcc taggtgaaga 660
ggctcaagtg gaggctcggt tc 682

<210> SEQ ID NO 319
<211> LENGTH: 146
<212> TYPE: DNA
<213> ORGANISM: Sorghum bicolor

<400> SEQUENCE: 319
ctccaaacag accgaactga gcttgcactt gagcctcttc atctaggagt ataaacaggt 60
gcgtcaaaaa tggtttctta gactatggtg cattaggcac aaactatgca cctatcttgc 120
accgaaacta acattgtctc caaaca 146

<210> SEQ ID NO 320
<211> LENGTH: 416
<212> TYPE: DNA
<213> ORGANISM: Sorghum bicolor

<400> SEQUENCE: 320
gcttcggttc gtttagagac agtgttagtt ttggtagaag atatgtgcac ggtttacgcc 60
taatgcacca taggctaaga aaccatttta gatgcatctg atggtactcg tagttcaaga 120
ggctcaagtg gaggctcgat ctggtctgtt tagatatagt gctaatcttg atgcaagata 180
gttgcacagt attcatggaa cgtaccatat gttaagaaat caatttggat gcaccaaatg 240
gaactcctag atgacgtgtg tcatatagaa tctcgcttcg gtctgtttgg agacaatgtt 300
agtttcggtg caagataggt gcatagtttg tgcctaatgc accatagtct aagaaaccat 360
ttttgacgca cctgtttgtc cttctagatg aagaggctca actggaagct cggttc 416

<210> SEQ ID NO 321
<211> LENGTH: 126
<212> TYPE: DNA
<213> ORGANISM: Sorghum bicolor

<400> SEQUENCE: 321

```
atttttgacg cacctgtttg tactcctaga tgaagaggct caagtggaag cttggttcgg     60

cgctttggtc tgtttagaaa tagtgttagt tttggtgcaa gatttgtgca tggtttgcgc    120

ctaatg                                                               126


<210> SEQ ID NO 322
<211> LENGTH: 147
<212> TYPE: DNA
<213> ORGANISM: Sorghum bicolor

<400> SEQUENCE: 322

gcatggaaca taccatatgc ttggaaataa ttttgggtgc acccgatgga attccttcac     60

gacgtgtgtc atatcaaatc tcgctttggt ctgtttagaa atattgttag tttcggtgca    120

agatatgtgc atgctttgcg cctaatg                                        147


<210> SEQ ID NO 323
<211> LENGTH: 128
<212> TYPE: DNA
<213> ORGANISM: Sorghum bicolor

<400> SEQUENCE: 323

gcatggaaca taccatatcg cttggaaatc aatttggatg cacccgatgg aactccttga     60

tgacatgtgt catatggaat ctcgcttcgg tccatttgga gacattgtta gtttcagtgc    120

aagataga                                                             128


<210> SEQ ID NO 324
<211> LENGTH: 177
<212> TYPE: DNA
<213> ORGANISM: Sorghum bicolor

<400> SEQUENCE: 324

gatctgtttc gagatagagc taatcttcat gcaagaatga tgcacagtct gcatggaatg     60

taccatatgc ttagaaatta atttggacac acccgataga actccttcat gacgtgtcat    120

acggaatctc gctttggtgt gcttacagat agtattagtt tgctgcaaga tatgtgc       177


<210> SEQ ID NO 325
<211> LENGTH: 196
<212> TYPE: DNA
<213> ORGANISM: Sorghum bicolor

<400> SEQUENCE: 325

gtttggagat aatgctaatc ttgatgcaag atagatgcac ggtctgcatg gaacatacca     60

tatgcttaga aattaattta gacacacccg atagaactcc ttcatgacct atgtcatatg    120

gaatctcgct ttggtgtgct tagagacagt attagttacg gtgcaagata tgtgcatgtt    180

ttgcgcataa tgcacc                                                    196


<210> SEQ ID NO 326
<211> LENGTH: 274
<212> TYPE: DNA
<213> ORGANISM: Sorghum bicolor

<400> SEQUENCE: 326

ggtctgtttg gagacagtgc taatcttgac gcaagatagg tgacggtttg catggacgta     60

ccatatgcta ggaaatcaat ttggacgcac ccgatagaac tcctagatga cgtgtgtcat    120

atgaaatctc acttcggtcc atttggagat agtgttagtt tcggtgtaag ataggtgcac    180
```

-continued

```
ggtatgcacc taatgcacca taggcttaga aacacttgtg gaagcacccg atggtactct    240

ttggagacag tgttagtttc ggtgcaagaa aggt                                274
```